United States Patent
Jiang et al.

(10) Patent No.: US 11,040,964 B2
(45) Date of Patent: Jun. 22, 2021

(54) COMPOUNDS AND METHODS OF USE

(71) Applicant: Ferro Therapeutics, Inc., Palo Alto, CA (US)

(72) Inventors: Chun Jiang, Hillsborough, CA (US); Anjali Pandey, Fremont, CA (US); Ruihong Chen, Burlingame, CA (US); Biswajit Kalita, Bangalore (IN); Athisayamani Jeyaraj Duraiswamy, Bangalore (IN)

(73) Assignee: Ferro Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 16/803,862

(22) Filed: Feb. 27, 2020

(65) Prior Publication Data

US 2020/0299283 A1 Sep. 24, 2020

Related U.S. Application Data

(63) Continuation-in-part of application No. PCT/US2019/019854, filed on Feb. 27, 2019, which is a continuation-in-part of application No. 16/287,805, filed on Feb. 27, 2019.

(60) Provisional application No. 62/893,092, filed on Aug. 28, 2019.

(51) Int. Cl.
| | |
|---|---|
| C07D 413/10 | (2006.01) |
| C07D 215/20 | (2006.01) |
| C07D 495/04 | (2006.01) |
| C07D 471/04 | (2006.01) |
| C07D 401/12 | (2006.01) |
| A61P 35/00 | (2006.01) |
| C07D 401/04 | (2006.01) |
| A61K 45/06 | (2006.01) |

(52) U.S. Cl.
CPC ............ *C07D 413/10* (2013.01); *A61P 35/00* (2018.01); *C07D 215/20* (2013.01); *C07D 401/04* (2013.01); *C07D 401/12* (2013.01); *C07D 471/04* (2013.01); *C07D 495/04* (2013.01); *A61K 45/06* (2013.01)

(58) Field of Classification Search
CPC .............................. C07D 413/10; A61P 35/00
See application file for complete search history.

(56) References Cited

U.S. PATENT DOCUMENTS

| 9,695,133 B2 | 7/2017 | Stockwell et al. |
| 10,519,148 B2 | 12/2019 | Guan et al. |
| 2003/0225092 A1 | 12/2003 | Orme et al. |
| 2003/0225902 A1 | 12/2003 | Orme et al. |
| 2010/0081654 A1 | 4/2010 | Stockwell et al. |
| 2016/0332974 A1 | 11/2016 | Stockwell et al. |
| 2019/0263802 A1 | 8/2019 | Chun et al. |
| 2020/0138829 A1 | 5/2020 | Chen et al. |

FOREIGN PATENT DOCUMENTS

| CN | 109796424 A | 5/2019 |
| FR | 2 916 200 A | 11/2008 |
| WO | WO 1997/03985 A1 | 2/1997 |
| WO | WO 2001/94347 A1 | 12/2001 |
| WO | WO 2002/28858 A2 | 4/2002 |
| WO | WO 2002/038563 A2 | 5/2002 |
| WO | WO 2007/016361 A2 | 2/2007 |
| WO | WO 2008/044144 A2 | 4/2008 |
| WO | WO 2008/103470 A2 | 8/2008 |
| WO | WO 2011/063223 A1 | 5/2011 |
| WO | WO 2014/011973 A2 | 1/2014 |
| WO | WO 2016/099452 A1 | 12/2014 |
| WO | WO 2015/051149 A1 | 4/2015 |
| WO | WO 2016/099452 A1 | 6/2016 |
| WO | WO 2016/196201 A1 | 12/2016 |
| WO | WO 2017/080338 A1 | 5/2017 |
| WO | WO 2017/120445 A1 | 7/2017 |
| WO | WO 2017/136688 A1 | 8/2017 |
| WO | WO 2018/118711 A1 | 6/2018 |
| WO | WO 2018/218087 A1 | 11/2018 |
| WO | WO 2019/016722 A2 | 1/2019 |
| WO | WO 2019/106434 A1 | 6/2019 |
| WO | WO 2019/113004 A1 | 6/2019 |
| WO | WO 2019/168999 | 9/2019 |
| WO | WO 2020/176757 | 9/2020 |

OTHER PUBLICATIONS

Database Entry [Online] Chemical Abstracts Service, Columbus, Ohio, US; May 22, 2001, XP002792599.
Eaton et al., "Selective covalent targeting of GPX4 using masked nitrile-oxide electrophiles." Natural Chemical Biology. May 2020; 16:497-506.
International Search Report and Written Opinion dated Aug. 8, 2018 for PCT/US2020/020150, 12 pages.
Smith et al., "Addition to Carbon-Hetero Multiple Bonds", March's Advanced Organic Chemistry: reactions, mechanisms, and structure, May 18, 2006, pp. 1430.
Sugita, et al. "Novel Phorbol Analogs Which Bind to Protein Kinase C (PKC) without Activation." Chem Pharm Bull. 1996; 44(2):463-465.
Wada et al., "Dramatic Switching of Protein Kinase C Agonist/Antagonist Activity by Modifying the 12-Ester Side Chain of Phorbol Esters." J. Am. Chem. Soc. 2002, 124, 10658-10659.
International Search Report and Written Opinion dated Jul. 17, 2019 for PCT/US2019/019854. 34 pages.
International Search Report and Written Opinion dated Aug. 8, 2018 for PCT/US2018/034491. 8 pages.
Beghyn et al.: "Drug-to-Genome-to-Drug, Step 2: Reversing Selectivity in a Series of Antiplasmodial Compounds", Journal of Medicinal Chemistry, vol. 55 No. 3, Jan. 24, 2012 (Jan. 24, 2012), pp. 1274-1286, XP055576643.
Chauhan et al.: "A Diversity Oriented Synthesis of Natural Product Inspired Molecular Libraries" Organic a& Biomolecular Chemistry, vol. 15, No. 43, Jan. 1, 2017, pp. 9108-9120, XP055601193.

(Continued)

*Primary Examiner* — Golam M Shameem
(74) *Attorney, Agent, or Firm* — Sheppard Mullin Richter & Hampton LLP

(57) ABSTRACT

This present disclosure relates to compounds with ferroptosis inducing activity, a method of treating a subject with cancer with the compounds, and combination treatments with a second therapeutic agent.

30 Claims, 1 Drawing Sheet

(56) References Cited

OTHER PUBLICATIONS

Chen et al.: "Diastereoselective Synthesis of Bridged Polycyclic Alkaloids via Tandem Acylation/Intramolecular Diels-Alder Reaction", Journal of Organic Chemistry, vol. 78, No. 19, Sep. 5, 2013, pp. 9738-9747, XP055601468.
Database CAPLUS [Online] Chemical Abstracts Service, Columbus, Ohio, US; 1987, Misztal, Stanislaw; Boksa, Jan; Chojnacka-Wojcik, Ewa; Tatarczynska, Ewa; Lewandowska, Anna: "Synthesis and pharmacological properties of some 2-substituted 1-(3-pyridyl)-1,2,3,4-tetrahydro-beta-carb olines", XP002792598.
Database CAPLUS [Online] Chemical Abstracts Service, Columbus, Ohio, US; 1989, Misztal, Stanislaw; Boska, Jan; Chojnacka-Wojcik, Ewa; Tatarczynska, Ewa; Russeva, S.: "Synthesis and pharmacological properties of some 2-(3-aminopropionyl)- and 2-(3-aminopropyl)-1-(3-pyridyl)-1,2,3,4-te trahydro-beta-carbolines", XP002792597.
Database CAPLUS [Online] Chemical Abstracts Service, Columbus, Ohio, US; 2000, You, Ye Cheng et al.; "Application of DDQ in the synthesis of .beta.-carboline alkaloid", XP002790284.
Database CAPLUS [Online] Chemical Abstracts Service, Columbus, Ohio, US; Dec. 29, 1991 Misztal, Stanislaw; Dukat, Malgorzata; Mokrosz, Jerzy L.: "Structure and spectral properties of beta-carbolines. Part 3. Synthesis and stereochemistry of 1,2,3,4,6,7,9,10,15b,15c-decahydropyrido [1", 2":1', 2'] pyrazino [4', 3':1]pyrido[3,4-b] indoles", XP002792596.
Database Registry [Online] Chemical Abstracts Service, Columbus, Ohio, US; May 10, 2001, XP002792592.
Database Registry [Online] Chemical Abstracts Service, Columbus, Ohio, US; May 10, 2001, XP002792593.
Database Registry [Online] Chemical Abstracts Service, Columbus, Ohio, US; May 10, 2001, XP002792594.
Database Registry [Online] Chemical Abstracts Service, Columbus, Ohio, US; May 10, 2001, XP002792595.
Database Registry [Online] Chemical Abstracts Service, Columbus, Ohio, US; May 22, 2881, XP002792599.
Database Registry [Online] Chemical Abstracts Service, Columbus, Ohio, US; Sep. 3, 2008, XP002792591.
Daugan et al.: "The Discovery of Tadalafil: A Novel and Highly Selective PDE5 Inhibitor. 2: 2,3,6,7,12,12A-Hexahydropytrazinoä1', 2': 1,6 Üpyrodoä3, 4-Büindole-1,4-Dione", Journal of American Chemical Society, US, vol. 46, No. 21, Jan. 1, 2003, pp. 4533-4542, XP008052656, ISSN: 0022-2623.
Desai et al.: "How hydrogen bonds impact P-glycoprotein transport and permeability", Bioorganic & Medicinal Chemistry Letters, vol. 22, Issue 21, Nov. 1, 2012, pp. 6540-6548.
Eaton et al.: "Targeting a Therapy-Resistant Cancer Cell State Using Masked Electrophiles as GPX4 Inhibitors", Jul. 24, 2018, https://www.biorxiv.org/content/10.1101/376764v3.
El-Gamil et al.: "Design of Novel [beta]-Carboline Derivatives with Pendant 5-Bromothienyl and Their Evaluation as Phosphodiesterase-5 Inhibitors", Archiv Der Pharmazie, vol. 346, No. 1, Jan. 1, 2013, pp. 23-33, XP055601459.
Hangauer et al.: "Drug-tolerant persister cancer cells are vulnerable to GPX4 inhibition", Nature International Journal of Science, vol. 551, Nov. 9, 2017, pp. 247-250.
Jiang et al: "Synthesis and SAR of Tetracyclic Pyrroloquinolones as Phosphodiesterase 5 Inhibitors", Bioorganic & Medicinal Chemi, Pergamon, GB, vol. 12, No. 6, Mar. 15, 2004 (Mar. 15, 2004), pp. 1505-1515, XP008105689.
Lemaire et al., Alternative Synthesis of the PDE5 Inhibitor RWJ387273 (R290629), Synlett, vol. 20007, No. 5, Mar. 1, 2007, pp. 0709-0712, XP055577124.
Lonsdale et. al.: "Expanding the Armory: Predicating and Tuning Covalent Warhead Reactivity", Journal of Chemical Information and Modeling, Nov. 13, 2017. Retrieved from the internet: URL: http://pubs.acs.org, retrieved on Nov. 15, 2017.
Misztal et al.: "Structure and Spectral Properties of p-Carbolines. Part 4. Synthesis of the New Ring System", J.Chem. Soc. Perkin Trans, Jan. 1, 1991, XP055601572.
Ooko et al.: [Abstract] "Artemisinin derivatives induce iron-dependent cell death (ferroptosis) in tumor cells", Internation Journal of Phytotherapy & Phytopharmacology, vol. 22, Issue 11, Oct. 15, 2015, pp. 1045-1054.
Roh et al.: [Abstract] "Induction of ferroptotic cell death for overcoming cisplatin resistance of head and neck cancer",Cancer Letters, vol. 381, Issue1, pp. 96-103,Oct. 10, 2016.
St. Jean Jr. et al.: "Mitigating Heterocycle Metabolism in Drug Discovery", Journal of Medicinal Chemistry, Apr. 25, 2012. Retrieved from the internet: URL: https://pubs.acs.org/sharingguidelines, retrieved Oct. 15, 2018.
Viswanathan et al.: "Dependency of a therapy-resistant state of cancer cells on a lipid peroxidase pathway", Nature International Journal of Science, vol. 547, Jul. 27, 2017, pp. 453-457.
Yang et al.: "Regulation of Ferroptotic Cancer Cell Death by GPX4", Cell, vol. 156, Jan. 16, 2014, pp. 317-331.
Zheng et al: " Discovery of furyl/thienyl [beta]-carboline derivatives as potent and selective PDE5 inhibitors with excellent vasorelaxant effect" , European Journal of Medicinal Chemistry, vol. 158, Sep. 15, 2018, pp. 767-788, XP055601520.
Zheng et al.: "S1 Supporting Information Discovery of Furyl/Thienyl [beta]-Carboline Derivatives as Potent and Selective PDE5 Inhibitors with Excellent Vasorelaxant Effect" , Sep. 15, 2018 (Sep. 15, 2018), pp. S1-S170, XP055601535, Retrieved from the Internet: URL: https://ars.els-cdn.com/content/image/1-s2.0-S0223523418308006-mmc1.pdf, retrieved on Jul. 2, 2019.

COMPOUNDS AND METHODS OF USE

CROSS-REFERENCE TO RELATED APPLICATIONS

This application is a continuation-in-part of PCT application number PCT/US2019/019,854, filed Feb. 27, 2019, a continuation-in-part of U.S. patent application Ser. No. 16/287,805, filed Feb. 27, 2019, and claims the benefit under 35 U.S.C. § 119(e) to U.S. Provisional Patent Application No. 62/893,092, filed Aug. 28, 2019, the contents of which are incorporated herein in their entirety.

BACKGROUND

Glutathione peroxidase 4 (GPX4) can directly reduce phospholipid hydroperoxide. Depletion of GPX4 induces lipid peroxidation-dependent cell death. Cancer cells in a drug-induced, therapy-resistant state have an enhanced dependence on the lipid peroxidase activity of GPX4 to prevent undergoing ferroptotic cell death. Studies have shown that lipophilic antioxidants, such as Ferrostatin, can rescue cells from GPX4 inhibition-induced ferroptosis. For instance, mesenchymal state GPX4-knockout cells can survive in the presence of Ferrostatin, however, when the supply of Ferrostatin is terminated, these cells undergo ferroptosis (see, e.g., Viswanathan et al., Nature 547:453-7, 2017). It has also been experimentally determined that that GPX4i can be rescued by blocking other components of the ferroptosis pathways, such as lipid ROS scavengers (Ferrostatin, Liproxstatin), lipoxygenase inhibitors, iron chelators and caspase inhibitors, which an apoptotic inhibitor does not rescue. These findings are suggestive of non-apoptotic, iron-dependent, oxidative cell death (i.e., ferroptosis). Accordingly, a GPX4 inhibitor can be useful to induce ferroptotic cancer cell death and thus treat cancer.

SUMMARY

The present disclosure relates to compounds having ferroptosis inducing activity, and methods of using the compounds for the treatment of cancer. In certain embodiments, provided herein is a compound of Formula I:

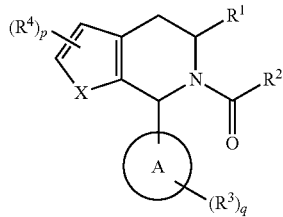

or a tautomer, stereoisomer, mixture of stereoisomers, isotopically enriched analog, or pharmaceutically acceptable salt thereof, wherein:

ring A is $C_4$-$C_{10}$cycloalkyl, heterocyclyl, aryl, or heteroaryl;

X is —O—, —S—, —$NR^9$—, —$CR^5$=$CR^5$—, or —$CR^5$=N—;

p is 0, 1 or 2;

q is 0, 1, 2 or 3;

$R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —$OR^7$, —C(O)$OR^6$, —C(O)N($R^7$)$_2$, —OC(O)$R^6$, —S(O)$_2R^8$, —S(O)$_2$N($R^7$)$_2$, —S(O)N($R^7$)$_2$, —S(O)$R^8$, —N($R^7$)$_2$, —$NO_2$, —$C_1$-$C_6$alkyl-$OR^7$, or—Si($R^{15}$)$_3$;

$R^2$ is —$C_1$-$C_2$haloalkyl, —$C_2$-$C_3$alkenyl, —$C_2$-$C_3$haloalkenyl, $C_2$alkynyl, or—$CH_2OS(O)_2$-phenyl, wherein the $C_1$-$C_2$alkylhalo and—$C_2$-$C_3$alkenylhalo are optionally substituted with one or two—$CH_3$, and the $C_2$alkynyl and phenyl are optionally substituted with one—$CH_3$;

each $R^3$ is independently halo, —CN, —OH, —$OR^8$, —$NH_2$, —$NHR^8$, —N($R^8$)$_2$, —S(O)$_2R^8$, —S(O)$R^8$, —S(O)$_2$N($R^7$)$_2$, —S(O)N($R^7$)$_2$, —$NO_2$, —Si($R^{12}$)$_3$, —$SF_5$, —C(O)$OR^6$, —C(O)N($R^7$)$_2$, —$NR^{12}$C(O)$R^8$, —$NR^{12}$C(O)$OR^8$, —OC(O)N($R^7$)$_2$, —OC(O)$R^8$, —C(O)$R^6$, —OC(O)$CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of $R^3$ is independently optionally substituted with one to three $R^{10}$;

each $R^4$ is independently halo, —CN, —OH, —$OR^8$, —$NH_2$, —$NHR^8$, —N($R^8$)$_2$, —S(O)$_2R^8$, —S(O)$R^8$, —S(O)$_2$N($R^7$)$_2$, —S(O)N($R^7$)$_2$, —$NO_2$, —Si($R^5$)$_3$, —C(O)$OR^6$, —C(O)N($R^7$)$_2$, —$NR^{12}$C(O)$R^8$, —OC(O)R, —C(O)$R^6$, —$NR^{12}$C(O)$OR^8$, —OC(O)N($R^7$)$_2$, —OC(O)$CHR^8$N($R^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of $R^4$ is optionally independently optionally substituted with one to three $R^{10}$;

each $R^5$ is independently hydrogen, halo, —CN, —OH, —$OR^8$, —$NH_2$, —$NHR^8$, —N($R^8$)$_2$, —S(O)$_2R^8$, —S(O)$R^8$, —S(O)$_2$N($R^7$)$_2$, —S(O)N($R^7$)$_2$, —$NO_2$, —Si($R^5$)$_3$, —C(O)$OR^6$, —C(O)N($R^7$)$_2$, —$NR^{12}$C(O)$R^8$, —OC(O)$R^8$, —C(O)$R^6$, —$NR^{12}$C(O)$OR^8$, —OC(O)N($R^7$)$_2$, —OC(O)$CHR^8$N($R^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of R is optionally independently optionally substituted with one to three $R^{10}$;

each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $R^6$ is independently further substituted with one to three $R^{11}$;

each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, —$C_2$-$C_6$alkenylheteroaryl, or two $R^7$ together with the nitrogen atom to which they are attached, form a 4 to 7 membered heterocyclyl; wherein each $R^7$ or ring formed thereby is independently further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl; wherein each $R^8$ is independently further substituted with one to three $R^{11}$;

$R^9$ is hydrogen or $C_1$-$C_6$alkyl;

each $R^{10}$ is independently halo, —CN, —$OR^{12}$, —$NO_2$, —$N(R^{12})_2$, —$S(O)R^3$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —$OR^{12}$, —$NO_2$, —$N(R^{12})_2$, —$S(O)R^3$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl or $C_3$-$C_{10}$cycloalkyl; and each $R^{15}$ is independently $C_1$-$C_6$alkyl, $C_2$-$C_6$alkenyl, aryl, heteroaryl, —$C_1$-$C_6$alkylaryl, —$C_2$-$C_6$alkenylaryl, —$C_1$-$C_6$alkylheteroaryl, and—$C_2$-$C_6$alkenylheteroaryl; provided that at least one of the following is true:

1) $R^1$ is other than—$C(O)OCH_3$;
2) $R^2$ is—$C_2$alkynyl optionally substituted with one—$CH_3$; or
3) when $R^1$ is—$C(O)OCH_3$ and $R^2$ is—$CH_2Cl$, then the moiety

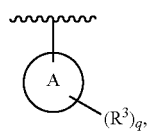

is other than 1,3-benzodioxol-5-yl, 4-nitrophenyl, 4-bromophenyl, cyclohexyl, furyl, or 4-methoxyphenyl.

In certain embodiments, the compounds, or a tautomer, stereoisomer, mixture of stereoisomers, isotopically enriched analog, or pharmaceutically acceptable salt thereof, or pharmaceutical compositions comprising the same, exhibit GPX4 inhibiting activity, and in certain embodiments, exhibit altered or enhanced stability (e.g., metabolic stability) and/or enhanced activity or other characteristics as compared to other GPX4 inhibitors. In certain embodiments, the compounds described herein, or a tautomer, stereoisomer, mixture of stereoisomers, isotopically enriched analog, or pharmaceutically acceptable salt thereof, or pharmaceutical compositions comprising the same, are selective for GPX4 over other GPXs. In certain embodiments, the compounds are used in a method of inhibiting GPX4 in a cell, comprising contacting a cell with an effective amount of the compound described herein, or a tautomer, stereoisomer, mixture of stereoisomers, isotopically enriched analog, or pharmaceutically acceptable salt thereof, or pharmaceutical compositions comprising the same, to inhibit GPX4 in the cell. In certain embodiments, the cell is a cancer cell.

In certain embodiments, provided is a method of inducing ferroptosis in a cell comprising contacting the cell with an effective amount of a compound of Formula I:

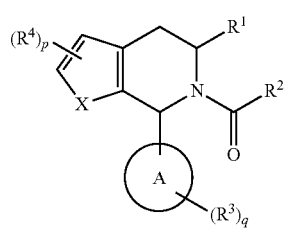

I or a tautomer, stereoisomer, mixture of stereoisomers, isotopically enriched analog, or pharmaceutically acceptable salt thereof, wherein:

ring A is $C_4$-$C_{10}$cycloalkyl, heterocyclyl, aryl, or heteroaryl;

X is—O—, —S—, —$NR^9$—, —$CR^5$=$CR^5$—, or—$CR^5$=N—;

p is 0, 1 or 2;

q is 0, 1, 2 or 3;

$R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —$OR^7$, —$C(O)OR^6$, —$C(O)N(R^7)_2$, —$OC(O)R^6$, —$S(O)_2R^8$, —$S(O)_2N(R^7)_2$, —$S(O)N(R^7)_2$, —$S(O)R^8$, —$N(R^7)_2$, —$NO_2$, —$C_1$-$C_6$alkyl-$OR^7$, or—$Si(R^{15})_3$;

$R^2$ is—$C_1$-$C_2$haloalkyl, —$C_2$-$C_3$alkenyl, —$C_2$-$C_3$haloalkenyl, $C_2$alkynyl, or—$CH_2OS(O)_2$-phenyl, wherein the $C_1$-$C_2$alkylhalo and—$C_2$-$C_3$alkenylhalo are optionally substituted with one or two—$CH_3$, and the $C_2$alkynyl and phenyl are optionally substituted with one—$CH_3$;

each $R^3$ is independently halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{12})_3$, —$SF_5$, —$C(O)OR^6$, —$C(O)N(R^7)_2$, —$NR^{12}C(O)R^8$, —$NR^{12}C(O)OR^8$, —$OC(O)N(R^7)_2$, —$OC(O)R^8$, —$C(O)R^6$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-

$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of $R^3$ is independently optionally substituted with one to three $R^{10}$;

each $R^4$ is independently halo, —CN, —OH, —$OR^8$, —$NH_2$, —$NHR^8$, —$N(R^8)_2$, —$S(O)_2R$, —$S(O)R^8$, —$S(O)_2N(R^7)_2$, —$S(O)N(R^7)_2$, —$NO_2$, —$Si(R^5)_3$, —$C(O)OR^6$, —$C(O)N(R^7)_2$, —$NR^{12}C(O)R^8$, —$OC(O)R$, —$C(O)R^6$, —$NR^{12}C(O)OR^8$, —$OC(O)N(R^7)_2$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of $R^4$ is optionally independently optionally substituted with one to three $R^{10}$;

each $R^5$ is independently hydrogen, halo, —CN, —OH, —$OR^8$, —$NH_2$, —$NHR^8$, —$N(R^8)_2$, —$S(O)_2R$, —$S(O)R^8$, —$S(O)_2N(R^7)_2$, —$S(O)N(R^7)_2$, —$NO_2$, —$Si(R^5)_3$, —$C(O)OR^6$, —$C(O)N(R^7)_2$, —$NR^{12}C(O)R^8$, —$OC(O)R^8$, —$C(O)R^6$, —$NR^{12}C(O)OR^8$, —$OC(O)N(R^7)_2$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of $R^5$ is optionally independently optionally substituted with one to three $R^{10}$;

each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $R^6$ is independently further substituted with one to three $R^{11}$;

each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl, or two $R^7$ together with the nitrogen atom to which they are attached, form a 4 to 7 membered heterocyclyl; wherein each $R^7$ or ring formed thereby is independently further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl; wherein each $R^8$ is independently further substituted with one to three $R^{11}$;

$R^9$ is hydrogen or $C_1$-$C_6$alkyl;

each $R^{10}$ is independently halo, —CN, —$OR^{12}$, —$NO_2$, —$N(R^{12})_2$, —$S(O)R^3$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl or $C_3$-$C_{10}$cycloalkyl; and each $R^{15}$ is independently $C_1$-$C_6$alkyl, $C_2$-$C_6$alkenyl, aryl, heteroaryl, —$C_1$-$C_6$alkylaryl, —$C_2$-$C_6$alkenylaryl, —$C_1$-$C_6$alkylheteroaryl, and—$C_2$-$C_6$alkenylheteroaryl, or pharmaceutical composition comprising the same.

In certain embodiments, provided is a method for treating a cancer in a patient in need thereof, comprising administering an effective amount of a compound, or a tautomer, stereoisomer, mixture of stereoisomers, isotopically enriched analog, or pharmaceutically acceptable salt thereof, or pharmaceutical composition provided herein. In certain embodiments, provided is a method for treating a malignant solid tumor in a patient in need thereof, comprising administering an effective amount of a compound, or a tautomer, stereoisomer, mixture of stereoisomers, isotopically enriched analog, or pharmaceutically acceptable salt thereof, or pharmaceutical composition provided herein to the patient. In certain embodiments, the malignant solid tumor is a sarcoma, carcinoma, or lymphoma. In certain embodiments, the method comprises a compound of Formula I:

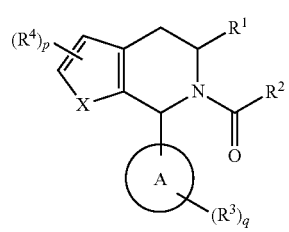

I or a tautomer, stereoisomer, mixture of stereoisomers, isotopically enriched analog, or pharmaceutically acceptable salt thereof, wherein:

ring A is $C_4$-$C_{10}$cycloalkyl, heterocyclyl, aryl, or heteroaryl;

X is —O—, —S—, —NR$^9$—, —CR$^5$=CR$^5$—, or —CR$^5$=N—;

p is 0, 1 or 2;

q is 0, 1, 2 or 3;

$R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —OR$^7$, —C(O)OR$^6$, —C(O)N(R$^7$)$_2$, —OC(O)R$^6$, —S(O)$_2$R$^8$, —S(O)$_2$N(R$^7$)$_2$, —S(O)N(R$^7$)$_2$, —S(O)R$^8$, —N(R$^7$)$_2$, —NO$_2$, —$C_1$-$C_6$alkyl-OR$^7$, or —Si(R$^{15}$)$_3$;

$R^2$ is —$C_1$-$C_2$haloalkyl, —$C_2$-$C_3$alkenyl, —$C_2$-$C_3$haloalkenyl, $C_2$alkynyl, or —CH$_2$OS(O)$_2$-phenyl, wherein the $C_1$-$C_2$alkylhalo and —$C_2$-$C_3$alkenylhalo are optionally substituted with one or two —CH$_3$, and the $C_2$alkynyl and phenyl are optionally substituted with one —CH$_3$;

each $R^3$ is independently halo, —CN, —OH, —OR$^8$, —NH$_2$, —NHR$^8$, —N(R$^8$)$_2$, —S(O)$_2$R$^8$, —S(O)R$^8$, —S(O)$_2$N(R$^7$)$_2$, —S(O)N(R$^7$)$_2$, —NO$_2$, —Si(R$^{12}$)$_3$, —SF$_5$, —C(O)OR$^6$, —C(O)N(R$^7$)$_2$, —NR$^{12}$C(O)R$^8$, —NR$^{12}$C(O)OR$^8$, —OC(O)N(R$^7$)$_2$, —OC(O)R$^8$, —C(O)R$^6$, —OC(O)CHR$^8$N(R$^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_{10}$cycloalkyl, —$C_2$-$C_6$alkenylC$_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_{10}$cycloalkyl, —$C_2$-$C_6$alkenylC$_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^3$ is independently optionally substituted with one to three $R^{10}$;

each $R^4$ is independently halo, —CN, —OH, —OR$^8$, —NH$_2$, —NHR$^8$, —N(R$^8$)$_2$, —S(O)$_2$R$^8$, —S(O)R$^8$, —S(O)$_2$N(R$^7$)$_2$, —S(O)N(R$^7$)$_2$, —NO$_2$, —Si(R$^5$)$_3$, —C(O)OR$^6$, —C(O)N(R$^7$)$_2$, —NR$^{12}$C(O)R$^8$, —OC(O)R, —C(O)R$^6$, —NR$^{12}$C(O)OR$^8$, —OC(O)N(R$^7$)$_2$, —OC(O)CHR$^8$N(R$^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_{10}$cycloalkyl, —$C_2$-$C_6$alkenylC$_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_{10}$cycloalkyl, —$C_2$-$C_6$alkenylC$_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^4$ is optionally independently optionally substituted with one to three $R^{10}$;

each $R^5$ is independently hydrogen, halo, —CN, —OH, —OR$^8$, —NH$_2$, —NHR$^8$, —N(R$^8$)$_2$, —S(O)$_2$R$^8$, —S(O)R$^8$, —S(O)$_2$N(R$^7$)$_2$, —S(O)N(R$^7$)$_2$, —NO$_2$, —Si(R$^5$)$_3$, —C(O)OR$^6$, —C(O)N(R$^7$)$_2$, —NR$^{12}$C(O)R$^8$, —OC(O)R$^8$, —C(O)R$^6$, —NR$^{12}$C(O)OR$^8$, —OC(O)N(R$^7$)$_2$, —OC(O)CHR$^8$N(R$^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_{10}$cycloalkyl, —$C_2$-$C_6$alkenylC$_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_{10}$cycloalkyl, —$C_2$-$C_6$alkenylC$_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^5$ is optionally independently optionally substituted with one to three $R^{10}$;

each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_{10}$cycloalkyl, —$C_2$-$C_6$alkenylC$_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $R^6$ is independently further substituted with one to three $R^{11}$;

each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_6$cycloalkyl, —$C_2$-$C_6$alkenylC$_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, —$C_2$-$C_6$alkenylheteroaryl, or two $R^7$ together with the nitrogen atom to which they are attached, form a 4 to 7 membered heterocyclyl; wherein each $R^7$ or ring formed thereby is independently further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkylC$_3$-$C_{10}$cycloalkyl, —$C_2$-$C_6$alkenylC$_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $R^8$ is independently further substituted with one to three $R^{11}$;

$R^9$ is hydrogen or $C_1$-$C_6$alkyl;

each $R^{10}$ is independently halo, —CN, —OR$^{12}$, —NO$_2$, —N(R$^{12}$)$_2$, —S(O)R$^{13}$, —S(O)$_2$R$^{13}$, —S(O)N(R$^{12}$)$_2$, —S(O)$_2$N(R$^{12}$)$_2$, —Si(R$^{12}$)$_3$, —C(O)R$^{12}$, —C(O)OR$^{12}$, —C(O)N(R$^{12}$)$_2$, —NR$^{12}$C(O)R$^{12}$, —OC(O)R$^{12}$, —OC(O)OR$^{12}$, —OC(O)N(R$^{12}$)$_2$, —NR$^{12}$C(O)OR$^{12}$, —OC(O)CHR$^{12}$N(R$^{12}$)$_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —OR$^{12}$, —NO$_2$, —N(R$^{12}$)$_2$, —S(O)R$^3$, —S(O)$_2$R$^{13}$, —S(O)N(R$^{12}$)$_2$, —S(O)$_2$N(R$^{12}$)$_2$, —Si(R$^{12}$)$_3$, —C(O)R$^{12}$, —C(O)OR$^{12}$, —C(O)N(R$^{12}$)$_2$, —NR$^{12}$C(O)R$^{12}$, —OC(O)R$^{12}$, —OC(O)OR$^{12}$, —OC(O)N(R$^{12}$)$_2$, —NR$^{12}$C(O)OR$^{12}$, —OC(O)CHR$^{12}$N(R$^{12}$)$_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl or $C_3$-$C_{10}$cycloalkyl; and each $R^{15}$ is independently $C_1$-$C_6$alkyl, $C_2$-$C_6$alkenyl, aryl, heteroaryl, —$C_1$-$C_6$alkylaryl, —$C_2$-$C_6$alkenylaryl, —$C_1$-$C_6$alkylheteroaryl, and —$C_2$-$C_6$alkenylheteroaryl.

DETAILED DESCRIPTION

Figure 1:
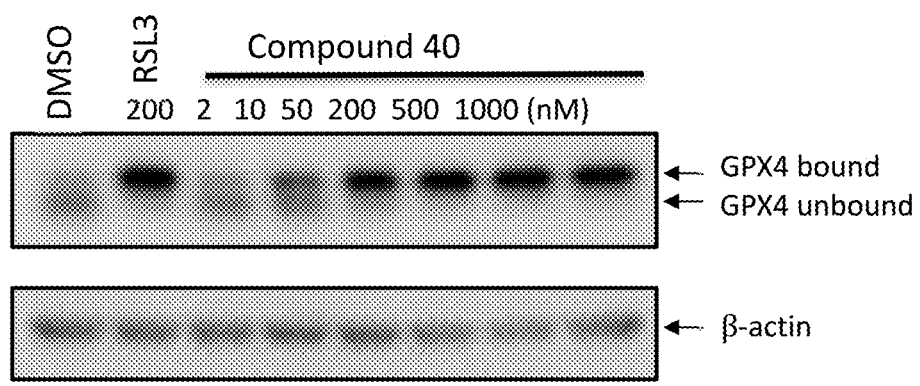
FIG. 1 shows compound 40 tested in cell-based Western blot analysis of GPX4.

As used in this specification and the appended claims, the singular forms "a," "an" and "the" include plural referents unless the context clearly indicates otherwise. Thus, for example, reference to "a protein" includes more than one protein, and reference to "a compound" refers to more than one compound.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure. The section headings used herein are for organizational purposes only and not to be construed as limiting the subject matter described.

1. Definitions

In reference to the present disclosure, the technical and scientific terms used in the descriptions herein will have the meanings commonly understood by one of ordinary skill in the art, unless specifically defined otherwise. Accordingly, the following terms are intended to have the meanings as described below.

"Ferroptosis" refers to a form of cell death understood in the art as involving generation of reactive oxygen species mediated by iron, and characterized by, in part, lipid peroxidation.

"Ferroptosis inducer" or "ferroptosis activator" refers to an agent which induces, promotes or activates ferroptosis.

"GPX4 inhibitor" refers to any agent that inhibits the activity of the enzyme glutathione peroxidase 4 (GPX4). A GPX4 inhibitor can be either a direct or indirect inhibitor. GPX4 is a phospholipid hydroperoxidase that in catalyzing the reduction of hydrogen peroxide and organic peroxides, thereby protects cells against membrane lipid peroxidation, or oxidative stress. GPX4 has a selenocysteine in the active site that is oxidized to a selenenic acid by the peroxide to afford a lipid-alcohol. The glutathione acts to reduce the selenenic acid (—SeOH) back to the selenol (—SeH). Should this catalytic cycle be disrupted, cell death occurs through an intracellular iron-mediated process known as ferroptosis.

"Subject" as used herein refers to a mammal, for example a dog, a cat, a horse, or a rabbit. In certain embodiments, the subject is a non-human primate, for example a monkey, chimpanzee, or gorilla. In certain embodiments, the subject is a human, sometimes referred to herein as a patient.

"Treating" or "treatment" of a disease, disorder, or syndrome, as used herein, includes (i) preventing the disease, disorder, or syndrome from occurring in a subject, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art, particularly in view of the guidance provided in the present disclosure.

"Therapeutically effective amount" refers to that amount which, when administered to an animal (e.g., human) for treating a disease, is sufficient to effect such treatment for the disease, disorder, or condition. In certain embodiments, the treatment provides a therapeutic benefit such as amelioration of symptoms or slowing of disease progression. For example, a therapeutically effective amount may be an amount sufficient to decrease a symptom of a disease or condition of as described herein.

"Alkyl" refers to a straight or branched chain hydrocarbon group of 1 to 20 carbon atoms ($C_1$-$C_{20}$ or $C_{1-20}$), 1 to 12 carbon atoms ($C_1$-$C_{12}$ or $C_{1-12}$), or 1 to 8 carbon atoms ($C_1$-$C_8$ or $C_{1-8}$). Exemplary "alkyl" includes, but are not limited to, methyl, ethyl, n-propyl, i-propyl, n-butyl, s-butyl, t-butyl, n-pentyl, and s-pentyl, and the like.

"Alkenyl" refers to a straight or branched chain hydrocarbon group of 2 to 20 carbon atoms ($C_2$-$C_{20}$ or $C_{2-20}$), 2 to 12 carbon atoms ($C_2$-$C_{12}$ or $C_{2-12}$), or 2 to 8 carbon atoms ($C_2$-$C_8$ or $C_2$-8), having at least one double bond. Exemplary "alkenyl" includes, but are not limited to, vinyl, ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl, and the like.

"Alkynyl" refers to a straight or branched chain hydrocarbon group of 2 to 12 carbon atoms ($C_2$-$C_{12}$ or $C_{2-12}$), 2 to 8 carbon atoms ($C_2$-$C_8$ or $C_{2-8}$), containing at least one triple bond. Exemplary "alkynyl" includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl, and the like.

"Alkylene," "alkenylene" and "alkynylene" refers to a straight or branched chain divalent hydrocarbon radical of the corresponding alkyl, alkenyl, and alkynyl, respectively. In certain embodiments, "alkyl," "alkenyl," and "alkynyl" can represent the corresponding "alkylene," "alkenylene" and "alkynylene," such as, by way of example and not limitation, cycloalkylalkyl-, heterocycloalkylalkyl-, arylalkyl-, heteroarylalkyl-, cycloalkylalkenyl-, heterocycloalkylalkenyl-, arylalkenyl-, heteroarylalkenyl-, cycloalkylalkynyl-, heterocycloalkylalkynyl-, arylalkynyl-, heteroarylalkynyl-, and the like, wherein the cycloalkyl, heterocycloalkyl, aryl, and heteroaryl group is connected, as a substituent via the corresponding alkylene, alkenylene, or alkynylene group.

"Lower" in reference to substituents refers to a group having between one and six carbon atoms.

"Alkylhalo" or "haloalkyl" refers to a straight or branched chain hydrocarbon group of 1 to 20 carbon atoms ($C_1$-$C_{20}$ or $C_{1-20}$), 1 to 12 carbon atoms ($C_1$-$C_{12}$ or $C_{1-12}$), or 1 to 8 carbon atoms ($C_1$-$C_8$ or $C_1$-8) wherein one or more (e.g., one to three, or one) hydrogen atom is replaced by a halogen (e.g., Cl, F, etc.). In certain embodiments, the term "alkylhalo" refers to an alkyl group as defined herein, wherein one hydrogen atom is replaced by a halogen (e.g., Cl, F, etc.). In certain embodiments, the term "alkylhalo" refers to an alkylchloride.

"Alkenylhalo" or "haloalkenyl" refers to a straight or branched chain hydrocarbon group of 2 to 20 carbon atoms ($C_2$-$C_{20}$ or $C_{2-20}$), 2 to 12 carbon atoms ($C_2$-$C_{12}$ or $C_{2-12}$), or 2 to 8 carbon atoms ($C_2$-$C_8$ or $C_{2-8}$), having at least one double bond, wherein one or more (e.g., one to three, or one) hydrogen atom is replaced by a halogen (e.g., Cl, F, etc.). In certain embodiments, the term "alkenylhalo" refers to an alkenyl group as defined herein, wherein one hydrogen atom is replaced by a halogen (e.g., Cl, F, etc.).

In certain embodiments, the term "alkenylhalo" refers to an alkenylchloride.

"Heteroalkyl" refers to a straight or branched chain hydrocarbon group of 1 to 20 carbon atoms ($C_1$-$C_{20}$ or $C_{1-20}$), 1 to 12 carbon atoms ($C_1$-$C_{12}$ or $C_{1-12}$), or 1 to 8 carbon atoms ($C_1$-$C_8$ or $C_{1-8}$), wherein 1 to 3 carbon atoms are replaced by a heteroatom. Heteroatoms and/or heteroatomic groups which can replace the carbon atoms include, but are not limited to, —O—, —S—, —NR$^{40}$—, —PH—, —C(O)—, —S(O)—, —S(O)$_2$—, —S(O)NR$^{40}$—, —S(O)$_2$NR$^{40}$—, and the like, including combinations thereof, wherein each R$^{40}$ is independently hydrogen or lower alkyl.

"Cycloalkyl" refers to any stable monocyclic or polycyclic system which consists of carbon atoms, any ring of which being saturated. "Cycloalkenyl" refers to any stable monocyclic or polycyclic system which consists of carbon atoms, with at least one ring thereof being partially unsaturated. Examples of cycloalkyls include, but are not limited to, cyclopropyl, cyclobutyl, cyclopentyl, cyclohexyl, cycloheptyl, cyclooctyl, bicycloalkyls and tricycloalkyls (e.g., adamantyl).

"Heterocycloalkyl" or "heterocyclyl" refers to a 4 to 14 membered, mono- or polycyclic (e.g., bicyclic), non-aromatic hydrocarbon ring, wherein 1 to 3 carbon atoms are replaced by a heteroatom. Heteroatoms and/or heteroatomic groups which can replace the carbon atoms include, but are not limited to, —O—, —S—, —S—O—, —NR$^{40}$—, —PH—, —C(O)—, —S(O)—, —S(O)$_2$—, —S(O)NR$^{40}$—, —S(O)$_2$NR$^{40}$—, and the like, including combinations thereof, where each R$^{40}$ is independently hydrogen or lower alkyl. Examples include thiazolidinyl, thiadiazolyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like. In certain embodiments, the "heterocycloalkyl" or "heterocyclyl" is a substituted or unsubstituted 4 to 7 membered monocyclic ring, wherein 1 to 3 carbon atoms are replaced by a heteroatom as described above.

In certain embodiments, the "heterocycloalkyl" or "heterocyclyl" is a 4 to 10, or 4 to 9, or 5 to 9, or 5 to 7, or 5 to 6 membered mono- or polycyclic (e.g., bicyclic) ring, wherein 1 to 3 carbon atoms are replaced by a heteroatom as described above. In certain embodiments, when the "heterocycloalkyl" or "heterocyclyl" is a substituted or unsubstituted bicyclic ring, one ring may be aromatic, provided at least one ring is non-aromatic, regardless of the point of attachment to the remainder of the molecule (e.g., indolinyl, isoindolinyl, and the like).

"Aryl" refers to a 6 to 14-membered, mono- or bicarbocyclic ring, wherein the monocyclic ring is aromatic and at least one of the rings in the bicyclic ring is aromatic. Unless stated otherwise, the valency of the group may be located on any atom of any ring within the radical, valency rules permitting. Examples of "aryl" groups include phenyl, naphthyl, indenyl, biphenyl, phenanthrenyl, naphthacenyl, and the like.

"Heteroaryl" means an aromatic heterocyclic ring, including monocyclic and polycyclic (e.g., bicyclic) ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In certain embodiments, the heteroaryl can be a 5 to 6 membered monocyclic, or 7 to 11 membered bicyclic ring systems. Examples of "heteroaryl" groups include pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinolyl, and the like.

"Bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In certain embodiments, a bridged bicyclic group has 5-12 ring members and 0-4 heteroatoms independently selected from nitrogen, oxygen, and sulfur. Such bridged bicyclic groups include those groups set forth below where each group is attached to the rest of the molecule at any substitutable carbon or nitrogen atom. Exemplary bridged bicyclics include, but are not limited to:

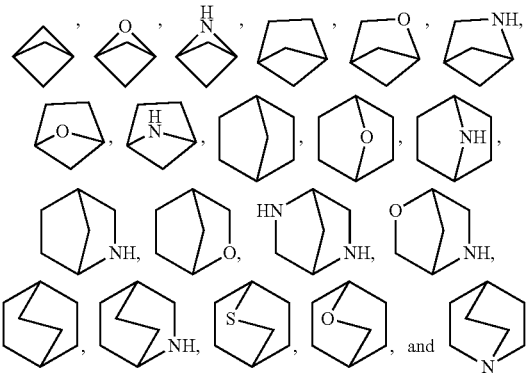

"Fused ring" refers a ring system with two or more rings having at least one bond and two atoms in common. A "fused aryl" and a "fused heteroaryl" refer to ring systems having at least one aryl and heteroaryl, respectively, that share at least one bond and two atoms in common with another ring.

"Halogen" or "halo" refers to fluorine, chlorine, bromine and iodine.

"Acyl" refers to —C(O)R$^{43}$, where R$^{43}$ is hydrogen, or an optionally substituted alkyl, heteroalkyl, cycloalkyl, cycloalkylalkyl, heterocycloalkyl, heterocycloalkylalkyl, aryl, arylalkyl, heteroaryl, or heteroarylalkyl as defined herein. Exemplary acyl groups include, but are not limited to, formyl, acetyl, cyclohexylcarbonyl, cyclohexylmethylcarbonyl, benzoyl, benzylcarbonyl, and the like.

"Alkyloxy" or "alkoxy" refers to —OR$^{44}$, wherein R$^{44}$ is an optionally substituted alkyl.

"Aryloxy" refers to —OR$^{45}$, wherein R$^{45}$ is an optionally substituted aryl.

"Carboxy" refers to —COO$^-$ or COOM, wherein M is H or a counterion (e.g., a cation, such as Na$^+$, Ca$^{2+}$, Mg$^{2+}$, etc.).

"Carbamoyl" refers to —C(O)NR$^{46}$R$^{46}$, wherein each R$^{46}$ is independently selected from H or an optionally substituted alkyl, cycloalkyl, cycloalkylalkyl, heterocycloalkyl, heterocylcoalkylalkyl, aryl, arylalkyl, heteroaryl, or heteroarylalkyl.

"Ester" refers to a group such as —C(=O)OR$^{47}$, alternatively illustrated as—C(O)OR$^{47}$, wherein R$^{47}$ is selected from an optionally substituted alkyl, cycloalkyl, cycloalkylalkyl, heterocycloalkyl, heterocyclolalkylalkyl, aryl, arylalkyl, heteroaryl, and heteroarylalkyl.

"Ether" refers to the group-alkyl-O-alkyl, where the term alkyl is as defined herein.

"Sulfanyl" refers to —SR$^{48}$, wherein R$^{48}$ is selected from an optionally substituted alkyl, cycloalkyl, cycloalkylalkyl, heterocycloalkyl, heterocycloalkylalkyl, aryl, arylalkyl, heteroaryl, and heteroarylalkyl.

For example, —SR$^{48}$, wherein R$^{48}$ is an alkyl is an alkylsulfanyl. "Sulfonyl" refers to —S(O)$_2$—, which may have various substituents to form different sulfonyl groups including sulfonic acids, sulfonamides, sulfonate esters, and sulfones. For example, —S(O)$_2$R$^{49}$, wherein R$^{49}$ is an alkyl refers to an alkylsulfonyl. In certain embodiments of —S(O)$_2$R$^{49}$, R$^{49}$ is selected from an optionally substituted alkyl, cycloalkyl, cycloalkylalkyl, heterocycloalkyl, heterocycloalkylalkyl, aryl, arylalkyl, heteroaryl, and heteroarylalkyl.

"Sulfinyl" refers to—S(O)—, which may have various substituents to form different sulfinyl groups including sulfinic acids, sulfinamides, and sulfinyl esters. For example, —S(O)R$^{50}$, wherein R$^{50}$ is an alkyl refers to an alkylsulfinyl. In certain embodiments of—S(O)R$^{50}$, R$^{50}$ is selected from an optionally substituted alkyl, cycloalkyl, cycloalkylalkyl, heterocycloalkyl, heterocycloalkylalkyl, aryl, arylalkyl, heteroaryl, and heteroarylalkyl.

"Silyl" refers to Si, which may have various substituents, for example—SiR$^{51}$R$^{51}$R$^{51}$, where each R$^{51}$ is independently selected from alkyl, cycloalkyl, cycloalkylalkyl, heterocycloalkyl, heterocycloalkylalkyl, aryl, arylalkyl, heteroaryl, and heteroarylalkyl. As defined herein, any heterocycloalkyl or heteroaryl group present in a silyl group has from 1 to 3 heteroatoms selected independently from O, N, and S.

"Amino" or "amine" refers to the group—NR$^{52}$R$^{52}$ or—N$^+$R$^{52}$R$^{52}$R$^{52}$, wherein each R$^{52}$ is independently selected from hydrogen and an optionally substituted alkyl, cycloalkyl, heterocycloalkyl, alkyloxy, aryl, heteroaryl, heteroarylalkyl, acyl, —C(O)—O-alkyl, sulfanyl, sulfinyl, sulfonyl, and the like. Exemplary amino groups include, but are not limited to, dimethylamino, diethylamino, trimethylammonium, triethylammonium, methylsulfonylamino, furanyl-oxy-sulfamino, and the like.

"Amide" refers to a group such as—C(=O)NR$^{53}$R$^{53}$, wherein each R$^{53}$ is independently selected from H and an optionally substituted alkyl, cycloalkyl, cycloalkylalkyl, heterocycloalkyl, heterocycloalkylalkyl, aryl, arylalkyl, heteroaryl, and heteroarylalkyl.

"Carbamate" refers to a group such as—O—C(=O) NR$^{53}$R$^{53}$ or—NR$^{53}$—C(=O)OR$^{53}$, wherein each R$^{53}$ is independently selected from H and an optionally substituted alkyl, cycloalkyl, cycloalkylalkyl, heterocycloalkyl, heterocycloalkylalkyl, aryl, arylalkyl, heteroaryl, and heteroarylalkyl.

"Sulfonamide" refers to—S(O)$_2$NR$^{54}$R$^{54}$, wherein each R$^{54}$ is independently selected from H and an optionally substituted alkyl, heteroalkyl, heteroaryl, heterocycle, alkenyl, alkynyl, arylalkyl, heteroarylalkyl, heterocyclylalkyl, alkylene-C(O)—OR$^{55}$, or alkylene-O—C(O)—OR$^{55}$, where R$^{55}$ is selected from H, alkyl, heteroalkyl, cycloalkyl, heterocyclyl, aryl, heteroaryl, alkenyl, alkynyl, arylalkyl, heterocycloalkyl, heteroarylalkyl, amino, and sulfinyl.

"Adamantyl" refers to tricyclo[3.3.1.1$^{3,7}$]decanyl, where bonding can be via a 3-coordinated carbon site or a 2-coordinated carbon site (i.e., 1-adamantyl or 2-adamantyl). In certain embodiments, "adamantyl" refers to a compound of structural formula:

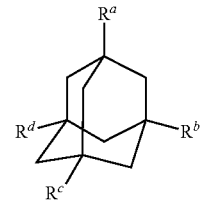

where optional substitutions can be present on one or more of R$^a$, R$^b$, R$^c$, and R$^d$. Adamantyl includes substituted adamantyl, e.g., 1- or 2-adamantyl, substituted by one or more substituents, including alkyl, halo, —OH, —NH$_2$, and alkoxy. Exemplary derivatives include methyladamatane, haloadamantane, hydroxyadamantane, and aminoadamantane (e.g., amantadine).

"N-protecting group" as used herein refers to those groups intended to protect a nitrogen atom against undesirable reactions during synthetic procedures. Exemplary N-protecting groups include, but is not limited to, acyl groups such acetyl and t-butylacetyl, pivaloyl, alkoxycarbonyl groups such as methyloxycarbonyl and t-butyloxycarbonyl (Boc), aryloxycarbonyl groups such as benzyloxycarbonyl (Cbz) and fluorenylmethoxycarbonyl (Fmoc) and aroyl groups such as benzoyl. N-protecting groups are described in Greene's Protective Groups in Organic Synthesis, 5th Edition, P. G. M. Wuts, ed., Wiley (2014).

"Optional" or "optionally" refers to a described event or circumstance may or may not occur, and that the description includes instances where the event or circumstance occurs and instances where the event or circumstance does not. For example, "optionally substituted alkyl" refers to an alkyl group that may or may not be substituted and that the description encompasses both substituted alkyl group and unsubstituted alkyl group.

"Substituted" as used herein means one or more hydrogen atoms of the group is replaced with a substituent atom or group commonly used in pharmaceutical chemistry. Each substituent can be the same or different. Examples of suitable substituents include, but are not limited to, alkyl, alkenyl, alkynyl, cycloalkyl, aryl, arylalkyl, heterocycloalkyl, heteroaryl, —OR$^{56}$ (e.g., hydroxyl, alkyloxy (e.g., methoxy, ethoxy, and propoxy), ether, ester, carbamate, etc.), hydroxyalkyl, —C(O)O-alkyl, —O-alkyl-O-alkyl, haloalkyl, alkyl-O-alkyl, SR$^{56}$ (e.g., —SH, —S-alkyl, —S-aryl, —S-heteroaryl, arylalkyl-S—, etc.), S$^+$R$^{56}_2$, S(O)R$^{56}$, SO$_2$R$^{56}$, NR$^{56}$R$^{57}$ (e.g., primary amine (i.e., NH$_2$), secondary amine, tertiary amine, amide, carbamate, urea, etc.), hydrazide, halo, nitrile, nitro, sulfide, sulfoxide, sulfone, sulfonamide, —SH, carboxy, aldehyde, keto, carboxylic acid, ester, amide, imine, and imide (e.g., —C(O)NR$^{56}$C(O) R$^{57}$), including seleno and thio derivatives thereof, wherein each $R^{56}$ and $R^{57}$ are independently alkyl, alkenyl, alkynyl, heteroalkyl, cycloalkyl, cycloalkylalkyl, heterocycloalkyl, heterocycloalkylalkyl, aryl, arylalkyl, heteroaryl, or heteroarylalkyl, and wherein each of the substituents can be optionally further substituted. In embodiments in which a functional group with an aromatic carbon ring is substituted, such substitutions will typically number less than about 10 substitutions, or about 1 to 5, with about 1 or 2 substitutions in certain embodiments.

"Pharmaceutically acceptable salt" is meant to include salts of the active compounds which are prepared with relatively nontoxic acids or bases, depending on the particular substituents found on the compounds described herein. When compounds as disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds as disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure may contain both basic and acidic functionalities that allow the compounds to be converted into either base or acid addition salts. Lists of suitable salts are found in Remington's Pharmaceutical Sciences, 17th Ed., Mack Publishing Company, Easton, Pa., (1985) and Journal of Pharmaceutical Science, 66:2 (1977), each of which is incorporated herein by reference in its entirety.

"Pharmaceutically acceptable carrier" or "pharmaceutically acceptable excipient" refers to an excipient, carrier or adjuvant that can be administered to a subject, together with at least one compound, and which does not destroy the pharmacological activity thereof and is generally safe, nontoxic and neither biologically nor otherwise undesirable when administered in doses sufficient to deliver a therapeutic amount of the agent.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Various isotopically labeled compounds of the present disclosure, for example those into which radioactive isotopes such as $^{3}H$, and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, e.g., a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^{3}H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Accordingly, in the compounds of this disclosure any atom specifically designated as a deuterium (D) is meant to represent deuterium.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds as disclosed herein, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)-for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are non-superimposable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

2. Compounds

In certain embodiments, provided herein is a compound of Formula I or a tautomer, stereoisomer, mixture of stereoisomers, isotopically enriched analog, or pharmaceutically acceptable salt thereof:

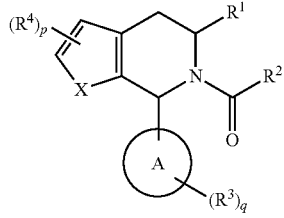

I wherein:
ring A is $C_4$-$C_{10}$cycloalkyl, heterocyclyl, aryl, or heteroaryl;
X is —O—, —S—, —NR$^9$—, —CR$^5$=CR$^5$—, or —CR$^5$=N—;
p is 0, 1 or 2;
q is 0, 1, 2 or 3;
R$^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —OR$^7$, —C(O)OR$^6$, —C(O)N(R$^7$)$_2$, —OC(O)R$^6$, —S(O)$_2$R$^8$, —S(O)$_2$N(R$^7$)$_2$, —S(O)N(R$^7$)$_2$, —S(O)R$^8$, —N(R$^7$)$_2$, —NO$_2$, —C$_1$-$C_6$alkyl-OR$^7$, or —Si(R$^5$)$_3$;
R$^2$ is —$C_1$-$C_2$haloalkyl, —$C_2$-$C_3$alkenyl, —$C_2$-$C_3$haloalkenyl, $C_2$alkynyl, or—CH$_2$OS(O)$_2$-phenyl, wherein the $C_1$-$C_2$haloalkyl and —$C_2$-$C_3$alkenylhalo are optionally substituted with one or two —CH$_3$, and the $C_2$alkynyl and phenyl are optionally substituted with one —CH$_3$;
each R$^3$ is independently halo, —CN, —OH, —OR$^8$, —NH$_2$, —NHR$^8$, —N(R$^8$)$_2$, —S(O)$_2$R$^8$, —S(O)R$^8$, —S(O)$_2$N(R$^7$)$_2$, —S(O)N(R$^7$)$_2$, —NO$_2$, —Si(R$^{12}$)$_3$, —SF$_5$, —C(O)OR$^6$, —C(O)N(R$^7$)$_2$, —NR$^{12}$C(O)R$^8$, —NR$^{12}$C(O) OR$^8$, —OC(O)N(R$^7$)$_2$, —OC(O)R$^8$, —C(O)R$^6$, —OC(O) CHR$^8$N(R$^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of R$^3$ is independently optionally substituted with one to three R$^{10}$;

each R$^4$ is independently halo, —CN, —OH, —OR$^8$, —NH$_2$, —NHR$^8$, —N(R$^8$)$_2$, —S(O)$_2$R, —S(O)R$^8$, —S(O)$_2$N(R$^7$)$_2$, —S(O)N(R$^7$)$_2$, —NO$_2$, —Si(R$^5$)$_3$, —C(O) OR$^6$, —C(O)N(R$^7$)$_2$, —NR$^{12}$C(O)R$^8$, —OC(O)R, —C(O) R$^6$, —NR$^{12}$C(O)OR$^8$, —OC(O)N(R$^7$)$_2$, —OC(O)CHR$^8$N (R$^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of R$^4$ is optionally independently optionally substituted with one to three R$^{10}$;

each R$^5$ is independently hydrogen, halo, —CN, —OH, —OR$^8$, —NH$_2$, —NHR$^8$, —N(R$^8$)$_2$, —S(O)$_2$R$^8$, —S(O)R$^8$, —S(O)$_2$N(R$^7$)$_2$, —S(O)N(R$^7$)$_2$, —NO$_2$, —Si(R$^5$)$_3$, —C(O) OR$^6$, —C(O)N(R$^7$)$_2$, —NR$^{12}$C(O)R$^8$, —OC(O)R$^8$, —C(O) R$^6$, —NR$^{12}$C(O)OR$^8$, —OC(O)N(R$^7$)$_2$, —OC(O)CHRN (R$^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl of R$^5$ is optionally independently optionally substituted with one to three R$^{10}$;

each R$^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl; wherein each R$^6$ is independently further substituted with one to three R$^{11}$;

each R$^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or—$C_2$-$C_6$alkenylheteroaryl, or two R$^7$ together with the nitrogen atom to which they are attached, form a 4 to 7 membered heterocyclyl; wherein each $R^7$ or ring formed thereby is independently further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl; wherein each $R^8$ is independently further substituted with one to three $R^{11}$;

$R^9$ is hydrogen or $C_1$-$C_6$alkyl;

each $R^{10}$ is independently halo, —CN, —$OR^{12}$, —$NO_2$, —$N(R^{12})_2$, —$S(O)R^3$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —$OR^2$, —$NO_2$, —$N(R^2)_2$, —$S(O)R^3$, —$S(O)_2R^{13}$, —$S(O)N(R^{12})_2$, —$S(O)_2N(R^{12})_2$, —$Si(R^2)_3$, —$C(O)R^2$, —$C(O)OR^2$, —$C(O)N(R^{12})_2$, —$NR^{12}C(O)R^2$, —$OC(O)R^2$, —$OC(O)OR^{12}$, —$OC(O)N(R^{12})_2$, —$NR^{12}C(O)OR^2$, —$OC(O)CHR^2N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl or $C_3$-$C_{10}$cycloalkyl; and each $R^{15}$ is independently $C_1$-$C_6$alkyl, $C_2$-$C_6$alkenyl, aryl, heteroaryl, —$C_1$-$C_6$alkylaryl, —$C_2$-$C_6$alkenylaryl, —$C_1$-$C_6$alkylheteroaryl, and —$C_2$-$C_6$alkenylheteroaryl.

In certain embodiments, provided is a compound of Formula I or a tautomer, stereoisomer, mixture of stereoisomers, isotopically enriched analog, or pharmaceutically acceptable salt thereof:

I wherein:

ring A is $C_4$-$C_{10}$cycloalkyl, heterocyclyl, aryl, or heteroaryl;

X is —O—, —S—, —$NR^9$—, —$CR^5$=$CR^5$—, or —$CR^5$=N—;

p is 0, 1 or 2;

q is 0, 1, 2 or 3;

$R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —$OR^7$, —$C(O)OR^6$, —$C(O)N(R^7)_2$, —$OC(O)R^6$, —$S(O)_2R^8$, —$S(O)_2N(R^7)_2$, —$S(O)N(R^7)_2$, —$S(O)R^8$, —$N(R^7)_2$, —$NO_2$, —$C_1$-$C_6$alkyl-$OR^7$, or —$Si(R^{15})_3$;

$R^2$ is —$C_1$-$C_2$haloalkyl, —$C_2$-$C_3$alkenyl, —$C_3$haloalkenyl, $C_2$alkynyl, or —$CH_2OS(O)_2$-phenyl, wherein the $C_1$-$C_2$alkylhalo and —$C_2$-$C_3$alkenylhalo are optionally substituted with one or two —$CH_3$, and the $C_2$alkynyl and phenyl are optionally substituted with one —$CH_3$;

each $R^3$ is independently halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{12})_3$, —$SF_5$, —$C(O)OR^6$, —$C(O)N(R^7)_2$, —$NR^{12}C(O)R^8$, —$NR^{12}C(O)OR^8$, —$OC(O)N(R^7)_2$, —$OC(O)R^8$, —$C(O)R^6$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^3$ is independently optionally substituted with one to three $R^{10}$;

each $R^4$ is independently halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^5)_3$, —$C(O)OR^6$, —$C(O)N(R^7)_2$, —$NR^{12}C(O)R^8$, —$OC(O)R^8$, —$C(O)R^6$, —$NR^{12}C(O)OR^8$, —$OC(O)N(R^7)_2$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^4$ is optionally independently optionally substituted with one to three $R^{10}$;

each $R^5$ is independently hydrogen, halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^5)_3$, —$C(O)OR^6$, —$C(O)N(R^7)_2$, —$NR^{12}C(O)R^8$, —$OC(O)R^8$, —$C(O)R^6$, —$NR^{12}C(O)OR^8$, —$OC(O)N(R^7)_2$, —$OC(O)CHRN(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^5$ is independently optionally optionally substituted with one to three $R^{10}$;

each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-

$C_6$alkenylheteroaryl; wherein each $R^6$ is independently further substituted with one to three $R^{11}$;

each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, —$C_2$-$C_6$alkenylheteroaryl, or two $R^7$ together with the nitrogen atom to which they are attached, form a 4 to 7 membered heterocyclyl; wherein each $R^7$ or ring formed thereby is independently further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl; wherein each $R^8$ is independently further substituted with one to three $R^{11}$;

$R^9$ is hydrogen or $C_1$-$C_6$alkyl;

each $R^{10}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —$OR^{12}$, —$NO_2$, —$N(R^{12})_2$, —$S(O)R^3$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl or $C_3$-$C_{10}$cycloalkyl; and each $R^{15}$ is independently $C_1$-$C_6$alkyl, $C_2$-$C_6$alkenyl, aryl, heteroaryl, —$C_1$-$C_6$alkylaryl, —$C_2$-$C_6$alkenylaryl, —$C_1$-$C_6$alkylheteroaryl, and—$C_2$-$C_6$alkenylheteroaryl; provided that at least one of the following is true:

1) $R^1$ is other than—$C(O)OCH_3$;
2) $R^2$ is—$C_2$alkynyl optionally substituted with one—$CH_3$; or
3) when $R^1$ is—$C(O)OCH_3$ and $R^2$ is—$CH_2Cl$, then the moiety

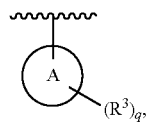

is other than 1,3-benzodioxol-5-yl, 4-nitrophenyl, 4-bromophenyl, cyclohexyl, furyl, or 4-methoxyphenyl.

In certain embodiments, $R^1$ is other than—$C(O)OR^6$ or $R^2$ is—$C_2$alkynyl optionally substituted with one—$CH_3$. In certain embodiments, $R^1$ is other than—$C(O)OCH_3$ or $R^2$ is—$C_2$alkynyl optionally substituted with one—$CH_3$. In certain embodiments, $R^1$ is other than—$C(O)OR^6$ and $R^2$ is—$C_2$alkynyl optionally substituted with one—$CH_3$. In certain embodiments, $R^1$ is other than—$C(O)OCH_3$ and $R^2$ is—$C_2$alkynyl optionally substituted with one—$CH_3$. In certain embodiments, $R^1$ is other than—$C(O)OR^6$. In certain embodiments, $R^1$ is other than—$C(O)OCH_3$. In certain embodiments, $R^2$ is—$C_2$alkynyl optionally substituted with one—$CH_3$. In certain embodiments, $R^2$ is—$C_2$alkynyl.

Also provided is a compound of Formula IA, or a tautomer, stereoisomer, mixture of stereoisomers, isotopically enriched analog, or pharmaceutically acceptable salt thereof:

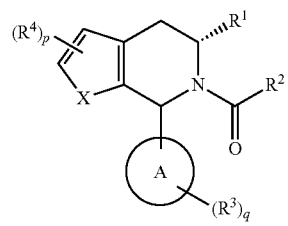

IA wherein each of ring A, X, $R^1$, $R^2$, $R^3$, $R^4$, p, and q are independently as defined herein.

Also provided is a compound of Formula IB, or a tautomer, stereoisomer, mixture of stereoisomers, isotopically enriched analog, or pharmaceutically acceptable salt thereof:

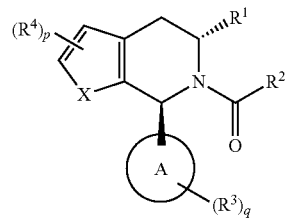

IB wherein each of ring A, X, $R^1$, $R^2$, $R^3$, $R^4$, p, and q are independently as defined herein.

Also provided is a compound of Formula II, or a tautomer, stereoisomer, mixture of stereoisomers, isotopically enriched analog, or pharmaceutically acceptable salt thereof:

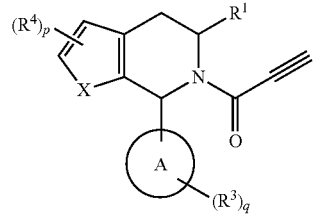

II wherein each of ring A, X, $R^1$, $R^3$, $R^4$, p, and q are independently as defined herein.

Also provided is a compound of Formula IIA, or a tautomer, stereoisomer, mixture of stereoisomers, isotopically enriched analog, or pharmaceutically acceptable salt thereof:

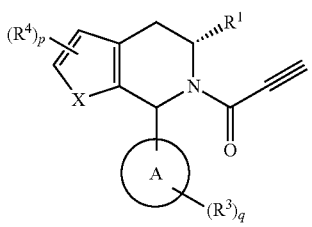

IIA wherein each of ring A, X, $R^1$, $R^3$, $R^4$, p, and q are independently as defined herein.

Also provided is a compound of Formula IIB, or a tautomer, stereoisomer, mixture of stereoisomers, isotopically enriched analog, or pharmaceutically acceptable salt thereof:

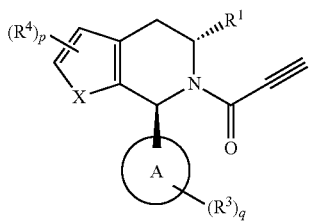

IIB wherein each of ring A, X, $R^1$, $R^3$, $R^4$, p, and q are independently as defined herein.

Also provided is a compound of Formula III, or a tautomer, stereoisomer, mixture of stereoisomers, isotopically enriched analog, or pharmaceutically acceptable salt thereof:

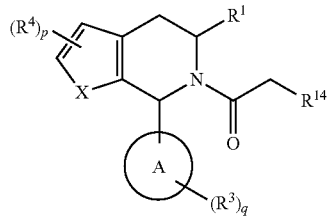

III wherein each of ring A, X, $R^1$, $R^3$, $R^4$, p, and q are independently as defined herein, and $R^{14}$ is halo.

Also provided is a compound of Formula IIIA, or a tautomer, stereoisomer, mixture of stereoisomers, isotopically enriched analog, or pharmaceutically acceptable salt thereof:

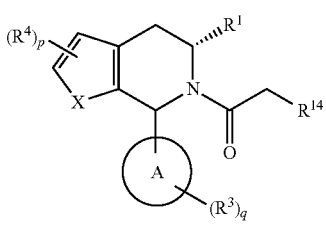

IIIA wherein each of ring A, X, $R^1$, $R^3$, $R^4$, p, and q are independently as defined herein, and $R^{14}$ is halo.

Also provided is a compound of Formula IIIB, or a tautomer, stereoisomer, mixture of stereoisomers, isotopically enriched analog, or pharmaceutically acceptable salt thereof:

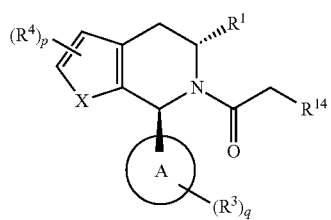

IIIB wherein each of ring A, X, $R^1$, $R^3$, $R^4$, p, and q are independently as defined herein, and $R^{14}$ is halo.

In certain embodiments,
ring A is aryl or heteroaryl;
X is —O—, —S—, —NH—, —CH=CH—, or —CH=N—;
p is 0, 1 or 2;
q is 1;
$R^1$ is $C_1$-$C_6$alkyl, —C(O)O—$C_1$-$C_6$alkyl, or —C(O)N($C_1$-$C_6$alkyl)$_2$;
$R^3$ is halo, —$NHR^8$, —$S(O)_2N(R^7)_2$, —$C(O)OR^6$, —$C(O)N(R^7)_2$, or heterocyclyl;
each $R^4$ is independently —$OR^8$;
$R^6$ is $C_1$-$C_6$alkyl;
each $R^7$ is independently hydrogen, $C_1$-$C_6$alkyl, or $C_3$-$C_{10}$cycloalkyl, wherein each $R^7$ is independently further substituted with one to three $R^{11}$;
each $R^8$ is independently $C_1$-$C_6$alkyl or $C_3$-$C_{10}$cycloalkyl; wherein each $R^8$ is independently further substituted with one to three $R^{11}$;
each $R^{11}$ is independently —O—$C_1$-$C_6$alkyl; and $R^{14}$ is halo.

In certain embodiments,
ring A is aryl or heteroaryl;
X is —O—, —S—, —NH—, —CH=CH—, or —CH=N—;
p is 0, 1 or 2;
q is 1;
$R^1$ is $C_1$-$C_6$alkyl or —C(O)N($C_1$-$C_6$alkyl)$_2$;
$R^3$ is halo, —$NHR^8$, —$S(O)_2N(R^7)_2$, —$C(O)OR^6$, —$C(O)N(R^7)_2$, or heterocyclyl;
each $R^4$ is independently —$OR^8$;
$R^6$ is $C_1$-$C_6$alkyl;
each $R^7$ is independently hydrogen, $C_1$-$C_6$alkyl, or $C_3$-$C_{10}$cycloalkyl, wherein each $R^7$ is independently further substituted with one to three $R^{11}$;
each $R^8$ is independently $C_1$-$C_6$alkyl or $C_3$-$C_{10}$cycloalkyl; wherein each $R^8$ is independently further substituted with one to three $R^{11}$;
each $R^{11}$ is independently —O—$C_1$-$C_6$alkyl; and
$R^{14}$ is halo.

In certain embodiments, X is —O—, —S—, or —$NR^9$—. In certain embodiments, X is —O—, —S—, or —NH—. In certain embodiments, X is —O—. In certain embodiments, X is —S—. In certain embodiments, X is —$NR^9$—. In certain embodiments, X is —NH—.

In certain embodiments, X is —$CR^5$=$CR^5$— or —$CR^5$=N—. In certain embodiments, X is —CH=CH— or —CH═N—. In certain embodiments, X is—CR⁵═CR⁵—. In certain embodiments, X is—CR⁵═N—.

In certain embodiments, R⁵ is R⁴.

In certain embodiments, when X is—CH═CH—, p is 1 or 2, each R⁴ is methoxy, ring A is phenyl, and q is 1, then R³ is other than adamantylamine, fluoro, or—C(O)NH-cyclopropyl. In certain embodiments, when X is—CH═CH—, p is 1 or 2, each R⁴ is methoxy, R¹ is methyl, n-butyl or—C(O)OCH₃, ring A is phenyl, and q is 1, then R³ is other than adamantylamine, fluoro, and—C(O)NH-cyclopropyl. In certain embodiments, when X is—CH═CH—, p is 1 or 2, each R⁴ is methoxy, R¹ is methyl, n-butyl or —C(O)OCH₃, R² is—CH₂Cl or C₂alkynyl, ring A is phenyl, and q is 1, then R³ is other than adamantylamine, fluoro, or—C(O)NH-cyclopropyl.

In certain embodiments, when X is—CR⁵═CR⁵—, p is 1 or 2, ring A is phenyl, cyclohexyl, or furyl, and q is 0 or 1, then at least one R⁴ is other than methoxy. In certain embodiments, when R¹ is—C(O)OCH₃ and R² is—CH₂Cl, ring A is phenyl, cyclohexyl, or furyl, q is 0 or 1, R³ is—NO₂, Br, or—OCH₃, and p is 1 or 2, then at least one R⁴ is other than methoxy. In certain embodiments, when R² is—CH₂Cl, X is—CR⁵═CR⁵—, p is 1 or 2, ring A is phenyl, cyclohexyl, or furyl, and q is 0 or 1, then at least one R⁴ is other than methoxy. In certain embodiments, when R¹ is—C(O)OCH₃, R² is—CH₂Cl, X is—CR⁵═CR⁵—, p is 1 or 2, ring A is phenyl, cyclohexyl, or furyl, and q is 0 or 1, then at least one R⁴ is other than methoxy.

In certain embodiments, when R¹ is—C(O)OCH₃ and R² is—CH₂Cl, then X is other than—CR⁵═CR⁵—. In certain embodiments, when X is—CH═CH—, p is 1 or 2, ring A is phenyl, and q is 1, then at least one R⁴ is other than methoxy.

In certain embodiments, the compound is not N-cyclopropyl-4-((1S,3S)-6-methoxy-3-methyl-2-propioloyl-1,2,3,4-tetrahydroisoquinolin-1-yl)benzamide, 4-((1S,3S)-2-(2-chloroacetyl)-6-methoxy-3-methyl-1,2,3,4-tetrahydroisoquinolin-1-yl)—N-cyclopropylbenzamide, 1-((1S,3S)-3-butyl-1-(4-fluorophenyl)-6-methoxy-3,4-dihydroisoquinolin-2(1H)-yl)-2-chloroethan-1-one, 4-((1S,3S)-3-butyl-2-(2-chloroacetyl)-6-methoxy-1,2,3,4-tetrahydroisoquinolin-1-yl)—N-cyclopropylbenzamide, 4-((1S,3S)-3-butyl-6-methoxy-2-propioloyl-1,2,3,4-tetrahydroisoquinolin-1-yl)—N-cyclopropylbenzamide, 1-((1S,3S)-1-(4-(adamantan-1-ylamino)phenyl)-3-butyl-6-methoxy-3,4-dihydroisoquinolin-2(1H)-yl)-2-chloroethan-1-one, 1-((1S,3S)-1-(4-(adamantan-1-ylamino)phenyl)-3-butyl-6-methoxy-3,4-dihydroisoquinolin-2(1H)-yl)prop-2-yn-1-one, methyl (1S,3R)-1-(4-(adamantan-1-ylamino)phenyl)-2-(2-chloroacetyl)-6-methoxy-1,2,3,4-tetrahydroisoquinoline-3-carboxylate, methyl (1S,3R)-1-(4-(adamantan-1-ylamino)phenyl)-6-methoxy-2-propioloyl-1,2,3,4-tetrahydroisoquinoline-3-carboxylate, 4-((1S,3S)-3-butyl-2-(2-chloroacetyl)-6,7-dimethoxy-1,2,3,4-tetrahydroisoquinolin-1-yl)—N-cyclopropylbenzamide, or 4-((1S,3S)-3-butyl-6,7-dimethoxy-2-propioloyl-1,2,3,4-tetrahydroisoquinolin-1-yl)—N-cyclopropylbenzamide.

In certain embodiments, when R² is—C₁-C₂haloalkyl, then ring A is not benzo[d][1,3]dioxole.

In certain embodiments, R⁵ is R⁴.

Also provided is a compound of Formula IV, or a tautomer, stereoisomer, mixture of stereoisomers, isotopically enriched analog, or pharmaceutically acceptable salt thereof:

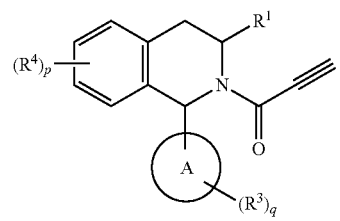

IV wherein each of ring A, R¹, R³, R⁴, p, and q are independently as defined herein.

Also provided is a compound of Formula IV, or a tautomer, stereoisomer, mixture of stereoisomers, isotopically enriched analog, or pharmaceutically acceptable salt thereof:

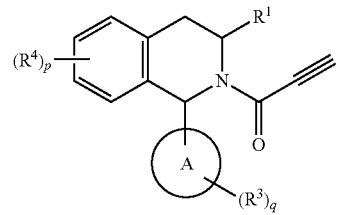

IV wherein:
ring A is aryl or heteroaryl;
p is 0, 1 or 2;
q is 1;
R¹ is C₁-C₆alkyl, —C(O)O—C₁-C₆alkyl, or—C(O)N(C₁-C₆alkyl)₂;
R³ is halo, —NHR⁸, —S(O)₂N(R⁷)₂, —C(O)OR⁶, —C(O)N(R⁷)₂, or heterocyclyl;
each R⁴ is independently—OR⁸;
R⁶ is C₁-C₆alkyl;
each R⁷ is independently hydrogen, C₁-C₆alkyl, or C₃-C₁₀cycloalkyl, wherein each R⁷ is independently further substituted with one to three R¹¹;
each R⁸ is independently C₁-C₆alkyl or C₃-C₁₀cycloalkyl, wherein each R⁸ is independently further substituted with one to three R¹¹; and each R¹¹ is independently—O—C₁-C₆alkyl.

Also provided is a compound of Formula IVA, or a tautomer, stereoisomer, mixture of stereoisomers, isotopically enriched analog, or pharmaceutically acceptable salt thereof:

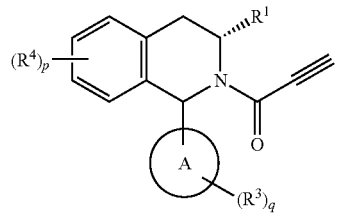

IVA wherein each of ring A, R¹, R³, R⁴, p, and q are independently as defined herein.

Also provided is a compound of Formula IVB, or a tautomer, stereoisomer, mixture of stereoisomers, isotopically enriched analog, or pharmaceutically acceptable salt thereof:

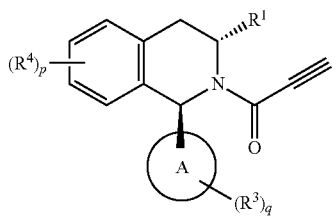

IVB wherein each of ring A, $R^1$, $R^3$, $R^4$, p, and q are independently as defined herein.

Also provided is a compound of Formula V, or a tautomer, stereoisomer, mixture of stereoisomers, isotopically enriched analog, or pharmaceutically acceptable salt thereof:

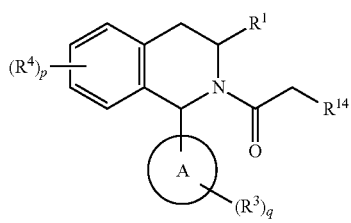

V wherein each of ring A, $R^1$, $R^3$, $R^4$, p, and q are independently as defined herein, and $R^{14}$ is halo.

Also provided is a compound of Formula V, or a tautomer, stereoisomer, mixture of stereoisomers, isotopically enriched analog, or pharmaceutically acceptable salt thereof:

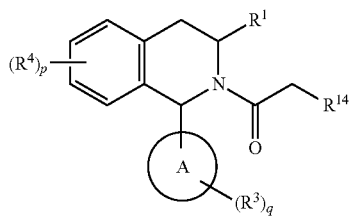

V wherein:
ring A is aryl or heteroaryl;
p is 0, 1 or 2;
q is 1;
$R^1$ is $C_1$-$C_6$alkyl, —C(O)O—$C_1$-$C_6$alkyl, or —C(O)N($C_1$-$C_6$alkyl)$_2$;
$R^3$ is halo, —NHR$^8$, —S(O)$_2$N(R$^7$)$_2$, —C(O)OR$^6$, —C(O)N(R$^7$)$_2$, or heterocyclyl;
each $R^4$ is independently —OR$^8$;
$R^6$ is $C_1$-$C_6$alkyl;
each $R^7$ is independently hydrogen, $C_1$-$C_6$alkyl, or $C_3$-$C_{10}$cycloalkyl, wherein each $R^7$ is independently further substituted with one to three $R^{11}$;
each $R^8$ is independently $C_1$-$C_6$alkyl or $C_3$-$C_{10}$cycloalkyl; wherein each $R^8$ is independently further substituted with one to three $R^{11}$;
each $R^{11}$ is independently —O—$C_1$-$C_6$alkyl; and
$R^{14}$ is halo.

In certain embodiments, $R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —OR$^7$, —C(O)OR$^6$, —C(O)N(R$^7$)$_2$, —OC(O)R$^6$, —S(O)$_2$R$^8$, —S(O)$_2$N(R$^7$)$_2$, —S(O)N(R$^7$)$_2$, —S(O)R$^8$, —N(R$^7$)$_2$, —NO$_2$, —$C_1$-$C_6$alkyl-OR$^7$, or —Si(R$^5$)$_3$. In certain embodiments, $R^1$ is $C_1$-$C_6$alkyl.

Also provided is a compound of Formula VA, or a tautomer, stereoisomer, mixture of stereoisomers, isotopically enriched analog, or pharmaceutically acceptable salt thereof:

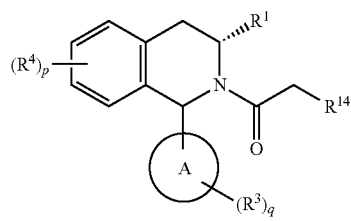

VA wherein each of ring A, $R^1$, $R^3$, $R^4$, p, and q are independently as defined herein, and $R^{14}$ is halo.

Also provided is a compound of Formula VB, or a tautomer, stereoisomer, mixture of stereoisomers, isotopically enriched analog, or pharmaceutically acceptable salt thereof:

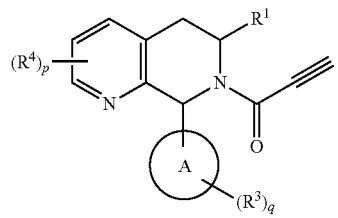

VB wherein each of ring A, $R^1$, $R^3$, $R^4$, p, and q are independently as defined herein, and $R^{14}$ is halo.

In certain embodiments, $R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —OR$^7$, —C(O)OR$^6$, —C(O)N(R$^7$)$_2$, —OC(O)R$^6$, —S(O)$_2$R$^8$, —S(O)$_2$N(R$^7$)$_2$, —S(O)N(R$^7$)$_2$, —S(O)R$^8$, —N(R$^7$)$_2$, —NO$_2$, —$C_1$-$C_6$alkyl-OR$^7$, or —Si(R$^5$)$_3$. In certain embodiments, $R^1$ is $C_1$-$C_6$alkyl.

Also provided is a compound of Formula VI, or a tautomer, stereoisomer, mixture of stereoisomers, isotopically enriched analog, or pharmaceutically acceptable salt thereof:

VI wherein each of ring A, $R^1$, $R^3$, $R^4$, p, and q are independently as defined herein.

Also provided is a compound of Formula VI, or a tautomer, stereoisomer, mixture of stereoisomers, isotopically enriched analog, or pharmaceutically acceptable salt thereof:

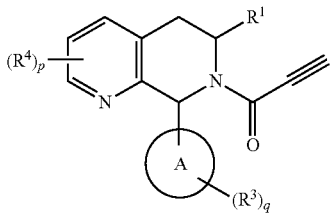

wherein:
ring A is aryl or heteroaryl;
p is 0, 1 or 2;
q is 1;
$R^1$ is $C_1$-$C_6$alkyl, —C(O)O—$C_1$-$C_6$alkyl, or —C(O)N($C_1$-$C_6$alkyl)$_2$;
$R^3$ is halo, —NHR$^8$, —S(O)$_2$N(R$^7$)$_2$, —C(O)OR$^6$, —C(O)N(R$^7$)$_2$, or heterocyclyl;
each $R^4$ is independently —OR$^8$;
$R^6$ is $C_1$-$C_6$alkyl;
each $R^7$ is independently hydrogen, $C_1$-$C_6$alkyl, or $C_3$-$C_{10}$cycloalkyl, wherein each $R^7$ is independently further substituted with one to three $R^{11}$;
each $R^8$ is independently $C_1$-$C_6$alkyl or $C_3$-$C_{10}$cycloalkyl; wherein each $R^8$ is independently further substituted with one to three $R^{11}$; and
each $R^{11}$ is independently —O—$C_1$-$C_6$alkyl.

Also provided is a compound of Formula VIA, or a tautomer, stereoisomer, mixture of stereoisomers, isotopically enriched analog, or pharmaceutically acceptable salt thereof:

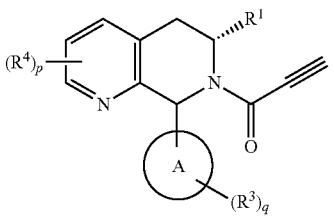

wherein each of ring A, $R^1$, $R^3$, $R^4$, p, and q are independently as defined herein.

Also provided is a compound of Formula VIB, or a tautomer, stereoisomer, mixture of stereoisomers, isotopically enriched analog, or pharmaceutically acceptable salt thereof:

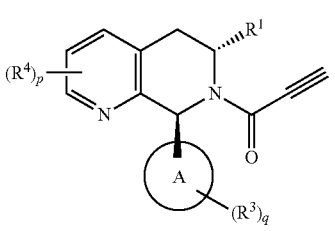

wherein each of ring A, $R^1$, $R^3$, $R^4$, p, and q are independently as defined herein.

Also provided is a compound of Formula VII, or a tautomer, stereoisomer, mixture of stereoisomers, isotopically enriched analog, or pharmaceutically acceptable salt thereof:

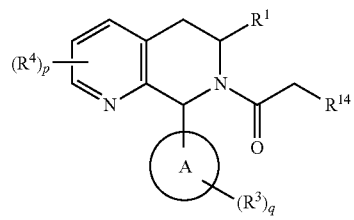

wherein each of ring A, $R^1$, $R^3$, $R^4$, p, and q are independently as defined herein, and $R^{14}$ is halo.

Also provided is a compound of Formula VII, or a tautomer, stereoisomer, mixture of stereoisomers, isotopically enriched analog, or pharmaceutically acceptable salt thereof:

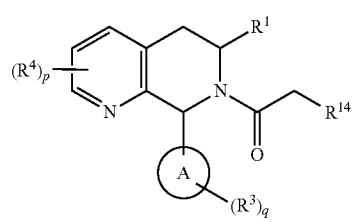

wherein:
ring A is aryl or heteroaryl;
p is 0, 1 or 2;
q is 1;
$R^1$ is $C_1$-$C_6$alkyl, —C(O)O—$C_1$-$C_6$alkyl, or —C(O)N($C_1$-$C_6$alkyl)$_2$;
$R^3$ is halo, —NHR$^8$, —S(O)$_2$N(R$^7$)$_2$, —C(O)OR$^6$, —C(O)N(R$^7$)$_2$, or heterocyclyl;
each $R^4$ is independently —OR$^8$;
$R^6$ is $C_1$-$C_6$alkyl;
each $R^7$ is independently hydrogen, $C_1$-$C_6$alkyl, or $C_3$-$C_{10}$cycloalkyl, wherein each $R^7$ is independently further substituted with one to three $R^{11}$;
each $R^8$ is independently $C_1$-$C_6$alkyl or $C_3$-$C_{10}$cycloalkyl; wherein each $R^8$ is independently further substituted with one to three $R^{11}$; and
each $R^{11}$ is independently —O—$C_1$-$C_6$alkyl; and
$R^{14}$ is halo.

Also provided is a compound of Formula VIIA, or a tautomer, stereoisomer, mixture of stereoisomers, isotopically enriched analog, or pharmaceutically acceptable salt thereof:

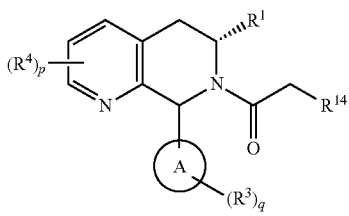

VIIA wherein each of ring A, $R^1$, $R^3$, $R^4$, p, and q are independently as defined herein, and $R^{14}$ is halo.

Also provided is a compound of Formula VIIB, or a tautomer, stereoisomer, mixture of stereoisomers, isotopically enriched analog, or pharmaceutically acceptable salt thereof:

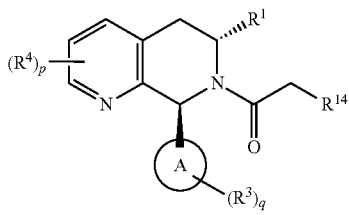

VIIB wherein each of ring A, $R^1$, $R^3$, $R^4$, p, and q are independently as defined herein, and $R^{14}$ is halo.

Also provided is a compound of Formula VIII, or a tautomer, stereoisomer, mixture of stereoisomers, isotopically enriched analog, or pharmaceutically acceptable salt thereof:

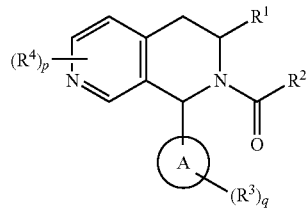

VIII wherein each of ring A, $R^1$, $R^2$, $R^3$, $R^4$, p, and q are independently as defined herein.

In certain embodiments, ring A, or the moiety

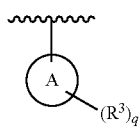

is:

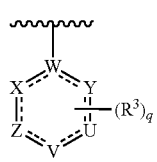

wherein 0 to 3 of U, V, W, X, Y, and Z is independently N, S, or O, and the remaining variables are CH or $CR^3$ and each ═══ independently represents a single or double bond, which comply with valency requirements based on U, V, W, X, Y and Z.

In certain embodiments, ring A, or the moiety

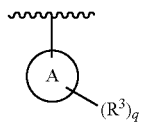

is:

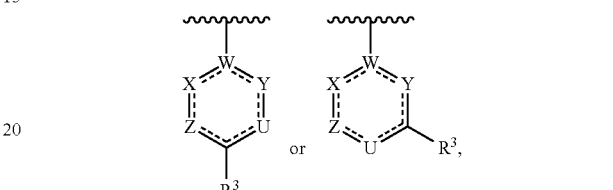

wherein 1 to 3 of U, W, X, Y, and Z is N, S, or O, and the remaining variables are CH or $CR^3$ and ═══ represents a single or double bond, which comply with valency requirements based on U, W, X, Y and Z.

In certain embodiments, ring A is aryl or heteroaryl. In certain embodiments, ring A is a monocyclic aryl or monocyclic heteroaryl. In certain embodiments, ring A is heterocyclyl. In certain embodiments, ring A is a 4 to 7 membered heterocyclyl. In certain embodiments, ring A is aryl. In certain embodiments, ring A is phenyl. In certain embodiments, ring A is heteroaryl. In certain embodiments, ring A is pyridyl. In certain embodiments, ring A is pyrazolyl. In certain embodiments, ring A is phenyl, pyridyl, piperidynyl, piperazinyl, or morpholinyl.

In certain embodiments, ring A is aryl or heteroaryl, each of which is substituted by one to three $R^3$. In certain embodiments, ring A is aryl or heteroaryl, each of which is substituted by one to three $R^3$, where at least one $R^3$ is $C_3$-$C_{10}$cycloalkyl, heterocyclyl, aryl, or heteroaryl; wherein each $C_3$-$C_{10}$cycloalkyl, heterocyclyl, aryl, and heteroaryl of $R^3$ is optionally substituted with one to three $R^{10}$.

In certain embodiments, ring A is aryl or heteroaryl, each of which is substituted by one to three $R^3$, where at least one $R^3$ is $C_3$-$C_{10}$cycloalkyl, heterocyclyl, aryl, or heteroaryl; and wherein each $C_3$-$C_{10}$cycloalkyl, heterocyclyl, aryl, and heteroaryl of $R^3$ is optionally substituted with one to three $R^{10}$;

each $R^{10}$ is independently —$OR^{12}$, —$N(R^{12})_2$, —$S(O)_2R^{13}$, —$OC(O)CHR^{12}N(R^{12})_2$, or $C_1$-$C_6$alkyl, wherein the $C_1$-$C_6$alkyl, of $R^{10}$ is optionally independently substituted with one to three $R^{11}$;

each $R^{11}$ is independently halo, —$OR^{12}$, —$N(R^{12})_2$, —Si$(R^{12})_3$, —$C(O)OR^{12}$, —$NR^{12}C(O)OR^{12}$, —$OC(O)CHR^{12}N(R^{12})_2$, $C_1$-$C_6$alkyl, or heterocyclyl;

each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, ring A is bicyclo[1.1.1]pentan-1-yl, phenyl, piperidinyl, pyrazolyl, pyridyl, or quinolinyl, each of which is optionally substituted by one, two or three $R^3$. In certain embodiments, ring A is bicyclo[1.1.1]pentan-1-yl, phenyl, piperidinyl, pyrazolyl, pyridyl, or quinolinyl, each of which is substituted by one, two or three $R^3$. In certain embodiments, ring A is bicyclo[1.1.1]pentan-1-yl, phenyl, piperidinyl, pyrazolyl, pyridyl, or quinolinyl, each of which is substituted by two or three $R^3$.

In certain embodiments, ring A is aryl or heteroaryl, each of which is substituted by two or three $R^3$. In certain embodiments, ring A is aryl or heteroaryl, each of which is substituted by two or three $R^3$; wherein at least one $R^3$ is halo.

In certain embodiments, ring A is cyclohexyl. In certain embodiments, ring A is $C_4$-$C_{10}$cycloalkyl. In certain embodiments, ring A is a $C_4$-$C_7$cycloalkyl. In certain embodiments, ring A is bicyclo[1.1.1]pentanyl. In certain embodiments, ring A is selected from cyclobutyl, cyclopentyl, cyclohexyl, and cycloheptyl.

In certain embodiments, ring A, or the moiety

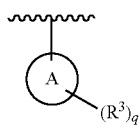

is:

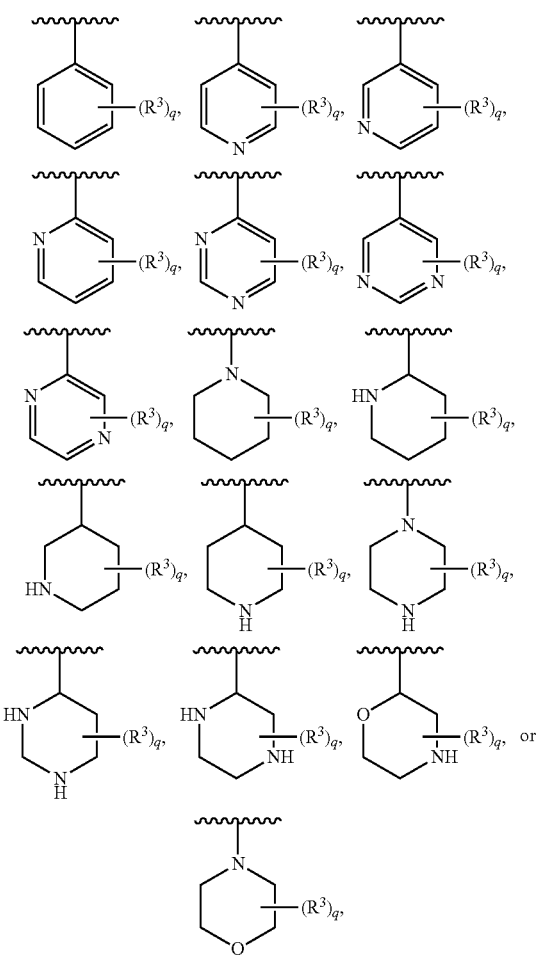

where q and each $R^3$ is independently as defined herein.

In certain embodiments, ring A, or the moiety

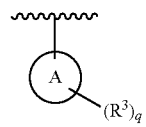

is:

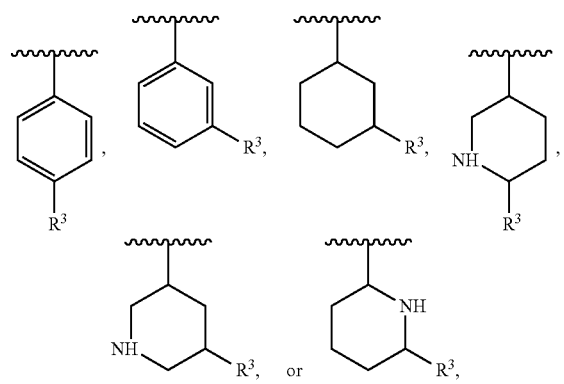

where $R^3$ is independently as defined herein.

In certain embodiments, ring A is a bridged bicyclic ring selected from:

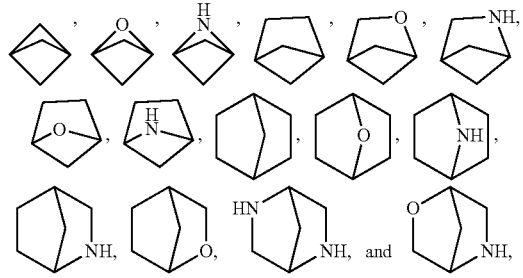

wherein each is substituted with one to three $R^3$. In certain embodiments, ring A is a bridged bicyclic ring selected from:

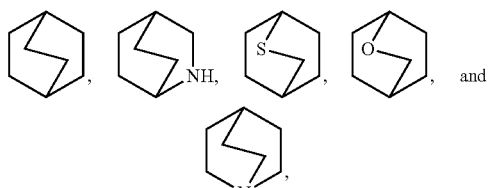

wherein each $R^3$ is attached to a carbon atom on the bridged bicyclic ring.

In certain embodiments, ring A, or the moiety

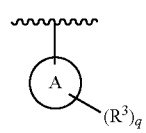

is:

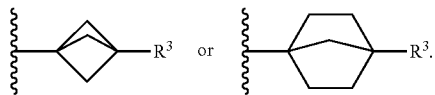

Also provided is a compound of Formula VIII, or a tautomer, stereoisomer, mixture of stereoisomers, isotopically enriched analog, or pharmaceutically acceptable salt thereof:

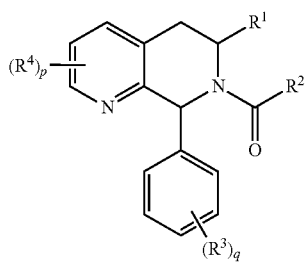

VIII wherein each of $R^1$, $R^2$, $R^3$, $R^4$, p, and q are independently as defined herein.

Also provided is a compound of Formula VIIIA, or a tautomer, stereoisomer, mixture of stereoisomers, isotopically enriched analog, or pharmaceutically acceptable salt thereof:

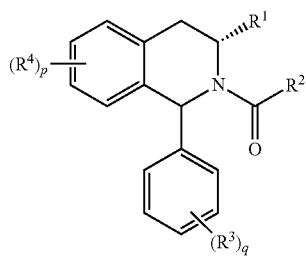

VIIIA wherein each of $R^1$, $R^2$, $R^3$, $R^4$, p, and q are independently as defined herein.

Also provided is a compound of Formula VIIIB, or a tautomer, stereoisomer, mixture of stereoisomers, isotopically enriched analog, or pharmaceutically acceptable salt thereof:

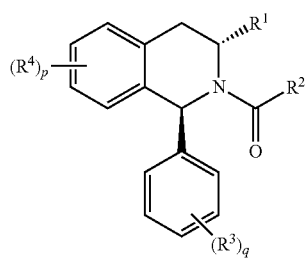

VIIIB wherein each of $R^1$, $R^2$, $R^3$, $R^4$, p, and q are independently as defined herein.

In certain embodiments, $R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —C(O)OR$^6$, —C(O)N(R$^7$)$_2$, —N(R$^7$)$_2$, —OR$^7$, or —$C_1$-$C_6$alkyl-OR$^7$.

In certain embodiments, $R^1$ is —C(O)OR$^6$ or —C(O)N(R$^7$)$_2$.

In certain embodiments, $R^1$ is $C_1$-$C_6$alkyl. In certain embodiments, In certain embodiments, $R^1$ is $C_2$-$C_6$alkyl. In certain embodiments, $R^1$ is $C_3$-$C_6$alkyl. In certain embodiments, $R^1$ is $C_5$-$C_6$alkyl. In certain embodiments, $R^1$ is $C_2$-$C_3$alkyl. In certain embodiments, $R^1$ is $C_4$-$C_6$alkyl. In certain embodiments, $R^1$ is methyl. In certain embodiments, $R^1$ is n-butyl.

In certain embodiments, $R^1$ is —CH$_2$—R$^{16}$, wherein $R^{16}$ is $C_1$-$C_5$alkyl, $C_2$-$C_5$alkenyl, $C_2$-$C_5$alkynyl, $C_1$-$C_5$haloalkyl, or —$C_1$-$C_5$alkyl-OR$^7$.

In certain embodiments, $R^1$ is $C_2$-$C_6$alkenyl, $C_2$-$C_6$alkynyl, $C_1$-$C_6$haloalkyl, $C_3$-$C_{10}$cycloalkyl, —CN, —OR$^7$, —C(O)N(R$^7$)$_2$, —OC(O)R$^6$, —S(O)$_2$R$^8$, —S(O)$_2$N(R$^7$)$_2$, —S(O)N(R$^7$)$_2$, —S(O)R$^8$, —N(R$^7$)$_2$, —NO$_2$, —$C_1$-$C_6$alkyl-OR$^7$, or —Si(R$^5$)$_3$.

In certain embodiments, $R^1$ is other than methyl. In certain embodiments, $R^1$ is other than n-butyl. In certain embodiments, $R^1$ is other than —C(O)OR$^6$. In certain embodiments, $R^1$ is other than —C(O)OCH$_3$.

Also provided is a compound of Formula IX, or a tautomer, stereoisomer, mixture of stereoisomers, isotopically enriched analog, or pharmaceutically acceptable salt thereof:

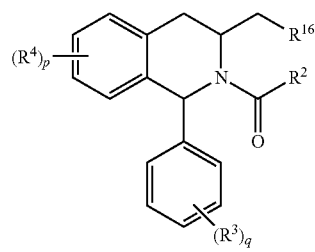

IX wherein each of $R^2$, $R^3$, $R^4$, $R^{16}$, p, and q are independently as defined herein. In certain embodiments, $R^{16}$ is hydrogen or $C_2$-$C_5$alkyl.

Also provided is a compound of Formula IXA, or a tautomer, stereoisomer, mixture of stereoisomers, isotopically enriched analog, or pharmaceutically acceptable salt thereof:

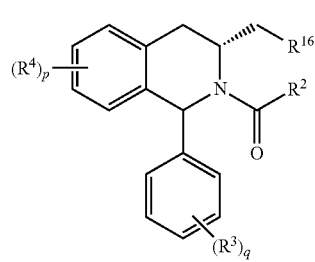

IXA wherein each of $R^2$, $R^3$, $R^4$, $R^{16}$, p, and q are independently as defined herein. In certain embodiments, $R^{16}$ is hydrogen or $C_2$-$C_5$alkyl.

Also provided is a compound of Formula IXB, or a tautomer, stereoisomer, mixture of stereoisomers, isotopically enriched analog, or pharmaceutically acceptable salt thereof:

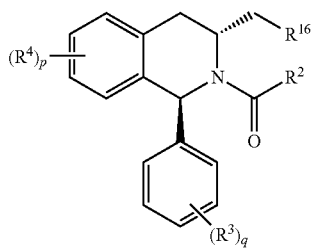

IXB wherein each of $R^2$, $R^3$, $R^4$, $R^{16}$, p, and q are independently as defined herein. In certain embodiments, $R^{16}$ is hydrogen or $C_2$-$C_5$alkyl.

In certain embodiments, $R^2$ is —$C_1$-$C_2$haloalkyl, —$C_2$-$C_3$alkenyl, —$C_2$-$C_3$haloalkenyl, $C_2$alkynyl, wherein the $C_1$-$C_2$haloalkyl and —$C_2$-$C_3$alkenylhalo are optionally substituted with one or two —$CH_3$, and the $C_2$alkynyl is optionally substituted with one —$CH_3$. In certain embodiments, $R^2$ is —$C_1$-$C_2$haloalkyl. In certain embodiments, $R^2$ is —$C_2$-$C_3$alkenyl. In certain embodiments, $R^2$ is $C_2$-$C_3$haloalkenyl. In certain embodiments, $R^2$ is $C_2$alkynyl.

In certain embodiments, at least one $R^3$ is halo, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{12})_3$, —$SF_5$, —$C(O)OR^6$, —$C(O)N(R^7)_2$, —$NR^{12}C(O)R$, —$NR^{12}C(O)OR^8$, —$OC(O)R^8$, —$C(O)R^6$, or—$OC(O)CHR^8N(R^{12})_2$.

In certain embodiments, at least one $R^3$ is halo.

In certain embodiments, at least one $R^3$ is —$NHR^8$. In certain embodiments, at least one $R^3$ is —$N(R^8)_2$. In certain embodiments, q is 2, and one $R^3$ is halo and the other $R^3$ is —$N(R^8)_2$. In certain embodiments, q is 3, and two $R^3$ are independently halo and one $R^3$ is —$N(R^8)_2$.

In certain embodiments, at least one $R^3$ is —$C(O)OR^6$ or—$C(O)R^6$.

In certain embodiments, at least one $R^3$ is —$S(O)_2N(R^7)_2$, —$S(O)N(R^7)_2$, or—$C(O)N(R^7)_2$.

In certain embodiments, at least one $R^3$ is —$S(O)_2R$, —$S(O)R^8$, —$NR^2C(O)R^8$, —$NR^{12}C(O)OR^8$, —$OC(O)R^8$, or—$OC(O)CHRN(R^{12})_2$.

In certain embodiments, each $R^3$ is independently halo, —CN, —$OR^8$, —$NHR^8$, —$S(O)_2R^8$, —$S(O)_2N(R^7)_2$, —$NO_2$, —$Si(R^{12})_3$, —$SF_5$, —$C(O)OR^6$, —$C(O)N(R^7)_2$, —$NR^{12}C(O)R^8$, —$NR^{12}C(O)OR^8$, —$OC(O)R^8$, —$OC(O)CHR^8N(R^{12})_2$, $C_1$-$C_6$alkyl, $C_3$-$C_{10}$cycloalkyl, heterocyclyl, heteroaryl, or—$C_1$-$C_6$alkylheterocyclyl; wherein each $C_1$-$C_6$alkyl, $C_3$-$C_{10}$cycloalkyl, heterocyclyl, heteroaryl, or—$C_1$-$C_6$alkylheterocyclyl of $R^3$ is independently optionally substituted with one to three $R^{10}$.

In certain embodiments, each $R^3$ is independently halo, —CN, —$OR^8$, —$NHR_8$, —$S(O)_2R$, —$S(O)_2N(R^7)_2$, —$NO_2$, —$Si(R^{12})_3$, —$SF_5$, —$C(O)OR^6$, —$C(O)N(R^7)_2$, —$NR^{12}C(O)R^8$, —$NR^{12}C(O)OR^8$, —$OC(O)R^8$, —$OC(O)CHR^8N(R^{12})_2$, $C_1$-$C_6$alkyl, $C_3$-$C_{10}$cycloalkyl, heterocyclyl, heteroaryl, or—$C_1$-$C_6$alkylheterocyclyl; wherein each $C_1$-$C_6$alkyl, $C_3$-$C_{10}$cycloalkyl, heterocyclyl, heteroaryl, or—$C_1$-$C_6$alkylheterocyclyl is independently optionally substituted with one to three substituents independently selected from—$OR^{12}$, —$N(R^{12})_2$, —$S(O)_2R^{13}$, —$OC(O)CHR^{12}N(R^{12})_2$, and $C_1$-$C_6$alkyl optionally substituted with one to three halo, —$OR^{12}$, —$N(R^{12})_2$, —$Si(R^{12})_3$, —$C(O)OR^{12}$, —$NR^{12}C(O)OR^{12}$, —$OC(O)CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, each $R^3$ is independently—$NH_2$, fluoro, methyl, pyridine-4-carboxamido, pyridin-3-amino, pentyloxycarbonylamino, N—(3-aminobicyclo[1.1.1]pentan-1-yl)amino, morpholin-4-yl, methoxycarbonyl, dimethylcarbamoyl, cyclopropylcarbamoyl, cyclohexyl, cyclobutylcarbamoyl, cyclobutylaminosulfonyl, adamantylamino, (adamantan-1-ylamino)methyl, 3-methyl-1,2,4-oxadiazol-5-yl, 2-methylpyridine-4-carboxamido, (bicyclo[1.1.1]pentan-1-ylamino)methyl, (adamantan-1-yl)carbamoyl, or (2-methoxyethyl)carbamoyl.

In certain embodiments, q is 0 or 1, and $R^3$ is—$NH_2$, fluoro, methyl, pyridine-4-carboxamido, pyridin-3-amino, pentyloxycarbonylamino, N—(3-aminobicyclo[.1.1.1]pentan-1-yl)amino, morpholin-4-yl, methoxycarbonyl, dimethylcarbamoyl, cyclopropylcarbamoyl, cyclohexyl, cyclobutylcarbamoyl, cyclobutylaminosulfonyl, adamantylamino, (adamantan-1-ylamino)methyl, 3-methyl-1,2,4-oxadiazol-5-yl, 2-methylpyridine-4-carboxamido, (bicyclo[1.1.1]pentan-1-ylamino)methyl, (adamantan-1-yl)carbamoyl, or (2-methoxyethyl)carbamoyl.

In certain embodiments, each $R^4$ is independently halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^5)_3$, —$C(O)OR^6$, —$C(O)N(R^7)_2$, —$NR^{12}C(O)R^8$, —$OC(O)R^8$, —$C(O)R^6$, $C_1$-$C_6$alkyl, $C_2$-$C_6$alkenyl, $C_2$-$C_6$alkynyl, or $C_3$-$C_{10}$cycloalkyl; wherein each $C_1$-$C_6$alkyl, $C_2$-$C_6$alkenyl, $C_2$-$C_6$alkynyl, or $C_3$-$C_{10}$cycloalkyl of $R^4$ is independently optionally substituted with one to three $R^{10}$.

In certain embodiments, each $R^4$ is independently halo, —CN, —$OR^7$, $C_1$-$C_6$alkyl, $C_2$-$C_6$alkynyl, or $C_3$-$C_{10}$cycloalkyl; wherein each $C_1$-$C_6$alkyl, $C_2$-$C_6$alkynyl, or $C_3$-$C_{10}$cycloalkyl of $R^4$ is independently optionally substituted with one to three $R^{10}$.

In certain embodiments, each $R^4$ is independently halo, —CN, —OH, $C_1$-$C_6$alkyl, $C_2$-$C_6$alkynyl, or $C_3$-$C_{10}$cycloalkyl.

In certain embodiments, each $R^4$ is independently halo, —CN, —OH, —$OR^8$, $C_1$-$C_6$alkyl, or $C_2$-$C_6$alkynyl; wherein the $C_1$-$C_6$alkyl of $R^4$ is optionally substituted with one to three $R^{10}$.

In certain embodiments, each $R^4$ is independently halo, —CN, —OH, —$OR^8$, $C_1$-$C_6$alkyl, $C_2$-$C_6$alkynyl; wherein the $C_1$-$C_6$alkyl of $R^4$ is optionally substituted with one to three substituents independently selected from—$OR^{12}$, —$N(R^{12})_2$, —$S(O)_2R^{13}$, —$OC(O)CHR^{12}N(R^{12})_2$, and $C_1$-$C_6$alkyl optionally substituted with one to three halo, —$OR^{12}$, —$N(R^{12})_2$, —$Si(R^{12})_3$, —$C(O)OR^{12}$, —$NR^{12}C(O)OR^{12}$, —$OC(O)CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, each $R^5$ is independently halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^5)_3$, —$C(O)OR^6$, —$C(O)N(R^7)_2$, —$NR^{12}C(O)R^8$, —$OC(O)R^8$, —$C(O)R^6$, $C_1$-$C_6$alkyl, $C_2$-$C_6$alkenyl, $C_2$-$C_6$alkynyl, or $C_3$-$C_{10}$cycloalkyl; wherein each $C_1$-$C_6$alkyl, $C_2$-$C_6$alkenyl, $C_2$-$C_6$alkynyl, or $C_3$-$C_{10}$cycloalkyl of $R^5$ is independently optionally substituted with one to three $R^{10}$.

In certain embodiments, each $R^5$ is independently halo, —CN, —$OR^7$, $C_1$-$C_6$alkyl, $C_2$-$C_6$alkynyl, or $C_3$-$C_{10}$cycloalkyl; wherein each $C_1$-$C_6$alkyl, $C_2$-$C_6$alkynyl, or $C_3$-$C_{10}$cycloalkyl of $R^5$ is independently optionally substituted with one to three $R^{10}$.

In certain embodiments, each $R^5$ is independently halo, —CN, —OH, $C_1$-$C_6$alkyl, $C_2$-$C_6$alkynyl, or $C_3$-$C_{10}$cycloalkyl.

In certain embodiments, each $R^5$ is independently halo, —CN, —OH, —$OR^8$, $C_1$-$C_6$alkyl, or $C_2$-$C_6$alkynyl; wherein the $C_1$-$C_6$alkyl of $R^5$ is optionally substituted with one to three $R^{10}$.

In certain embodiments, each $R^5$ is independently halo, —CN, —OH, —$OR^8$, $C_1$-$C_6$alkyl, $C_2$-$C_6$alkynyl; wherein the $C_1$-$C_6$alkyl of $R^5$ is optionally substituted with one to three substituents independently selected from —$OR^{12}$, —$N(R^{12})_2$, —$S(O)_2R^{13}$, —$OC(O)CHR^{12}N(R^{12})_2$, and $C_1$-$C_6$alkyl optionally substituted with one to three halo, —$OR^{12}$, —$N(R^{12})_2$, —$Si(R^{12})_3$, —$C(O)OR^{12}$, —$NR^{12}C(O)OR^{12}$, —$OC(O)CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, each $R^6$ is independently hydrogen, $C_1$-$C_6$alkyl, $C_2$-$C_6$alkenyl, or —$C_1$-$C_6$alkyl$C_3$-$C_{10}$cycloalkyl; wherein each $R^6$ is independently further substituted with one to three $R^{11}$.

In certain embodiments, each $R^6$ is independently hydrogen, $C_1$-$C_6$alkyl, $C_2$-$C_6$alkenyl, or —$C_1$-$C_6$alkyl$C_3$-$C_{10}$cycloalkyl; wherein each $R^6$ is independently further substituted with one to three halo, —$OR^{12}$, —$N(R^{12})_2$, —$Si(R^{12})_3$, —$C(O)OR^{12}$, —$NR^{12}C(O)OR^{12}$, —$OC(O)CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl.

In certain embodiments, each $R^7$ is independently hydrogen, $C_1$-$C_6$alkyl, $C_3$-$C_{10}$cycloalkyl, heterocyclyl, heteroaryl, —$C_1$-$C_6$alkyl$C_3$-$C_6$cycloalkyl, —$C_1$-$C_6$alkylheterocyclyl, or two $R^7$ together with the nitrogen atom to which they are attached, form a 4 to 7 membered heterocyclyl; wherein each $R^7$ or ring formed thereby is independently further substituted with one to three $R^{11}$.

In certain embodiments, each $R^7$ is independently hydrogen, $C_1$-$C_6$alkyl, $C_3$-$C_{10}$cycloalkyl, heterocyclyl, heteroaryl, —$C_1$-$C_6$alkyl$C_3$-$C_6$cycloalkyl, —$C_1$-$C_6$alkylheterocyclyl, or two $R^7$ together with the nitrogen atom to which they are attached, form a 4 to 7 membered heterocyclyl; wherein each $R^7$ or ring formed thereby is independently further substituted with one to three halo, —$OR^{12}$, —$N(R^{12})_2$, —$Si(R^{12})_3$, —$C(O)OR^{12}$, —$NR^{12}C(O)OR^{12}$, —$OC(O)CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl.

In certain embodiments, each $R^8$ is independently $C_1$-$C_6$alkyl, $C_2$-$C_6$alkynyl, $C_3$-$C_{10}$cycloalkyl, —$C_1$-$C_6$alkyl$C_3$-$C_{10}$cycloalkyl, or —$C_1$-$C_6$alkylaryl; wherein each $R^8$ is independently further substituted with one to three $R^{11}$.

In certain embodiments, each $R^8$ is independently $C_1$-$C_6$alkyl, $C_2$-$C_6$alkynyl, $C_3$-$C_{10}$cycloalkyl, —$C_1$-$C_6$alkyl$C_3$-$C_{10}$cycloalkyl, or —$C_1$-$C_6$alkylaryl; wherein each $R^8$ is independently further substituted with one to three halo, —$OR^{12}$, —$N(R^{12})_2$, —$Si(R^{12})_3$, —$C(O)OR^{12}$, —$NR^{12}C(O)OR^{12}$, —$OC(O)CHR^{12}N(R^{12})_2$, $C_1$-$C_6$alkyl, or heterocyclyl; wherein each $R^{12}$ is independently hydrogen, $C_1$-$C_6$alkyl or $C_3$-$C_{10}$cycloalkyl.

In certain embodiments, each $R^{10}$ is independently —$OR^{12}$, —$N(R^{12})_2$, —$S(O)_2R^{13}$, —$OC(O)CHR^{12}N(R^{12})_2$, or $C_1$-$C_6$alkyl, wherein the $C_1$-$C_6$alkyl, of $R^{10}$ is optionally independently substituted with one to three $R^{11}$;

each $R^{11}$ is independently halo, —$OR^{12}$, —$N(R^{12})_2$, —$Si(R^{12})_3$, —$C(O)OR^{12}$, —$NR^{12}C(O)OR^{12}$, —$OC(O)CHR^{12}N(R^{12})_2$, $C_1$-$C_6$alkyl, or heterocyclyl;

each $R^{12}$ is independently hydrogen, $C_1$-$C_6$alkyl or $C_3$-$C_{10}$cycloalkyl; and each $R^{13}$ is independently $C_1$-$C_6$alkyl or $C_3$-$C_{10}$cycloalkyl.

In certain embodiments, each $R^5$ is independently $C_1$-$C_6$alkyl.

In certain embodiments, p is 0. In certain embodiments, p is 0 or 1. In certain embodiments, p is 1 or 2. In certain embodiments, p is 1. In certain embodiments, p is 2.

In certain embodiments, q is 0. In certain embodiments, q is 0 or 1. In certain embodiments, q is 1 or 2. In certain embodiments, q is 1. In certain embodiments, q is 2. In certain embodiments, q is 3.

Also provided is a compound, or a tautomer, stereoisomer, mixture of stereoisomers, isotopically enriched analog, or pharmaceutically acceptable salt thereof, selected from Table 1:

TABLE 1

| No. | Structure |
|---|---|
| 1 | 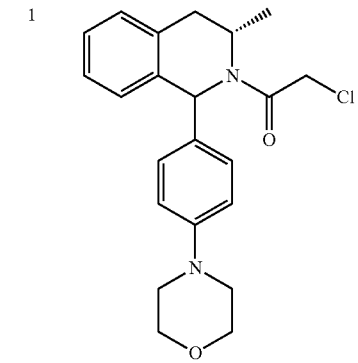 |
| 2 | 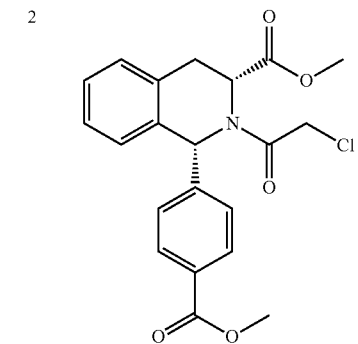 |

TABLE 1-continued

| No. | Structure |
|---|---|
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |

TABLE 1-continued
| No. | Structure |
|-----|-----------|
| 12 | 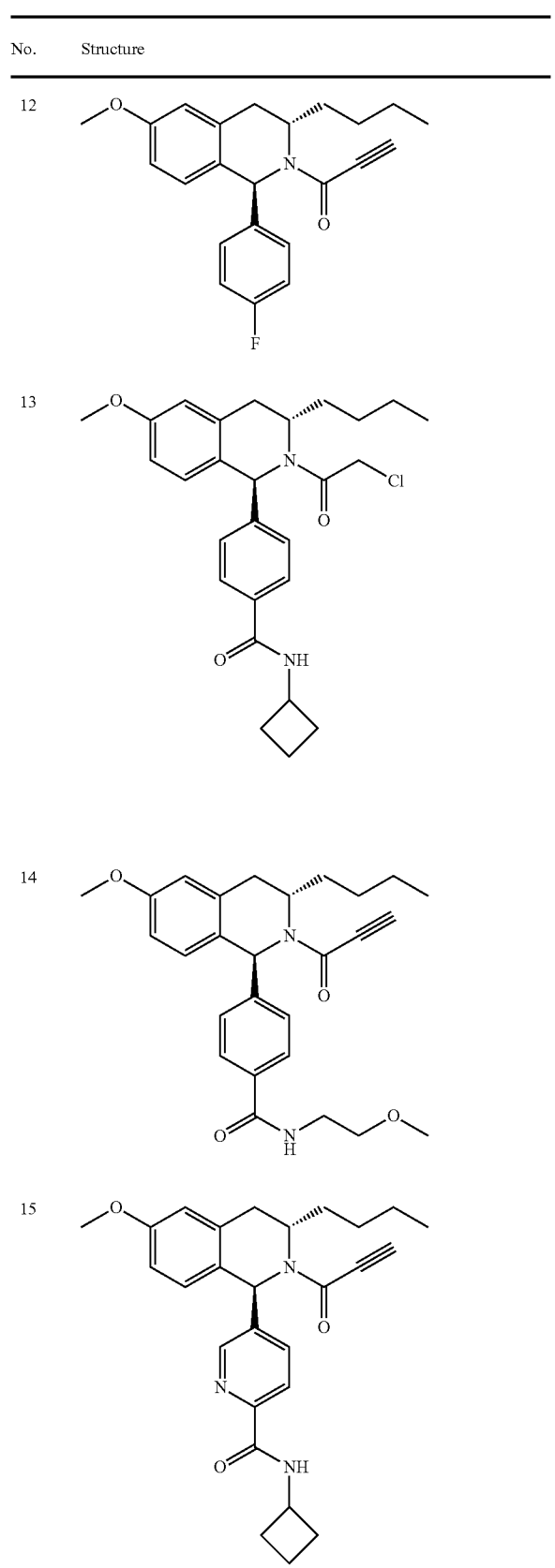 |
| 13 | 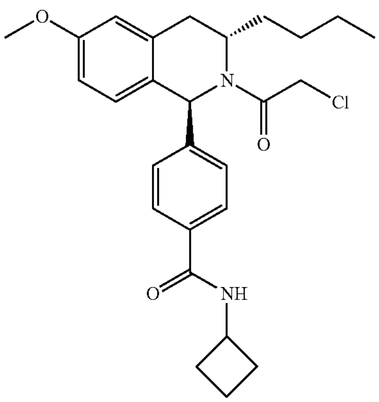 [SMILES: CCCC[C@H]1Cc2cc(OC)ccc2[C@H](c2ccc(C(=O)NC3CCC3)cc2)N1C(=O)CCl] |
| 14 | 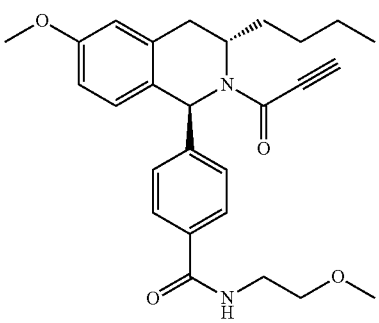 |
| 15 | 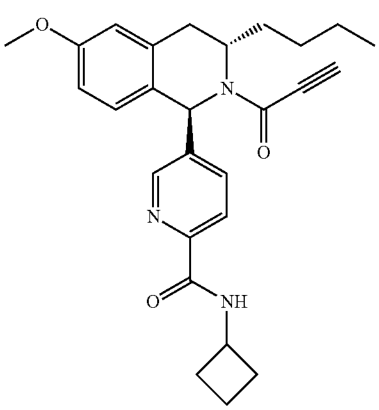 [SMILES: C#CC(=O)N1[C@@H](CCCC)Cc2cc(OC)ccc2[C@@H]1c1ccc(C(=O)NC2CCC2)nc1] |
| 16 | 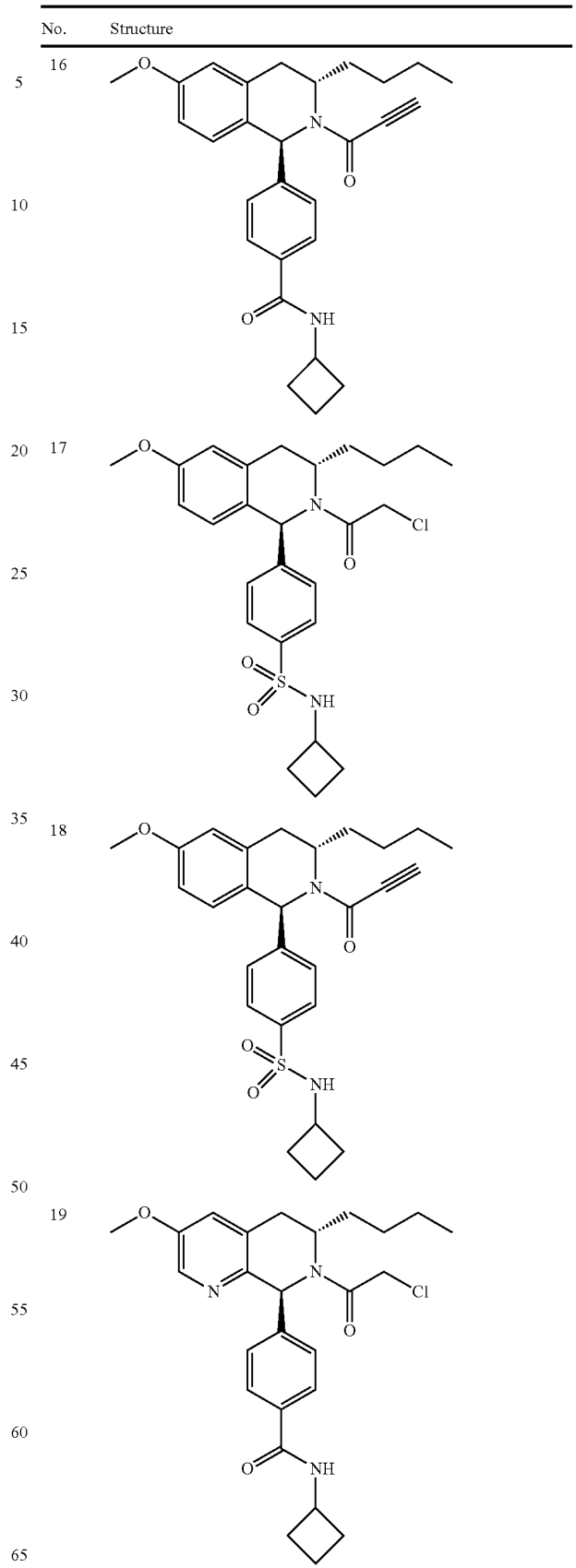 |
| 17 | |
| 18 | |
| 19 | |

TABLE 1-continued

| No. | Structure |
|---|---|
| 20 | (structure) |
| 21 | (structure) |
| 22 | (structure) |
| 23 | (structure) |
| 24 | (structure) |
| 25 | (structure) |
| 26 | (structure) |
| 27 | (structure) |

TABLE 1-continued
| No. | Structure |
|---|---|
| 28 | 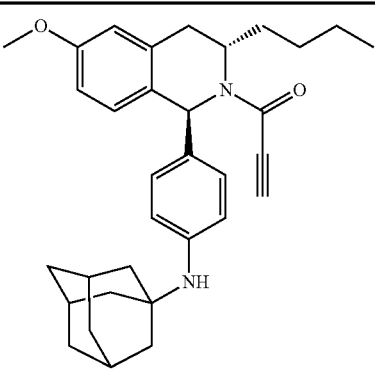 |
| 29 | 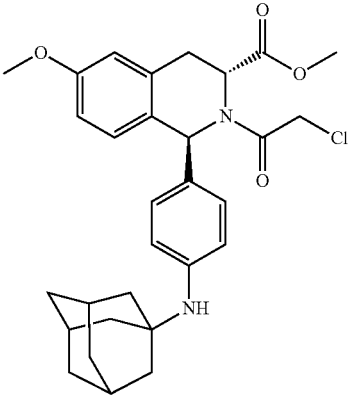 [SMILES: COC(=O)[C@H]1Cc2cc(OC)ccc2[C@H](c2ccc(NC34CC5CC(CC(C5)C3)C4)cc2)N1C(=O)CCl] |
| 30 | 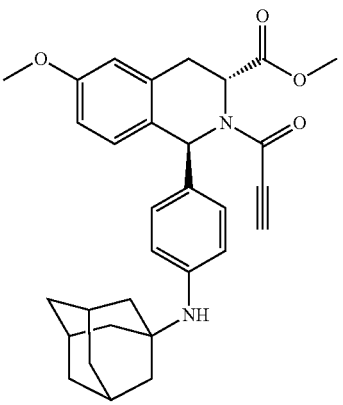 |
| 31 | 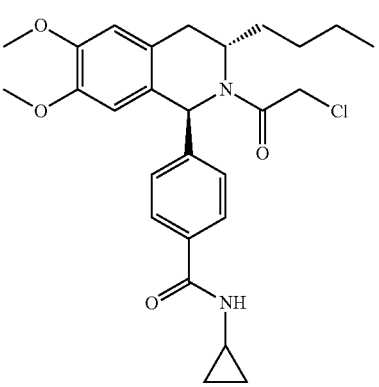 [SMILES: CCCC[C@H]1Cc2cc(OC)c(OC)cc2[C@H](c2ccc(C(=O)NC3CC3)cc2)N1C(=O)CCl] |
| 32 | 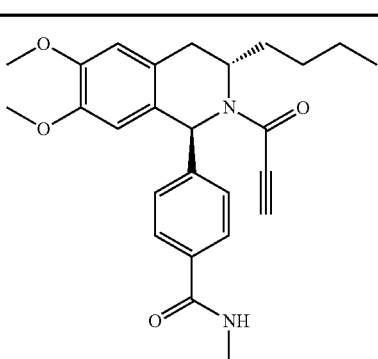 |
| 33 | 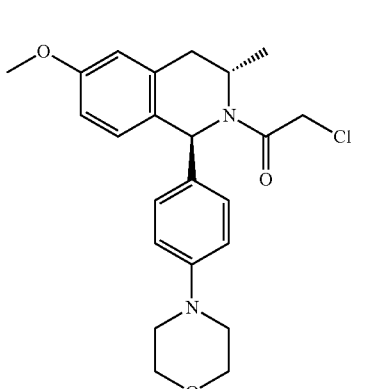 |
| 34 | 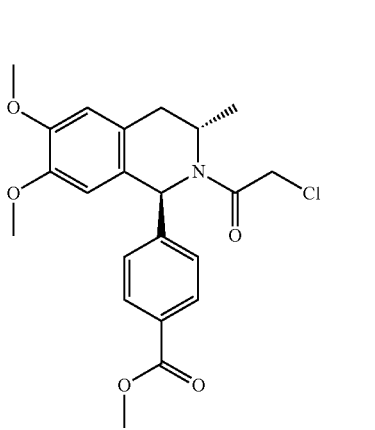 [SMILES: COC(=O)c1ccc([C@H]2c3cc(OC)c(OC)cc3C[C@H](C)N2C(=O)CCl)cc1] |
| 35 | 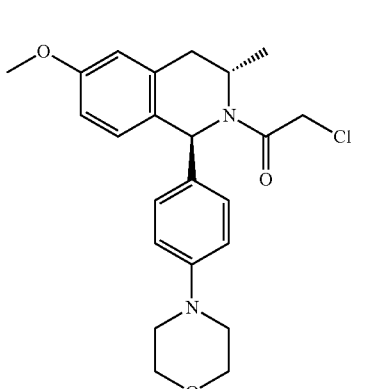 |

TABLE 1-continued
| No. | Structure |
|---|---|
| 36 | 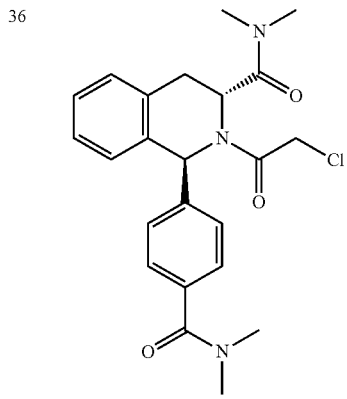 |
| 37 | 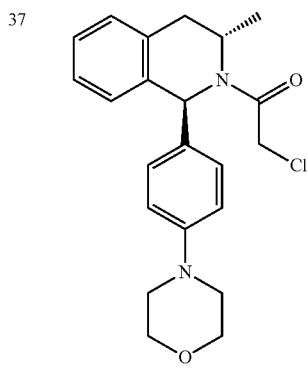 |
| 38 | 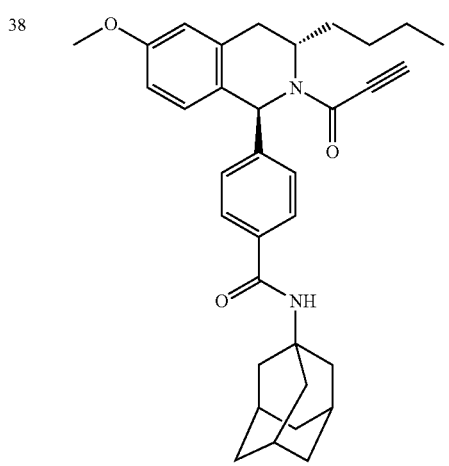 |
| 39 | 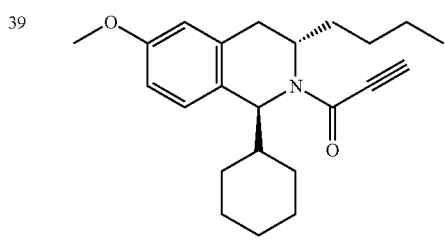 |
| 40 | 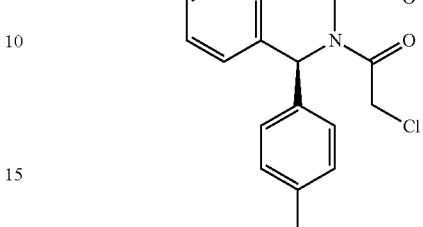 |
| 41 | 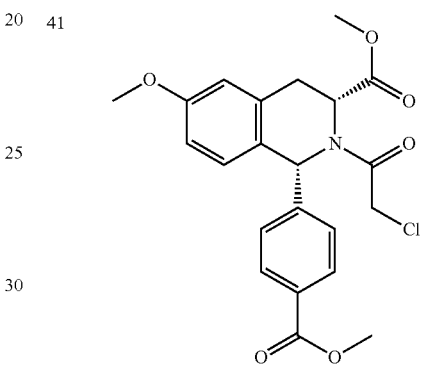 |
| 42 | 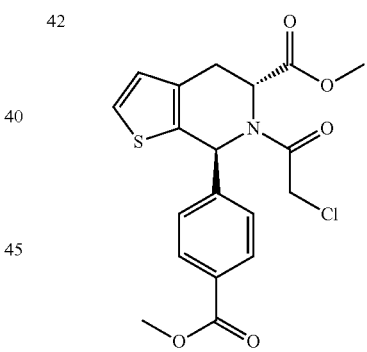 |
| 43 | 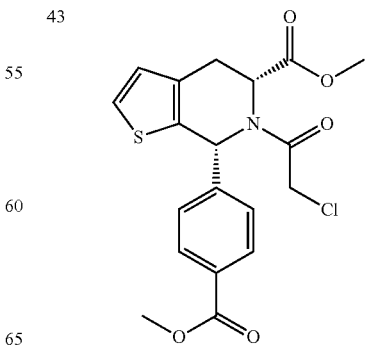 |

TABLE 1-continued
| No. | Structure |
|---|---|
| 44 | 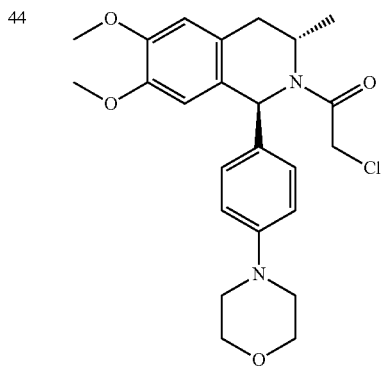 |
| 45 | 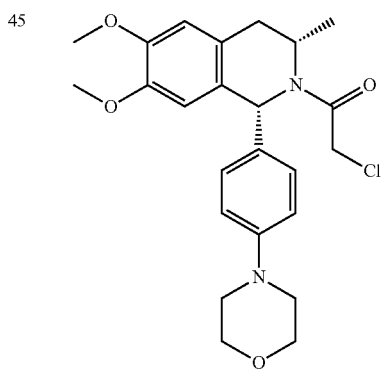 |
| 46 | 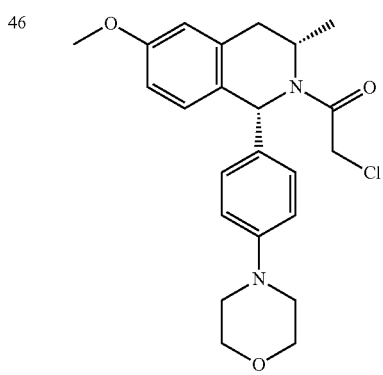 |
| 47 | 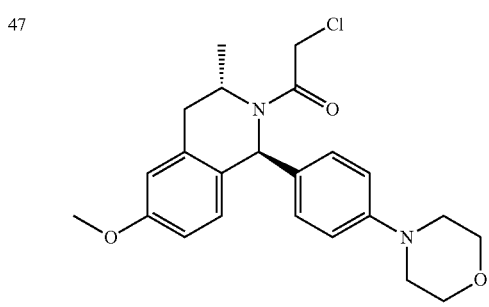 |
| 48 | 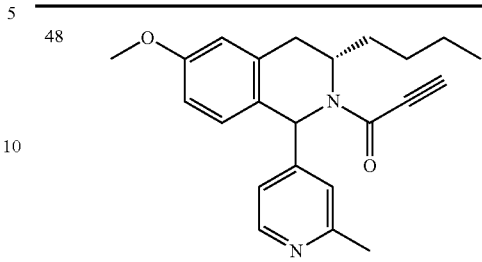 |
| 49 | 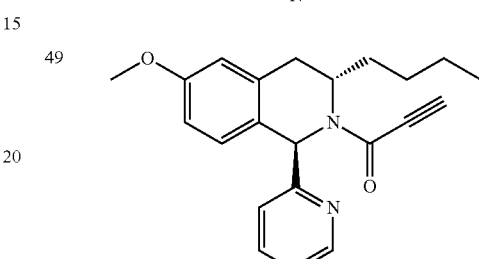 |
| 50 | 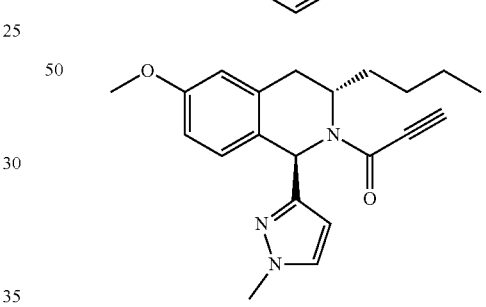 |
| 51 | 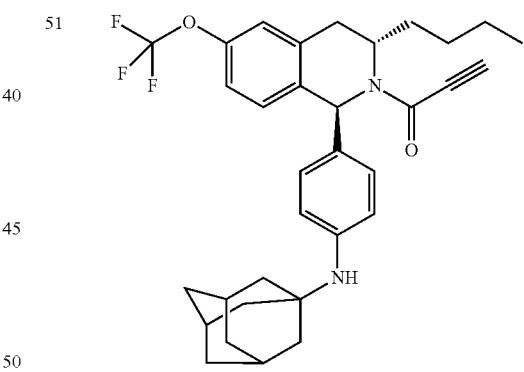 |
| 52 | 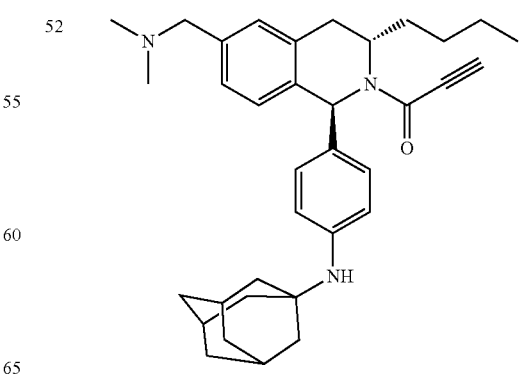 |

TABLE 1-continued

| No. | Structure |
|-----|-----------|
| 53 | (6-methoxy-1-(pyridin-4-yl)-3-butyl-3,4-dihydroisoquinolin-2(1H)-yl)(propargyl) ketone |
| 54 | (6-methoxy-1-(1-methylpiperidin-4-yl)-3-butyl-3,4-dihydroisoquinolin-2(1H)-yl)(propargyl) ketone |
| 55 | (6-methoxy-1-(4-(3-methyl-1,2,4-oxadiazol-5-yl)phenyl)-3-butyl-3,4-dihydroisoquinolin-2(1H)-yl)(propargyl) ketone |
| 56 | (6-(2-(dimethylamino)ethoxy)-1-(4-fluorophenyl)-3-butyl-3,4-dihydroisoquinolin-2(1H)-yl)(propargyl) ketone |
| 57 | (6-methoxy-1-(pyridin-2-yl)-3-butyl-3,4-dihydroisoquinolin-2(1H)-yl)(propargyl) ketone |
| 58 | 1,8-naphthyridine pyridin-2-yl butyl propargyl ketone analog |
| 59 | (6-methoxy-1-(pyridin-3-yl)-3-butyl-3,4-dihydroisoquinolin-2(1H)-yl)(propargyl) ketone |
| 60 | 1,8-naphthyridine pyridin-3-yl butyl propargyl ketone analog |
| 61 | (6-methoxy-1-(1-methyl-1H-pyrazol-5-yl)-3-butyl-3,4-dihydroisoquinolin-2(1H)-yl)(propargyl) ketone |
| 62 | 1,8-naphthyridine 1-methyl-1H-pyrazol-5-yl butyl propargyl ketone analog |
| 63 | (6-methoxy-1-(4-((3-aminobicyclo[1.1.1]pentan-1-yl)amino)phenyl)-3-butyl-3,4-dihydroisoquinolin-2(1H)-yl)(propargyl) ketone |

TABLE 1-continued

| No. | Structure |
|-----|-----------|
| 64 | 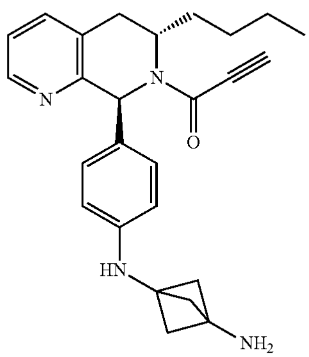 [SMILES: C#CC(=O)N1[C@@H](CCCC)Cc2cccnc2[C@@H]1c1ccc(NC23CC(N)(C2)C3)cc1] |
| 65 | 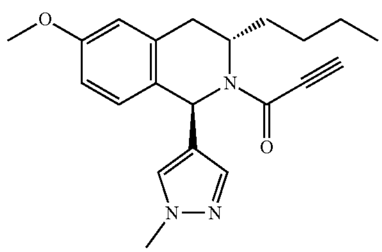 [SMILES: C#CC(=O)N1[C@@H](CCCC)Cc2cc(OC)ccc2[C@@H]1c1cnn(C)c1] |
| 66 | 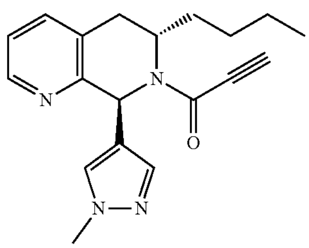 [SMILES: C#CC(=O)N1[C@@H](CCCC)Cc2cccnc2[C@@H]1c1cnn(C)c1] |
| 67 | 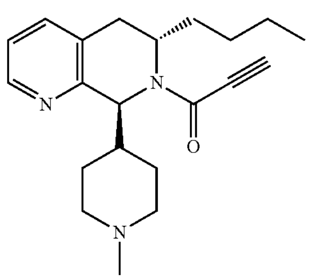 [SMILES: C#CC(=O)N1[C@@H](CCCC)Cc2cccnc2[C@@H]1C1CCN(C)CC1] |
| 68 | 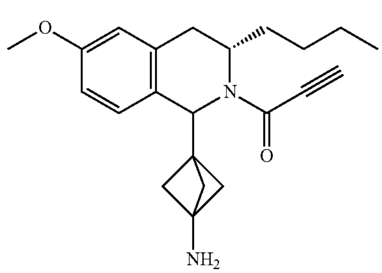 [SMILES: C#CC(=O)N1C(C23CC(N)(C2)C3)c2ccc(OC)cc2C[C@@H]1CCCC] |
| 69 | 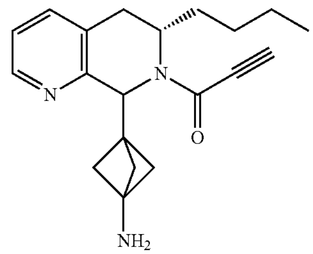 [SMILES: C#CC(=O)N1C(C23CC(N)(C2)C3)c2ncccc2C[C@@H]1CCCC] |
| 70 | 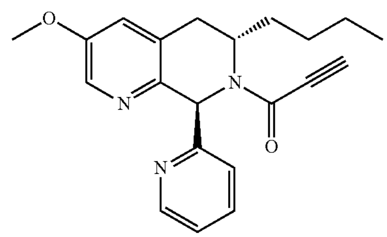 [SMILES: C#CC(=O)N1[C@@H](CCCC)Cc2cc(OC)cnc2[C@@H]1c1ccccn1] |
| 71 | 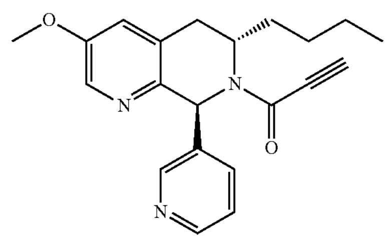 [SMILES: C#CC(=O)N1[C@@H](CCCC)Cc2cc(OC)cnc2[C@@H]1c1cccnc1] |
| 72 | 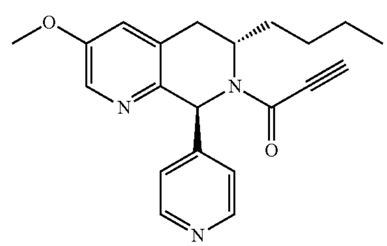 [SMILES: C#CC(=O)N1[C@@H](CCCC)Cc2cc(OC)cnc2[C@@H]1c1ccncc1] |
| 73 | 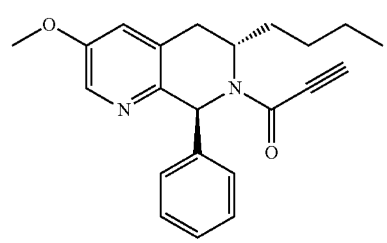 [SMILES: C#CC(=O)N1[C@@H](CCCC)Cc2cc(OC)cnc2[C@@H]1c1ccccc1] |
| 74 | 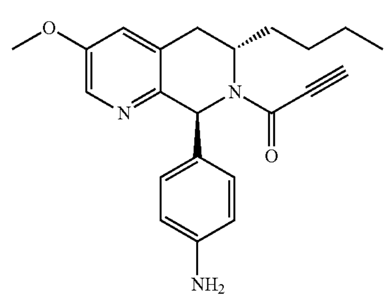 [SMILES: C#CC(=O)N1[C@@H](CCCC)Cc2cc(OC)cnc2[C@@H]1c1ccc(N)cc1] |

TABLE 1-continued
| No. | Structure |
|-----|-----------|
| 75 | 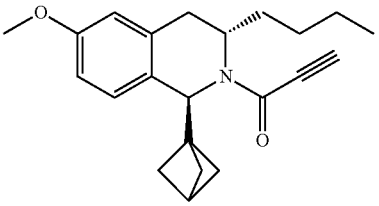 [SMILES: C#CC(=O)N1[C@@H](CCCC)Cc2cc(OC)ccc2[C@@H]1C12CC(C1)C2] |
| 76A | 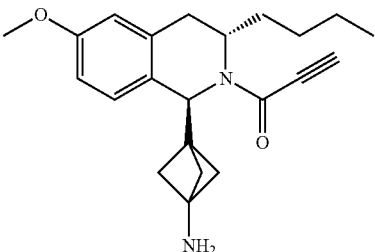 |
| 76 | 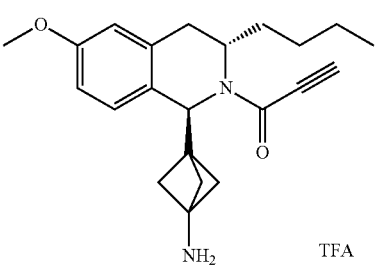 [SMILES: C#CC(=O)N1[C@@H](CCCC)Cc2cc(OC)ccc2[C@@H]1C12CC(N)(C1)C2] TFA |
| 77 | 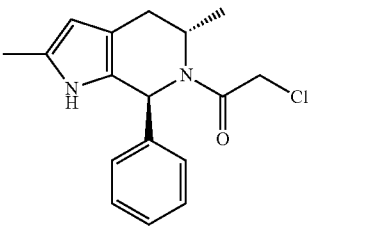 [SMILES: Cc1cc2c([nH]1)[C@H](c1ccccc1)N(C(=O)CCl)[C@@H](C)C2] |
| 78 | 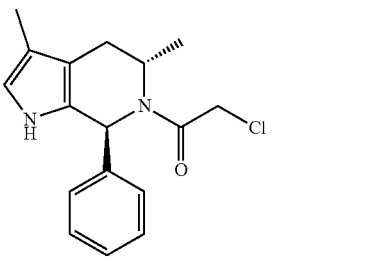 [SMILES: Cc1c[nH]c2c1C[C@H](C)N(C(=O)CCl)[C@H]2c1ccccc1] |
| 79 | 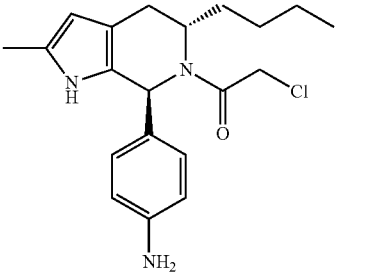 [SMILES: CCCC[C@H]1Cc2cc(C)[nH]c2[C@H](c2ccc(N)cc2)N1C(=O)CCl] |
| 80 | 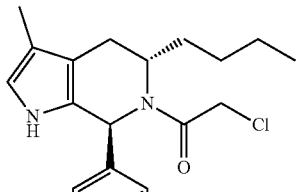 |
| 81 | 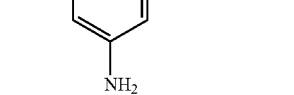 |
| 82 | 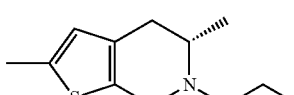 |
| 83 | 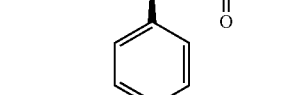 |
| 84 |  |

TABLE 1-continued

| No. | Structure |
|-----|-----------|
| 85 | 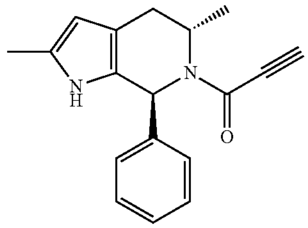 [SMILES: C#CC(=O)N1[C@@H](c2ccccc2)c2[nH]c(C)cc2C[C@@H]1C] |
| 86 | 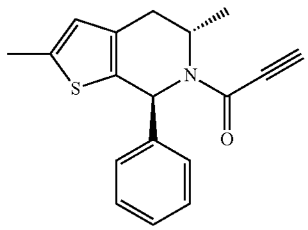 [SMILES: C#CC(=O)N1[C@@H](c2ccccc2)c2sc(C)cc2C[C@@H]1C] |
| 87 | 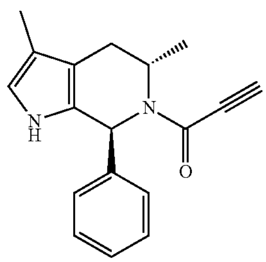 [SMILES: C#CC(=O)N1[C@@H](c2ccccc2)c2[nH]cc(C)c2C[C@@H]1C] |
| 88 | 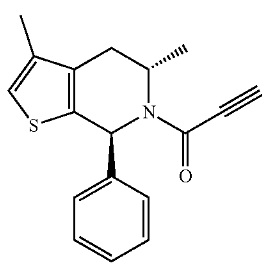 [SMILES: C#CC(=O)N1[C@@H](c2ccccc2)c2scc(C)c2C[C@@H]1C] |
| 89 | 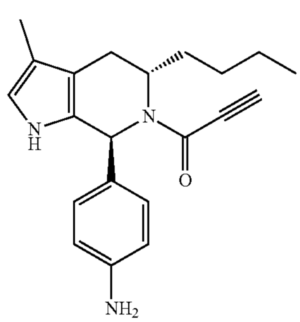 [SMILES: C#CC(=O)N1[C@@H](CCCC)Cc2c(C)c[nH]c2[C@@H]1c1ccc(N)cc1] |
| 90 | |
| 91 | |
| 92 | |
| 93 | |

TABLE 1-continued
| No. | Structure |
|---|---|
| 94 | 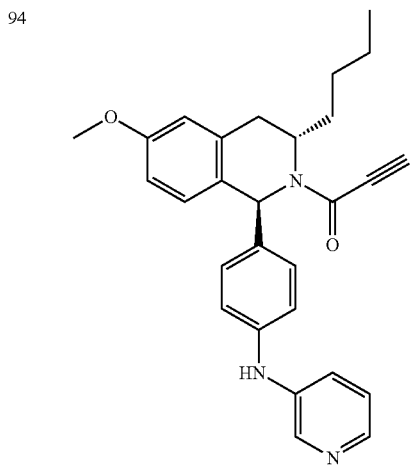 |
| 95 | 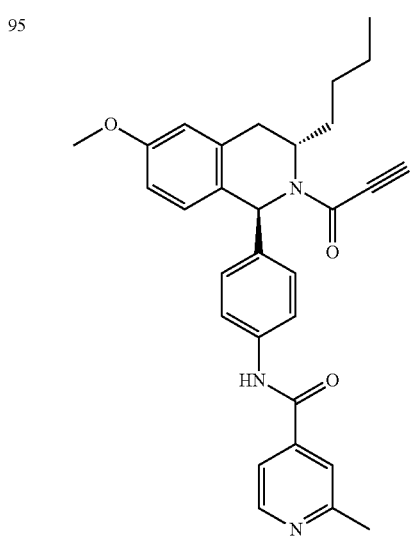 |
| 96 | 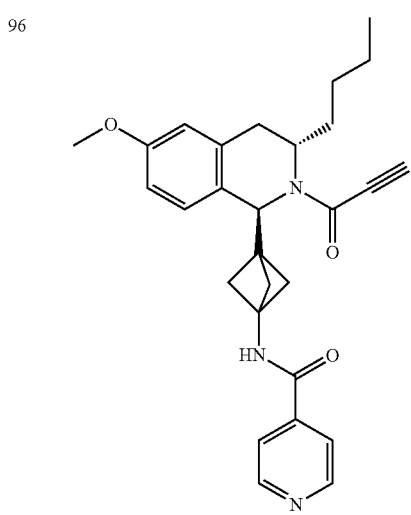 |
TABLE 1-continued
| No. | Structure |
|---|---|
| 97 | 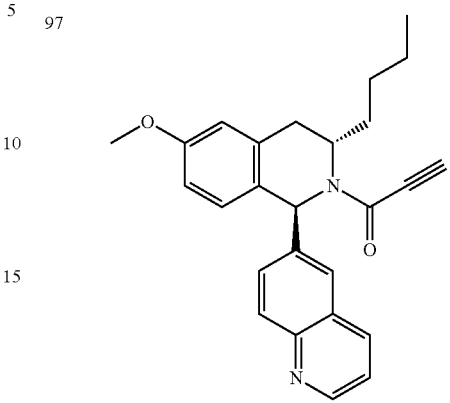 |
| 98 | 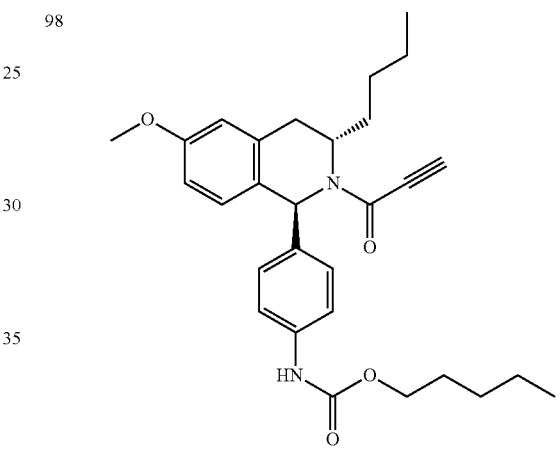 |
| 99A | 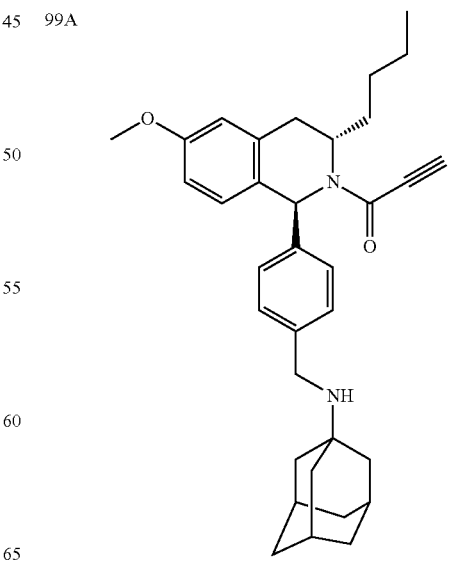 |

TABLE 1-continued

| No. | Structure |
|---|---|
| 99 | (structure with methoxy-tetrahydroisoquinoline, propiolyl, phenyl-CH2-NH-adamantyl, TFA) |
| 100A | (structure with methoxy-tetrahydroisoquinoline, propiolyl, phenyl-CH2-NH-bicyclopentyl) |
| 100 | (structure with methoxy-tetrahydroisoquinoline, propiolyl, phenyl-CH2-NH-bicyclopentyl, TFA) |
| 101 | (structure with methoxy-tetrahydroisoquinoline, propiolyl, phenyl-NH-adamantyl·HCl) |
| 102 | (structure with methoxy-tetrahydroisoquinoline, propiolyl, phenyl-NH-C(O)-cyclobutyl) |

3. Methods of Use

In certain embodiments, the compounds described herein are used in a method of treating cancer. In certain embodiments, the method of treating cancer comprises administering to a subject in need thereof a therapeutically effective amount any of the compounds described herein.

In certain embodiments, the compounds are used in a method of inhibiting GPX4 in a cell, comprising contacting a cell with an effective amount of a compound or composition described herein to inhibit GPX4 in the cell. In certain embodiments, the cell is a cancer cell. In certain embodiments, the method comprises administering an effective amount of a compound or composition described herein to a patient in need thereof.

In certain embodiments, the compounds are used in a method of inducing ferroptosis in a cell comprising contacting the cell with an effective amount of a compound or composition provided herein. In certain embodiments, the method comprises administering an effective amount of a compound or composition described herein to a patient in need thereof.

In certain embodiments, provided is a method for treating a cancer in a patient in need thereof, comprising administering an effective amount of a compound or composition provided herein.

In certain embodiments, the compounds are used in a method of treating cancer in a subject in need thereof, comprising administering to a subject having cancer a therapeutically effective amount of a ferroptosis inducing compound disclosed herein. Various cancers for treatment with the compounds include, but are not limited to, adrenocortical cancer, anal cancer, biliary cancer, bladder cancer, bone cancer, gliomas, astrocytoma, neuroblastoma, breast cancer, cervical cancer, colon cancer, endometrial cancer, esophageal cancer, head and neck cancer, intestinal cancer, liver cancer, lung cancer, oral cancer, ovarian cancer, pancreatic cancer, renal cancer, prostate cancer, salivary gland cancer, skin cancer, stomach cancer, testicular cancer, throat cancer, thyroid cancer, uterine cancer, vaginal cancer, sarcoma, and soft tissue carcinomas. In certain embodiments, the compound is used to treat pancreatic cancer.

In certain embodiments, the cancer is renal cell carcinoma (RCC), pancreatic cancer, lung cancer, breast cancer, or prostate cancer. In certain embodiments, provided is a method for treating renal cell carcinoma (RCC) in a patient in need thereof, comprising administering an effective amount of a compound or composition provided herein. In certain embodiments, provided is a method for treating pancreatic cancer in a patient in need thereof, comprising administering an effective amount of a compound or composition provided herein. In certain embodiments, provided is a method for treating lung cancer in a patient in need thereof, comprising administering an effective amount of a compound or composition provided herein. In certain embodiments, provided is a method for treating breast cancer in a patient in need thereof, comprising administering an effective amount of a compound or composition provided herein. In certain embodiments, provided is a method for treating prostate cancer in a patient in need thereof, comprising administering an effective amount of a compound or composition provided herein.

In certain embodiments, provided is a method for treating a malignant solid tumor in a patient in need thereof, comprising administering an effective amount of a compound or composition provided herein to the patient. In certain embodiments, the malignant solid tumor is a carcinoma. In certain embodiments, the malignant solid tumor is a lymphoma. In certain embodiments, the malignant solid tumor is a sarcoma.

In certain embodiments, the cancer for treatment with the compound can be selected from, among others, adrenocortical cancer, anal cancer, biliary cancer, bladder cancer, bone cancer (e.g., osteosarcoma), brain cancer (e.g., gliomas, astrocytoma, neuroblastoma, etc.), breast cancer, cervical cancer, colon cancer, endometrial cancer, esophageal cancer, head and neck cancer, hematologic cancer (e.g., leukemia and lymphoma), intestinal cancer (small intestine), liver cancer, lung cancer (e.g., bronchial cancer, small cell lung cancer, non-small cell lung cancer, etc.), oral cancer, ovarian cancer, pancreatic cancer, renal cancer, prostate cancer, salivary gland cancer, skin cancer (e.g., basal cell carcinoma, melanoma), stomach cancer, testicular cancer, throat cancer, thyroid cancer, uterine cancer, vaginal cancer, sarcoma, and soft tissue carcinomas. In certain embodiments, the cancer is renal cell carcinoma (RCC). In certain embodiments, the cancer is pancreatic cancer. In certain embodiments, the cancer is lung cancer. In certain embodiments, the cancer is breast cancer. In certain embodiments, the cancer is prostate cancer.

In certain embodiments, the cancer for treatment with the compound is pancreatic cancer. In certain embodiments, the pancreatic cancer for treatment with the compounds is pancreatic adenocarcinoma or metastatic pancreatic cancer.

In certain embodiments, the cancer for treatment with the compounds is stage I, stage II, stage III, or stage IV pancreatic adenocarcinoma.

In certain embodiments, the cancer for treatment with the compounds is lung cancer. In certain embodiments, the lung cancer for treatment with the compounds is small cell lung cancer or non-small cell lung cancer. In certain embodiments, the non-small cell lung cancer for treatment with the compounds is an adenocarcinoma, squamous cell carcinoma, or large cell carcinoma. In certain embodiments, the lung cancer for treatment with the compounds is metastatic lung cancer.

In certain embodiments, the cancer for treatment with the compounds is a hematologic cancer. In certain embodiments, the hematologic cancer is selected from acute lymphoblastic leukemia (ALL), acute myeloid leukemia (AML), lymphoma (e.g., Hodgkin's lymphoma, Non-Hodgkin's lymphoma, Burkitt's lymphoma), chronic lymphocytic leukemia (CLL), chronic myelogenous leukemia (CML), Hairy Cell chronic myelogenous leukemia (CML), and multiple myeloma.

In certain embodiments, the cancer for treatment with the compounds is a leukemia selected from acute lymphoblastic leukemia (ALL), acute myeloid leukemia (AML), chronic lymphocytic leukemia (CLL), chronic myelogenous leukemia (CML), Hairy Cell chronic myelogenous leukemia (CML), and multiple myeloma.

In certain embodiments, the cancer for treatment with the compound is a lymphoma selected from Hodgkin's lymphoma, Non-Hodgkin's lymphoma, and Burkitt's lymphoma.

In certain embodiments, the cancer for treatment with the compound is a cancer characterized by mesenchymal features or mesenchymal phenotype. In some cancers, gain of mesenchymal features is associated with migratory (e.g., intravasation) and invasiveness of cancers. Mesenchymal features can include, among others, enhanced migratory capacity, invasiveness, elevated resistance to apoptosis, and increased production of extracellular matrix (ECM) components. In addition to these physiological characteristics, the mesenchymal features can include expression of certain biomarkers, including among others, E-cadherin, N-cadherin, integrins, FSP-1, α-SMA, vimentin, β-catenin, collagen I, collagen II, collagen III, collagen IV, fibronectin, laminin 5, SNAIL-1, SNAIL-2, Twist-1, Twist-2, and Lef-1. In certain embodiments, the cancer selected for treatment with the compounds herein include, among others, breast cancer, lung cancer, head and neck cancer, prostate cancer, and colon cancer. In certain embodiments, the mesenchymal features can be inherent to the cancer type or induced by or selected for by treatment of cancers with chemotherapy and/or radiation therapy.

In certain embodiments, the cancer for treatment with the compound is identified as having or determined to have an activating or oncogenic RAS activity. In certain embodiments, the RAS is K-RAS, H-RAS or N-RAS. In certain embodiments, the activating or oncogenic RAS is an activating or oncogenic RAS mutation.

In certain embodiments, the cancer selected for treatment with the compounds are determined to have or identified as having an activating or oncogenic RAS activity. In certain embodiments, the activating or oncogenic RAS activity is an activating or oncogenic RAS mutations. In certain embodiments, the activating or oncogenic RAS activity is an activating or activating K-RAS activity, particularly an activating or oncogenic K-RAS mutation. In certain embodiments, the activating or oncogenic RAS activity is an activating or activating N-RAS activity, particularly an activating or oncogenic N-RAS mutation. In certain embodiments, the activating or oncogenic RAS activity is an activating or activating H-RAS activity, particularly an activating or oncogenic H-RAS mutation.

In certain embodiments, the compounds can be used to treat a cancer that is refractory to one or more other chemotherapeutic agents, particularly cytotoxic chemotherapeutic agents; or treat a cancer resistant to radiation treatment. In certain embodiments, the compounds are used to treat cancers that have developed tolerance to chemotherapeutic agents activating other cell death pathways, such as apoptosis, mitotic catastrophe, necrosis, senescence and/or autophagy.

In certain embodiments, the cancer for treatment with the compounds is identified as being refractory or resistant to chemotherapy. In certain embodiments, the cancer is refractory or resistant to one or more of alkylating agents, anticancer antibiotic agents, antimetabolic agents (e.g., folate antagonists, purine analogs, pyrimidine analogs, etc.), topoisomerase inhibiting agents, anti-microtubule agents (e.g., taxanes, vinca alkaloids), hormonal agents (e.g., aromatase inhibitors), plant-derived agents and their synthetic derivatives, anti-angiogenic agents, differentiation inducing agents, cell growth arrest inducing agents, apoptosis inducing agents, cytotoxic agents, agents affecting cell bioenergetics i.e., affecting cellular ATP levels and molecules/activities regulating these levels, biologic agents, e.g., monoclonal antibodies, kinase inhibitors and inhibitors of growth factors and their receptors.

In certain embodiments, the cancer for treatment with the compounds is a cancer identified as being refractory or resistant to one or more of afatinib, afuresertib, alectinib, alisertib, alvocidib, amsacrine, amonafide, amuvatinib, axitinib, azacitidine, azathioprine, bafetinib, barasertib, bendamustine, bleomycin, bosutinib, bortezomib, busulfan, cabozantinib, camptothecin, canertinib, capecitabine, cabazitaxel, carboplatin, carmustine, cenisertib, ceritinib, chlorambucil, cisplatin, cladribine, clofarabine, crenolanib, crizotinib, cyclophosphamide, cytarabine, dabrafenib, dacarbazine, dacomitinib, dactinomycin, danusertib, dasatinib, daunorubicin, decitabine, dinaciclib, docetaxel, dovitinib, doxorubicin, epirubicin, epitinib, eribulin mesylate, errlotinib, etirinotecan, etoposide, everolimus, exemestane, floxuridine, fludarabine, fluorouracil, gefitinib, gemcitabine, hydroxyurea, ibrutinib, icotinib, idarubicin, ifosfamide, imatinib, imetelstat, ipatasertib, irinotecan, ixabepilone, lapatinib, lenalidomide, lestaurtinib, lomustine, lucitanib, masitinib, mechlorethamine, melphalan, mercaptopurine, methotrexate, midostaurin, mitomycin, mitoxantrone, mubritinib, nelarabine, neratinib, nilotinib, nintedanib, omacetaxine mepesuccinate, orantinib, oxaliplatin, paclitaxel, palbociclib, palifosfamide tris, pazopanib, pelitinib, pemetrexed, pentostatin, plicamycin, ponatinib, poziotinib, pralatrexate, procarbazine, quizartinib, raltitrexed, regorafenib, ruxolitinib, seliciclib, sorafenib, streptozocin, sulfatinib, sunitinib, tamoxifen, tandutinib, temozolomide, temsirolimus, teniposide, theliatinib, thioguanine, thiotepa, topotecan, uramustine, valrubicin, vandetanib, vemurafenib (Zelborae), vincristine, vinblastine, vinorelbine, and vindesine.

In certain embodiments, the cancer for treatment with the compound is identified as being refractory or resistant to one or more chemotherapeutics agents selected from cyclophosphamide, chlorambucil, melphalan, mechlorethamine, ifosfamide, busulfan, lomustine, streptozocin, temozolomide, dacarbazine, cisplatin, carboplatin, oxaliplatin, procarbazine, uramustine, methotrexate, pemetrexed, fludarabine, cytarabine, fluorouracil, floxuridine, gemcitabine, capecitabine, vinblastine, vincristine, vinorelbine, etoposide, paclitaxel, docetaxel, doxorubicin, daunorubicin, epirubicin, idarubicin, mitoxantrone, bleomycin, mitomycin, hydroxyurea, topotecan, irinotecan, amsacrine, teniposide, and erlotinib.

In certain embodiments, the cancer for treatment with the compounds is a cancer resistant to ionizing radiation therapy. The radioresistance of the cancer can be inherent or as a result of radiation therapy. In certain embodiments, the cancers for treatment with the compounds is, among others, a radioresistant adrenocortical cancer, anal cancer, biliary cancer, bladder cancer, bone cancer (e.g., osteosarcoma), brain cancer (e.g., gliomas, astrocytoma, neuroblastoma, etc.), breast cancer, cervical cancer, colon cancer, endometrial cancer, esophageal cancer, head and neck cancer, hematologic cancer (e.g., leukemia and lymphoma), intestinal cancer (small intestine), liver cancer, lung cancer (e.g., bronchial cancer, small cell lung cancer, non-small cell lung cancer, etc.), oral cancer, ovarian cancer, pancreatic cancer, renal cancer, prostate cancer, salivary gland cancer, skin cancer (e.g., basal cell carcinoma, melanoma), stomach cancer, testicular cancer, throat cancer, thyroid cancer, uterine cancer, or vaginal cancer. In certain embodiments, the cancer is pancreatic cancer, breast cancer, glioblastoma, advanced non-small-cell lung cancer, bladder cancer, sarcoma, or soft tissue carcinoma.

4. Combination Treatments

In certain embodiments, the compounds described herein are used in combination with one or more of other (e.g., second therapeutic agent) therapeutic treatments for cancer. In certain embodiments, the compounds can be used as monotherapy, or as further provided below, in a combination therapy with one or more therapeutic treatments, particularly in combination with one or more chemotherapeutic agents. In certain embodiments, the compounds are used in combination with a second therapeutic agent, where the compounds are used at levels that sensitizes the cancer or cancer cell to the second therapeutic agent, for example at levels of the compound that do not cause significant cell death. In certain embodiments, the compounds can be used in combination with radiation therapy, either to sensitize the cells to radiation therapy or as an adjunct to radiation therapy (e.g., at doses sufficient to activate cell death pathway).

In certain embodiments, a subject with cancer is treated with a combination of a compound described herein and radiation therapy. In certain embodiments, the method comprises administering to a subject with cancer a therapeutically effective amount of a compound of the disclosure, and adjunctively treating the subject with an effective amount of radiation therapy. In certain embodiments, the compound is administered to the subject in need thereof prior to, concurrently with, or subsequent to the treatment with radiation.

In certain embodiments, the method comprises administering an effective amount of a compound described herein to a subject with cancer to sensitize the cancer to radiation treatment, and administering a therapeutically effective amount of radiation therapy to treat the cancer. In certain embodiments, an effective amount of X-ray and gamma ray is administered to the subject. In certain embodiments, an effective amount of particle radiation is administered to the subject, where the particle radiation is selected from electron beam, proton beam, and neutron beam radiation. In certain embodiments, the radiation therapy is fractionated.

In certain embodiments, a subject with cancer is administered a therapeutically effective amount of a compound described herein, or a first pharmaceutical composition thereof, and adjunctively administered a therapeutically effective amount of a second chemotherapeutic agent, or a second pharmaceutical composition thereof.

In certain embodiments, the second chemotherapeutic agent is selected from an platinating agent, alkylating agent, anti-cancer antibiotic agent, antimetabolic agent (e.g., folate antagonists, purine analogs, pyrimidine analogs, etc.), topoisomerase I inhibiting agent, topoisomerase II inhibiting agent antimicrotubule agent (e.g., taxanes, vinca alkaloids), hormonal agent (e.g., aromatase inhibitors), plant-derived agent and synthetic derivatives thereof, anti-angiogenic agent, differentiation inducing agent, cell growth arrest inducing agent, apoptosis inducing agent, cytotoxic agent, agent affecting cell bioenergetics, i.e., affecting cellular ATP levels and molecules/activities regulating these levels, anti-cancer biologic agent (e.g., monoclonal antibodies), kinase inhibitors and inhibitors of growth factors and their receptors.

In certain embodiments, the second chemotherapeutic agent is an angiogenesis inhibitor, such as but not limited to, an inhibitor of soluble VEGFR-1, NRP-1, angiopoietin 2, TSP-1, TSP-2, angiostatin and related molecules, endostatin, vasostatin, calreticulin, platelet factor-4, TIMP, CDAI, Meth-1, Meth-2, IFN-α, IFN-β, IFN-γ, CXCL10, IL-4, IL-12, IL-18, prothrombin (kringle domain-2), antithrombin III fragment, prolactin, VEGI, SPARC, osteopontin, maspin, canstatin (a fragment of COL4A2), or proliferin-related protein. In certain embodiments, the angiogenesis inhibitor is bevacizumab (Avastin), itraconazole, carboxyamidotriazole, TNP-470 (an analog of fumagillin), CM101, IFN-α, IL-12, platelet factor-4, suramin, SU5416, thrombospondin, a VEGFR antagonist, an angiostatic steroid plus heparin, cartilage-derived angiogenesis inhibitory factor (CDAI), a matrix metalloproteinase inhibitor, angiostatin, endostatin, 2-methoxyestradiol, tecogalan, tetrathiomolybdate, thalidomide, thrombospondin, prolactin, a αVβ3 inhibitor, linomide, ramucirumab, tasquinimod, ranibizumab, sorafenib (Nexavar), sunitinib (Sutent), pazopanib (Votrient), or everolimus (Afinitor).

In certain embodiments, the second chemotherapeutic agent is a cyclin-dependent kinase (CDK) inhibitor (e.g., a CDK4/CDK6 inhibitor). Examples include, but are not limited to, palbociclib (Ibrance), Ribociclib (optionally further in combination with letrozole), abemaciclib (LY2835219; Verzenio), P1446A-05, and Trilaciclib (G1T28).

In certain embodiments, the second chemotherapeutic agent is a Bruton's tyrosine kinase (BTK) inhibitor, such as but not limited to, Ibrutinib (PCI-32765), acalabrutinib, ONO-4059 (GS-4059), spebrutinib (AVL-292, CC-292), BGB-3111, and HM71224.

In certain embodiments, the second chemotherapeutic agent is a BRAF inhibitor. Examples include, but are not limited to, BAY43-9006 (Sorafenib, Nexavar), PLX-4032 (Vemurafenib), GDC-0879, PLX-4720, dabrafenib and LGX818.

In certain embodiments, the second chemotherapeutic agent is a EGFR inhibitor. Examples include, but are not limited to, gefitinib, erlotinib, afatinib, brigatinib, icotinib, cetuximab, osimertinib, panitumumab, brigatinib, lapatinib, cimaVax-EGF, and veristrat.

In certain embodiments, the second chemotherapeutic agent is a human epidermal growth factor receptor 2 (HER2) inhibitor. Examples include, but are not limited to, trastuzumab, pertuzumab (optionally further in combination with trastuzumab), margetuximab, and NeuVax.

In certain embodiments, disclosed herein is a method of increasing a subject's responsiveness to an immunotherapeutic or immunogenic chemotherapeutic agent, the method comprising administering to the subject in need thereof an effective amount of a compound described herein and an effective amount of an immunotherapeutic agent and/or an immunogenic chemotherapeutic agent. In certain embodiments, the method further includes administering to the subject a lipoxygenase inhibitor. In certain embodiments, the subject has a tumor whose cellular microenvironment is stromal cell rich. In certain embodiments, the administration of compound described herein results in killing one or more stromal cells in the tumor cells' microenvironment. In certain embodiments, the administration of an effective amount of an immunotherapeutic agent and/or an immunogenic chemotherapeutic agent results in killing one or more tumor cells. Also provided herein is a combination comprising a compound described herein and an immunotherapeutic agent, lipoxygenase inhibitor, or immunogenic chemotherapeutic agent. In certain embodiments, the immunotherapeutic agent is selected from a CTLA4, PDL1 or PD1 inhibitor. In certain embodiments, the immunotherapeutic agent can be selected from CTLA4 inhibitor such as ipilimumab, a PD1 inhibitor such as pembrolizumab or nivolumab or a PDL1 inhibitor such as atezolizumab or durvalumab. In certain embodiments, the immunotherapeutic agent is pembrolizumab. In other embodiments, the immunogenic chemotherapeutic agent is a compound selected from anthracycline, doxorubicin, cyclophosphamide, paclitaxel, docetaxel, cisplatin, oxaliplatin or carboplatin. In certain embodiments, provided herein is a combination comprising a compound described herein and a lipoxygenase inhibitor. In certain embodiments, the lipoxygenase inhibitor is selected from PD147176 and/or ML351. In certain embodiments, the lipoxygenase inhibitor may be a 15-lipoxygenase inhibitor (see, e.g., Sadeghian et al., Expert Opinion on Therapeutic Patents, 2015, 26:1, 65-88).

In certain embodiments, the second chemotherapeutic agent is selected from an alkylating agent, including, but not limiting to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosfamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, paradox breakers (such as PLX8394 or PLX7904), LGX818, BGB-283, pexidartinib (PLX3397) and vatalanib; a targeted signal transduction inhibitor including, but not limiting to bortezomib, geldanamycin, and rapamycin; a biological response modifier, including, but not limiting to, imiquimod, interferon-α, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus, INK28, AZD8055, PI3K inhibitors (e.g. BEZ235, GDC-0941, XL147, XL765, BMK120), cyclin dependent kinase (CDK) inhibitors (e.g., a CDK4 inhibitor or a CDK6 inhibitor, such as Palbociclib (PD-0332991), Ribocyclib (LEE011), Abemaciclib (LY2835219), P1446A-05, Abemaciclib (LY2835219), Trilaciclib (G1T28), etc.), AKT inhibitors, Hsp90 inhibitors (e.g. geldanamycin, radicicol, tanespimycin), farnesyltransferase inhibitors (e.g. tipifarnib), Aromatase inhibitors (anastrozole letrozole exemestane); an MEK inhibitor including, but are not limited to, AS703026, AZD6244 (Selumetinib), AZD8330, BIX 02188, CI-1040 (PD184352), GSK1120212 (also known as trametinib or JTP-74057), cobimetinib, PD0325901, PD318088, PD98059, RDEA119 (BAY 869766), TAK-733 and U0126-EtOH; tyrosine kinase inhibitors, including, but are not limited to, AEE788, AG-1478 (Tyrphostin AG-1478), AG-490, Apatinib (YN968D1), AV-412, AV-951 (Tivozanib), Axitinib, AZD8931, BIBF1120 (Vargatef), BIBW2992 (Afatinib), BMS794833, BMS-599626, Brivanib (BMS-540215), Brivanib alaninate (BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib (TAK 165), Neratinib (HKI-272), NVP-BHG712, OSI-420 (Desmethyl Erlotinib,CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, quizartinib, Cabozantinib, XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), DPP4 inhibitors (sitagliptin, vildagliptin, saxagliptin, dutogliptin, gemigliptin, alogliptin) or an EGFR inhibitor, including, but not limited to, AEE-788, AP-26113, BIBW-2992 (Tovok), CI-1033, GW-572016, Iressa, LY2874455, RO-5323441, Tarceva (Erlotinib, OSI-774), CUDC-101 and WZ4002.

In certain embodiments, the second chemotherapeutic agent is selected from afatinib, afuresertib, alectinib, alisertib, alvocidib, amsacrine, amonafide, amuvatinib, axitinib, azacitidine, azathioprine, bafetinib, barasertib, bendamustine, bleomycin, bosutinib, bortezomib, busulfan, cabozantinib, camptothecin, canertinib, capecitabine, cabazitaxel, carboplatin, carmustine, cenisertib, ceritinib, chlorambucil, cisplatin, cladribine, clofarabine, crenolanib, crizotinib, cyclophosphamide, cytarabine, dabrafenib, dacarbazine, dacomitinib, dactinomycin, danusertib, dasatinib, daunorubicin, decitabine, dinaciclib, docetaxel, dovitinib, doxorubicin, epirubicin, epitinib, eribulin mesylate, errlotinib, etirinotecan, etoposide, everolimus, exemestane, floxuridine, fludarabine, fluorouracil, gefitinib, gemcitabine, hydroxyurea, ibrutinib, icotinib, idarubicin, idelalisib, ifosfamide, imatinib, imetelstat, ipatasertib, irinotecan, ixabepilone, lapatinib, lenalidomide, lestaurtinib, lomustine, lucitanib, masitinib, mechlorethamine, melphalan, mercaptopurine, methotrexate, midostaurin, mitomycin, mitoxantrone, mubritinib, nelarabine, neratinib, nilotinib, nintedanib, omacetaxine mepesuccinate, olaparib, orantinib, oxaliplatin, paclitaxel, palbociclib, palifosfamide tris, pazopanib, pelitinib, pemetrexed, pentostatin, plicamycin, ponatinib, poziotinib, pralatrexate, procarbazine, quizartinib, raltitrexed, regorafenib, ruxolitinib, seliciclib, sorafenib, streptozocin, sulfatinib, sunitinib, tamoxifen, tandutinib, temozolomide, temsirolimus, teniposide, theliatinib, thioguanine, thiotepa, topotecan, uramustine, valrubicin, vandetanib, vemurafenib (Zelboraf), vincristine, vinblastine, vinorelbine, vindesine, and the like. In certain embodiments, the compounds herein are administered prior to, concurrently with, or subsequent to the treatment with the chemotherapeutic agent.

In certain embodiments, the method of treating a cancer comprises administering a therapeutically effective amount of a compound described herein and a therapeutically effective amount a biologic agent used to treat cancer. In certain embodiments, the biologic agent is selected from anti-BAFF (e.g., belimumab); anti-CCR4 (e.g., mogamulizumab); anti-CD19/CD3 (e.g., blinatumomab); anti-CD20 (e.g., obinutuzumab, rituximab, ibritumomab tiuxetan, ofatumumab, tositumomab); anti-CD22 (e.g., moxetumomab pasudotox); anti-CD30 (e.g., brentuximab vedotin); anti-CD33 (e.g., gemtuzumab); anti-CD37 (e.g., otlertuzumab); anti-CD38 (e.g., daratumumab); anti-CD52 (e.g., alemtuzumab); anti-CD56 (e.g., lorvotuzumab mertansine); anti-CD74 (e.g., milatuzumab); anti-CD105; anti-CD248 (TEM1) (e.g., ontuxizumab); anti-CTLA4 (e.g., tremelimumab, ipilimumab); anti-EGFL7 (e.g., parsatuzumab); anti-EGFR (HER1/ERBB1) (e.g., panitumumab, nimotuzumab, necitumumab, cetuximab, imgatuzumab, futuximab); anti-FZD7 (e.g., vantictumab); anti-HER2 (ERBB2/neu) (e.g., margetuximab, pertuzumab, ado-trastuzumab emtansine, trastuzumab); anti-HER3 (ERBB3); anti-HGF (e.g., rilotumumab, ficlatuzumab); anti-IGF-1R (e.g., ganitumab, figitumumab, cixutumumab, dalotuzumab); anti-IGF-2R; anti-KIR (e.g., lirilumab, onartuzumab); anti-MMP9; anti-PD-1 (e.g., nivolumab, pidilizumab, lambrolizumab); anti-PD-L1 (e.g. Atezolizumab); anti-PDGFRa (e.g., ramucirumab, tovetumab); anti-PD-L2; anti-PIGF (e.g., ziv-aflibercept); anti-RANKL (e.g., denosumab); anti-TNFRSF 9 (CD 137/4-1 BB) (e.g., urelumab); anti-TRAIL-RI/DR4,R2/D5 (e.g., dulanermin); anti-TRAIL-R1/D4 (e.g., mapatumumab); anti-TRAIL-R2/D5 (e.g., conatumumab, lexatumumab, apomab); anti-VEGFA (e.g., bevacizumab, ziv-aflibercept); anti-VEGFB (e.g., ziv-aflibercept); and anti-VEGFR2 (e.g., ramucirumab).

5. Formulations and Administration

In certain embodiments, the pharmaceutical compositions of the compounds can be formulated by standard techniques using one or more physiologically acceptable carriers or excipients. Suitable pharmaceutical carriers are described herein and in Remington: The Science and Practice of Pharmacy, 21$^{st}$ Ed. (2005). The therapeutic compounds and their physiologically acceptable salts, hydrates and solvates can be formulated for administration by any suitable route, including, among others, topically, nasally, orally, parenterally, rectally or by inhalation. In certain embodiments, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets, capsules, and solutions can be administered orally, rectally or vaginally.

For oral administration, a pharmaceutical composition can take the form of, for example, a tablet or a capsule prepared by conventional means with a pharmaceutically acceptable excipient. Tablets and capsules comprising the active ingredient can be prepared together with excipients such as: (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; (c) binders, e.g., magnesium aluminum silicate, starch paste, gelatin, tragacanth, methylcellulose, sodium carboxymethylcellulose, polyvinylpyrrolidone and/or hydroxypropyl methylcellulose; (d) disintegrants, e.g., starches (including potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners. The compositions are prepared according to conventional mixing, granulating or coating methods.

In certain embodiments, the carrier is a cyclodextrin, such as to enhance solubility and/or bioavailability of the compounds herein. In certain embodiments, the cyclodextrin for use in the pharmaceutical compositions can be selected from α-cyclodextrin, β-cyclodextrin, γ-cyclodextrin, derivatives thereof, and combinations thereof. In certain embodiments, the cyclodextrin is selected from β-cyclodextrin, γ-cyclodextrin, derivatives thereof, and combinations thereof.

In certain embodiments, the compounds can be formulated with a cyclodextrin or derivative thereof selected from carboxyalkyl cyclodextrin, hydroxyalkyl cyclodextrin, sulfoalkylether cyclodextrin, and an alkyl cyclodextrin. In various embodiments, the alkyl group in the cyclodextrin is methyl, ethyl, propyl, butyl, or pentyl.

When used in a formulation with the compound of the present disclosure, the cyclodextrin can be present at about 0.1 w/v to about 30% w/v, about 0.1 w/v to about 20% w/v, about 0.5% w/v to about 10% w/v, or about 1% w/v to about 5% w/v. In certain embodiments, the cyclodextrin is present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v or more.

Tablets may be either film coated or enteric coated according to methods known in the art. Liquid preparations for oral administration can take the form of, for example, solutions, syrups, or suspensions, or they can be presented as a dry product for reconstitution with water or other suitable vehicle before use. Such liquid preparations can be prepared by conventional means with pharmaceutically acceptable carriers and additives, for example, suspending agents, e.g., sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

The compounds can be formulated for parenteral administration, for example by bolus injection or continuous infusion. Formulations for injection can be presented in unit dosage form, for example, in ampoules or in multi-dose containers, with an optionally added preservative. Injectable compositions can be aqueous isotonic solutions or suspensions. In certain embodiments for parenteral administration, the compounds can be prepared with a surfactant, such as Cremaphor, or lipophilic solvents, such as triglycerides or liposomes. The compositions may be sterilized and/or contain adjuvants, such as preserving, stabilizing, wetting or emulsifying agents, solution promoters, salts for regulating the osmotic pressure and/or buffers. Alternatively, the compound can be in powder form for reconstitution with a suitable vehicle, for example, sterile pyrogen-free water, before use. In addition, they may also contain other therapeutically effective substances.

For administration by inhalation, the compound may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound with a carrier. Preferred carriers include absorbable pharmacologically acceptable solvents to assist passage through the skin of the subject. For example, transdermal devices are in the form of a bandage or patch comprising a backing member, a reservoir containing the compound optionally with carriers, optionally a rate controlling barrier to deliver the compound to the skin of the host at a controlled and predetermined rate over a prolonged period of time, and a means to secure the device to the skin. Matrix transdermal formulations may also be used.

Suitable formulations for topical application, e.g., to the skin and eyes, are preferably aqueous solutions, ointments, creams or gels well-known in the art. The formulations may contain solubilizers, stabilizers, tonicity enhancing agents, buffers and preservatives.

In certain embodiments, the compound can also be formulated as a rectal composition, for example, suppositories or retention enemas, for example, containing conventional suppository bases, for example, cocoa butter or other glycerides, or gel forming agents, such as carbomers.

In certain embodiments, the compound can be formulated as a depot preparation. Such long-acting formulations can be administered by implantation (for example, subcutaneously or intramuscularly) or by intramuscular injection. The compound can be formulated with suitable polymeric or hydrophobic materials (for example as an emulsion in an acceptable oil), ion exchange resins, biodegradable polymers, or as sparingly soluble derivatives, for example, as a sparingly soluble salt.

The pharmaceutical compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

6. Effective Amount and Dosing

In certain embodiments, a pharmaceutical composition of the compound is administered to a subject, preferably a human, at a therapeutically effective dose to prevent, treat, or control a condition or disease as described herein. The pharmaceutical composition is administered to a subject in an amount sufficient to elicit an effective therapeutic response in the subject. An effective therapeutic response is a response that at least partially arrests or slows the symptoms or complications of the condition or disease. An amount adequate to accomplish this is defined as "therapeutically effective dose" or "therapeutically effective amount." The dosage of compounds can take into consideration, among others, the species of warm-blooded animal (mammal), the body weight, age, condition being treated, the severity of the condition being treated, the form of administration, route of administration. The size of the dose also will be determined by the existence, nature, and extent of any adverse effects that accompany the administration of a particular therapeutic compound in a particular subject.

In certain embodiments, a suitable dosage of the compounds of the disclosure or a composition thereof is from about 1 ng/kg to about 1000 mg/kg, from 0.01 mg/kg to 900 mg/kg, 0.1 mg/kg to 800 mg/kg, from about 1 mg/kg to about 700 mg/kg, from about 2 mg/kg to about 500 mg/kg, from about 3 mg/kg to about 400 mg/kg, 4 mg/kg to about 300 mg/kg, or from about 5 mg/kg to about 200 mg/kg. In certain embodiments, the suitable dosages of the compound can be about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg. In certain embodiments, the dose of the compound can be administered once per day or divided into subdoses and administered in multiple doses, e.g., twice, three times, or four times per day.

In certain embodiments, the compounds can be administered with one or more of a second compound, sequentially or concurrently, either by the same route or by different routes of administration. When administered sequentially, the time between administrations is selected to benefit, among others, the therapeutic efficacy and/or safety of the combination treatment. In certain embodiments, the compounds herein can be administered first followed by a second compound, or alternatively, the second compound administered first followed by the compounds of the present disclosure. By way of example and not limitation, the time between administrations is about 1 hr, about 2 hr, about 4 hr, about 6 hr, about 12 hr, about 16 hr or about 20 hr. In certain embodiments, the time between administrations is about 1, about 2, about 3, about 4, about 5, about 6, or about 7 more days. In certain embodiments, the time between administrations is about 1 week, 2 weeks, 3 weeks, or 4 weeks or more. In certain embodiments, the time between administrations is about 1 month or 2 months or more.

When administered concurrently, the compound can be administered separately at the same time as the second compound, by the same or different routes, or administered in a single composition by the same route. In certain embodiments, the amount and frequency of administration of the second compound can used standard dosages and standard administration frequencies used for the particular compound. See, e.g., Physicians' Desk Reference, 70th Ed., PDR Network, 2015; incorporated herein by reference.

In certain embodiments where the compounds of the present disclosure is administered in combination with a second compound, the dose of the second compound is administered at a therapeutically effective dose. In certain embodiments, a suitable dose can be from about 1 ng/kg to about 1000 mg/kg, from about 0.01 mg/kg to about 900 mg/kg, from about 0.1 mg/kg to about 800 mg/kg, from about 1 mg/kg to about 700 mg/kg, from about 2 mg/kg to about 500 mg/kg, from about 3 mg/kg to about 400 mg/kg, from about 4 mg/kg to about 300 mg/kg, or from about 5 mg/kg to about 200 mg/kg. In certain embodiments, the suitable dosages of the second compound can be about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg. In certain embodiments, guidance for dosages of the second compound is provided in Physicians' Desk Reference, $70^{th}$ Ed, PDR Network (2015), incorporated herein by reference.

It to be understood that optimum dosages, toxicity, and therapeutic efficacy of such compounds may vary depending on the relative potency of individual compound and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. compounds or combinations thereof that exhibit large therapeutic indices are preferred. While certain agents that exhibit toxic side effects can be used, care should be used to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods disclosed herein, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

7. Methods of Preparation

The following examples are provided to further illustrate the methods of the present disclosure, and the compounds and compositions for use in the methods. The examples described are illustrative only and are not intended to limit the scope of the invention(s) in any way. The disclosures of all articles and references mentioned in this application, including patents, are incorporated herein by reference in their entirety.

The compounds of the present disclosure can be synthesized in view of the guidance provided herein, incorporating known chemical reactions and related procedures such as separation and purification. Representative methods and procedures for preparation of the compounds in this disclosure are described below and in the Examples. Acronyms are abbreviations are used per convention which can be found in literature and scientific journals.

In certain embodiments, provided is a process for preparing a compound of Formula I, or a tautomer, stereoisomer, mixture of stereoisomers, isotopically enriched analog, or salt thereof:

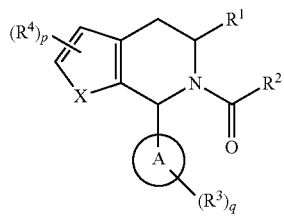

I wherein each of ring A, X, $R^1$, $R^2$, $R^3$, $R^4$, p, and q are independently as defined herein, comprising contacting a compound of Formula 1-5 with a compound of Formula 1-6:

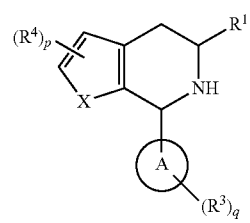

1-5

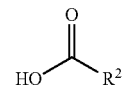

1-6 under reaction conditions sufficient to provide the compound of Formula I, or a tautomer, stereoisomer, mixture of stereoisomers, isotopically enriched analog, or salt thereof.

In certain embodiments, provided is a process for preparing a compound of Formula 1-5, or a tautomer, stereoisomer, mixture of stereoisomers, isotopically enriched analog, or salt thereof:

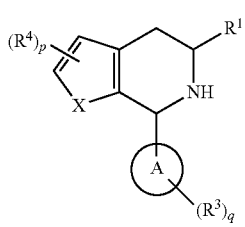

1-5 wherein each of ring A, X, $R^1$, $R^3$, $R^4$, p, and q are independently as defined herein, comprising cyclizing a compound of Formula 1-3:

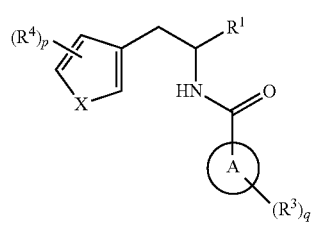

1-3 under reaction conditions sufficient to provide the compound of Formula 1-5, or a tautomer, stereoisomer, mixture of stereoisomers, isotopically enriched analog, or salt thereof.

It is understood that the starting materials and reaction conditions may be varied, the sequence of the reactions altered, and additional steps employed to produce compounds encompassed by the present disclosure, as demonstrated by the following examples. General references for known chemical reactions useful for synthesizing the disclosed compounds are available (see, e.g., Smith and March, March's Advanced Organic Chemistry: Reactions, Mechanisms, and Structure, Fifth Edition, Wiley Interscience, 2001; or Carey and Sundberg, Advanced Organic Chemistry, Part B. Reaction and Synthesis; Fifth Edition, Springer, 2007; or Li, J. J. Name Reactions, A Collection of Detailed Mechanisms and Synthetic Applications; Fifth Edition, Springer, 2014).

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

General Synthesis

In certain embodiments, compounds disclosed herein can be according to the general schemes shown below. For example, compounds of Formula I can be prepared according to the general syntheses outlined below in Scheme 1, where suitable reagents can be purchased form commercial sources or synthesized via known methods or methods adapted from the examples provided herein. In Scheme 1, each of ring A, X, $R^1$, $R^2$, $R^3$, $R^4$, p, and q are independently as defined herein.

Scheme 1

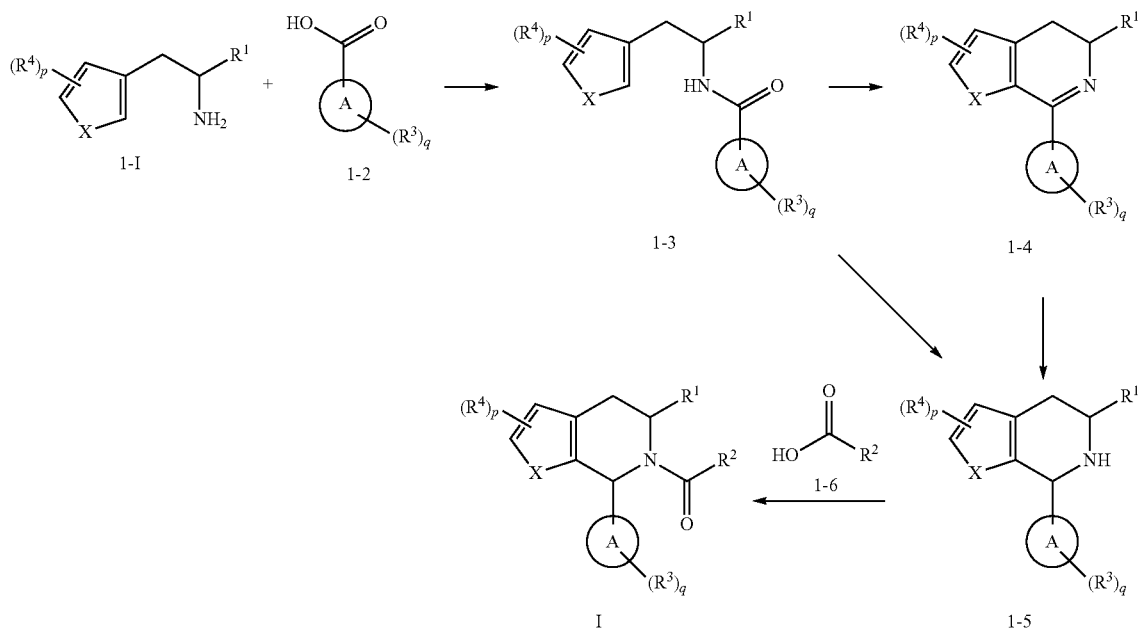

In Scheme 1, compound 1-3 can be provided by coupling amine 1-1 with acid 1-2 under standard amide bond forming reaction conditions. Cyclization of compound 1-3 to provide compound 1-5 can be achieved by first forming compound 1-4 followed by reduction using a hydride (e.g., $NaBH_4$, $LiAlH_4$, etc.). Alternatively, compound 1-5 can be provided directly from compound 1-3 under suitable conditions, such as an aprotic solvent in the presence of an acid catalyst. Compounds of Formula I can then be provided by coupling compound 1-5 with compound 1-6 under reaction conditions suitable to provide compounds of Formula I. Upon each reaction completion, each of the intermediate or final compounds can be recovered, and optionally purified, by conventional techniques such as neutralization, extraction, precipitation, chromatography, filtration and the like.

Appropriate starting materials and reagents for use in Scheme 1 can be purchased or prepared by methods known to one of skill in the art. As shown in Scheme 2, chiral or enantiomerically enriched starting materials can be provided for use in the method of Scheme 1 by converting a chiral or enantiomerically enriched amino alcohol to a oxathiazolidine dioxide 2-2. In Scheme 2, X, R¹, R⁴, and p are independently as defined herein, M is a metal halide (e.g., MgBr) and PG is a protecting group (e.g., Boc).

Scheme 2

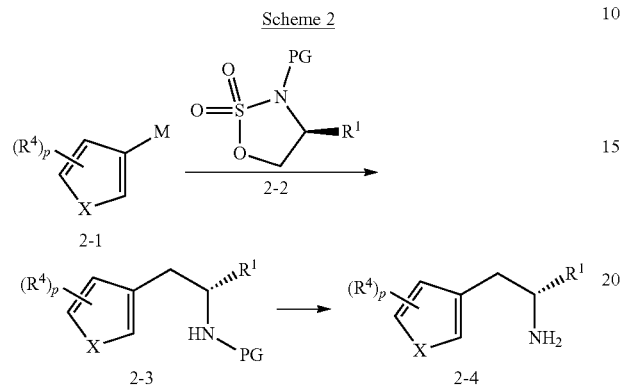

Referring to Scheme 2, compound 2-1 is coupled to compound 2-2 under standard coupling conditions to produce compound 2-3. The reaction is typically conducted in the presence of suitable catalyst (e.g., CuI) using suitable solvents/solvent mixtures. Deprotection of compound 2-3 provides compound 2-4. Upon reaction completion, each intermediate can be recovered by conventional techniques such as neutralization, extraction, precipitation, chromatography, filtration and the like.

In some embodiments of the methods of Scheme 1 and Scheme 2, the various substituents on the starting compound (e.g., compound I-1 and compound 1-2, (e.g., ring A, R¹, R², R³, etc.) are as defined for Formula I. However, it should also be appreciated that chemical derivatization and/or functional group interconversion, can be used to further modify of any of the compounds of Scheme 1 or Scheme 2 in order to provide the various compounds of Formula I.

Other compounds of the disclosure can be synthesized using the synthetic routes above and adapting chemical synthetic procedures available to the skilled artisan. Exemplary methods of synthesis are provided in the Examples. It is to be understood that each of the procedures describing synthesis of exemplary compounds are part of the specification, and thus incorporated herein into the Detailed Description of this disclosure.

SYNTHETIC EXAMPLES

Intermediate 1: Synthesis of Intermediate (S)-1-(3-methoxyphenyl)hexan-2-amine

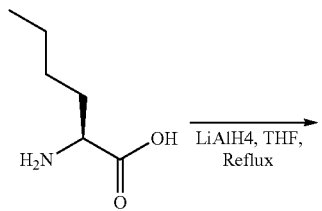

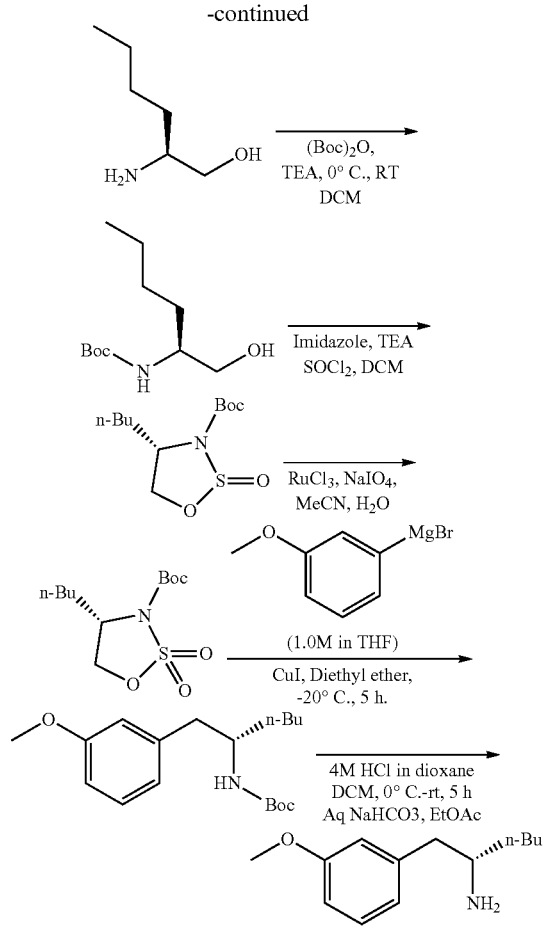

(S)-2-aminohexan-1-ol: To a solution of (S)-2-aminohexanoic acid (30.0 g, 228.6 mmol, 1 eq) in THF (300 mL) at 0° C. was added lithium aluminiumhydride (1M in THF, 458 mL, 457.3 mmol, 2 eq) over a period of 1 h. Reaction mixture was warm to room temperature, then the mixture was stirred at 70° C. for 14 h under N2 atmosphere. Reaction mixture was cooled to room temperature, the reaction was diluted with Diethyl ether (50 mL), after fisher-workup, reaction mixture was filtered through sintered funnel, using diethyl ether, filtrate was concentrated under reduced pressure to get the product, without further purification crude product was forward to next step. ¹H NMR (400 MHz, CDCl3) δ ppm 0.89 (s, 3H), 1.29-1.39 (m, 6H), 2.00 (s, 3H), 2.81 (s, 1H), 3.23-3.25 (m, 1H), 3.55-3.56 (m, 1H).

tert-butyl (S)-(1-hydroxyhexan-2-yl)carbamate: To a solution of (S)-2-aminohexan-1-ol (24.5 g, 209.06 mmol, 1 eq) in DCM (250 mL) was added TEA (58.76 mL, 418.12 mmol, 2 eq) at 0° C. drop wise, it was stirred for 5 mins, then di-tert-butyl dicarbonate (57.63 mL, 250.87 mmol, 1.2 eq). After stirring at room temperature for 14 h, diluted with water (30 mL), extracted with DCM (2×150 mL). Combined organic layer was washed with water, then with aq NaHCO₃ solution (~30 mL) and finally with brine solution (75 mL), dried over Na₂SO₄, and concentrated in-vacuo. The residue was subjected to Combiflash silica gel chromatography equipped MeOH in DCM as an eluent to give the tert-butyl (S)-(1-hydroxyhexan-2-yl)carbamate. ¹H NMR (400 MHz, CDCl3) δ ppm 0.90 (s, 3H), 1.25-1.33 (m, 6H), 1.38-1.41 (m, 9H), 3.48-3.55 (m, 1H), 3.62-3.68 (m, 2H), 4.57 (bs, 1H).

1H-imidazole (25 g, 368.1 mmol, 4 equiv) and triethlamine (39 mL, 276.1 mmol, 3 eq) were dissolved in anhydrous dichloromethane (200 mL, commercial dry solvent) at rt and the mixture was cooled to 0° C. (external temp, maintained with ice). Then thionyl chloride (7.3 mL, 101.2 mmol, 1.1 eq) was added slowly dropwise through an additional funnel over a period of ~30 minutes while maintaining the bath temperature at 0° C. The reaction mixture was then stirred for additional 10 mins at 0° C. Then the reaction mixture was cooled −78° C. Then a solution of tert-butyl (S)-(1-hydroxyhexan-2-yl)carbamate (20 g, 92.03 mmol, 1 eq) made in anhydrous dichloromethane (100 mL, commercial dry solvent) at rt was added through an additional funnel dropwise to the reaction mixture stirred at −78° C. over a period of 45 mins. The reaction mixture was stirred at −78° C. for additional 3 hours. Then the dry ice-acetone bath was removed and the reaction mixture was allowed to stir at room temperature for 16 h. After completion of the reaction (TLC, 10% EA in hexane) the mixture was diluted with DCM, washed with water (200 mL×3) and brine (200 mL). The organic phase was dried over anhydrous Na$_2$SO$_4$, filtered and concentrated under reduced pressure at rotavapor to obtain the crude product. The crude was purified by silica gel column chromatography using ethyl acetate in hexane as eluent. Product was eluted at 10-25% of EA in hexane to give the tert-butyl (4S)-4-butyl-1,2,3-oxathiazolidine-3-carboxylate 2-oxide. $^1$H NMR (400 MHz, CDCl3) δ ppm 0.91 (t, J=6.8 Hz, 3H), 1.27-1.38 (m, 4H), 1.52 (s, 9H), 1.67-1.73 (m, 1H), 1.99-2.10 (m, 1H), 3.97-4.02 (m, 1H), 4.70-4.78 (m, 2H).

tert-butyl (S)-4-butyl-1,2,3-oxathiazolidine-3-carboxylate 2,2-dioxide: This reaction was performed 20 g×2 batches. Ruthenium(III)chloride (0.463 g, 2.23 mmol, 0.014 eq), was added to a stirred solution of tert-butyl (4S)-4-butyl-1,2,3-oxathiazolidine-3-carboxylate 2-oxide (42.0 g, 159.48 mmol, 1 eq), in acetonitrile (400 mL) and water (200 mL) at 0° C., followed by portion wise addition of sodium metaperiodate (37.43 g, 175.43 mmol, 1.1 eq). The biphasic mixture was stirred at rt for 2 hours. Reaction mixture was filtered through sintered, washed with ethyl acetate. Water (250 mL) was added and the mixture was extracted in to ethyl acetate (2×150 mL). The combined organics were washed with water (150 mL), brine (150 mL), dried over with Na2SO4, filtered and concentrated under reduced pressure to obtain the crude product, which was purified by column chromatography using 10% ethylacetate in hexane as an eluent to give the tert-butyl (S)-4-butyl-1,2,3-oxathiazolidine-3-carboxylate 2,2-dioxide. $^1$H NMR (400 MHz, CDCl3) δ ppm 0.89-0.92 (m, 3H), 1.24-1.37 (m, 4H), 1.53 (s, 9H), 1.77-1.83 (m, 1H), 1.88-1.89 (m, 1H), 4.26-4.30 (m, 2H), 4.59-4.63 (m, 1H).

tert-butyl (S)-(1-(3-methoxyphenyl)hexan-2-yl)carbamate: To a solution of copper iodide (0.95 g, 5.017 mmol, 0.1 eq) in diethyl ether (150 mL) was added (3-methoxyphenyl)magnesium bromide (1M in THF) (98.5 mL, 100.35 mmol, 2 eq) drop wise over a period of 15 min at −20° C. (salt & Ice mixture bath). The reaction mixture stirred for 30 min at −20° C. (salt & Ice mixture bath). After this time, a solution of tert-butyl (S)-4-butyl-1,2,3-oxathiazolidine-3-carboxylate 2,2-dioxide (14 g, 50.172 mmol, 1 eq) in diethyl ether (100 mL) was added at −20° C. (salt & Ice mixture bath) drop wise over a period of 25 min to the reaction mass. The resulting mixture stirred for 4 h at −20° C. Finally, the reaction quenched with 10% aqueous citric acid solution (70 mL) at −20° C. (salt & Ice mixture bath). The mixture was allowed to warm to RT and stirred for 10 min. The mixture was filtered through celite pad, washed with ethyl acetate thoroughly. The filtrate was washed with water (100 mL), brine (100 mL), dried over anhydrous sodium sulfate, filtered and concentrated to give the crude product, which was purified by flash column chromatography using 15% ethyl acetate in n-hexane as an eluent to obtain tert-butyl (S)-(1-(3-methoxyphenyl)hexan-2-yl)carbamate. LCMS (ES) m/z=208.2 [M+H]$^+$ without boc mass observed. $^1$H NMR (400 MHz, CDCl3) δ ppm 0.86-0.87 (m, 3H), 1.25-1.28 (m, 6H), 1.40 (s, 9H), 2.73 (bs, 2H), 3.79 (s, 3H), 4.29 (bs, 1H), 6.71-6.76 (m, 3H), 7.17-7.21 (m, 1H), amide NH was not observed.

(S)-1-(3-methoxyphenyl)hexan-2-amine: To a solution of tert-butyl (S)-(1-(3-methoxyphenyl)hexan-2-yl)carbamate (12.0 g, 39.033 mmol, 1 eq) in dichloromethane (50 mL) was added 4M HCl in 1,4-dioxane (150 mL) slowly at 0° C. The mixture was allowed to stir at room temperature for 5 h. Progress of the reaction was monitored by TLC, after completion of reaction; the reaction mixture was concentrated under reduced pressure. The obtained crude was basified by saturated aqueous solution of NaHCO$_3$. The compound was extracted with EtOAc (3×200 mL). Organic layer was washed with brine (100 mL), dried over anhydrous sodium sulfate, filtered and concentrated to get (S)-1-(3-methoxyphenyl)hexan-2-amine. LCMS (ES) m/z=208.1 [M+H]$^+$ Procedure 1: Synthesis of Compound 1

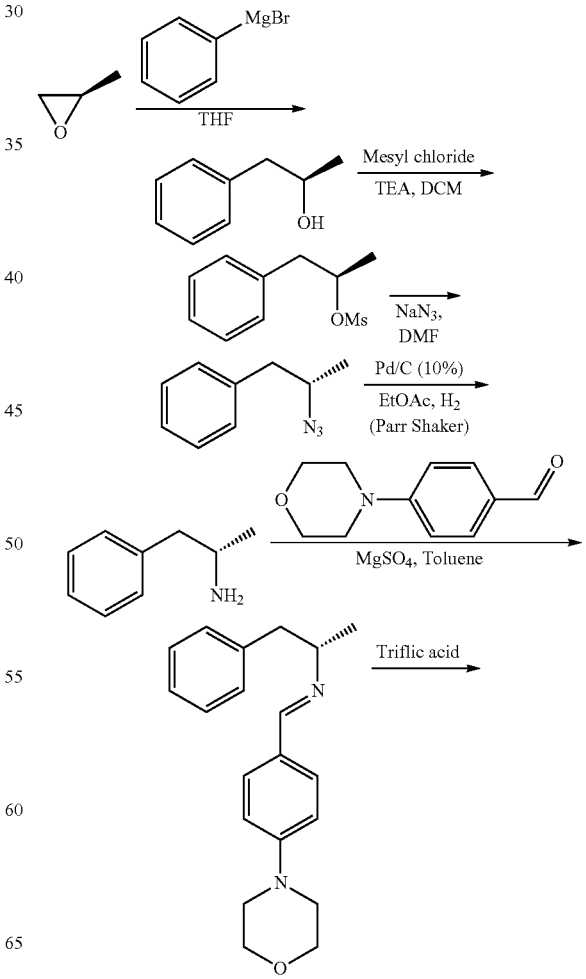

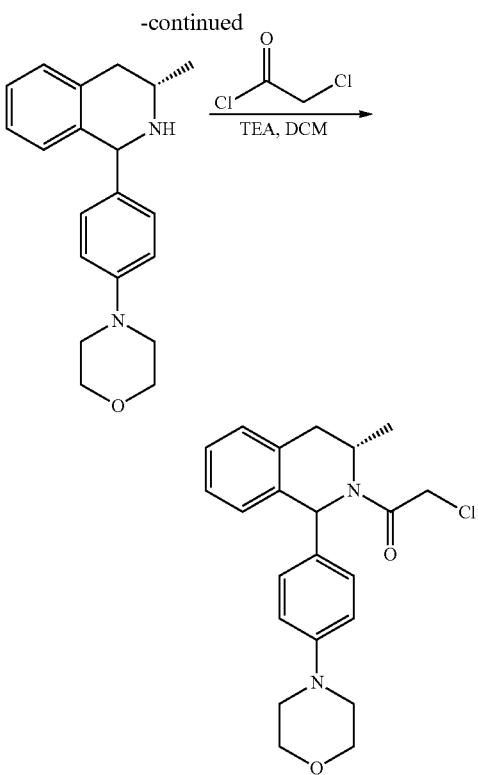

To a stirred mixture of (R)-2-methyloxirane (10 g, 172 mmol, 1 eq) in dry tetrahydrofuran (100 mL) was added phenyl magnesium bromide (3M in diethyl ether) (63 mL, 183 mmol, 1.1 eq) at −10° C. under nitrogen atmosphere. The resulting mixture was allowed to warm to room temperature gradually and stirred for 16 h. The progress of the reaction was monitored by TLC (15% Ethyl acetate in hexane). The reaction mixture was quenched with saturated ammonium chloride solution. The crude product was extracted with ethyl acetate (3×300 mL), the combined organics were washed with water (200 mL), brine (100 mL), dried over anhydrous sodium sulfate, filtered and concentrated under reduced pressure to provide the crude product, which was purified by flash column chromatography using 15% of ethyl acetate in hexane as eluent to obtain (R)-1-phenylpropan-2-ol. $^1$H NMR (400 MHz, CDCl$_3$) δ ppm 1.23 (d, J=2.0 Hz, 3H), 1.48 (s, 1H), 2.66-2.71 (m, 1H), 2.77-2.80 (m, 1H), 4.02 (bs, 1H), 7.21-7.31 (m, 5H).

To a stirred mixture of (R)-1-phenylpropan-2-ol (0.5 g, 3.671 mmol, 1 eq) and triethyl amine (1.54 mL, 11 mmol, 3 eq) in dichloromethane (10 mL) was added methane sulfonyl chloride (0.42 mL, 5.5 mmol, 1.5 eq) at 0° C. under nitrogen atmosphere. The resulting mixture was allowed to warm to room temperature gradually and stirred for 2 h. The progress of the reaction was monitored by TLC (50% dichloromethane in hexane). The reaction mixture was quenched with water. The crude product was extracted with dichloromethane (3×30 mL), the combined organics were washed with water (50 mL), brine (20 mL), dried over anhydrous Na$_2$SO$_4$, concentrated under reduced pressure to provide crude product (R)-1-phenylpropan-2-yl methanesulfonate, which was taken as such without purification to next step. 1H NMR (400 MHz, CDCl$_3$) δ ppm 1.47 (d, J=6.4 Hz, 3H), 2.51 (s, 3H), 2.89-2.99 (m, 2H), 4.85-4.95 (m, 1H), 7.16-7.40 (m, 5H).

To a stirred solution of (R)-1-phenylpropan-2-yl methanesulfonate (0.5 g crude, 2 mmol, 1 eq) in N,N-dimethyl formamide (10 mL) was added sodium azide (0.18 g, 2.80 mmol, 1.2 eq) at room temperature under nitrogen atmosphere. The resulting mixture was heated to 80° C. and stirred for 16 h. The progress of the reaction was monitored by TLC (5% ethyl acetate in hexane). After completion of reaction, the reaction mixture was allowed to cool to room temperature and quenched with water. The mixture was extracted with ethyl acetate (3×30 mL), the combined organics were washed with water (4×30 mL), brine (20 mL), dried over anhydrous Na$_2$SO$_4$, concentrated under reduced pressure to crude product, which was purified by flash column chromatography using 5% of ethyl acetate in hexane as eluent to obtain (S)-(2-azidopropyl)benzene. $^1$H NMR (400 MHz, CDCl$_3$) δ ppm 1.29 (d, J=6.8 Hz, 3H), 2.69-2.74 (m, 1H), 2.81-2.86 (m, 1H), 3.66-3.72 (m, 1H), 7.18-7.32 (m, 5H).

To a stirred solution of (S)-(2-azidopropyl)benzene (0.24 g, 1.5 mmol, 1 eq) in ethyl acetate (10 mL) was added Palladium, (10% on activated carbon powder, 50% water wet) (0.05 g) at room temperature under nitrogen atmosphere. The resulting mixture was subjected to hydrogenation by using hydrogen pressure (balloon, if large scale parr apparatus is suitable) stirred for 8 h. The progress of the reaction was monitored by TLC (10% ethyl acetate in hexane). After completion of reaction, the reaction mixture was filtered through celite pad, washed the celite pad with ethyl acetate, the filtrated was concentrated under reduced pressure to obtain (S)-1-phenylpropan-2-amine. $^1$H NMR (400 MHz, CDCl$_3$) δ ppm 1.12 (d, J=6.8 Hz, 3H), 2.49-2.59 (m, 1H), 2.68-2.77 (m, 1H), 3.12-3.20 (m, 1H), 4.68 (s, 2H), 7.09-7.31 (m, 5H).

To a solution of (S)-1-phenylpropan-2-amine (0.2 g, 1.5 mmol, 1 eq) and 4-morpholinobenzaldehyde (0.28 g, 1.5 mmol, 1 eq) in toluene (10 mL) was added MgSO$_4$ anhydrous (0.2 g) at room temperature. The reaction mixture was stirred at 110° C. for 4 h. TLC (70% ethyl acetate in hexane) showed the reaction was completed. The solid portion was removed from reaction mixture by filtration and filtrate was concentrated under reduced pressure. The obtained crude (S)-1-(4-morpholinophenyl)—N—(1-phenylpropan-2-yl) methanimine was carried to next step without further purification.

To a solution of (S)-1-(4-morpholinophenyl)—N—(1-phenylpropan-2-yl)methanimine (0.5 g crude) in triflic acid (0.5 mL) was stirred at 130° C. for 24 h. TLC 5% (methanol in dichloromethane) showed the reaction was completed. The reaction was cooled to room temperature and was diluted with ice cold water (5 mL), and then basified with 10% aqueous sodium hydroxide solution up to pH=12. The product was extracted in to ethyl acetate (30 mL), the organic layer dried over anhydrous sodium sulfate, filtered and concentrated under reduced pressure to obtain the crude product. The obtained crude product was purified by flash chromatography using 5% methanol in dichloromethane as an eluent. The isolated product was re-purified by preparative HPLC [Analytical conditions: Column: Inertsil ODS 3V (250 mm×4.6 mm×5 μm), mobile phase (A): 0.1% ammonia in water, mobile phase (B): CH$_3$CN, flow rate: 1.0 mL/min, composition of B: 0/10, 12/80, 25/90, 27/10, 30/10] to obtain 4-(4-((3S)-3-methyl-1,2,3,4-tetrahydroisoquinolin-1-yl)phenyl)morpholine. LCMS (ES) m/z=309.2 [M+H]+; 1H NMR (400 MHz, CDCl3): δ ppm 1.24 (d, J=4.4 Hz, 3H), 2.69-2.81 (m, 2H), 3.14-3.20 (m, 5H), 3.85 (bs, 4H), 5.05 (s, 1H), 6.69 (d, J=8.0 Hz, 1H), 6.87 (d, J=6.8 Hz, 2H), 6.99 (s, 1H), 7.09 (s, 2H), 7.21-7.25 (m, 2H).

To a solution of 4-(4-((3S)-3-methyl-1,2,3,4-tetrahydroisoquinolin-1-yl)phenyl)morpholine (0.04 g, 0.129 mmol, 1 eq) in chloroform (5 mL) was added sodium bicarbonate (0.021 g, 0.259 mmol, 2.0 eq) at 0° C., followed by 2-chloroacetyl chloride (0.015 mL, 0.194 mmol, 1.5 eq). The mixture was allowed to warm to room temperature and stirred for 3 h under $N_2$ atmosphere. TLC (40% ethyl acetate in hexane) showed the reaction was completed. Then the reaction was diluted with dichloromethane (20 mL) and washed with water (20 mL), brine (20 mL), dried over anhydrous $Na_2SO_4$, filtered and concentrated under reduced pressure to obtain the crude product. The crude product was purified by flash column chromatography using 50% EtOAc in n-hexane as mobile phase to obtain 2-chloro-1-((3S)-3-methyl-1-(4-morpholinophenyl)-3,4-dihydroisoquinolin-2 (1H)-yl)ethan-1-one. LCMS (ES) m/z=385.3 [M+H]+; 1H NMR (400 MHz, CDCl3): δ ppm 1.25 (bs, 3H), 2.3-2.5 (m, 1H), 2.75-2.95 (m, 1H), 3.14 (bs, 4H), 3.85 (bs, 4H), 4.16-4.26 (m, 3H), 5.97 (bs, 1H), 6.83 (bs, 2H), 7.07 (bs, 2H), 7.19-7.25 (m, 4H). chiral HPLC purity: 48.93 (trans): 47.12% (cis).

Procedure 2: Synthesis of Compounds 2 and 3

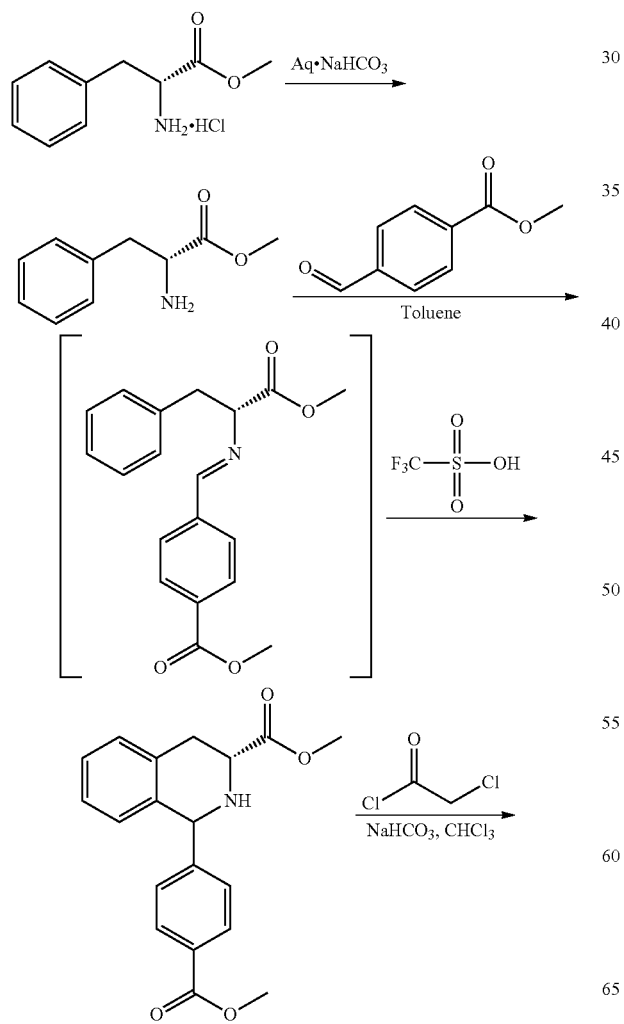

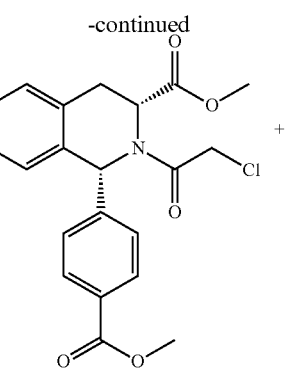

+

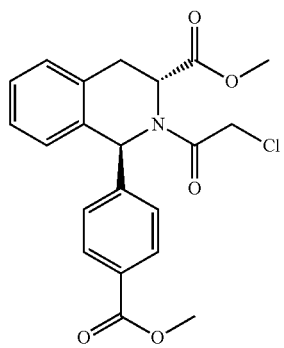

methyl D-phenylalaninate hydrochloride (0.3 g, 1.391 mmol, 1 eq) was portioned between ethyl acetate and sodium bicarbonate solution and stirred for 15 min, the ethyl acetate layer was separated and the aqueous layer was extracted with ethyl acetate (2×50 mL). The combined ethyl acetate fractions were washed with water (50 mL), brine (50 mL), dried over anhydrous sodium sulfate, and concentrated under reduced pressure to obtain methyl D-phenylalaninate. LCMS (ES) m/z=180.1 [M+H]+; 1H NMR (400 MHz, CDCl3) δ ppm, 2.83-2.88 (m, 1H), 3.07-3.11 (m, 1H), 3.71-3.75 (m, 4H), 7.18-7.32 (m, 5H).

To a solution of methyl D-phenylalaninate (0.1 g, 0.557 mmol, 1 eq) in toluene (10 mL) was added methyl 4-formylbenzoate (0.0.09 g, 0.557 mmol, 1 eq). The reaction mixture was heated to 120° C. and stirred for 1 h. The mixture was concentrated under reduced pressure to obtain methyl (R,E)-4-(((1-methoxy-1-oxo-3-phenylpropan-2-yl) imino)methyl)benzoate and the obtained crude product was carried to next step without any further purification.

methyl (R,E)-4-(((1-methoxy-1-oxo-3-phenylpropan-2-yl)imino)methyl)benzoate (0.3 g crude) was mixed with triflic acid (2 mL) and the mixture was heated to 130° C. and stirred for 18 h and the mixture was analyzed by LCMS (LCMS showed hydrolyzed product (3R)-1-(4-carboxyphenyl)-1,2,3,4-tetrahydroisoquinoline-3-carboxylic acid). The mixture was cooled to 0° C. and 10 mL of anhydrous methanol was added. The resulting mixture was heated to 80° C. and stirred for 2 h. The mixture was cooled to 0° C. and neutralized with triethylamine and concentrated under reduced pressure. The obtained crude was dissolved with ethyl acetate, washed with water (3×20 mL), brine (20 mL), dried over anhydrous sodium sulfate, filtered and concentrated under reduced pressure. The crude product was purified by flash chromatography using 20% ethyl acetate in hexane as the eluent to provide methyl (3R)-1-(4-(methoxycarbonyl)phenyl)-1,2,3,4-tetrahydroisoquinoline-3-carboxylate. LCMS (ES) m/z=326.2 [M+H]$^+$.

To a stirred mixture of methyl (3R)-1-(4-(methoxycarbonyl)phenyl)-1,2,3,4-tetrahydroisoquinoline-3-carboxylate (0.12 g, 0.368 mmol, 1 eq) and sodium bicarbonate (0.06 g, 0.737 mmol, 2 eq) in chloroform (5 mL), was added 2-chloroacetyl chloride (0.044 mL, 0.553 mmol, 1.5 eq) at 0° C. under nitrogen atmosphere. The resulting mixture was allowed to warm to room temperature and stirred for 2 h. The progress of the reaction was monitored by TLC (20% ethyl acetate in hexane). After completion of reaction, the mixture was diluted with dichloromethane (50 mL), washed with water (2×20 mL), dried over anhydrous sodium sulfate, filtered and concentrated under reduced pressure to obtain the crude product. The crude product was purified by preparative HPLC [Analytical Conditions:—Column: Inertsil ODS 3V (250 mm×4.6 mm×5 μm), mobile phase (A): 0.1% ammonia in water, mobile phase (B): CH$_3$CN, flow rate: 1.0 mL/min, composition of B: 0/20, 12/80, 25/90, 27/20, 30/20] to obtain methyl (1S,3R)-2-(2-chloroacetyl)-1-(4-(methoxycarbonyl)phenyl)-1,2,3,4-tetrahydroisoquinoline-3-carboxylate (3). In TLC, polar spot compared to corresponding to the other isomer. LCMS (ES) m/z=402 [M+H]+; 1H NMR (400 MHz, DMSO-d6) δ ppm 3.04-3.15 (m, 1H), 3.30 (m, 1H), 3.46 (m, 3H), 3.78-3.79 (s, 3H), 3.98, 4.30 (m, 0.5H, 0.5H), 4.67-4.73 (m, 1H), 5.21, 5.37 (m, 0.5H, 0.5H), 6.28, 6.52 (s, 0.5H, 0.5H), 7.11-7.21 (m, 3H), 7.51-7.60 (m, 3H), 7.88-7.89 (m, 2H). Chiral HPLC purity with 2 peaks with 61.1% & 36.7%;

and methyl (1R,3R)-2-(2-chloroacetyl)-1-(4-(methoxycarbonyl)phenyl)-1,2,3,4-tetrahydroisoquinoline-3-carboxylate (2). In TLC, non-polar spot compared to corresponding to the other isomer. LCMS (ES) m/z=402 [M+H]+; 1H NMR (400 MHz, DMSO-d6) δ ppm 2.98-3.02 (m, 0.5H), 3.07-3.12 (m, 1H), 3.21-3.22 (m, 0.5H), 3.27 (s, 1H), 3.66 (s, 2H), 3.80 (s, 3H), 4.22-4.26 (m, 1H), 4.31-4.40 (m, 1H), 4.65-4.75, 5.02 (m, 1H), 6.42, 6.77 (m, 0.8H, 0.3H), 7.11-7.38 (m, 4H), 7.63 (d, J=7.2 Hz, 2H), 7.83-7.89 (m, 2H). Chiral HPLC purity with 2 peaks with 74.37% & 25.6%.

Procedure 3: Synthesis of Compounds 4 and 5

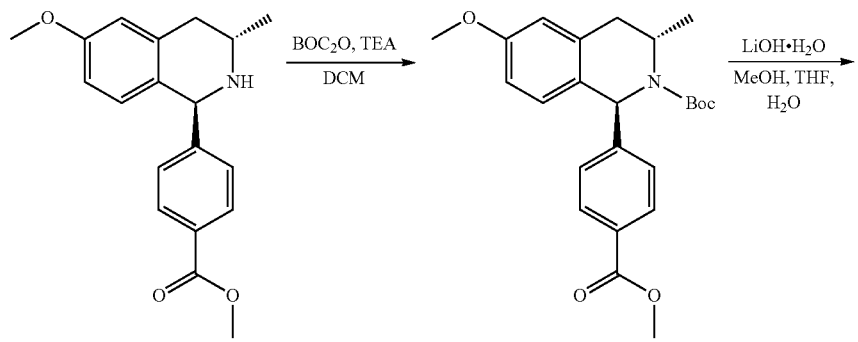

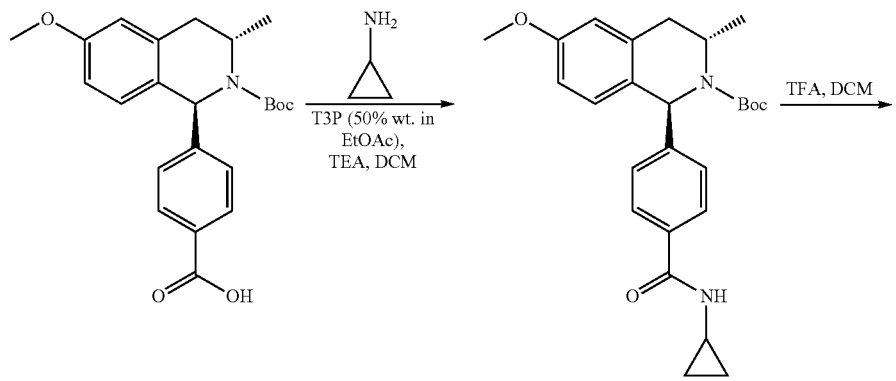

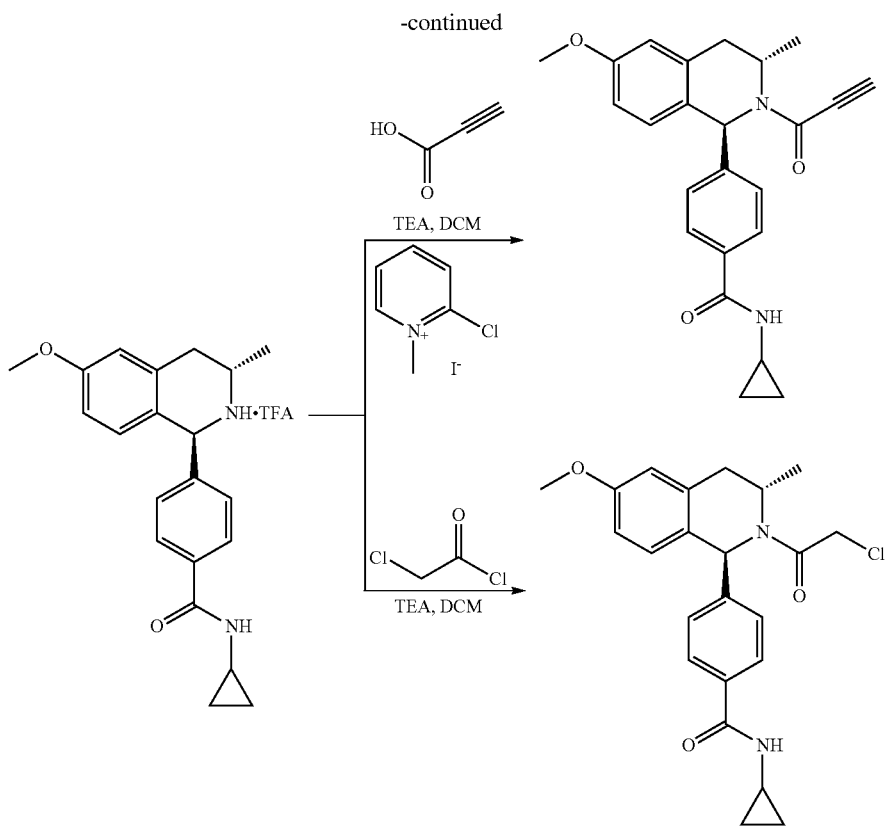

To a solution of compound methyl 4-((1S,3S)-6-methoxy-3-methyl-1,2,3,4-tetrahydroisoquinolin-1-yl)benzoate (0.35 g, 1.12 mmol, 1.0 eq) in DCM (10 mL) was added triethylamine (0.45 g, 4.49 mmol, 4.0 eq) and di-tert-butyl dicarbonate (0.715 g, 2.24 mmol, 2.0 eq) at room temperature and the mixture was stirred for 16 h. TLC (50% EtOAc in hexane) showed the reaction was completed. The reaction mixture was concentrated under reduced pressure, and the crude was diluted with EtOAc (50 mL), washed with water (2×50 mL). The organic layer was dried over anhydrous $Na_2SO_4$, concentrated under reduced pressure to crude product tert-butyl (1S,3S)-6-methoxy-1-(4-(methoxycarbonyl)phenyl)-3-methyl-3,4-dihydroisoquinoline-2(1H)-carboxylate. LC-MS (m/z): 356.0 [M-$^t$Bu+H]$^+$.

To a solution of compound tert-butyl (1S,3S)-6-methoxy-1-(4-(methoxycarbonyl)phenyl)-3-methyl-3,4-dihydroisoquinoline-2(1H)-carboxylate (0.650 g, 1.57 mmol, 1.0 eq) in a mixture of THF:MeOH:$H_2O$ (9 mL: 1 mL) were added lithium hydroxide (0.331 g, 7.89 mmol, 5.0 eq) and allowed to stirrer at room temperature for 16 h. TLC (50% EtOAc in hexane) showed the reaction was completed. The reaction mixture was concentrated under reduced pressure, and the crude was acidified with 5% citric acid solution (pH=9). Reaction mixture was diluted with EtOAc (50 mL) and the organic layer was separated and dried over anhydrous $Na_2SO_4$, concentrated under reduced pressure to give crude 4-((1S,3S)-2-(tert-butoxycarbonyl)-6-methoxy-3-methyl-1,2,3,4-tetrahydroisoquinolin-1-yl)benzoic acid. LC-MS (m/z): 396.0 [M+H]$^+$.

To a solution of compound 4-((1S,3S)-2-(tert-butoxycarbonyl)-6-methoxy-3-methyl-1,2,3,4-tetrahydroisoquinolin-1-yl)benzoic acid (0.38 g, 0.957 mmol, 1.0 eq) in DCM (10 mL) was added triethylamine (0.4 mL, 2.87 mmol, 3.0 eq) and cyclopropanamine (0.65 g, 1.14 mmol, 1.2 eq) at 0° C. and the mixture was stirred for 15 min. To the above reaction mixture T3P (50% wt in EtOAc) (1.4 mL, 1.97 mmol, 1.2 eq) was added at the same temperature and stirred for 16 h. TLC (50% EtOAc in hexane) showed the reaction was completed. The reaction mixture was concentrated under reduced pressure, and the crude was diluted with EtOAc (50 mL), washed with water (2×50 mL). The organic layer was dried over anhydrous $Na_2SO_4$, and concentrated under reduced pressure to give crude tert-butyl (1S,3S)-1-(4-(cyclopropylcarbamoyl)phenyl)-6-methoxy-3-methyl-3,4-dihydroisoquinoline-2(1H)-carboxylate. LC-MS (m/z): 381.0 [M-$^t$Bu+H]$^+$.

To a solution of compound tert-butyl (1S,3S)-1-(4-(cyclopropylcarbamoyl)phenyl)-6-methoxy-3-methyl-3,4-dihydroisoquinoline-2(1H)-carboxylate (0.27 g, 0.61 mmol, 1.0 eq) in DCM (10 mL) was added trifluoroacetic acid (0.084 g, 0.74 mmol, 1.2 eq) at 0° C. and the mixture was stirred for 2 h. TLC (50% EtOAc in hexane) showed the reaction was completed. The reaction mixture was concentrated under reduced pressure to give crude N-cyclopropyl-4-((1S,3S)-6-methoxy-3-methyl-2-(2,2,2-trifluoroacetyl)-1,2,3,4-tetrahydro-2$\lambda^4$-isoquinolin-1-yl)benzamide. LC-MS (m/z): 337.0 [M+H]$^+$.

To a solution of N-cyclopropyl-4-((1S,3S)-6-methoxy-3-methyl-2-(2,2,2-trifluoroacetyl)-1,2,3,4-tetrahydro-2$\lambda^4$-isoquinolin-1-yl)benzamide (0.2 g, 0.59 mmol, 1.0 eq) in DCM (8.0 mL) was added TEA (0.12 g, 1.18 mmol, 2.0 eq) at 0° C., stirred for 15 mins and then and 2-chloroacetyl chloride (0.08 g, 0.71 mmol, 1.2 eq) was added at 0° C. The mixture was allowed to stir at room temperature for 1 hr. LCMS and TLC (50% EtOAc in hexane) showed the reaction was completed. The reaction mixture was diluted with saturated NaHCO₃ solution (10 mL) and was extracted with DCM (2×50 mL). The organic layers were dried over Na₂SO₄ and concentrated to give the crude product. The crude product was purified by flash column chromatography using 15% EtOAc/hexane as an eluent followed by preparative TLC with 30% EtOAc in hexane as eluent to give 4-((1S,3S)-2-(2-chloroacetyl)-6-methoxy-3-methyl-1,2,3,4-tetrahydroisoquinolin-1-yl)—N-cyclopropylbenzamide. LC-MS (m/z): 413.3 [M+H]⁺, ¹H NMR (400 MHz, DMSO-d₆): δ 0.49-0.52 (m, 2H), 0.52-0.64 (m, 2H), 0.66 (bs, 3H), 2.65-2.66 (m, 1H), 2.77-2.81 (m, 1H), 3.71 (s, 3H), 4.37-4.74 (bs, 3H), 6.13 (s, 1H), 6.74-6.75 (m, 1H), 6.79-6.81 (m, 1H), 7.320-7.302 (m, 2H), 7.48 (d, J=8.4 Hz, 1H), 7.64 (s, 2H), 8.13 (s, 1H).

The reaction mixture was diluted with water (10 mL) and organic layer was separated, dried over Na₂SO₄ and concentrated under reduced pressure to give the crude product. The crude product was purified by preparative TLC with 70% EtOAc in hexane as an eluent to give N-cyclopropyl-4-((1S,3S)-6-methoxy-3-methyl-2-propioloyl-1,2,3,4-tetrahydroisoquinolin-1-yl)benzamide. LC-MS (m/z): 389.0 [M+H]⁺, ¹H NMR (400 MHz, DMSO-d₆): δ 0.49-0.51 (m, 2H), 0.52-0.65 (m, 2H), 0.66 (bs, 3H), 2.65-2.66 (m, 1H), 2.78-2.82 (m, 1H), 3.71 (s, 3H), 4.37-4.74 (bs, 3H), 6.13 (s, 1H), 6.75-6.78 (m, 1H), 6.79-6.81 (m, 1H), 7.32-7.30 (m, 2H), 7.48 (d, J=8.4 Hz, 1H), 7.64 (s, 2H), 8.13 (s, 1H).

Procedure 4: Synthesis of Compounds 6 and 7

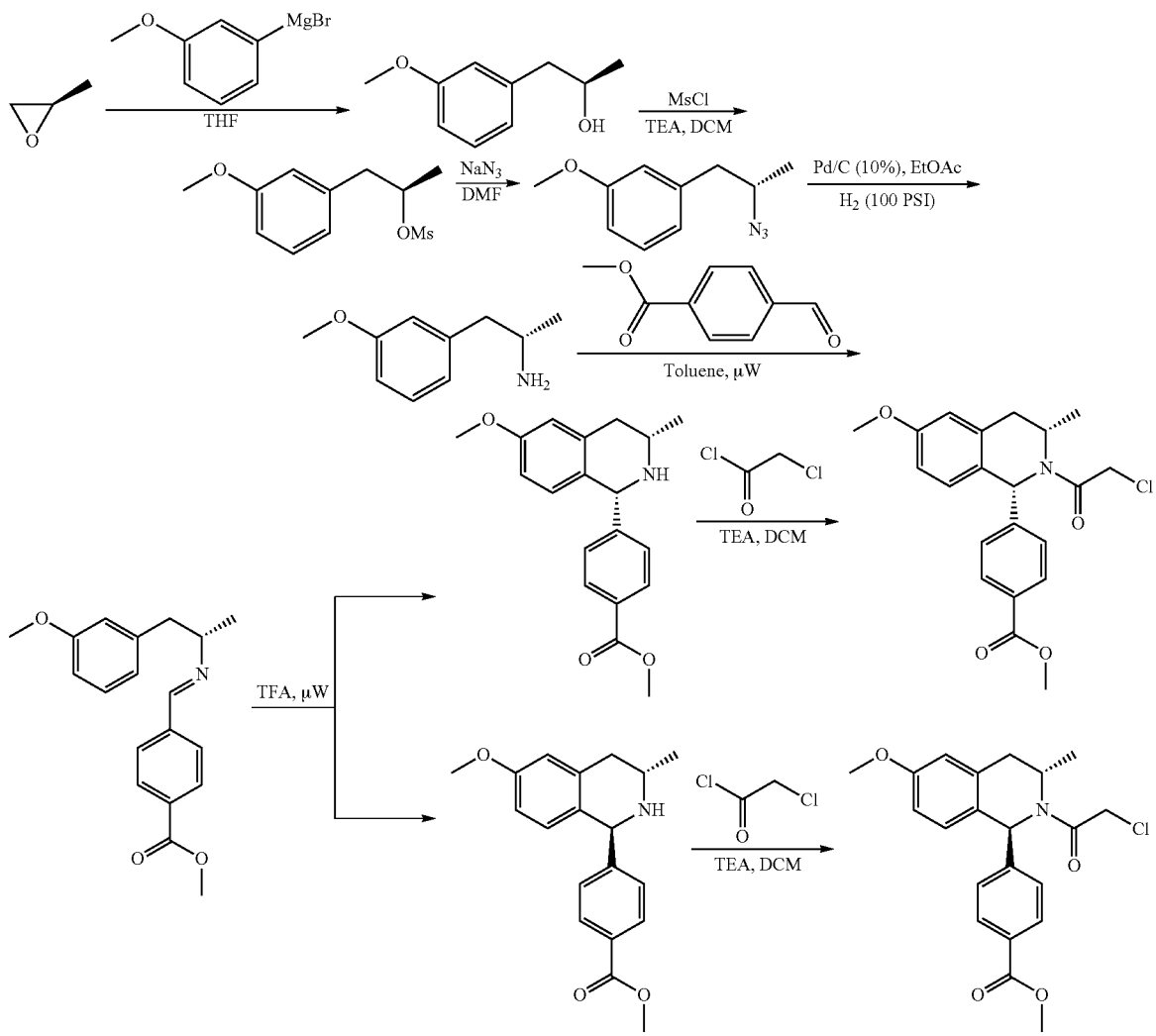

To a solution of N-cyclopropyl-4-((1S,3S)-6-methoxy-3-methyl-2-(2,2,2-trifluoroacetyl)-1,2,3,4-tetrahydro-2λ⁴-isoquinolin-1-yl)benzamide (0.2 g, 0.59 mmol, 1.0 eq) in DCM (10.0 mL) was added triethylamine (0.162 g, 1.42 mmol, 2.4 eq) and propiolic acid (0.041 mL, 0.59 mmol, 1.0 eq) and stirred for 15 minutes. To the above reaction mixture 2-chloro-1-methylpyridin-1-iumiodide (0.182 g, 0.71 mmol, 1.2 eq) was added and stirred for 16 hours. LCMS and TLC (5% MeOH in DCM) showed the reaction was completed.

To a solution of (R)-2-methyloxirane (3.0 g, 51.72 mmol, 1.0 eq) in THF (30 mL) was added (3-methoxyphenyl) magnesium bromide (62 mL, 62.06 mmol, 1.2 eq) drop wise at 0° C. The reaction mixture was stirred at room temperature for 6 hours. After this time, the reaction mixture was quenched with aqueous ammonium chloride solution (10 mL) and product was extracted in to ethyl acetate (100 mL). The organic layer was washed with water (2×20 mL), brine (15 mL), dried over anhydrous MgSO₄, filtered and concentrated under reduced pressure to obtain the crude product which was purified by silica gel flash column chromatography (n-hexane/EtOAc=8:1, $R_f$=0.24) to give (R)-1-(3-methoxyphenyl)propan-2-ol. $^1$H NMR (400 MHz, DMSO-$d_6$) δ ppm 1.00 (d, J=6.4 Hz, 3H), 2.49-2.51 (m, 1H), 2.61-2.66 (m, 1H), 3.70 (s, 3H), 3.76-3.81 (m, 1H), 4.51 (d, J=4.8 Hz, 1H), 6.71-6.74 (m, 3H), 7.14 (t, J=7.8 Hz, 1H).

To a solution of (R)-1-(3-methoxyphenyl)propan-2-ol (2.8 g, 16.86 mmol, 1.0 eq) in DCM (30 mL) was added triethyl amine (5.1 g, 50.58 mmol, 3.0 eq) at 0° C., followed by mesylchloride (2.8 g, 25.30 mmol, 1.5 eq). The mixture was stirred at 0° C. for 1.0 h under a $N_2$ atmosphere. TLC (30% EtOAc in n-hexane) showed the reaction was completed. The reaction was diluted with saturated aqueous solution of $NaHCO_3$ (15 mL) and was extracted with DCM (50 mL). The organic layer was dried over anhydrous $Na_2SO_4$, filtered and concentrated under reduced pressure to give (R)-1-(3-methoxyphenyl)propan-2-ylmethanesulfonate. $^1$H NMR (400 MHz, $CDCl_3$) δ ppm 1.47 (d, J=6.0 Hz, 3H), 2.56 (s, 3H), 2.84-2.89 (m, 1H), 2.93-2.99 (m, 1H), 3.79 (s, 3H), 4.87-4.92 (m, 1H), 6.77-6.82 (m, 3H), 7.21-7.23 (m, 1H).

To a solution of (R)-1-(3-methoxyphenyl)propan-2-yl-methanesulfonate (3.8 g, 15.57 mmol, 1.0 eq) in DMF (38 mL) was added sodium azide (1.2 g, 18.68 mmol, 1.2 eq) at room temperature. The mixture was stirred at 80° C. for 16 h. TLC (5% EtOAc in n-hexane) showed the reaction was completed. The reaction was diluted with water (15 mL) and EtOAc (50 mL), the organic layer was separated, washed with water (5×25 mL), brine (10 mL), dried over anhydrous $MgSO_4$, filtered and concentrated under reduced pressure to provide the crude product. The crude product was purified by silica gel flash column chromatography (n-hexane/EtOAc=9.7:0.2, $R_f$=0.6) to give (S)-1-(2-azidopropyl)-3-methoxybenzene. $^1$H NMR (400 MHz, $CDCl_3$) δ ppm 1.26 (d, J=6.0 Hz, 3H), 2.66-2.71 (m, 1H), 2.78-2.83 (m, 1H), 3.62-3.71 (m, 1H), 3.80 (s, 3H), 6.74-6.79 (m, 3H), 7.20-7.22 (m, 1H).

To a solution of (S)-1-(2-azidopropyl)-3-methoxybenzene (2.37 g, 12.40 mmol, 1.0 eq) in ethyl acetate (23 mL) was added Pd/C (150 mg of 10 percent Pd) at room temperature. The resulting reaction mixture was hydrogenated at 100 PSI in parr shaker at room temperature for 20 h. After this time, catalyst was removed by filtration through Celite, filtrate was concentrated under reduced pressure to provide (S)-1-(3-methoxyphenyl)propan-2-amine. LCMS (ES) m/z=343.3 [M+H]$^+$. $^1$H NMR (400 MHz, $CDCl_3$) δ ppm 1.13 (d, J=6.0 Hz, 3H), 2.44-2.54 (m, 1H), 2.67-2.72 (m, 1H), 3.16-3.21 (m, 1H), 3.79 (s, 3H), 6.74-6.78 (m, 3H), 7.21 (t, J=7.8 Hz, 1H). $NH_2$ Protons were not observed in $^1$H NMR.

To a solution of (S)-1-(3-methoxyphenyl)propan-2-amine (0.3 g, 1.81 mmol, 1.0 eq) and methyl 4-formylbenzoate (0.36 g, 2.18 mmol, 1.2 eq) in toluene (4 mL) was irradiated in microwave at 90° C. for 20 min. After this time, the volatile portion was concentrated under reduced pressure to provide methyl (S)-4-(((1-(3-methoxyphenyl)propan-2-yl)imino)methyl)benzoate. This product was taken forward for cyclization step as such.

To a solution of methyl (S)-4-(((1-(3-methoxyphenyl)propan-2-yl)imino)methyl)benzoate (previous step product) in TFA (2 mL) was irradiated in microwave at 140° C. for 45 min. After this time, the volatile portion was concentrated under reduced pressure and diluted with saturated aqueous solution of $NaHCO_3$ (10 mL) and EtOAc (40 mL). The organic layer was separated, washed with brine (10 mL), dried over anhydrous $MgSO_4$, filtered and concentrated under reduced pressure to obtain the crude product. The obtained crude product was purified by silica gel flash column chromatography (n-hexane/EtOAc=3:2, $R_f$=0.4— for non-polar spot, $R_f$=0.3— for polar spot) to give methyl 4-((1R,3S)-6-methoxy-3-methyl-1,2,3,4-tetrahydroisoquinolin-1-yl)benzoate (less polar spot) and methyl 4-((1S,3S)-6-methoxy-3-methyl-1,2,3,4-tetrahydroisoquinolin-1-yl)benzoate (polar spot).

methyl 4-((1R,3S)-6-methoxy-3-methyl-1,2,3,4-tetrahydroisoquinolin-1-yl)benzoate: LCMS (ES) m/z=312.2 [M+H]$^+$, $^1$H NMR (400 MHz, $CDCl_3$) δ ppm 1.26 (d, J=6.0 Hz, 3H), 2.74-2.76 (m, 2H), 3.19-3.20 (m, 1H), 3.76 (s, 3H), 3.90 (s, 3H), 5.12 (s, 1H), 6.49-6.64 (m, 3H), 7.41 (d, J=8.0 Hz, 2H), 8.00 (d, J=7.6 Hz, 2H). NH Proton was not observed in $^1$H NMR.

methyl 4-((1S,3S)-6-methoxy-3-methyl-1,2,3,4-tetrahydroisoquinolin-1-yl)benzoate: LCMS (ES) m/z=312.2 [M+H]$^+$. $^1$H NMR (400 MHz, $CDCl_3$) δ ppm 1.11 (d, J=6.4 Hz, 3H), 2.53-2.60 (m, 1H), 2.82-2.87 (m, 1H), 3.04-3.07 (m, 1H), 3.80 (s, 3H), 3.89 (s, 3H), 5.24 (s, 1H), 6.67-6.69 (m, 2H), 6.79 (d, J=8.8 Hz, 1H), 7.20 (d, J=8.4 Hz, 2H), 7.94 (d, J=8.0 Hz, 2H). NH Proton was not observed in $^1$H NMR.

To a solution of methyl 4-((1R,3S)-6-methoxy-3-methyl-1,2,3,4-tetrahydroisoquinolin-1-yl)benzoate (0.2 g, 0.64 mmol, 1 eq) in DCM (5.0 mL) was added triethyl amine (0.19 g, 1.92 mmol, 3.0 eq) at 0° C., followed by 2-chloroacetyl chloride (0.095 g, 0.83 mmol, 1.3 eq). The mixture was stirred at 0° C. for 2.0 h under $N_2$ atmosphere. TLC (35% EtOAc in n-hexane) showed the reaction was completed. Then the reaction was diluted with saturated aqueous solution of $NaHCO_3$ (5 mL) and was extracted with DCM (25 mL). The organic layer was dried over anhydrous $Na_2SO_4$, filtered and concentrated under reduced pressure. The crude product was purified by preparative TLC using 40% EtOAc in n-hexane as mobile phase to give methyl 4-((1R,3S)-2-(2-chloroacetyl)-6-methoxy-3-methyl-1,2,3,4-tetrahydroisoquinolin-1-yl)benzoate (6): LCMS (ES) m/z=388.1 [M+H]$^+$. $^1$H NMR (400 MHz, DMSO-$d_6$) (at 70° C.) δ ppm 1.10 (d, J=5.6 Hz, 3H), 3.00 (bs, 2H), 3.77 (m, 3H), 3.82 (s, 3H), 4.21 (bs, 1H), 4.47 (q, J=13.6 Hz, 2H), 6.45 (bs, 1H), 6.83-6.85 (m, 2H), 7.16 (bs, 1H), 7.26 (d, J=8.0 Hz, 2H), 7.88 (d, J 8.0 Hz, 2H).

To a solution of methyl 4-((1S,3S)-6-methoxy-3-methyl-1,2,3,4-tetrahydroisoquinolin-1-yl)benzoate (0.11 g, 0.35 mmol, 1 eq) in DCM (4.0 mL) was added triethyl amine (0.1 g, 1.05 mmol, 3.0 eq) at 0° C., followed by 2-chloroacetyl chloride (0.05 g, 0.45 mmol, 1.3 eq). The mixture was stirred at 0° C. for 2.0 h under $N_2$ atmosphere. TLC (35% EtOAc in n-hexane) showed the reaction was completed. Then the reaction was diluted with saturated aqueous solution of $NaHCO_3$ (5 mL) and was extracted with DCM (25 mL). The organic layer was dried over anhydrous $Na_2SO_4$, filtered and concentrated under reduced pressure. The crude product was purified by preparative TLC using 40% EtOAc in n-hexane as mobile phase to give methyl 4-((1S,3S)-2-(2-chloroacetyl)-6-methoxy-3-methyl-1,2,3,4-tetrahydroisoquinolin-1-yl)benzoate (7): LCMS (ES) m/z=388.0 [M+H]$^+$. $^1$H NMR (400 MHz, DMSO-$d_6$) (at 70° C.) δ ppm 0.97 (bs, 3H), 2.65 (bs, 2H), 3.71 (s, 3H), 3.79 (s, 3H), 4.40 (bs, 1H), 4.75 (bs, 2H), 6.17 (bs, 1H), 6.76-6.82 (m, 2H), 7.40-7.49 (m, 3H), 7.81 (bs, 2H).

Procedure 5: Compounds 8, 9, and 10

Procedure 6: Synthesis of Compound 11

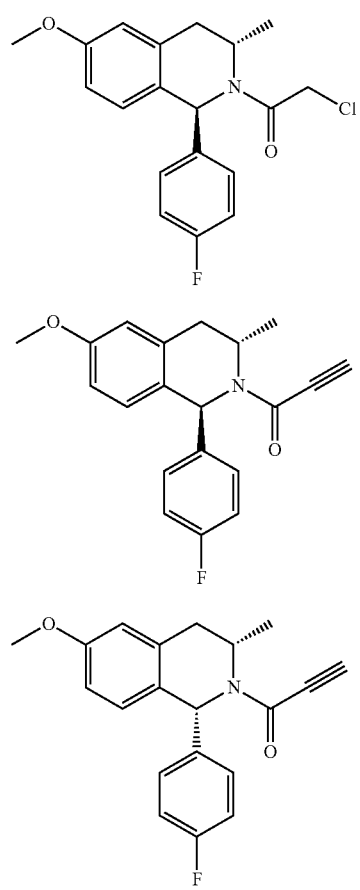

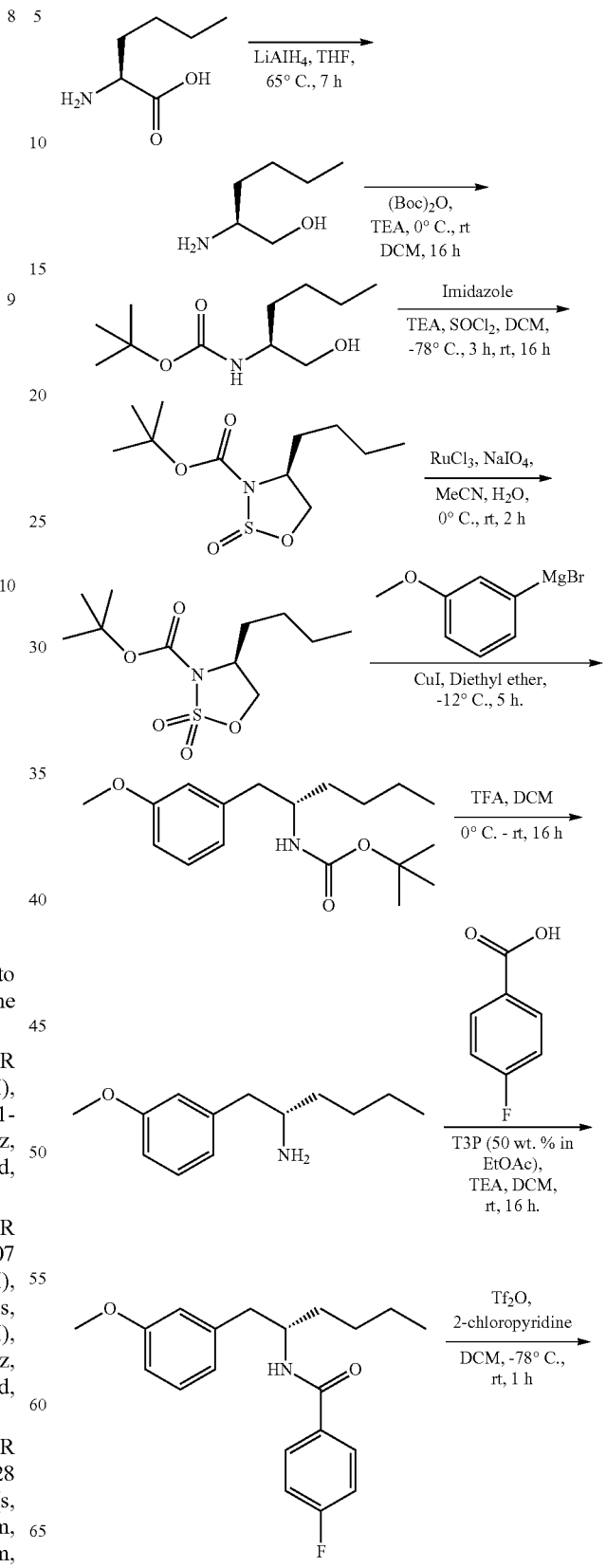

Compounds 8, 9, and 10 were synthesized according to the procedure provided in Examples 6 and 7 using the appropriate starting material.

Compound 8: LC-MS (m/z): 348.3 [M+H]$^+$. $^1$H NMR (400 MHz, DMSO-d$_6$) δ ppm 0.95 (d, J=5.2 Hz, 3H), 2.58-2.65 (m, 1H), 3.02-3.12 (m, 1H), 3.71 (s, 3H), 4.41-4.72 (m, 3H), 6.11 (s, 1H), 6.76 (s, 1H), 6.80 (d, J=8.4 Hz, 1H), 7.04 (bs, 2H), 7.27 (dd, J=8.4, 5.6 Hz, 2H), 7.45 (d, J=8.4 Hz, 1H). This NMR was recorded at 60° C.

Compound 9: LC-MS (m/z): 324.0 [M+H]$^+$. $^1$H NMR (400 MHz, DMSO-d$_6$) δ ppm 0.92 (d, J=6.0 Hz, 1H), 1.07 (d, J=6.0 Hz, 2H), 2.57-2.73 (m, 1H), 2.82-2.90 (m, 1H), 3.72-3.73 (m, 3H), 4.22 (s, 0.4H), 4.49 (s, 0.6H), 4.70 (bs, 0.5H), 4.92 (bs, 0.5H), 6.09 (s, 0.6H), 6.31 (s, 0.4H), 6.78-6.85 (m, 2H), 7.01 (t, J=9.0 Hz, 1H), 7.08 (t, J=8.4 Hz, 1H), 7.21-7.23 (m, 2H), 7.40 (d, J=8.0 Hz, 0.6H), 7.57 (d, J=8.4 Hz, 0.4H). This NMR was recorded at 60° C.

Compound 10: LC-MS (m/z): 324.3 [M+H]$^+$. $^1$H NMR (400 MHz, DMSO-d$_6$) δ ppm 1.09-1.13 (m, 3H), 2.21-2.28 (m, 0.5H), 2.90-2.94 (m, 0.5H), 3.07-3.08 (m, 1H), 3.77 (s, 3H), 4.07 (bs, 0.5H), 4.49-4.57 (m, 1.5H), 6.53-6.56 (m, 1H), 6.82-6.88 (m, 2H), 7.02-7.14 (m, 4.5H), 7.32-7.36 (m, 0.5H). This NMR was recorded at 60° C.

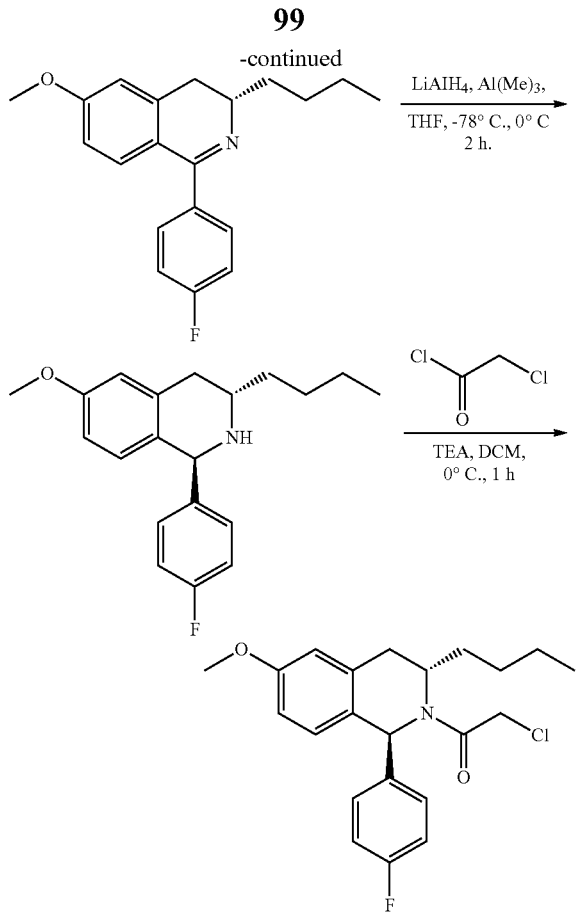

To a solution of (S)-2-aminohexanoic acid (5 g, 38.14 mmol, 1 eq) in THF (140 mL) at 0° C. was added 1 M LAH solution in THF (76.28 mL, 76.28 mmol, 2 eq). Reaction mixture was warmed to room temperature, then the mixture was stirred at 65° C. for 7 h under N2 atmosphere. TLC (10% MeOH in DCM) showed the reaction was completed. Reaction mixture was cooled to room temperature, the reaction was diluted with diethyl ether (50 mL), after fisher-workup, reaction mixture was filtered through sintered funnel, using diethyl ether, the filtrate was concentrated under reduced pressure and without further purification, the crude (S)-2-aminohexan-1-ol was forward to next step. $^1$H NMR (400 MHz, CDCl$_3$) δ ppm 0.83-0.91 (m, 3H), 1.2-1.42 (m, 6H), 2.82-2.83 (m, 1H), 3.24-3.29 (m, 1H), 3.57-3.61 (m, 1H).

To a solution of (S)-2-aminohexan-1-ol (4.2 g, 35.83 mmol, 1 eq) in DCM (40 mL) was added TEA (10 mL, 71.67 mmol, 2 eq) at 0° C. dropwise, it was stirred for 5 mins, then di-tert-butyl dicarbonate (9.86 mL, 43.00 mmol, 1.2 eq). After stirring at room temperature for 18 h, washed with water (75 mL) and brine (75 mL), dried over Na$_2$SO$_4$, and concentrated in vacuo. The residue was subjected to combiflash silica gel chromatography MeOH in DCM as an eluent to give tert-butyl (S)-(1-hydroxyhexan-2-yl)carbamate. $^1$H NMR (400 MHz, CDCl$_3$) δ ppm 0.89 (s, 3H), 1.32-1.43 (m, 6H), 1.44 (s, 9H), 3.50-3.54 (m, 1H), 3.61-3.67 (m, 2H), 4.59 (bs, 1H).

To a solution of 1H-imidazole (5.1 g, 75.57 mmol, 4 eq) and triethylamine (7.9 mL, 56.68 mmol, 3 eq) in anhydrous dichloromethane (30 mL) at −78° C. was added thionyl chloride (1.5 mL, 20.78 mmol, 1.1 eq) dropwise. The reaction mixture was stirred for 5 min while cooling −78° C. and tert-butyl (S)-(1-hydroxyhexan-2-yl)carbamate (4.1 g, 18.89 mmol, 1 eq) in anhydrous dichloromethane (30 mL) was added dropwise over 30 min. The reaction mixture was stirred at −78° C. for 3 hours. The reaction mixture was stirred while warming to room temperature overnight. Water was added (100 mL) and phase separated. The aqueous phase was further extracted into dichloromethane (150 mL), the combined organics were washed with water (100 mL), dried over with anhydrous Na$_2$SO$_4$, filtered and concentrated under reduced pressure. The tert-butyl (4S)-4-butyl-1,2,3-oxathiazolidine-3-carboxylate 2-oxide was taken on to the next step without further purification.

Ruthenium(III)chloride hydrate (0.002 g, 0.013 mmol, 0.007 eq), was added to a stirred solution of tert-butyl (4S)-4-butyl-1,2,3-oxathiazolidine-3-carboxylate 2-oxide (5 g, 19 mmol, 1 eq), in acetonitrile (50 mL) and water (50 mL) at 0° C., followed by portion-wise addition of sodium periodate (4.4 g, 20.91 mmol, 1.1 eq). The biphasic mixture was stirred at 20° C. for 2 hours. Water (250 mL) was added and the mixture was extracted into ethyl acetate (2×150 mL). The combined organics were washed with water (150 mL), brine (150 mL), dried over with Na$_2$SO$_4$, filtered and concentrated under reduced pressure to obtain the crude product, crude product was purified by column chromatography using 10% ethylacetate in hexane as an eluent to give the tert-butyl (S)-4-butyl-1,2,3-oxathiazolidine-3-carboxylate 2,2-dioxide. $^1$H NMR (400 MHz, CDCl$_3$) δ ppm 0.90-1.25 (m, 3H), 1.31-1.38 (m, 6H), 1.48 (s, 9H), 1.75-1.95 (m, 2H), 4.27-4.32 (m, 2H), 4.61-4.65 (m, 1H).

To a solution of copper iodide (0.238 g, 1.25 mmol, 0.1 eq) in diethyl ether (25 mL) was added (3-methoxyphenyl)magnesium bromide (1M in THF) (25 mL, 25.08 mmol, 2.0 eq) dropwise over a period of 10 min at −12° C. The reaction mixture was stirred for 30 min at −12° C. After this time, a solution of tert-butyl (S)-4-butyl-1,2,3-oxathiazolidine-3-carboxylate 2,2-dioxide (3.5 g, 12.54 mmol, 1.0 eq) in diethyl ether (15 mL) was added at −12° C. dropwise to the reaction. The resulting mixture was stirred for 4 h at −12° C. Finally, the reaction was quenched with 10% aqueous citric acid solution (15 mL) at −12° C. and diluted with ethyl acetate (100 mL). The organic layer was separated and washed with brine (20 mL), dried over anhydrous sodium sulfate, filtered and concentrated to give the crude product, which was purified by flash column chromatography using 15% ethyl acetate in n-hexane as an eluent to obtain tert-butyl (S)-(1-(3-methoxyphenyl)hexan-2-yl)carbamate. LC-MS (m/z)=252.0 [M+H]$^+$. $^1$H NMR (400 MHz, CDCl$_3$) δ ppm 0.86-0.87 (m, 3H), 1.23-1.35 (m, 6H), 1.40 (s, 9H), 2.73 (bs, 2H), 3.78 (s, 3H), 4.29 (bs, 1H), 6.71-6.76 (m, 3H), 7.19 (t, J=7.8 Hz, 1H). Amide NH was not observed.

To a solution of tert-butyl (S)-(1-(3-methoxyphenyl)hexan-2-yl)carbamate (3.7 g, 12.05 mmol, 1 eq) in dichloromethane (30 mL) was added trifluoroacetic acid (2.7 g, 24.10 mmol, 2 eq) at 0° C. The mixture was allowed to stir at room temperature for 16 h. The progress of the reaction was monitored by TLC, after completion of reaction; the reaction mixture was concentrated under reduced pressure. The obtained product was dissolved with ice cold water (10 mL) and basified with saturated aqueous solution of NaHCO$_3$. The compound was extracted with EtOAc (100 mL). The Organic layer was washed with brine (10 mL), dried over anhydrous sodium sulfate, filtered and concentrated to obtain (S)-1-(3-methoxyphenyl)hexan-2-amine. LC-MS (m/z)=208.1 [M+H]$^+$. $^1$H NMR (400 MHz, CDCl$_3$) δ ppm 0.82-0.90 (m, 3H), 1.23-1.42 (m, 4H), 1.57-1.62 (m, 2H), 2.69-2.91 (m, 2H), 3.25-3.58 (m, 1H), 3.80 (s, 3H), 6.69-6.78 (m, 3H), 7.21 (t, J=8.0 Hz, 1H). NH$_2$ protons not observed.

To a solution of 4-fluorobenzoic acid (1.62 g, 11.59 mmol, 1.2 eq) in DCM (25 mL) was added TEA (3.9 g, 38.64 mmol, 4 eq), the reaction stirred for 15 min and then T3P (50 wt % in EtOAc) (4.6 g, 14.49 mmol, 1.5 eq) was added at 0° C. and stirred for another 5 min. (S)-1-(3-methoxyphenyl) hexan-2-amine (2.0 g, 9.66 mmol, 1 eq) was added to the reaction mixture and then reaction mixture was stirred at room temperature. The progress of the reaction was monitored by TLC (20% ethyl acetate in hexane). After 16 h, the reaction mixture was diluted with DCM (50 mL) and saturated sodium bicarbonate solution (20 mL). The organic layer was separated, washed with brine solution (20 mL), dried over anhydrous sodium sulfate, filtered and concentrated under reduced pressure to obtain (S)-4-fluoro—N—(1-(3-methoxyphenyl)hexan-2-yl)benzamide. LC-MS (m/z)=330.0 [M+H]$^+$. $^1$H NMR (400 MHz, CDCl$_3$) δ ppm 0.88-0.89 (m, 3H), 1.26-1.48 (m, 6H), 2.83-2.93 (m, 2H), 3.76 (s, 3H), 4.36-4.38 (m, 1H), 5.74 (d, J=7.6 Hz, 1H), 6.69-6.80 (m, 3H), 7.08 (t, J=8.4 Hz, 2H), 7.21 (t, J=7.6 Hz, 1H), 7.68 (t, J=6.4 Hz, 2H).

Trifluoromethanesulfonic anhydride (2.5 mL, 14.89 mmol, 2.0 eq) was added via syringe over 1 min to a stirred mixture of amide (S)-4-fluoro—N—(1-(3-methoxyphenyl) hexan-2-yl)benzamide (2.45 g, 7.44 mmol, 1 eq) and 2-chloropyridine (1.4 mL, 14.89 mmol, 2.0 eq) in dichloromethane (25 mL) at −78° C. After 5 min, the reaction mixture was placed in an ice-water bath and warmed to 0° C. After 5 min, the resulting solution was allowed to warm to 23° C. After 1 h, aqueous sodium hydroxide solution (5 mL, 1N) was introduced to neutralize the trifluoromethanesulfonate salts. Dichloromethane (50 mL) was added to dilute the mixture and the layers were separated. The organic layer was washed with brine (2 mL), was dried over anhydrous sodium sulfate, and was filtered. The volatiles were removed under reduced pressure to give the (S)-3-butyl-1-(4-fluorophenyl)-6-methoxy-3,4-dihydroisoquinoline. LC-MS (m/z)=312.0 [M+H]$^+$.

A solution of the (S)-3-butyl-1-(4-fluorophenyl)-6-methoxy-3,4-dihydroisoquinoline (0.8 g, 2.57 mmol, 1 eq) in anhydrous THF (5 mL) was added drop wise to a mixture of lithium aluminum hydride 1M in THF (25.7 mL, 25.72 mmol, 10 eq) and trimethylaluminum 25% w/w in hexane (3.7 mL, 12.85 mmol, 5 eq) in THF (20 mL) at −78° C. under nitrogen. The suspension was stirred at −78° C. for 1 h, and warmed to 0° C. over 3 h. The reaction mixture was quenched with saturated aqueous sodium chloride (5 mL) followed by diluted with EtOAc (30 mL) and the precipitate was filtered off. Finally, filtrate was dried over anhydrous sodium sulfate, filtered and evaporated under reduced pressure. The residue was purified by silica gel flash chromatography (EtOAc/n-hexane=75/25) to give the (1S,3S)-3-butyl-1-(4-fluorophenyl)-6-methoxy-1,2,3,4-tetrahydroisoquinoline (trans confirmed by nOe experiment).

The isolated pure product was treated with metal scavenger Quadrasil® TA (compound was dissolved in THF (5 mL) and Quadrasil® TA (100 mg) was added, the mixture was stirred for 0.5 h, filtered. This was repeated one more time and concentrated). LC-MS (m/z)=314.0 [M+H]$^+$. $^1$H NMR (400 MHz, CDCl$_3$) δ ppm 0.85 (bs, 3H), 1.26 (bs, 4H), 1.45 (bs, 2H), 2.60-2.69 (m, 1H), 2.87-2.92 (m, 2H), 3.80 (s, 3H), 5.20 (s, 1H), 6.69 (s, 2H), 6.79-6.81 (m, 1H), 6.97-7.05 (m, 2H), 7.13 (s, 2H).

To a solution of (1S,3S)-3-butyl-1-(4-fluorophenyl)-6-methoxy-1,2,3,4-tetrahydroisoquinoline (0.1 g, 0.31 mmol, 1 eq) in DCM (4 mL) was added triethyl amine (0.08 g, 0.77 mmol, 2.5 eq) at 0° C., followed by 2-chloroacetyl chloride (0.054 g, 0.47 mmol, 1.5 eq). The mixture was stirred at 0° C. for 1 h under N$_2$ atmosphere. TLC (25% EtOAc in hexane) showed the reaction was completed. Then the reaction was diluted with saturated aqueous solution of NaHCO$_3$ (5 mL) and product was extracted with DCM (25 mL). The organic layer was dried over anhydrous Na$_2$SO$_4$, filtered and concentrated under reduced pressure to obtain the crude product. The obtained crude product was purified by preparative TLC using 25% EtOAc in n-hexane as mobile phase to give 1-((1S,3S)-3-butyl-1-(4-fluorophenyl)-6-methoxy-3,4-dihydroisoquinolin-2(1H)-yl)-2-chloroethan-1-one. LC-MS (m/z)=390.1 [M+H]$^+$. $^1$H NMR (400 MHz, DMSO-d$_6$): (recorded at 70° C. due to rotameric behavior was seen with RT NMR) δ 0.79-0.81 (m, 3H), 1.00 (bs, 1H), 1.20 (bs, 4H), 1.40 (bs, 1H), 2.78-2.83 (m, 1H), 2.87-2.90 (m, 2H), 3.71 (s, 3H), 4.50 (bs, 2H), 6.09 (s, 1H), 6.77-6.80 (m, 2H), 7.03 (bs, 2H), 7.28 (t, J=6.6 Hz, 2H), 7.41 (d, J=8.0 Hz, 1H).

Procedure 7: Synthesis of Compound 12

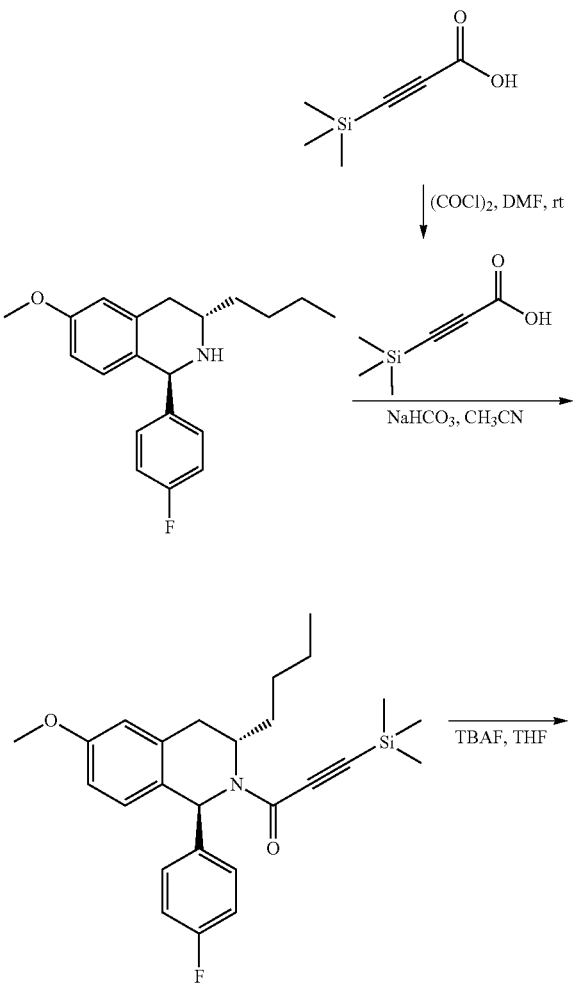

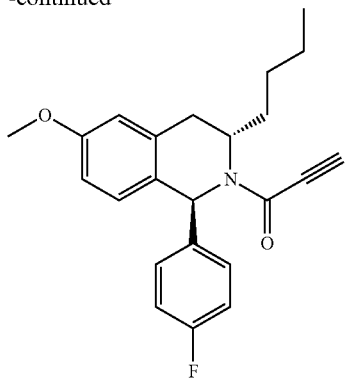

To a solution of 3-(trimethylsilyl)propiolic acid (0.1 g, 0.7 mmol, 1.0 eq) in DMF (0.003 mL, 0.0038 mmol, 0.04 eq) was added oxalyl chloride (0.066 mL, 0.77 mmol, 1.1 eq) at room temperature and stirred for 30 minutes. After this time, reaction mixture was concentrated under reduced pressure to provide 3-(trimethylsilyl)propioloyl chloride, which was carried to next step without any further purification.

To a solution of (1S,3S)-3-butyl-1-(4-fluorophenyl)-6-methoxy-1,2,3,4-tetrahydroisoquinoline (0.15 g, 0.47 mmol, 1.0 eq) in acetonitrile (3.5 mL) was added sodium bicarbonate (0.3 g, 3.57 mmol, 7.5 eq) at 0° C. After stirring for 5 minutes, a solution of 3-(trimethylsilyl)propioloyl chloride (0.113 g, 0.69 mmol, 1.5 eq) in acetonitrile (1.5 mL) was added. The resulting mixture was stirred at 0° C. for 15 min, and progress of the reaction was monitored by TLC (20% ethyl acetate in n-hexane). After this time, the solid portion from the reaction mass was removed by passing through a Celite pad, which was washed with acetonitrile. The obtained filtrate was concentrated under reduced pressure to provide 1-((1S,3S)-3-butyl-1-(4-fluorophenyl)-6-methoxy-3,4-dihydroisoquinolin-2(1H)-yl)-3-(trimethylsilyl)prop-2-yn-1-one which was carried to next step without any further purification. LC-MS (m/z)=438.2 [M+H]+.

To a solution of 1-((1S,3S)-3-butyl-1-(4-fluorophenyl)-6-methoxy-3,4-dihydroisoquinolin-2(1H)-yl)-3-(trimethylsilyl)prop-2-yn-1-one (0.2 g, 0.45 mmol, 1 eq) in THF (4.0 mL) was added tetra-butyl ammonium fluoride (1M in solution THF) (0.5 mL, 0.5 mmol, 1.1 eq) at −78° C. This reaction mixture was stirred at −78° C. for 15 minutes. The progress of the reaction was monitored by TLC (20% ethyl acetate in n-hexane). After this time, the reaction mixture was diluted with water (5 mL) and the product was extracted with ethyl acetate (25 mL). Combined organic layers were dried over anhydrous sodium sulfate, filtered and concentrated under reduced pressure to obtain crude product, which was purified by preparative TLC using 20% ethyl acetate in n-hexane as an eluent to provide 1-((1S,3S)-3-butyl-1-(4-fluorophenyl)-6-methoxy-3,4-dihydroisoquinolin-2(1H)-yl) prop-2-yn-1-one. LC-MS (m/z)=366.1 [M+H]+. 1H NMR (400 MHz, DMSO-$d_6$) δ ppm 0.81-0.88 (m, 3H), 1.20-1.24 (m, 5H), 1.50 (bs, 1H), 2.78-2.89 (s, 2H), 3.72 (s, 3H), 4.18 (s, 0.3H), 4.54 (s, 0.5H), 4.50 (bs, 0.5H), 4.70 (bs, 0.7H), 6.05 (s, 0.6H), 6.31 (s, 0.4H), 6.77-6.84 (m, 2H), 6.98-7.10 (m, 2H), 7.23-7.24 (m, 2H), 7.36 (d, J=8.0 Hz, 0.7H), 7.53 (d, J=7.6 Hz, 0.3H).

Procedure 8: Synthesis of Compound 13

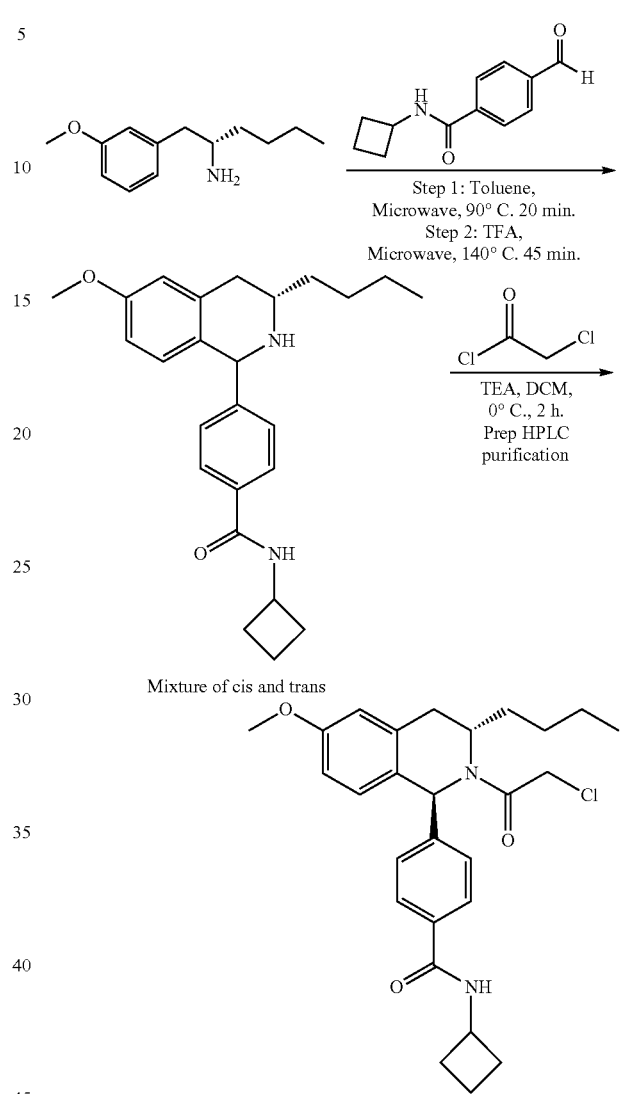

To a solution of (S)-1-(3-methoxyphenyl)hexan-2-amine (1.0 g, 1.27 mmol, 1 eq) and N-cyclobutyl-4-formylbenzamide (1.17 g, 5.79 mmol, 1.2 eq) in toluene (4 mL) was irradiated in microwave at 90° C. for 20 min. After this time, volatile portion was concentrated under reduced pressure and taken forward for cyclization step in TFA (4 mL) and irradiated in microwave at 140° C. for 45 min. After this time, volatile portion was concentrated under reduced pressure and the obtained crude was diluted with saturated aqueous solution of $NaHCO_3$ (10 mL) and EtOAc (40 mL). The organic layer was separated, washed with brine (10 mL), dried over anhydrous $MgSO_4$, filtered and concentrated under reduced pressure to obtain the crude product. The obtained crude product was purified by silica gel flash column chromatography (n-hexane/EtOAc) to give 4-((1S,3S)-3-butyl-2-(2-chloroacetyl)-6-methoxy-1,2,3,4-tetrahydroisoquinolin-1-yl)—N-cyclobutylbenzamide. LC-MS (m/z): 393.3 [M+H]+.

To a solution of 4-((3S)-3-butyl-6-methoxy-1,2,3,4-tetrahydroisoquinolin-1-yl)—N-cyclobutylbenzamide (0.5 g, 1.27 mmol, 1 eq) in DCM (10 mL) was TEA (0.4 g, 3.18 mmol, 2.5 eq) followed by the addition 2-chloroacetyl chloride (0.091 mL, 1.14 mmol, 0.9 eq) stirred at 0° C. for 6 h. TLC 30% (ethylacetate in hexane) showed the reaction was completed. The reaction mixture was concentrated under reduced pressure, and the crude was diluted with EtOAc (50 mL), washed with water (2×50 mL). The organic layer was dried over anhydrous $Na_2SO_4$, concentrated under reduced pressure to give crude product. The obtained crude product was purified by Prep HPLC purification [Analytical conditions: Column: Inertsil ODS 3V (250 mm×4.6 mm×5 µm), mobile phase (A): 0.1% Ammonia in water, mobile phase (B): $CH_3CN$, flow rate: 1.0 mL/min, composition of B: 0/10, 12/80, 25/90, 27/10, 30/10] to obtain 4-((1S,3S)-3-butyl-2-(2-chloroacetyl)-6-methoxy-1,2,3,4-tetrahydroisoquinolin-1-yl)—N-cyclobutylbenzamide. LCMS (ES) m/z: 469.0 $[M+H]^+$, HPLC Purity: 99.8%, Chiral HPLC Purity: 99.92%. $^1H$ NMR (400 MHz, $CDCl_3$): δ ppm 0.78-0.81 (m, 3H), 1.22-1.41 (m, 6H), 1.60-1.69 (m, 2H), 1.99-2.06 (m, 2H), 2.18-2.20 (m, 2H), 2.80-2.84 (m, 2H), 3.09-3.10 (m, 1H), 3.71 (s, 3H), 4.31-4.37 (m, 1H), 4.55 (bs, 2H), 6.13 (s, 1H), 6.77-6.81 (m, 2H), 7.32-7.34 (m, 2H), 7.43 (m, 1H), 7.66 (s, 1H).

Procedure 9: Synthesis of Compound 14

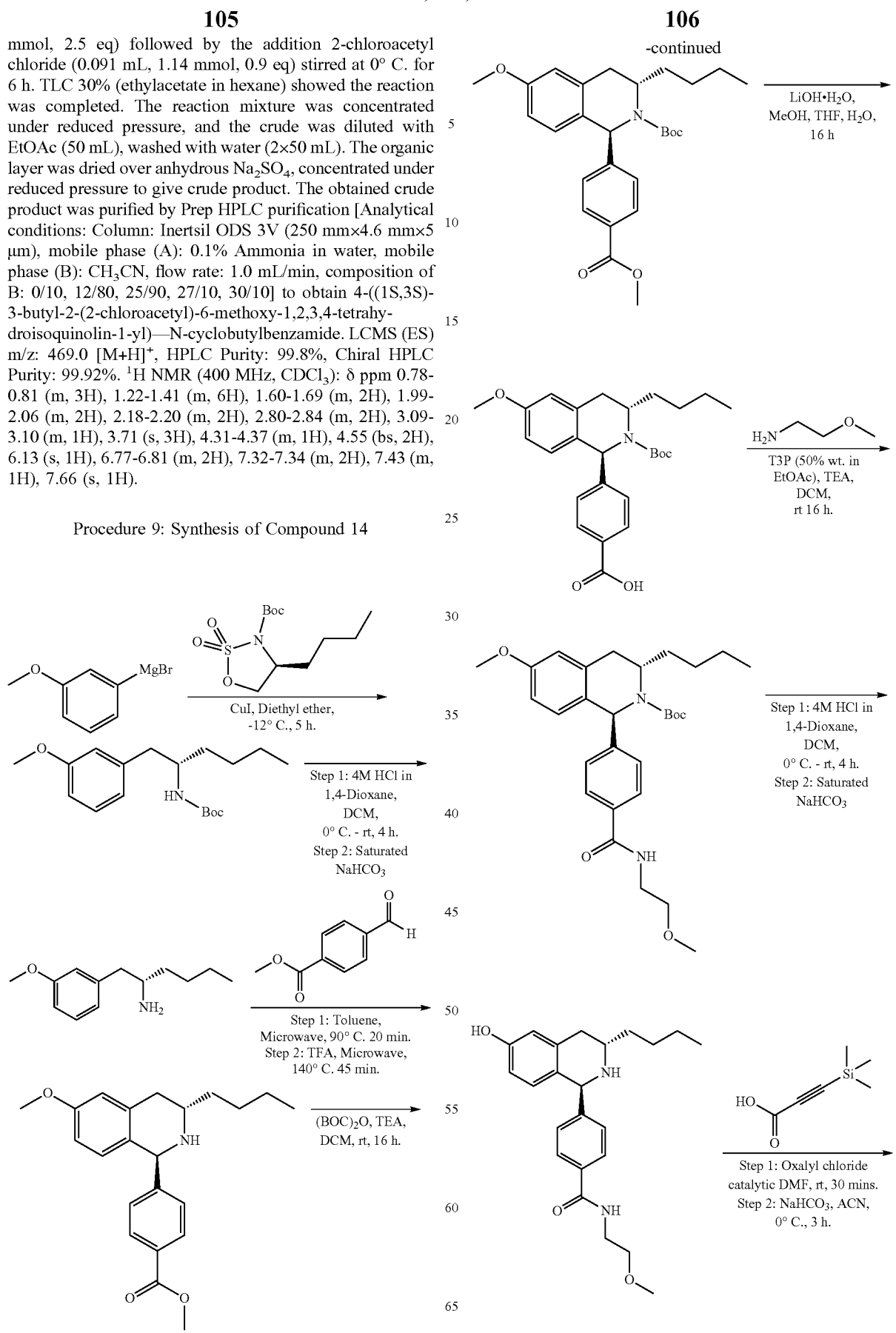

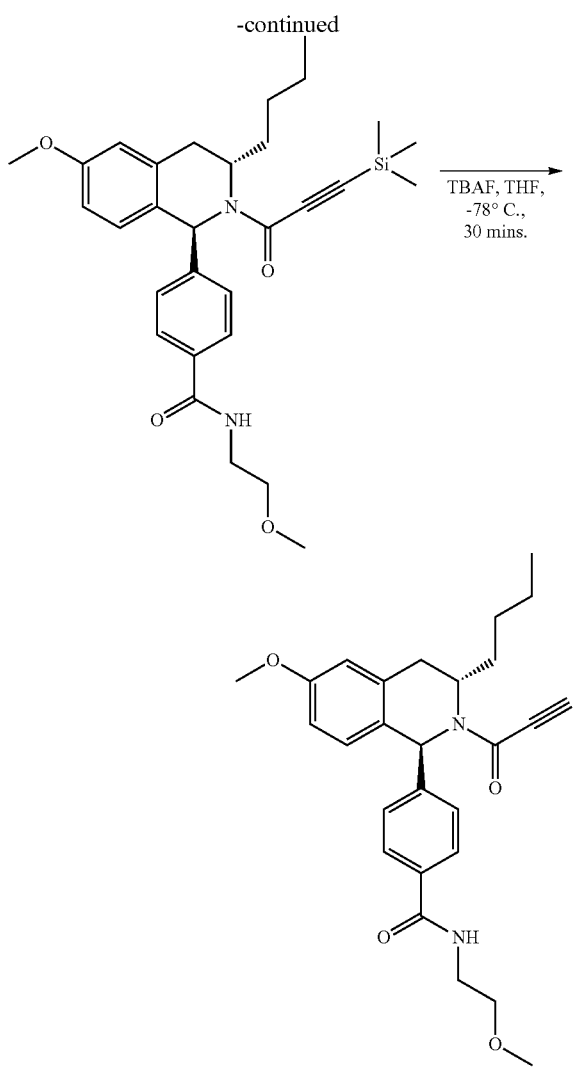

To a solution of copper iodide (0.510 g, 2.68 mmol, 0.1 eq) in diethyl ether (50 mL) was added (3-methoxyphenyl)magnesium bromide (1M in THF) (53 mL, 53.76 mmol, 2 eq) drop wise over a period of 10 min at −12° C. The reaction mixture was stirred for 30 min at −12° C. After this time, a solution of tert-butyl (S)-4-butyl-1,2,3-oxathiazolidine-3-carboxylate 2,2-dioxide (7.5 g, 26.88 mmol, 1 eq) in diethyl ether (15 mL) was added at −12° C. drop wise to the reaction mass. The resulting mixture was stirred for 4 h at −12° C. Finally, the reaction was quenched with 10% aqueous citric acid solution (15 mL) at −12° C. and diluted with ethyl acetate (100 mL). The organic layer was separated and washed with brine (50 mL), dried over anhydrous sodium sulfate, filtered and concentrated to give the crude product, which was purified by flash column chromatography using 15% ethyl acetate in n-hexane as an eluent to obtain tert-butyl (S)-(1-(3-methoxyphenyl)hexan-2-yl)carbamate. LC-MS (m/z): 252.0 [M+H]$^+$. $^1$H NMR (400 MHz, CDCl$_3$): δ ppm 0.86-0.87 (m, 3H), 1.23-1.35 (m, 6H), 1.40 (s, 9H), 2.73 (bs, 2H), 3.78 (s, 3H), 4.29 (bs, 1H), 6.71-6.76 (m, 3H), 7.19 (t, J=7.8 Hz, 1H) Amide NH was not observed.

To a solution of tert-butyl (S)-(1-(3-methoxyphenyl)hexan-2-yl)carbamate (10 g, 32.57 mmol, 1 eq) in dichloromethane (50 mL) was added 4M HCl in 1,4-Dioxane (20 mL, 64.10 mmol, 2 eq) at 0° C. The mixture was allowed to stir at room temperature for 16 h. The progress of the reaction was monitored by TLC, after completion of reaction; the reaction mixture was concentrated under reduced pressure. The obtained crude was dissolved with ice cold water (10 mL) and was basified by saturated aqueous solution of NaHCO$_3$. The compound was extracted with EtOAc (100 mL). Organic layer was washed with brine (10 mL), dried over anhydrous sodium sulfate, filtered and concentrated to obtain (S)-1-(3-methoxyphenyl)hexan-2-amine. LC-MS (m/z): 208.1 [M+H]$^+$. $^1$H NMR (400 MHz, CDCl$_3$): δ ppm 0.82-0.90 (m, 3H), 1.23-1.42 (m, 4H), 1.57-1.62 (m, 2H), 2.69-2.91 (m, 2H), 3.25-3.58 (m, 1H), 3.80 (s, 3H), 6.69-6.78 (m, 3H), 7.21 (t, J=8.0 Hz, 1H)(NH$_2$ protons not observed).

To a solution of (S)-1-(3-methoxyphenyl)hexan-2-amine (0.7 g, 3.37 mmol, 1 eq) and methyl 4-formylbenzoate (0.664 g, 4.05 mmol, 1 eq) in toluene (4 mL) was irradiated in microwave at 90° C. for 20 min. After this time, volatile portion was concentrated under reduced pressure and taken forward for cyclization step as such in TFA (4 mL) and irradiated in microwave at 140° C. for 45 min. After this time, volatile portion was concentrated under reduced pressure and obtained crude was diluted with saturated aqueous solution of NaHCO$_3$ (10 mL) and EtOAc (40 mL). The organic layer was separated, washed with brine (10 mL), dried over anhydrous MgSO4, filtered and concentrated under reduced pressure to obtain the crude product. The obtained crude product was purified by silica gel flash column chromatography (n-hexane/EtOAc) to give methyl 4-((1S,3S)-3-butyl-6-methoxy-1,2,3,4-tetrahydroisoquinolin-1-yl)benzoate. LC-MS (m/z): 208.1 [M+H]$^+$. $^1$H NMR (400 MHz, CDCl$_3$): δ ppm 0.84-0.86 (m, 3H), 1.23-1.24 (m, 6H), 2.55-2.59 (m, 1H), 2.85-2.88 (m, 2H), 3.75 (s, 3H), 3.80 (s, 3H), 5.29 (s, 3H), 6.67-6.69 (m, 2H), 6.70-6.80 (m, 1H), 7.21-7.26 (s, 2H), 7.94-8.0 (m, 2H).

To a solution of compound methyl 4-((1S,3S)-6-methoxy-3-methyl-1,2,3,4-tetrahydroisoquinolin-1-yl)benzoate (0.35 g, 1.12 mmol, 1 eq) in DCM (10 mL) was added triethylamine (0.45 g, 4.49 mmol, 4 eq) and di-tert-butyl dicarbonate (0.715 g, 2.24 mmol, 2 eq) at room temperature and the mixture was stirred for 16 h. TLC (50% EtOAc in hexane) showed the reaction was completed. The reaction mixture was concentrated under reduced pressure, and the crude was diluted with EtOAc (50 mL), washed with water (2×50 mL). The organic layer was dried over anhydrous Na$_2$SO$_4$, concentrated under reduced pressure to crude product tert-butyl (1S,3S)-6-methoxy-1-(4-(methoxycarbonyl)phenyl)-3-methyl-3,4-dihydroisoquinoline-2(1H)-carboxylate. LC-MS (m/z): 356.0 [M-$^t$Bu+H]$^+$.

To a solution of compound tert-butyl (1S,3S)-6-methoxy-1-(4-(methoxycarbonyl)phenyl)-3-methyl-3,4-dihydroisoquinoline-2(1H)-carboxylate (0.650 g, 1.57 mmol, 1 eq) in a mixture of THF:MeOH:H$_2$O (9 mL: 1 mL) were added Lithium hydroxide (0.331 g, 7.89 mmol, 5 eq) and allowed to stirrer at room temperature for 16 h. TLC (50% EtOAc in hexane) showed the reaction was completed. The reaction mixture was concentrated under reduced pressure, and the crude was acidified with 5% citric acid solution (pH=9). Reaction mixture was diluted with EtOAc (50 mL) and the organic layer was separated and dried over anhydrous Na$_2$SO$_4$, concentrated under reduced pressure to give crude product 4-((1S,3S)-2-(tert-butoxycarbonyl)-6-methoxy-3-methyl-1,2,3,4-tetrahydroisoquinolin-1-yl)benzoic acid. LC-MS (m/z): 396.0 [M+H]$^+$.

To a solution of compound 4-((1S,3S)-2-(tert-butoxycarbonyl)-3-butyl-6-methoxy-1,2,3,4-tetrahydroisoquinolin-1-yl)benzoic acid (0.520 g, 1.18 mmol, 1 eq) in DCM (10 mL)

was added triethylamine (0.6 mL, 4.73 mmol, 4 eq) and 2-methoxyethan-1-amine (0.106 g, 1.42 mmol, 1.2 eq) at 0° C. and the mixture was stirred for 15 min. To the above reaction mixture T3P (50% wt in EtOAc) (1.4 mL, 1.7 mmol, 1.5 eq) was added at the same temperature and stirred for 16 h. TLC (30% EtOAc in hexane) showed the reaction was completed. The reaction mixture was concentrated under reduced pressure, and the crude was diluted with EtOAc (50 mL), washed with water (2×50 mL). The organic layer was dried over anhydrous $Na_2SO_4$, concentrated under reduced pressure to give crude product tert-butyl (1S,3S)-3-butyl-6-methoxy-1-(4-((2-methoxyethyl)carbamoyl)phenyl)-3,4-dihydroisoquinoline-2(1H)-carboxylate. LC-MS (m/z): 497.0 [M-$^t$Bu+H]$^+$.

To a solution of tert-butyl (1S,3S)-3-butyl-6-methoxy-1-(4-((2-methoxyethyl)carbamoyl)phenyl)-3,4-dihydroisoquinoline-2(1H)-carboxylate (0.380 g, 0.76 mmol, 1 eq) in dichloromethane (50 mL) was added 4M HCl in 1,4-Dioxane (10 mL, 1.52 mmol, 2 eq) at 0° C. The mixture was allowed to stir at room temperature for 16 h. The progress of the reaction was monitored by TLC, after completion of reaction; the reaction mixture was concentrated under reduced pressure. The obtained crude was dissolved with ice cold water (20 mL) and was basified by saturated aqueous solution of $NaHCO_3$. The compound was extracted with EtOAc (100 mL). Organic layer was washed with brine (10 mL), dried over anhydrous sodium sulfate, filtered and concentrated to obtain 4-((1S,3S)-3-butyl-6-methoxy-1,2,3,4-tetrahydroisoquinolin-1-yl)—N—(2-methoxyethyl)benzamide. LC-MS (m/z): 397.0 [M+H]$^+$.

To 3-(trimethylsilyl)propiolic acid (0.172 g, 1.20 mmol, 1 eq), DMF (0.003 g, 0.048 mmol, 0.04 eq) and oxalyl chloride (0.114 mL, 1.33 mmol, 1.1 eq) was added and stirred for 30 mins. After this time reaction mixture was concentrated under reduced pressure to obtain crude 3-(trimethylsilyl)propioloyl chloride and this crude was diluted with ACN (1 mL) and added to a reaction mixture containing a stirred solution of 4-((1S,3S)-3-butyl-6-methoxy-1,2,3,4-tetrahydroisoquinolin-1-yl)—N—(2-methoxyethyl)benzamide (0.320 g, 0.807 mmol, 1 eq) and $NaHCO_3$ (0.508 g, 6.05 mmol, 7.5 eq) in ACN (5 mL) at 0° C. and stirred for 15 mins. LCMS and TLC (70% EtOAc in hexane) showed the reaction was completed. The reaction was filtered and concentrated under reduced pressure to give the crude product 4-((1S,3S)-3-butyl-6-methoxy-2-(3-(trimethylsilyl)propioloyl)-1,2,3,4-tetrahydroisoquinolin-1-yl)—N—(2 methoxyethyl)benzamide which was taken to next step without further purification. LC-MS (m/z): 521.0 [M+H]$^+$.

To 4-((1S,3S)-3-butyl-6-methoxy-2-(3-(trimethylsilyl)propioloyl)-1,2,3,4-tetrahydroisoquinolin-1-yl)—N—(2-methoxyethyl)benzamide (0.360 g, 0.69 mmol, 1 eq) in THF (10.0 mL) TBAF (1M solution in THF) (0.48 mL, 0.48 mmol, 2 eq) was added and stirred for 30 mins. After this time reaction mixture was concentrated under reduced pressure, diluted with ethylacetate (100 mL) and was washed with water (2×10 mL). The organic layers were dried over $Na_2SO_4$ and concentrated to give to obtain the crude product which was further purified by preparative TLC chromatography using 70% EtOAc in hexane as an eluent to 4-((1S,3S)-3-butyl-6-methoxy-2-propioloyl-1,2,3,4-tetrahydroisoquinolin-1-yl)—N—(2 methoxyethyl)benzamide. LC-MS (m/z): 449.2 [M+H]$^+$; HPLC Purity: 98.6%, Chiral HPLC Purity: 99.98%. $^1$H NMR (400 MHz, DMSO-d$_6$): δ 0.80-0.83 (m, 3H), 0.92-1.24 (m, 5H), 1.50 (bs, 1H), 2.80-2.90 (m, 2H), 3.10 (s, 1H), 3.24 (s, 3H), 3.38-3.42 (m, 4H), 3.71-3.72 (m, 2H), 4.16-4.46 (s, 1H), 4.58-4.75 (bs, 1H), 6.07-6.34 (s, 1H), 6.77-6.84 (m, 2H), 7.29-7.31 (m, 2H), 7.38-7.58 (m, 1H), 7.64-7.73 (m, 2H), 8.13-8.19 (m, 1H).

Procedure 10: Synthesis of Compound 15

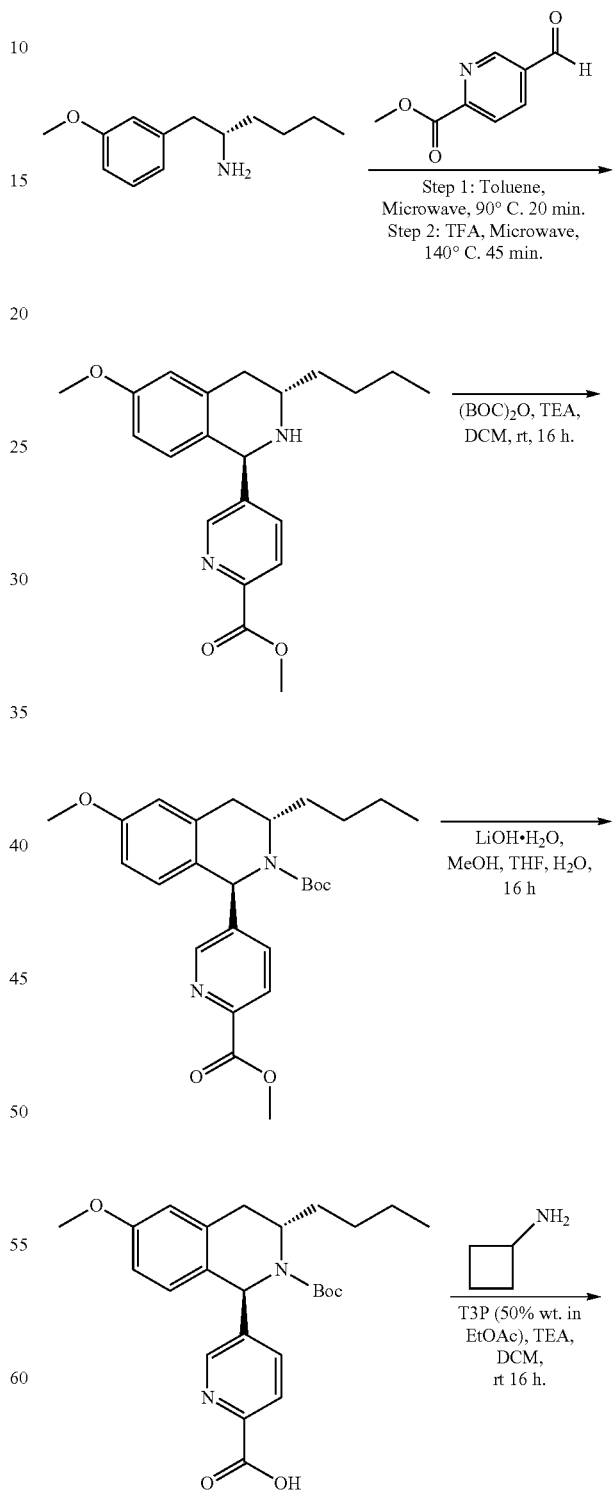

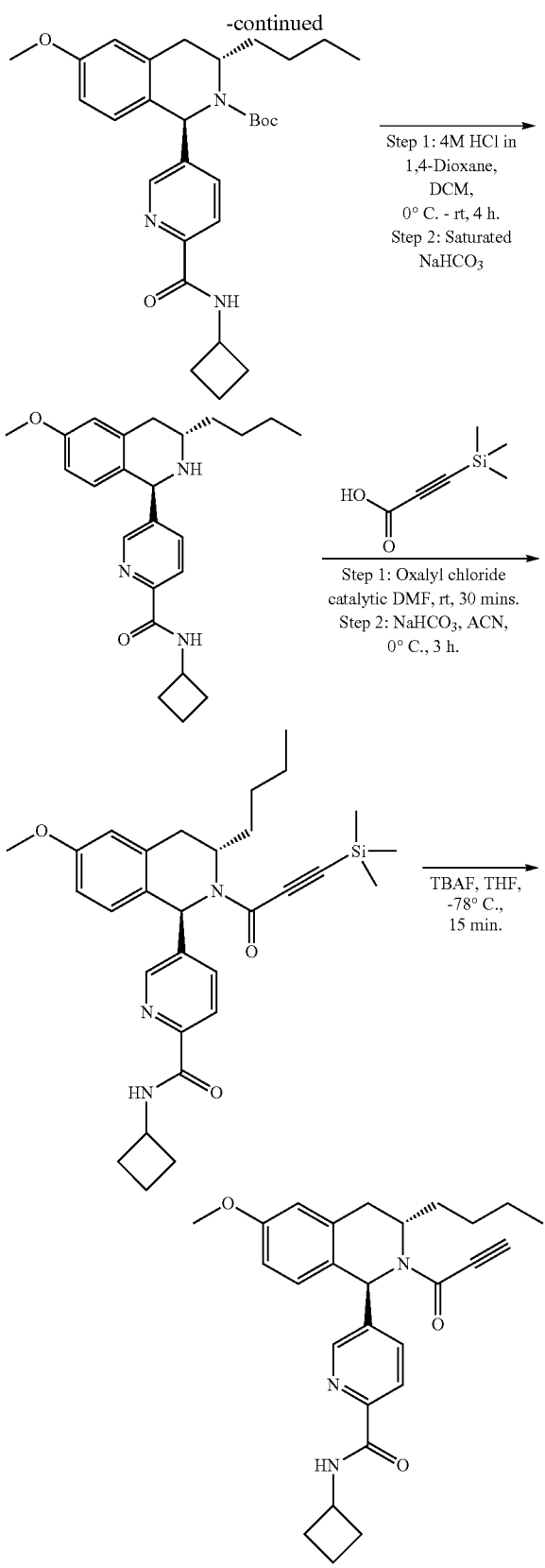

Step 1: 4M HCl in 1,4-Dioxane, DCM, 0° C. - rt, 4 h.
Step 2: Saturated NaHCO₃

Step 1: Oxalyl chloride catalytic DMF, rt, 30 mins.
Step 2: NaHCO₃, ACN, 0° C., 3 h.

TBAF, THF, -78° C., 15 min.

To a solution of (S)-1-(3-methoxyphenyl)hexan-2-amine (0.890 g, 4.29 mmol, 1 eq) and methyl 5-formylpicolinate (0.850 g, 5.15 mmol, 1.2 eq) in toluene (4 mL) was irradiated in microwave at 90° C. for 20 min. After this time, volatile portion was concentrated under reduced pressure and taken forward for cyclization step as such in TFA (4 mL) and irradiated in microwave at 140° C. for 45 min. After this time, volatile portion was concentrated under reduced pressure and obtained crude was diluted with saturated aqueous solution of NaHCO₃ (10 mL) and EtOAc (40 mL). The organic layer was separated, washed with brine (10 mL), dried over anhydrous MgSO₄, filtered and concentrated under reduced pressure to obtain the crude product. The obtained crude product was purified by silica gel flash column chromatography (n-hexane/EtOAc) to give methyl 5-((1R,3S)-3-butyl-6-methoxy-1,2,3,4-tetrahydroisoquinolin-1-yl)picolinate. LC-MS (m/z): 355.4 [M+H]⁺. ¹H NMR (400 MHz, CDCl₃): δ ppm 0.83-0.87 (s, 3H), 1.23-1.25 (m, 6H), 2.58-2.62 (m, 1H), 2.81-2.91 (m, 2H), 3.80 (s, 3H), 3.99 (s, 3H), 5.31 (s, 1H), 6.69-6.71 (m, 2H), 6.67-6.80 (m, 1H), 7.54-7.55 (m, 1H), 8.01-8.03 (m, 1H), 8.67 (s, 1H).

To a solution of compound methyl 5-((1R,3S)-3-butyl-6-methoxy-1,2,3,4-tetrahydroisoquinolin-1-yl)picolinate (0.320 g, 0.18 mmol, 1 eq) in DCM (10 mL) was added triethylamine (0.50 g, 3.61 mmol, 4 eq) and di-tert-butyl dicarbonate (0.394 g, 1.80 mmol, 2 eq) at room temperature and the mixture was stirred for 16 h. TLC (50% EtOAc in hexane) showed the reaction was completed. The reaction mixture was concentrated under reduced pressure, and the crude was diluted with EtOAc (50 mL), washed with water (2×50 mL). The organic layer was dried over anhydrous Na₂SO₄, concentrated under reduced pressure to crude product tert-butyl (1R,3S)-3-butyl-6-methoxy-1-(6-(methoxycarbonyl)pyridin-3-yl)-3,4-dihydroisoquinoline-2(1H)-carboxylate. LC-MS (m/z): 455.0 [M-ᵗBu+H]⁺.

To a solution of compound tert-butyl (1R,3S)-3-butyl-6-methoxy-1-(6-(methoxycarbonyl)pyridin-3-yl)-3,4-dihydroisoquinoline-2(1H)-carboxylate (0.450 g, 0.99 mmol, 1 eq) in a mixture of THF:MeOH:H₂O (9 mL:1 mL) were added Lithium hydroxide (0.208 g, 4.96 mmol, 5 eq) and allowed to stirrer at room temperature for 16 h. TLC (50% EtOAc in hexane) showed the reaction was completed. The reaction mixture was concentrated under reduced pressure, and the crude was acidified with 5% citric acid solution (pH=9). Reaction mixture was diluted with EtOAc (50 mL) and the organic layer was separated and dried over anhydrous Na₂SO₄, concentrated under reduced pressure to give crude product 5-((1R,3S)-2-(tert-butoxycarbonyl)-3-butyl-6-methoxy-1,2,3,4-tetrahydroisoquinolin-1-yl)picolinic acid. LC-MS (m/z): 441.0 [M+H]⁺.

To a solution of compound 5-((1R,3S)-2-(tert-butoxycarbonyl)-3-butyl-6-methoxy-1,2,3,4-tetrahydroisoquinolin-1-yl)picolinic acid (0.300 g, 0.68 mmol, 1 eq) in DCM (10 mL) was added triethylamine (0.38 mL, 2.72 mmol, 4 eq) and cyclobutanamine (0.058 g, 0.817 mmol, 1.2 eq) at 0° C. and the mixture was stirred for 15 min. To the above reaction mixture T3P (50% wt in EtOAc) (0.72 mL, 0.81 mmol, 1.5 eq) was added at the same temperature and stirred for 16 h. TLC (30% EtOAc in hexane) showed the reaction was completed. The reaction mixture was concentrated under reduced pressure, and the crude was diluted with EtOAc (50 mL), washed with water (2×50 mL). The organic layer was dried over anhydrous Na₂SO₄, concentrated under reduced pressure to give crude product tert-butyl (1R,3S)-3-butyl-1-(6-(cyclobutylcarbamoyl)pyridin-3-yl)-6-methoxy-3,4-dihydroisoquinoline-2(1H)-carboxylate. LC-MS (m/z): 494.0 [M-ᵗBu+H]⁺.

To a solution of tert-butyl (1R,3S)-3-butyl-1-(6-(cyclobutylcarbamoyl)pyridin-3-yl)-6-methoxy-3,4-dihydroisoquinoline-2(1H)-carboxylate (0.220 g, 0.445 mmol, 1 eq) in dichloromethane (50 mL) was added 4M HCl in 1,4-dioxane (10 mL, 0.89 mmol, 2 eq) at 0° C. The mixture was allowed to stir at room temperature for 16 h. The progress of the reaction was monitored by TLC, after completion of reaction; the reaction mixture was concentrated under reduced pressure. The obtained crude was dissolved with ice cold water (20 mL) and was basified by saturated aqueous solution of NaHCO$_3$. The compound was extracted with EtOAc (100 mL). Organic layer was washed with brine (10 mL), dried over anhydrous sodium sulfate, filtered and concentrated to obtain 5-((1R,3S)-3-butyl-6-methoxy-1,2,3,4-tetrahydroisoquinolin-1-yl)—N-cyclobutylpicolinamide. LC-MS (m/z): 394.0 [M+H]$^+$.

To 3-(trimethylsilyl)propiolic acid (0.084 g, 0.59 mmol, 1 eq), DMF (0.003 g, 0.048 mmol, 0.04 eq) and oxalyl chloride (0.055 mL, 0.64 mmol, 1.1 eq) was added and stirred for 30 mins. After this time reaction mixture was concentrated under reduced pressure to obtain crude 3-(trimethylsilyl)propioloyl chloride which was diluted with ACN (1 mL) and added to a reaction mixture containing a stirred solution of 5-((1R,3S)-3-butyl-6-methoxy-1,2,3,4-tetrahydroisoquinolin-1-yl)—N-cyclobutylpicolinamide (0.155 g, 0.394 mmol, 1 eq) and NaHCO$_3$ (0.248 g, 2.95 mmol, 7.5 eq) in ACN (5 mL) at 0° C. and stirred for 15 mins. LCMS and TLC (70% EtOAc in hexane) showed the reaction was completed. The reaction was filtered and concentrated under reduced pressure to give the crude product 5-((1R,3S)-3-butyl-6-methoxy-2-(3-(trimethylsilyl)propioloyl)-1,2,3,4-tetrahydroisoquinolin-1-yl)—N-cyclobutylpicolinamide which was taken to next step without further purification. LC-MS (m/z): 518.0 [M+H]$^+$.

To 5-((1R,3S)-3-butyl-6-methoxy-2-(3-(trimethylsilyl)propioloyl)-1,2,3,4-tetrahydroisoquinolin-1-yl)—N-cyclobutylpicolinamide (0.210 g, 0.405 mmol, 1 eq) in THF (10.0 mL) TBAF (1M solution in THF) (0.81 mL, 0.81 mmol, 2 eq) was added and stirred for 30 mins. After this time reaction mixture was concentrated under reduced pressure, diluted with Ethylacetate (100 mL) and was washed with water (2×10 mL). The organic layers were dried over Na$_2$SO$_4$ and concentrated to give to obtain the crude product, which was further purified by preparative TLC chromatography using 70% EtOAc in hexane as an eluent to 5-((1R,3S)-3-butyl-6-methoxy-2-propioloyl-1,2,3,4-tetrahydroisoquinolin-1-yl)—N-cyclobutylpicolinamide.
LC-MS (m/z): 446.2 [M+H]$^+$; HPLC Purity: 99.45%, Chiral HPLC Purity: 99.8%. $^1$H NMR (400 MHz, DMSO-d$_6$): δ 0.79-0.83 (m, 3H), 1.20-1.24 (m, 5H), 1.46 (bs, 1H), 1.57-1.63 (m, 2H), 2.09-2.16 (m, 4H), 2.81-2.95 (m, 1H), 3.15-3.19 (m, 1H), 4.35-4.41 (m, 1H), 4.63 (s, 1H), 4.77 (bs, 1H), 6.15 (s, 0.7H), 6.47 (s, 0.39H), 6.78-6.83 (m, 2H), 7.42-7.44 (m, 1H), 7.78-7.88 (m, 3H), 8.56-8.60 (m, 1H), 8.68-8.70 (m, 1H).

Procedure 11: Synthesis of Compounds 40 and 41

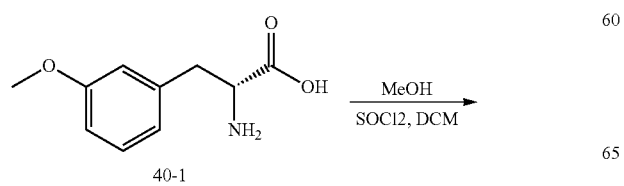

40-1

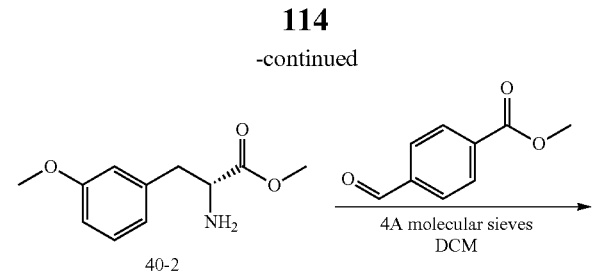

40-2

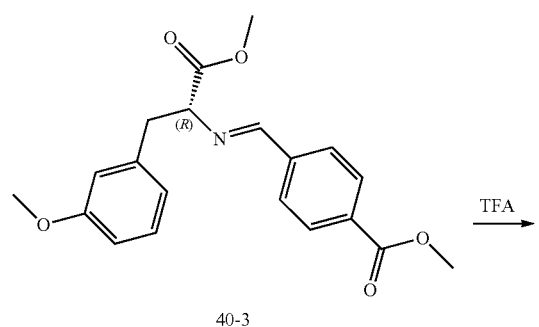

40-3

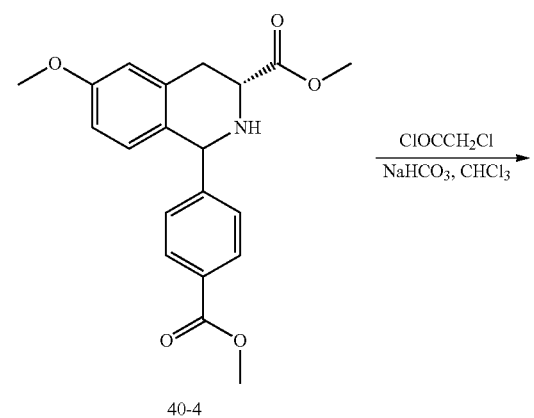

40-4

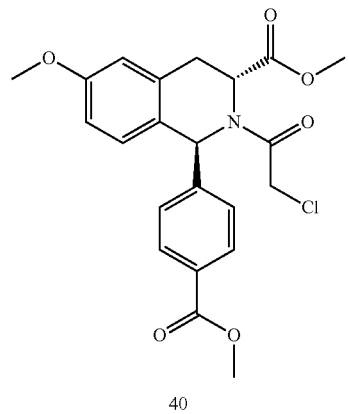

40

115

-continued

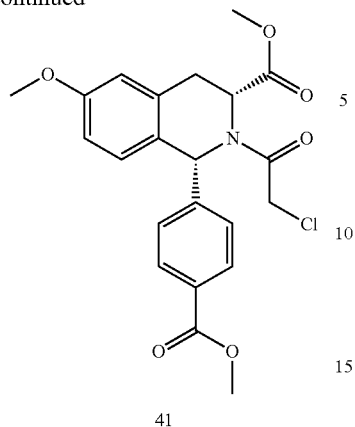

41

To a solution of 40-1 (200 mg, 1.02 mmol, 1 eq) in MeOH (8 mL) was added SOCl₂ (609.43 mg, 5.12 mmol, 371.60 µL, 5 eq) in DCM (1 mL) at 40° C. Then the mixture was stirred at 40° C. for 3 h to give a yellow solution. TLC (quenched with water, eluting with: PE/MeOH=20/1) showed the reaction was completed. The mixture was concentrated under reduced pressure to give 40-2.

To a solution of 40-2 (80 mg, 382.33 umol, 1 eq), 4A MS (700 mg, 382.33 umol, 1 eq) and methyl 4-formylbenzoate (62.76 mg, 382.33 umol, 1 eq) in DCM (15 mL) at 20° C. with stirring for 0.5 h to give a yellow solution. TLC (eluting with: PE/EA=3/1) showed the reaction was completed. The reaction solution was diluted with DCM (10 mL), washed with water (10 mL*3). The organic layer was dried over anhydrous Na₂SO₄, concentrated under reduced pressure to give 40-3.

To a solution of 40-3 (150 mg, 422.08 umol, 1 eq) in TFA (4.81 g, 42.21 mmol, 3.13 mL, 100 eq) was stirred at 80° C. for 16 h to give a yellow solution. TLC (quenched with water, eluting with: PE/EA=3/1) showed the reaction was completed. The reaction solution was diluted with DCM (10 mL), washed with NaHCO₃ solution until pH=8. The organic layer was dried over anhydrous Na₂SO₄, concentrated under reduced pressure to give 40-4.

To a solution of 40-4 (150 mg, 422.08 umol, 1 eq) and Et₃N (85.42 mg, 844.16 umol, 117.50 µL, 2 eq) in DCM (5 mL) was added 2-chloroacetyl chloride (71.51 mg, 633.12 umol, 50.36 µL, 1.5 eq) at 0° C. for 1 h to give a yellow solution. TLC (quenched with water, eluting with: PE/EA=3/1) showed the reaction was completed. The reaction was purified by prep-TLC to give 40 and 41.

Compound 40: LC-MS (m/z): 432.0[M]⁺. ¹H NMR (400 MHz, CHLOROFORM-d) δ ppm 3.08-3.13 (m, 1H) 3.28 (br s, 1H) 3.59 (s, 4H) 3.77 (s, 4H) 3.85-3.90 (m, 5H) 3.93-3.99 (m, 1H) 4.07 (br s, 1H) 4.11-4.18 (m, 1H) 5.17 (br s, 1H) 5.28 (br s, 1H) 6.13 (s, 1H) 6.42 (s, 1H) 6.61-6.69 (m, 2H) 6.77-6.86 (m, 2H) 7.28-7.36 (m, 5H) 7.91 (br d, J=8.28 Hz, 1H) 7.98 (br d, J=8.03 Hz, 2H).

Compound 41: LC-MS (m/z): 432.0[M]⁺. ¹H NMR (400 MHz, CHLOROFORM-d) δ ppm 2.59-2.71 (m, 1H) 2.99 (brdd, J=14.81, 4.52 Hz, 1H) 3.20 (brs, 1H) 3.33 (brs, 1H) 3.79 (s, 3H) 3.77-3.80 (m, 1H) 3.83 (s, 4H) 3.89 (s, 4H) 4.07-4.26 (m, 3H) 4.40 (br dd, J=12.92, 4.64 Hz, 1H) 4.68-4.77 (m, 1H) 4.73 (br s, 1H) 6.10 (s, 1H) 6.76-6.85 (m, 2H) 6.89 (br d, J=8.53 Hz, 1H) 7.00 (br d, J=7.28 Hz, 2H) 7.35 (br d, J=8.28 Hz, 1H) 7.63 (br d, J=8.28 Hz, 2H) 7.89 (br d, J=7.53 Hz, 1H) 7.99 (br d, J=8.28 Hz, 2H).

116

Procedure 12: Synthesis of Compounds 42 and 43

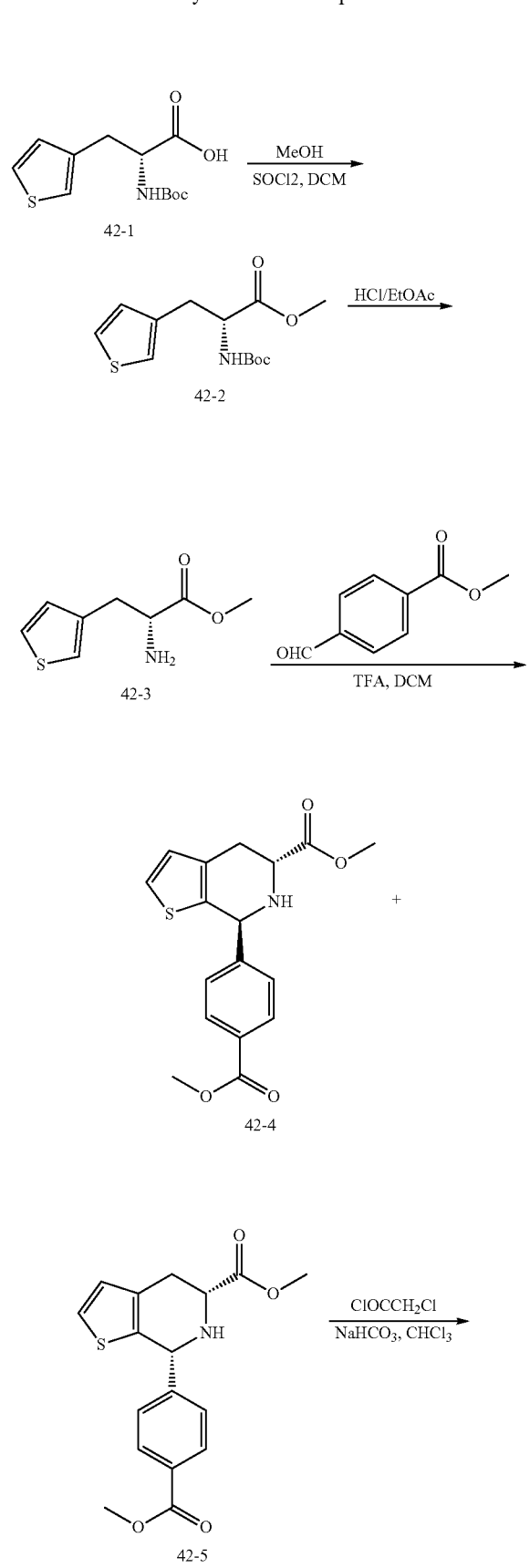

-continued

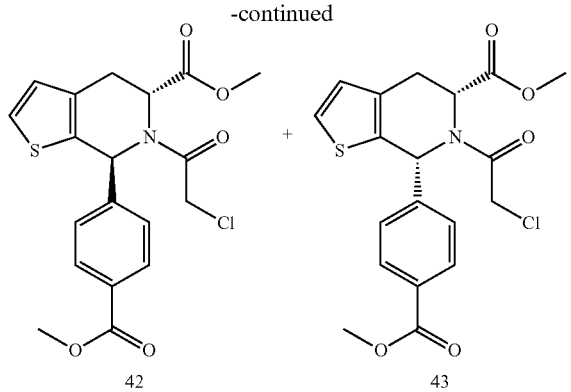

Procedure 13: Synthesis of Compounds 44 and 45

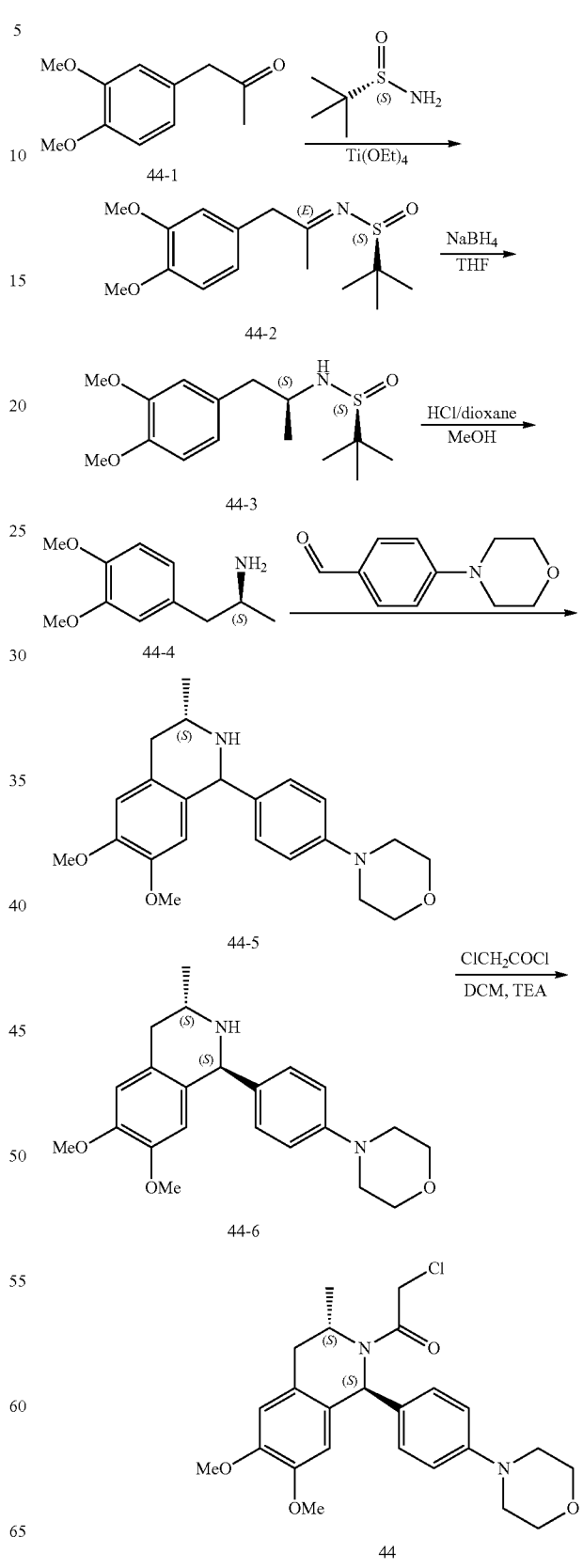

To a solution of 42-1 (150 mg, 552.83 umol, 1 eq) in MeOH (4 mL) was added SOCl$_2$ (65.77 mg, 552.83 umol, 40.10 μL, 1 eq) in DCM (1 mL). The mixture was stirred at 30° C. for 16 h to give a colorless solution. TLC showed the reaction was completed. The reaction mixture was distilled (40° C.) to give 42-3 (HCl salt). $^1$H NMR (400 MHz, CHLOROFORM-d) δ ppm 2.25 (br s, 5H) 3.44 (br d, J=4.52 Hz, 2H) 3.75 (s, 3H) 4.40 (br s, 1H) 6.97 (br d, J=4.52 Hz, 1H) 7.28 (br s, 1H) 7.33 (br s, 1H) 8.61 (br s, 3H)

To a solution of 42-3 (50 mg, 269.92 umol, 1 eq) and methyl 4-formylbenzoate (44.31 mg, 269.92 umol, 1 eq) in toluene (3 mL) was added TFA (15.39 mg, 134.96 umol, 9.99 μL, 0.5 eq) at 20° C. The mixture was stirred at 80° C. for 16 h to give a yellow solution. TLC showed the reaction was completed. The reaction mixture was purified by prep-TLC to give 42-4 and 42-5. $^1$H NMR (400 MHz, CHLOROFORM-d) δ ppm 2.96-3.05 (m, 1H) 3.10-3.18 (m, 1H) 3.73 (s, 3H) 3.83-3.88 (m, 1H) 3.86 (dd, J=7.15, 5.65 Hz, 1H) 3.91 (s, 3H) 5.44 (s, 1H) 6.85 (d, J=5.02 Hz, 1H) 7.19 (d, J=5.02 Hz, 1H) 7.40 (d, J=8.28 Hz, 2H) 8.00 (d, J=8.28 Hz, 2H).

To a solution of 42-4 (40 mg, 120.71 umol, 1 eq) and TEA (18.32 mg, 181.06 umol, 25.20 μL, 1.5 eq) in DCM (3 mL) was added 2-chloroacetyl chloride (20.45 mg, 181.06 umol, 14.40 μL, 1.5 eq) at 0° C. The mixture was stirred at 30° C. for 1 h to give a yellow solution. TLC (quenched with water, eluting with: PE/EA=0/1) showed the reaction was completed. The reaction was purified by prep-TLC to give 42. $^1$H NMR (400 MHz, CHLOROFORM-d) δ ppm 3.02-3.59 (m, 2H) 3.60-3.70 (m, 3H) 3.88 (br d, J=5.52 Hz, 3H) 4.06 (br d, J=13.30 Hz, 1H) 5.03-5.27 (m, 1H) 6.27 (br s, 1H) 6.77 (d, J=5.02 Hz, 1H) 7.09-7.20 (m, 1H) 7.32-7.52 (m, 2H) 7.88-8.10 (m, 2H). LC-MS (m/z): 407.9[M]$^+$.

To a solution of 42-5 (60.00 mg, 181.06 umol, 1 eq) and TEA (27.48 mg, 271.59 umol, 37.80 μL, 1.5 eq) in DCM (3 mL) was added 2-chloroacetyl chloride (30.67 mg, 271.59 umol, 21.60 μL, 1.5 eq) at 0° C. The mixture was stirred at 30° C. for 1 h to give a yellow solution. TLC (quenched with water, eluting with: PE/EA=3/1) showed the reaction was completed. The mixture was re-purified by prep-TLC to give 43. $^1$H NMR (400 MHz, CHLOROFORM-d) δ ppm 2.01 (s, 1H) 2.99-3.17 (m, 5H) 3.56 (br d, J=16.06 Hz, 1H) 3.89 (s, 4H) 4.18 (d, J=12.30 Hz, 1H) 4.30 (br s, 1H) 4.87 (br s, 1H) 6.88-7.05 (m, 2H) 7.28 (br s, 1H) 7.39 (br s, 2H) 7.94 (br s, 2H). LC-MS (m/z): 407.9[M]$^+$.

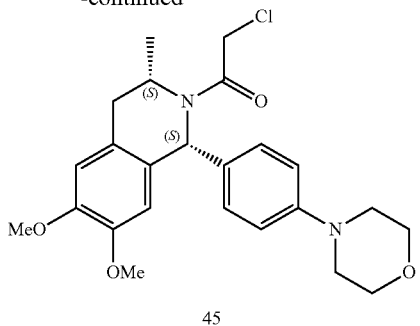

45

To this solution of 2-methylpropane-2-sulfinamide (6.24 g, 51.49 mmol, 2 eq) in THF (120 mL) was added Ti(OEt)$_4$ (58.72 g, 257.43 mmol, 53.38 mL, 10 eq), 44-1 (5 g, 25.74 mmol, 1 eq) in THF (100 mL). The brown solution was heated to 75° C. and monitored by TLC. After 5 hrs the reaction was allowed to cool to 25° C. to give crude 44-2. The reaction was then cooled down to −20° C., NaBH$_4$ (973.93 mg, 25.74 mmol, 1 eq) was added and the reaction was stirred for 3 hr at −20° C., then warmed to 25° C. and stirred for 12 hrs. LCMS showed the reaction was completed. An equal volume of sat. aq. NaCl (60 mL) was added to precipitate titanium salts. After stirring for 5 min, the suspension was filtered through celite and the filter cake was washed with EtOAc (100 mL×2). The organic layers were separated, and the aqueous layer was extracted with EtOAc (2×100 mL). The combined organic layers were dried over anhydrous sodium sulfate, and concentrated to yield a residue. The residue was purified by flash chromatography (silica) eluting with ethyl acetate in petroleum ether (0% to 80%) to give 44-3. $^1$H NMR (400 MHz, CDCl$_3$) δ=6.77-6.62 (m, 3H), 3.80 (d, J=4.8 Hz, 6H), 3.64-3.49 (m, 1H), 3.18 (br d, J=4.8 Hz, 1H), 2.78-2.59 (m, 2H), 1.14-1.05 (m, 12H).

To a mixture of 44-3 (2 g, 6.68 mmol, 1 eq) in MeOH (20 mL) was added HCl/dioxane (4 M, 20 mL, 11.98 eq) dropwise. The mixture was stirred at 20° C. for 12 h to give brown mixture. LCMS showed the reaction was completed. The reaction mixture was diluted with 60 mL HCl (0.1 M). The resulting mixture was extracted with ethyl acetate (30 mL×2). The aqueous phase was adjust pH=8. The aqueous phase was extracted with ethyl acetate (30 mL×3). The combined organic phase dried with anhydrous Na$_2$SO$_4$, filtered and concentrated in vacuum to afford 44-4. $^1$H NMR (400 MHz, CDCl$_3$) δ=6.78-6.83 (m, 1H), 6.70-6.75 (m, 2H), 3.86 (d, J=4.4 Hz, 6H), 3.07-3.21 (m, 1H), 2.78-2.59 (m, 2H), 2.67 (m, 1H), 2.44 (m, 1H), 1.64 (brs, 2H), 1.12 (d, J=6.4 Hz, 3H).

4A molecular sieve (3 g, 2.56 mmol, 1 eq) was added to a solution of 44-4 (500 mg, 2.56 mmol, 1 eq) and 4-morpholinobenzaldehyde (489.68 mg, 2.56 mmol, 1 eq) in toluene (20 mL), the mixture was stirred at 120° C. for 4 hr. LCMS showed starting material was not consumed completely. The reaction mixture was stirred at 120° C. for another 4 h. LCMS showed starting material was consumed completely. The reaction mixture was filtered and the filter was concentrated in vacuum. The residue was dissolved in TFA (32.58 g, 285.73 mmol, 21.16 mL, 111.58 eq) and the solution was heated at 120° C. for 20 h. LC-MS showed starting material was consumed completely. The reaction mixture was concentrated under reduced pressure. The mixture was adjust to pH=9 by 2N NaOH aqueous solution and extracted with EtOAc (30 mL×3). The combined organic layers were washed with brine (30 mL), dried over anhydrous sodium sulfate, filtered and concentrated under reduced pressure to give a residue. The residue was purified by column chromatography (SiO$_2$, Dichloromethane:Methanol=100:1 to 100:5) to afford N136-6 and 44-5. $^1$H NMR (400 MHz, CHLOROFORM-d) δ ppm 1.25 (d, J=6.4 Hz, 3H), 2.58-2.80 (m, 2H), 3.12-3.22 (m, 5H), 3.57-3.64 (m, 3H), 3.84-3.91 (m, 7H), 5.01 (s, 1H), 6.18-6.25 (m, 1H), 6.57-6.66 (m, 1H), 6.89 (d, J=8.8 Hz, 2H), 7.23 (d, J=8.8 Hz, 2H).

To a mixture of 44-6 (122 mg, 331.10 umol, 1 eq) and TEA (335.04 mg, 3.31 mmol, 460.85 µL, 10 eq) in DCM (6 mL) was added 2-chloroacetyl chloride (112.19 mg, 993.30 umol, 79.00 µL, 3 eq) at 0° C. The mixture was stirred at 0° C. for 30 min to give a brown mixture. LCMS showed starting material was consumed completely. The reaction mixture was concentrated in reduced pressure to give a residue. The residue was purified by prep-TLC and then dried by lyophilization to afford 44 and 45.

Compound 44: LC-MS (m/z): 445.0 [M+H]$^+$ $^1$H NMR (400 MHz, CHLOROFORM-d) δ 0.99 (br s, 3H), 2.41 (br d, J=14.8 Hz, 1H), 2.80-3.28 (m, 5H), 3.60-4.57 (m, 12H), 4.83 (br s, 1H), 5.74 (br s, 1H), 6.57 (s, 1H), 6.65-6.90 (m, 3H), 7.03 (d, J=8.8 Hz, 2H)

Compound 45: LC-MS (m/z): 445.0 [M+H]$^+$ $^1$H NMR (400 MHz, CHLOROFORM-d) δ 0.99 (br s, 3H), 2.41 (br d, J=14.8 Hz, 1H), 2.80-3.28 (m, 5H), 3.60-4.57 (m, 12H), 4.83 (br s, 1H), 5.74 (br s, 1H), 6.57 (s, 1H), 6.65-6.90 (m, 3H), 7.03 (d, J=8.8 Hz, 2H)

Procedure 14: Synthesis of Compound 46

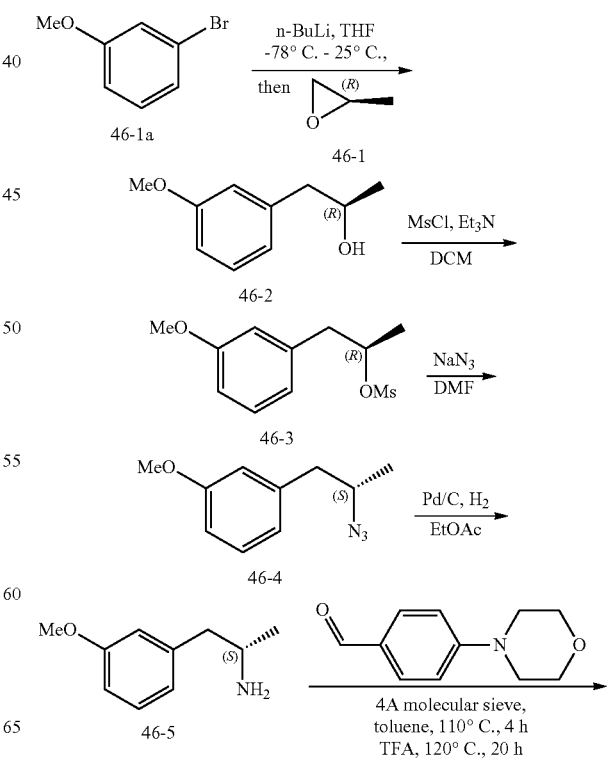

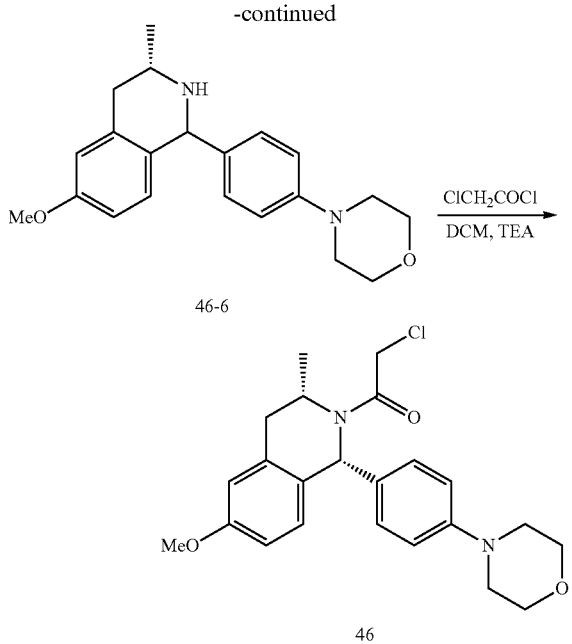

To a solution of 46-1a (5 g, 26.73 mmol, 3.38 mL, 1 eq) in THF (150 mL) at −78° C. was added n-BuLi (2.5 M, 16.04 mL, 1.5 eq) dropwise. After stirring 30 min, 46-1 (1.71 g, 29.41 mmol, 2.06 mL, 1.1 eq) was added all at once. The mixture was stirred at −78° C. for 1 hr, then warmed to 25° C. and stirred for 12 hr. TLC showed the reaction was completed. The reaction was quenched by adding saturated $NH_4Cl$ (50 mL) aqueous solution. The aqueous phase was extracted with ethyl acetate (3×50 mL) and the combined organic layers were washed with brine (100 mL), dried over anhydrous $Na_2SO_4$, filtered and concentrated under reduced pressure. The crude product was purified by flash chromatography (silica) eluting with ethyl acetate in petroleum ether (0% to 30%) to give 46-2. $^1$H NMR (400 MHz, $CDCl_3$) δ=7.15 (t, J=8.0 Hz, 1H), 6.79-6.59 (m, 3H), 3.99-3.89 (m, 1H), 3.72 (s, 3H), 2.74-2.53 (m, 2H), 1.63 (br s, 1H), 1.19-1.14 (m, 1H), 1.17 (d, J=6.0 Hz, 2H).

To a solution of 46-2 (1 g, 6.02 mmol, 1 eq) and $Et_3N$ (1.83 g, 18.05 mmol, 2.51 mL, 3 eq) in DCM (20 mL) at 0° C. was added MsCl (1.03 g, 9.02 mmol, 698.48 μL, 1.5 eq). The mixture was stirred at 25° C. for 1 h. TLC showed the reaction was completed. The reaction was poured into sat. aq. $NaHCO_3$ (50 mL) solution, the mixture was extracted with $CH_2Cl_2$ (3×50 mL). The combined organic layers were washed with brine (50 mL), dried over anhydrous sodium sulfate, filtered and concentrated under reduced pressure to give 46-3, which was used for next step directly without further purification. $^1$H NMR (400 MHz, $CDCl_3$) δ=7.22-7.12 (m, 1H), 6.82-6.62 (m, 3H), 4.89-4.73 (m, 1H), 3.73 (s, 3H), 2.95-2.74 (m, 2H), 2.49 (s, 3H), 1.40 (d, J=6.0 Hz, 3H).

To a solution of 46-3 (1.5 g, 6.14 mmol, 1 eq) in DMF (8 mL) was added $NaN_3$ (798.30 mg, 12.28 mmol, 2 eq). The mixture was heated at 80° C. for 2 h. TLC showed the reaction was completed. 90 mL of water was added, the mixture was extracted with 120 mL of EtOAc/hexane (1:1) mixture. The extract was dried over anhydrous $Na_2SO_4$ and evaporated to give crude 46-4, which was used for next step directly without further purification.

To a solution of 46-4 (1.1 g, 5.75 mmol, 1 eq) in EtOAc (100 mL) was added Pd/C (500 mg, 10% purity) under $N_2$. The suspension was degassed under vacuum and purged with $H_2$ several times. The mixture was stirred under $H_2$ (15 psi) at 25° C. for 1 hours. TLC showed the reaction was completed. The reaction mixture was filtered and the filter was concentrated. The crude product was purified by flash chromatography (silica) eluting with MeOH in $CH_2Cl_2$ (0% to 20%) to give 46-5. $^1$H NMR (400 MHz, $CDCl_3$) δ=7.20-7.08 (m, 1H), 6.74-6.61 (m, 3H), 3.72 (s, 3H), 3.17-3.03 (m, 1H), 2.62 (dd, J=5.6, 13.6 Hz, 1H), 2.42 (dd, J=8.0, 13.2 Hz, 1H), 1.42 (s, 2H), 1.05 (d, J=6.4 Hz, 3H).

4A MS (600 mg) was added to a solution of 46-5 (100 mg, 605.21 umol, 1 eq) and 4-morpholinobenzaldehyde (115.73 mg, 605.21 umol, 1 eq) in toluene (4 mL) and the mixture was stirred at 120° C. for 4 hrs. The reaction mixture was filtered and the filter was concentrated in vacuum. The residue was dissolved in TFA (5.00 mL) and the solution was heated at 120° C. for 20 hrs. TLC showed the reaction was completed. The reaction mixture was concentrated under reduced pressure. The mixture was basified by 2N NaOH aqueous solution and extracted with EtOAc (30 mL×3). The combined organic layers were washed with brine (30 mL), dried over anhydrous sodium sulfate, filtered and concentrated under reduced pressure to give 46-6, which was used for next step directly without further purification. $^1$H NMR (400 MHz, $CDCl_3$) δ=7.19-7.13 (m, 2H), 6.80 (d, J=8.4 Hz, 2H), 6.58-6.47 (m, 3H), 4.93 (s, 1H), 3.80-3.77 (m, 4H), 3.69 (s, 3H), 3.16-3.11 (m, 1H), 3.10-3.05 (m, 4H), 2.71-2.63 (m, 2H), 1.97 (s, 1H), 1.16 (d, J=6.0 Hz, 3H)

To a solution of 46-6 (250.00 mg, 738.68 umol, 1 eq) and $Et_3N$ (224.24 mg, 2.22 mmol, 308.45 μL, 3 eq) in DCM (5 mL) at 0° C. was added 2-chloroacetyl chloride (166.86 mg, 1.48 mmol, 117.51 μL, 2 eq). The mixture was stirred at 25° C. for 1 h. LCMS showed the reaction was completed. The reaction was poured into sat. $NaHCO_3$ (50 mL) solution, the mixture was extracted with $CH_2Cl_2$ (3×50 mL). The combined organic layers were washed with brine (50 mL), dried over anhydrous sodium sulfate, filtered and concentrated under reduced pressure. The residue was purified by flash chromatography (silica) eluting with ethyl acetate in petroleum ether (0% to 40%) to give 46. $^1$H NMR (400 MHz, DMSO-$d_6$) δ=7.15 (br d, J=8.8 Hz, 1H), 7.00 (d, J=8.4 Hz, 2H), 6.90-6.79 (m, 4H), 6.31 (br s, 1H), 4.53-4.35 (m, 2H), 4.28-4.18 (m, 1H), 3.79 (s, 3H), 3.76-3.70 (m, 2H), 3.76-3.70 (m, 1H), 3.76-3.70 (m, 1H), 3.12-3.08 (m, 4H), 3.01-2.93 (m, 1H), 2.49-2.37 (m, 1H), 1.14 (d, J=6.4 Hz, 3H).

Procedure 15: Synthesis of Compound 47

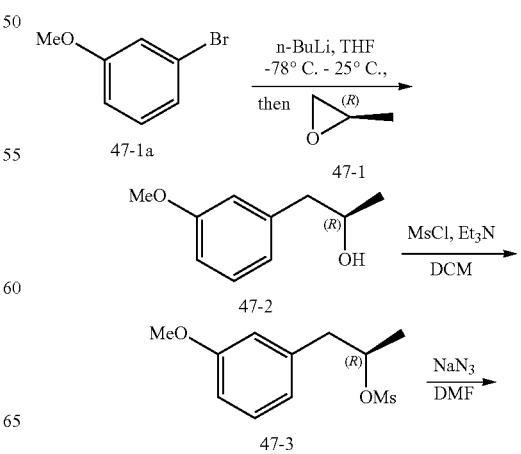

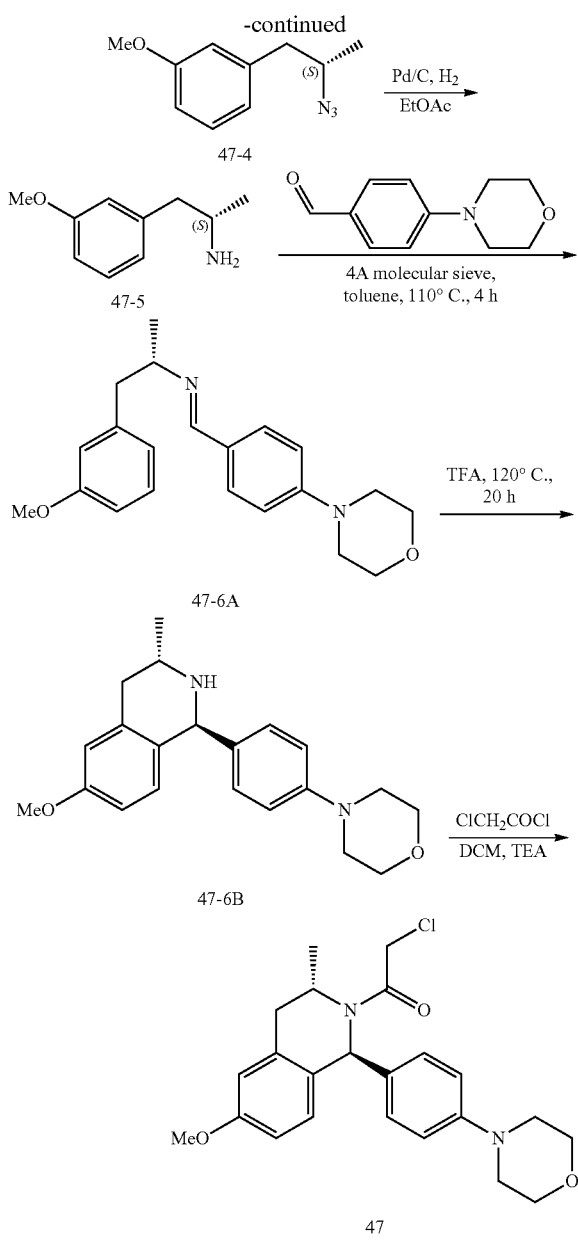

C. was added MsCl (1.03 g, 9.02 mmol, 698.48 μL, 1.5 eq). The mixture was stirred at 25° C. for 1 h. TLC showed the reaction was completed. The reaction was poured into sat. aq. NaHCO$_3$ (50 mL) solution, the mixture was extracted with CH$_2$Cl$_2$ (3×50 mL). The combined organic layers were washed with brine (50 mL), dried over anhydrous sodium sulfate, filtered and concentrated under reduced pressure to give 47-3, which was used for next step directly without further purification. $^1$H NMR (400 MHz, CDCl$_3$) δ=7.22-7.12 (m, 1H), 6.82-6.62 (m, 3H), 4.89-4.73 (m, 1H), 3.73 (s, 3H), 2.95-2.74 (m, 2H), 2.49 (s, 3H), 1.40 (d, J=6.0 Hz, 3H).

To a solution of 47-3 (1.5 g, 6.14 mmol, 1 eq) in DMF (8 mL) was added NaN$_3$ (798.30 mg, 12.28 mmol, 2 eq). The mixture was heated at 80° C. for 2 h. TLC showed the reaction was completed. 90 mL of water was added, the mixture was extracted with 120 mL of EtOAc/hexane (1:1) mixture. The extract was dried over anhydrous Na$_2$SO$_4$ and evaporated to give crude 47-4, which was used for next step directly without further purification.

To a solution of 47-4 (1.1 g, 5.75 mmol, 1 eq) in EtOAc (100 mL) was added Pd/C (500 mg, 10% purity) under N$_2$. The suspension was degassed under vacuum and purged with H$_2$ several times. The mixture was stirred under H$_2$ (15 psi) at 25° C. for 1 hours. TLC showed the reaction was completed. The reaction mixture was filtered and the filter was concentrated. The crude product was purified by flash chromatography (silica) eluting with MeOH in CH$_2$Cl$_2$ (0% to 20%) to give 47-5. $^1$H NMR (400 MHz, CDCl$_3$) δ=7.20-7.08 (m, 1H), 6.74-6.61 (m, 3H), 3.72 (s, 3H), 3.17-3.03 (m, 1H), 2.62 (dd, J=5.6, 13.6 Hz, 1H), 2.42 (dd, J=8.0, 13.2 Hz, 1H), 1.42 (s, 2H), 1.05 (d, J=6.4 Hz, 3H).

4A molecular sieve (3 g, 3.03 mmol, 1.00 eq) was added to a solution of 47-5 (500 mg, 3.03 mmol, 1 eq) and 4-morpholinobenzaldehyde (578.66 mg, 3.03 mmol, 1 eq) in toluene (25 mL), the mixture was stirred at 120° C. for 4 hr. LCMS showed the reaction was completed. After cooling to room temperature, the mixture was filtered and the filtrate to concentrated to a small volume under vacuum to give crude N135-6A, which was used for next step directly without further purification.

47-6A (1 g, 2.95 mmol, 1 eq) was dissolved in TFA (46.20 g, 405.19 mmol, 30.00 mL, 137.13 eq), the solution was heated at 120° C. for 20 hrs to give a brown solution. LCMS showed the reaction was completed. The reaction mixture was concentrated under reduced pressure. The mixture was basified by 2N NaOH aqueous solution and extracted with EtOAc (50 mL×3). The combined organic layers were washed with brine (50 mL), dried over anhydrous sodium sulfate, filtered and concentrated under reduced pressure. The residue was purified by flash chromatography (silica) eluting with MeOH in CH$_2$Cl$_2$ (0% to 5%). The crude product was purified by prep-TLC (DCM/MeOH=10/1, Rf1=0.5, Rf2=0.45) to give cis-product as major product.

Trace trans-product was obtained by further prep-TLC purification (95% purity) and the structure was confirmed by 2D NMR clearly.

To a solution of 47-6B (10 mg, 29.55 umol, 1 eq) and Et$_3$N (8.97 mg, 88.64 umol, 12.34 μL, 3 eq) in DCM (2 mL) at 0° C. was added 2-chloroacetyl chloride (6.67 mg, 59.09 umol, 4.70 μL, 2 eq). The mixture was stirred at 25° C. for 1 h to give brown solution. LCMS showed the reaction was completed. The reaction was concentrated under reduced pressure. The residue was purified by prep-TLC (PE/EA=2/1, Rf=0.4) to give 47. $^1$H NMR (400 MHz, CDCl$_3$) δ=7.24 (br d, J=8.0 Hz, 1H), 7.02 (d, J=8.4 Hz, 2H), 6.78-6.69 (m, 3H), 6.61 (s, 1H), 5.78 (br s, 1H), 4.84 (br s, 1H), 4.04 (br d, J=12.4 Hz, 1H), 3.81 (br d, J=12.4 Hz, 1H), 3.77-3.73 (m, To a solution of 47-1a (5 g, 26.73 mmol, 3.38 mL, 1 eq) in THF (150 mL) at −78° C. was added n-BuLi (2.5 M, 16.04 mL, 1.5 eq) dropwise. After stirring 30 min, 47-1 (1.71 g, 29.41 mmol, 2.06 mL, 1.1 eq) was added all at once. The mixture was stirred at −78° C. for 1 hr, then warmed to 25° C. and stirred for 12 hr. TLC showed the reaction was completed. The reaction was quenched by adding saturated NH$_4$Cl (50 mL) aqueous solution. The aqueous phase was extracted with ethyl acetate (3×50 mL) and the combined organic layers were washed with brine (100 mL), dried over anhydrous Na$_2$SO$_4$, filtered and concentrated under reduced pressure. The crude product was purified by flash chromatography (silica) eluting with ethyl acetate in petroleum ether (0% to 30%) to give 47-2. $^1$H NMR (400 MHz, CDCl$_3$) δ=7.15 (t, J=8.0 Hz, 1H), 6.79-6.59 (m, 3H), 3.99-3.89 (m, 1H), 3.72 (s, 3H), 2.74-2.53 (m, 2H), 1.63 (br s, 1H), 1.19-1.14 (m, 1H), 1.17 (d, J=6.0 Hz, 2H).

To a solution of 47-2 (1 g, 6.02 mmol, 1 eq) and Et$_3$N (1.83 g, 18.05 mmol, 2.51 mL, 3 eq) in DCM (20 mL) at 0°

4H), 3.72 (s, 3H), 3.06-2.99 (m, 4H), 2.96 (br s, 1H), 2.44 (br d, J=16.0 Hz, 1H), 0.97 (br d, J=5.6 Hz, 3H).

Procedure 16: Synthesis of Compound 39

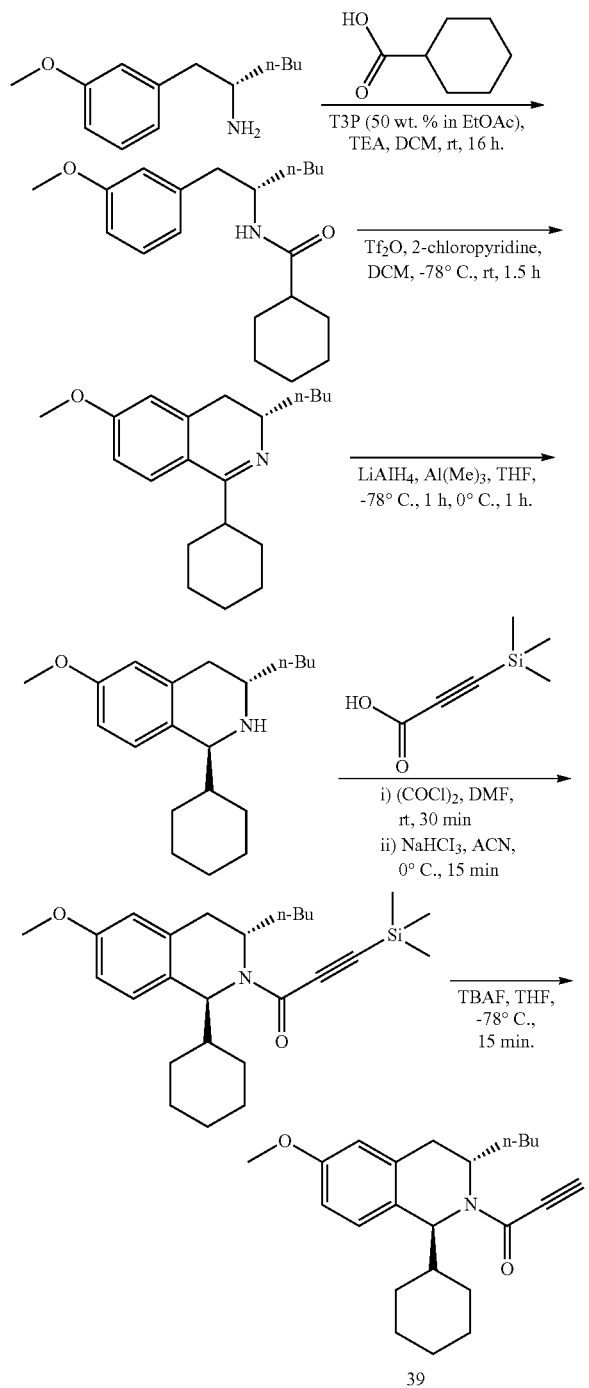

39

(S)—N—(1-(3-methoxyphenyl)hexan-2-yl)cyclohexanecarboxamide: To a solution of cyclohexanecarboxylic acid (0.78 g, 6.11 mmol, 1.15 eq) in DCM (15 mL) was added TEA (2.14 g, 21.24 mmol, 4 eq), stirred for 5 minutes, and then T3P (50 wt. % in EtOAc) (2.53 g, 7.96 mmol, 1.5 eq) was added at 0° C. and stirred for another 5 minutes. (S)-1-(3-methoxyphenyl)hexan-2-amine (1.1 g, 5.31 mmol, 1 eq) was added to the reaction mixture and the reaction mixture was stirred at room temperature for 16 hours. The progress of the reaction was monitored by TLC (20% ethyl acetate in hexane). The reaction mixture was diluted with DCM (50 mL) and saturated sodium bicarbonate solution (20 mL), the organic layer was separated, washed with brine solution (20 mL), dried over anhydrous sodium sulfate, filtered and concentrated under reduced pressure to obtain (S)—N—(1-(3-methoxyphenyl)hexan-2-yl)cyclohexanecarboxamide. LC-MS (m/z)=318.3 [M+H]$^+$.

$^1$H NMR (400 MHz, CDCl$_3$) δ ppm 0.84-0.92 (m, 3H), 1.16-1.38 (m, 9H), 1.49-1.51 (m, 1H), 1.65-1.80 (m, 6H), 1.92-2.03 (m, 1H), 2.70-2.79 (m, 2H), 3.78 (s, 3H), 4.12-4.17 (m, 1H), 5.11 (d, J=8.4 Hz, 1H), 6.70-6.75 (m, 3H), 7.18 (t, J=7.8 Hz, 1H).

(S)-3-butyl-1-cyclohexyl-6-methoxy-3,4-dihydroisoquinoline: Trifluoromethanesulfonic anhydride (1.45 mL, 8.64 mmol, 2.0 eq) was added via syringe over a period of 1 minute to a stirred mixture of (S)—N—(1-(3-methoxyphenyl)hexan-2-yl)cyclohexanecarboxamide (1.37 g, 4.32 mmol, 1 eq) and 2-chloropyridine (0.81 mL, 8.64 mmol, 2.0 eq) in dichloromethane (13 mL) at −78° C. After 5 minutes, the reaction mixture was placed in an ice-water bath and warmed to 0° C. After 5 minutes, the resulting solution was allowed to warm to 23° C. After 1 h, aqueous sodium hydroxide solution (5 mL, 1N) was introduced to neutralize the trifluoromethanesulfonate salts. Dichloromethane (50 mL) was added to dilute the mixture and the layers were separated. The organic layer was washed with brine (10 mL), was dried over anhydrous sodium sulfate, and was filtered. The volatiles were removed under reduced pressure to give the crude product. The obtained crude product was taken forward to next step without further purification. LC-MS (m/z)=300.3 [M+H]$^+$.

(1S,3S)-3-butyl-1-cyclohexyl-6-methoxy-1,2,3,4-tetrahydroisoquinoline: A solution of the (S)-3-butyl-1-cyclohexyl-6-methoxy-3,4-dihydroisoquinoline (1.37 g, 4.58 mmol, 1 eq) in anhydrous THF (20 mL) was added drop wise to a mixture of lithium aluminum hydride 1M in THF (22.9 mL, 22.90 mmol, 5.0 eq) and trimethylaluminum 2M solution in toluene (11.45 mL, 22.90 mmol, 5 eq) in THF (20 mL) at −78° C. under nitrogen atmosphere. The suspension was stirred at −78° C. for 1 h, and warmed to 0° C. over 30 minutes. The reaction mixture was quenched with saturated aqueous sodium chloride (5 mL) followed by diluted with EtOAc (30 mL) and the obtained precipitate was filtered off. Finally, filtrate was dried over anhydrous sodium sulfate, filtered and evaporated under reduced pressure. The residue was purified by flash chromatography (EtOAc/n-hexane=20/80) to give the (1S,3S)-3-butyl-1-cyclohexyl-6-methoxy-1,2,3,4-tetrahydroisoquinoline (trans isomer confirmed by nOe experiment). The isolated pure product was treated with metal scavenger QuadraSil® AP (compound was dissolved in THF (10 mL) and QuadraSil® AP (1 g) was added, the mixture was stirred for 0.5 h, filtered. This is repeated one more time and concentrated). LC-MS (m/z)=302.3 [M+H]$^+$ $^1$H NMR (400 MHz, CDCl$_3$) δ ppm 0.90-0.93 (m, 3H), 1.02-1.04 (m, 1H), 1.17 (bs, 3H), 1.25-1.29 (m, 1H), 1.34-1.35 (s, 3H), 1.36-1.42 (m, 3H), 1.66-1.68 (m, 3H), 1.68-1.77 (m, 3H), 2.41-2.47 (m, 1H), 2.80-2.85 (m, 1H), 3.10 (bs, 1H), 3.58 (d, J=6.4 Hz, 1H), 3.76 (s, 3H), 6.60 (s, 1H), 6.66 (d, J=8.4 Hz, 1H), 6.98 (d, J=8.4 Hz, 1H).

1-((1S,3S)-3-butyl-1-cyclohexyl-6-methoxy-3,4-dihydroisoquinolin-2(1H)-yl)-3-(trimethylsilyl)prop-2-yn-1-one: First step:— To a solution of 3-(trimethylsilyl)propiolic acid (141 mg, 0.99 mmol, 1.5 eq) in DMF (1.9 mg, 0.026 mmol, 0.04 eq) was added oxalyl chloride (0.13 g, 1.05 mmol, 1.6 eq) at room temperature and stirred for 30 minutes. After this time, reaction mixture was concentrated under reduced pressure to get 3-(trimethylsilyl)propioloyl chloride. This acid chloride was carried to next step without any further purification.

Second step:— To a solution of (1S,3S)-3-butyl-1-cyclohexyl-6-methoxy-1,2,3,4-tetrahydroisoquinoline (0.2 g, 0.66 mmol, 1.0 eq) in acetonitrile (5.0 mL) was added sodium bicarbonate (0.42 g, 4.98 mmol, 7.5 eq) at 0° C. After stirring for 5 minutes, a solution of 3-(trimethylsilyl)propioloyl chloride in acetonitrile (2.0 mL) was added to the above reaction mass. The resulting mixture stirred at 0° C. for 15 min, progress of the reaction was monitored by TLC (15% ethyl acetate in n-hexane). After this time, reaction mass was diluted with EtOAc (30 mL) and water (5 mL). Organic layer was separated, washed with brine solution (10 mL), dried over anhydrous sodium sulfate, filtered and concentrated under reduced pressure to obtain the crude product. This crude product was carried to next step without any further purification. LC-MS (m/z)=426.7 [M+H]$^+$ 1-((1S,3S)-3-butyl-1-cyclohexyl-6-methoxy-3,4-dihydroisoquinolin-2(1H)-yl)prop-2-yn-1-one: To a solution of 1-((1S,3S)-3-butyl-1-cyclohexyl-6-methoxy-3,4-dihydroisoquinolin-2(1H)-yl)-3-(trimethylsilyl)prop-2-yn-1-one (0.29 g, 0.68 mmol, 1.0 eq) in THF (5.0 mL) was added TBAF (1M solution in THF) (0.75 mL, 0.75 mmol, 1.1 eq) at −78° C. This reaction mixture was stirred at −78° C. for 15 minutes. Progress of the reaction was monitored by TLC (15% ethyl acetate in n-hexane). After this time, the reaction mixture was quenched with saturated aqueous NaHCO$_3$ solution (5 mL) and product was extracted with ethyl acetate (30 mL). Organic layers were dried over anhydrous sodium sulfate, filtered and concentrated under reduced pressure. The obtained crude product was purified by preparative TLC using 15% ethyl acetate in n-hexane as an eluent to get 1-((1S,3S)-3-butyl-1-cyclohexyl-6-methoxy-3,4-dihydroisoquinolin-2(1H)-yl)prop-2-yn-1-one. LC-MS (m/z)=354.6 [M+H]$^+$ $^1$H NMR (400 MHz, DMSO-d$_6$) δ ppm 0.54-0.68 (m, 1H), 0.76-0.77 (m, 3H), 0.82-0.99 (m, 3H), 1.08-1.14 (m, 6H), 1.38-1.66 (m, 7H), 2.74-2.78 (m, 1H), 2.96-3.08 (m, 1H), 3.72 (s, 3H), 4.16 (bs, 0.5H), 4.35-4.38 (m, 0.5H), 4.50-4.52 (m, 1H), 4.75-4.78 (m, 1H), 6.74 (d, J=8.4 Hz, 1H), 6.84 (d, J=12.8 Hz, 1H), 7.01-7.08 (m, 1H).

Procedure 17: Synthesis of Compound 28

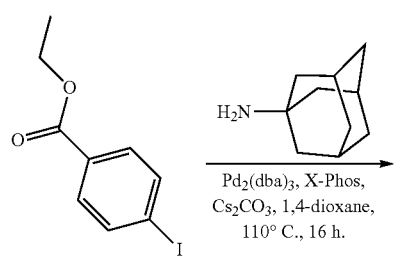

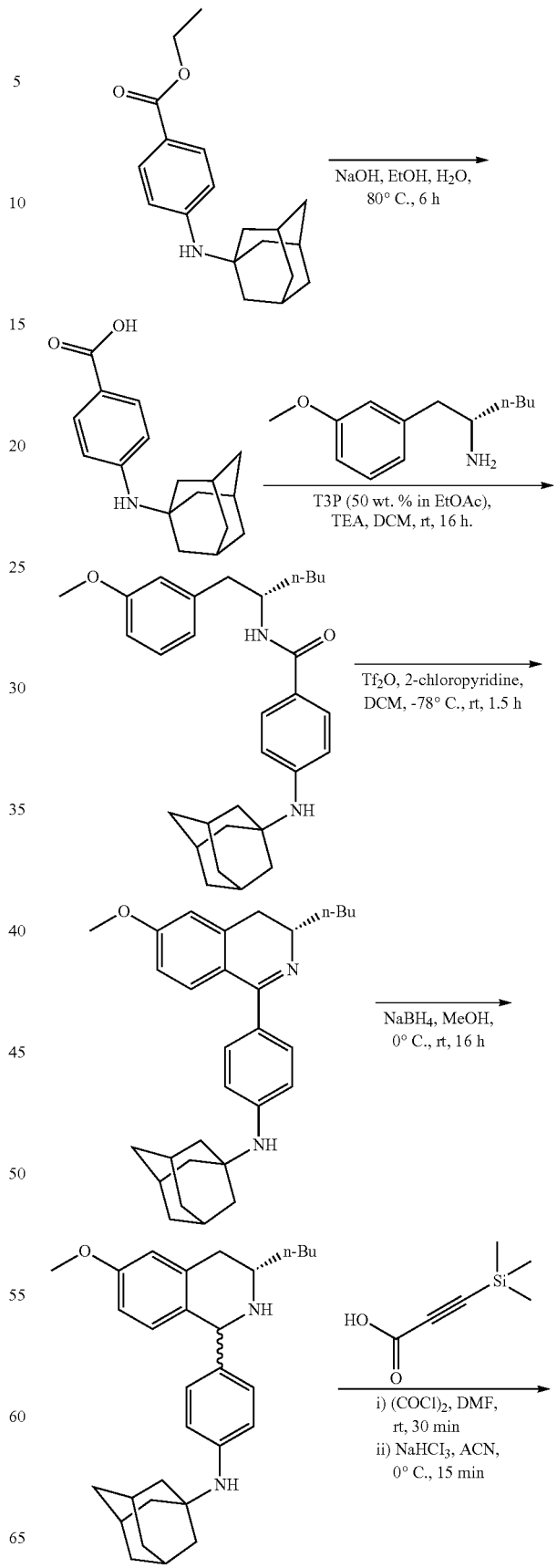

-continued

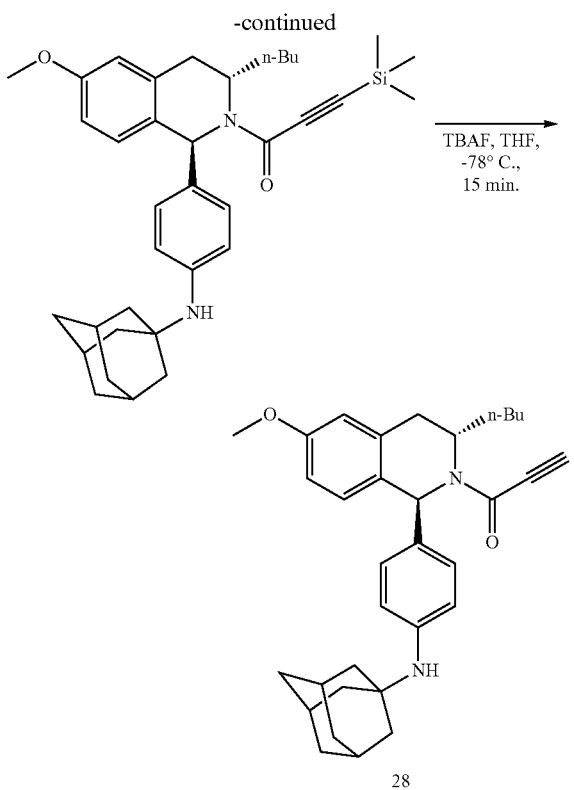

ethyl 4-(((3s,5s,7s)-adamantan-1-yl)amino)benzoate: To a stirred solution of ethyl 4-iodobenzoate (6.0 g, 21.73 mmol, 1 eq) and (3s,5s,7s)-adamantan-1-amine (3.93 g, 26.08 mmol, 1.2 eq) in 1,4-dioxane was added XPhos (0.51 g, 1.08 mmol, 0.05 eq) and Cs$_2$CO$_3$ (14.26 g, 43.26 mmol, 2 eq) at room temperature. The reaction mixture was purged under argon for 15 mins, then added Pd$_2$(dba)$_3$ (0.516 g, 0.65 mmol, 0.03 eq) to the reaction and stirred at 110° C. for 16 h. The progress of the reaction was monitored by TLC (15% ethyl acetate in hexane). After completion of reaction, the reaction mixture was filtered through celite bed and the celite bed was washed with ethyl acetate (150 mL). The filtrate was concentrated under reduced pressure to obtain crude. The obtained crude product was purified by flash chromatography using ethyl acetate in hexane as an eluent to obtain ethyl 4-(((3s,5s,7s)-adamantan-1-yl)amino)benzoate. LC-MS (m/z)=300.0 [M+H]$^+$ $^1$H NMR (400 MHz, CDCl$_3$) δ ppm 1.34 (t, J=7.0 Hz, 3H), 1.67-1.74 (m, 6H), 1.97 (s, 6H), 2.14 (s, 3H), 4.29 (q, J=6.9 Hz, 2H), 6.67 (d, J=8.4 Hz, 2H), 7.80 (d, J=8.4 Hz, 2H).

4-(((3s,5s,7s)-adamantan-1-yl)amino)benzoic acid: To a solution of ethyl 4-(((3s,5s,7s)-adamantan-1-yl)amino)benzoate (1.6 g, 5.37 mmol, 1 eq) in EtOH (29 mL) and water (11 mL) was added sodium hydroxide (0.43 g, 10.70 mmol, 2 eq) and stirrer at 80° C. for 6 h. TLC (15% ethyl acetate in hexane) showed the reaction was completed. The reaction mixture was concentrated under reduced pressure and the obtained crude was acidified with 5% aqueous citric acid solution (pH=4). Finally, the product was extracted with EtOAc (75 mL) from aqueous layer, dried over anhydrous Na$_2$SO$_4$, filtered and concentrated under reduced pressure to get the product 4-(((3s,5s,7s)-adamantan-1-yl)amino)benzoic acid. LC-MS (m/z)=272.0 [M+H]$^+$ $^1$H NMR (400 MHz, DMSO-d$_6$) δ ppm 1.61-1.68 (m, 6H), 1.91 (s, 6H), 2.06 (s, 3H), 5.87 (bs, 1H), 6.72 (d, J=8.8 Hz, 2H), 7.58 (d, J=8.8 Hz, 2H), 12.00 (bs, 1H).

4-(((3R,5R,7R)-adamantan-1-yl)amino)—N—((S)-1-(3-methoxyphenyl)hexan-2-yl)benzamide: To a solution of 4-(((3s,5s,7s)-adamantan-1-yl)amino)benzoic acid (1.05 g, 3.88 mmol, 1.2 eq) in DCM (20 mL) was added TEA (1.3 g, 12.92 mmol, 4 eq), stirred for 5 min and then T3P (50 wt. % in EtOAc) (1.53 g, 4.84 mmol, 1.5 eq) was added at 0° C. and stirred for another 5 mins. Then (S)-1-(3-methoxyphenyl)hexan-2-amine (0.67 g, 3.23 mmol, 1 eq) was added to the reaction mixture and then reaction mixture was stirred at room temperature for 16 h. The progress of the reaction was monitored by TLC (30% ethyl acetate in hexane). The reaction mixture was diluted with DCM (50 mL) and saturated sodium bicarbonate solution (20 mL) Organic layer was separated, washed with brine solution (20 mL), dried over anhydrous sodium sulfate, filtered and concentrated under reduced pressure to obtain the crude product. The obtained crude product was purified by flash chromatography using ethyl acetate in hexane as an eluent to get 4-(((3R,5R,7R)-adamantan-1-yl)amino)—N—((S)-1-(3-methoxyphenyl)hexan-2-yl)benzamide. LC-MS (m/z)=461.0 [M+H]$^+$ $^1$H NMR (400 MHz, DMSO-d$_6$) δ ppm 0.80 (bs, 3H), 1.22 (bs, 4H), 1.45 (bs, 2H), 1.64 (s, 6H), 1.89 (s, 6H), 2.05 (s, 3H), 2.65-2.76 (m, 2H), 3.16 (d, J=4.0 Hz, 1H), 3.66 (s, 3H), 4.07 (bs, 1H), 5.49 (s, 1H), 6.68-6.75 (m, 4H), 7.11-7.12 (m, 1H), 7.50 (d, J=7.2 Hz, 2H), 7.57-7.64 (m, 1H).

(3R,5R,7R)—N—(4-((S)-3-butyl-6-methoxy-3,4-dihydroisoquinolin-1-yl)phenyl)adamantan-1-amine: Trifluoromethanesulfonic anhydride (0.547 mL, 3.26 mmol, 3.0 eq) was added via syringe over a period of 1 min to a stirred mixture of 4-(((3R,5R,7R)-adamantan-1-yl)amino)—N—((S)-1-(3-methoxyphenyl)hexan-2-yl)benzamide (0.5 g, 1.08 mmol, 1 eq) and 2-chloropyridine (0.3 mL, 3.26 mmol, 3.0 eq) in dichloromethane (3.6 mL) at −78° C. After 5 min, the reaction mixture was placed in an ice-water bath and warmed to 0° C. After 5 min, the resulting solution was allowed to warm to 23° C. After 1 h, aqueous sodium hydroxide solution (5 mL, 1N) was introduced to neutralize the trifluoromethanesulfonate salts. Dichloromethane (50 mL) was added to dilute the mixture and the layers were separated. The organic layer was washed with brine (7 mL), was dried over anhydrous sodium sulfate, and was filtered. The volatiles were removed under reduced pressure to give the crude product. The obtained crude product was purified by flash chromatography using ethyl acetate in hexane as an eluent to get the desired product ((3R,5R,7R)—N—(4-((S)-3-butyl-6-methoxy-3,4-dihydroisoquinolin-1-yl)phenyl)adamantan-1-amine. LC-MS (m/z)=443.3 [M+H]$^+$ (3R,5R,7R)—N—(4-((1S,3S)-3-butyl-6-methoxy-1,2,3,4-tetrahydroisoquinolin-1-yl)phenyl)adamantan-1-amine: A solution of the (3R,5R,7R)—N—(4-((S)-3-butyl-6-methoxy-3,4-dihydroisoquinolin-1-yl)phenyl)adamantan-1-amine (0.5 g, 1.13 mmol, 1 eq) in methanol (9 mL) was added sodium borohydride (0.128 g, 33.93 mmol, 3 eq) at 0° C. The suspension was stirred at room temperature for 16 h. After this time, the reaction mixture was concentrated and obtained crude was diluted with EtOAc (30 mL) and water (10 mL). Organic layer was separated, washed with brine solution (10 mL), dried over anhydrous sodium sulfate, filtered and concentrated under reduced pressure to obtain the crude product. The obtained crude product was purified by flash chromatography using ethyl acetate in hexane as an eluent to get (3R,5R,7R)—N—(4-((1S,3S)-3-butyl-6-methoxy-1,2,3,4-tetrahydroisoquinolin-1-yl)phenyl)adamantan-1-amine. The isolated pure product was treated with metal scavenger QuadraSil® AP (compound was dissolved in THF (5 mL) and QuadraSil® AP (50 mg) was added, the mixture was stirred for 0.5 h, filtered. This is repeated one more time and concentrated). LC-MS (m/z)=445.3 [M+H]+

$^1$H NMR (400 MHz, CDCl$_3$) δ ppm 0.84-088 (m, 3H), 1.22-1.30 (m, 4H), 1.42-1.43 (m, 2H), 1.60-1.70 (m, 6H), 1.85 (s, 6H), 2.09 (bs, 3H), 2.53-2.60 (m, 1H), 2.82-2.86 (m, 1H), 2.87-2.97 (m, 1H), 3.78 (s, 3H), 5.13 (s, 1H), 6.66-6.70 (m, 4H), 6.84-6.90 (m, 3H).

1-((1S,3S)-1-(4-(((3R,5R,7R)-adamantan-1-yl)amino) phenyl)-3-butyl-6-methoxy-3,4-dihydroisoquinolin-2(1H)-yl)-3-(trimethylsilyl)prop-2-yn-1-one: First step:— To a solution of 3-(trimethylsilyl)propiolic acid (11.8 mg, 0.083 mmol, 1.0 eq) in DMF (0.24 mg, 0.003 mmol, 0.04 eq) was added oxalyl chloride (11.5 mg, 0.091 mmol, 1.1 eq) at room temperature and stirred for 30 minutes. After this time, reaction mixture was concentrated under reduced pressure to get 3-(trimethylsilyl)propioloyl chloride. This acid chloride was carried to next step without any further purification.

Second step:— To a solution of (3R,5R,7R)—N—(4-((1S,3S)-3-butyl-6-methoxy-1,2,3,4-tetrahydroisoquinolin-1-yl)phenyl)adamantan-1-amine (37 mg, 0.083 mmol, 1.0 eq) in acetonitrile (1.0 mL) was added sodium bicarbonate (52.5 mg, 0.62 mmol, 7.5 eq) at 0° C. After stirring for 5 minutes, a solution of 3-(trimethylsilyl)propioloyl chloride in acetonitrile (1.0 mL) was added to the above reaction mass. The resulting mixture stirred at 0° C. for 15 min, progress of the reaction was monitored by TLC (70% ethyl acetate in n-hexane). After this time, reaction mass was diluted with EtOAc (30 mL) and water (10 mL). Organic layer was separated, washed with brine solution (10 mL), dried over anhydrous sodium sulfate, filtered and concentrated under reduced pressure to obtain the crude product. This crude product was carried to next step without any further purification. LC-MS (m/z)=569.4 [M+H]+

1-((1S,3S)-1-(4-(((3R,5R,7R)-adamantan-1-yl)amino) phenyl)-3-butyl-6-methoxy-3,4-dihydroisoquinolin-2(1H)-yl)prop-2-yn-1-one: To a solution of 1-((1S,3S)-1-(4-(((3R,5R,7R)-adamantan-1-yl)amino)phenyl)-3-butyl-6-methoxy-3,4-dihydroisoquinolin-2(1H)-yl)-3-(trimethylsilyl)prop-2-yn-1-one (48 mg, 0.084 mmol, 1.0 eq) in THF (1.5 mL) was added TBAF (1M solution in THF) (0.092 mL, 0.092 mmol, 1.1 eq) at −78° C. This reaction mixture was stirred at −78° C. for 15 minutes. Progress of the reaction was monitored by TLC (25% ethyl acetate in n-hexane). After this time, the reaction mixture was quenched with saturated aqueous NaHCO$_3$ solution (5 mL) and product was extracted with ethyl acetate (25 mL). Organic layers were dried over anhydrous sodium sulfate, filtered and concentrated under reduced pressure. The obtained crude product was purified by preparative TLC using 25% ethyl acetate in n-hexane as an eluent to get 1-((1S,3S)-1-(4-(((3R,5R,7R)-adamantan-1-yl)amino)phenyl)-3-butyl-6-methoxy-3,4-dihydroisoquinolin-2(1H)-yl)prop-2-yn-1-one. LC-MS (m/z)=497.3 ([M+H]+

$^1$H NMR (400 MHz, DMSO-d6) δ ppm 0.79-0.80 (m, 3H), 1.18-1.24 (m, 6H), 1.51 (bs, 1H), 1.61 (s, 5H), 1.79 (s, 6H), 2.01 (s, 3H), 2.71-2.83 (m, 1H), 3.00-3.09 (m, 2H), 3.72-3.73 (m, 3H), 4.15 (bs, 0.3H), 4.40 (bs, 1H), 4.61 (bs, 0.7H), 5.95 (s, 0.5H), 6.16 (s, 0.5H), 6.59-6.66 (m, 2H), 6.76-6.85 (m, 4H), 7.29 (d, J=8.4 Hz, 0.5H), 7.40 (d, J=7.6 Hz, 0.5H).

Procedure 18: Synthesis of Compound 55

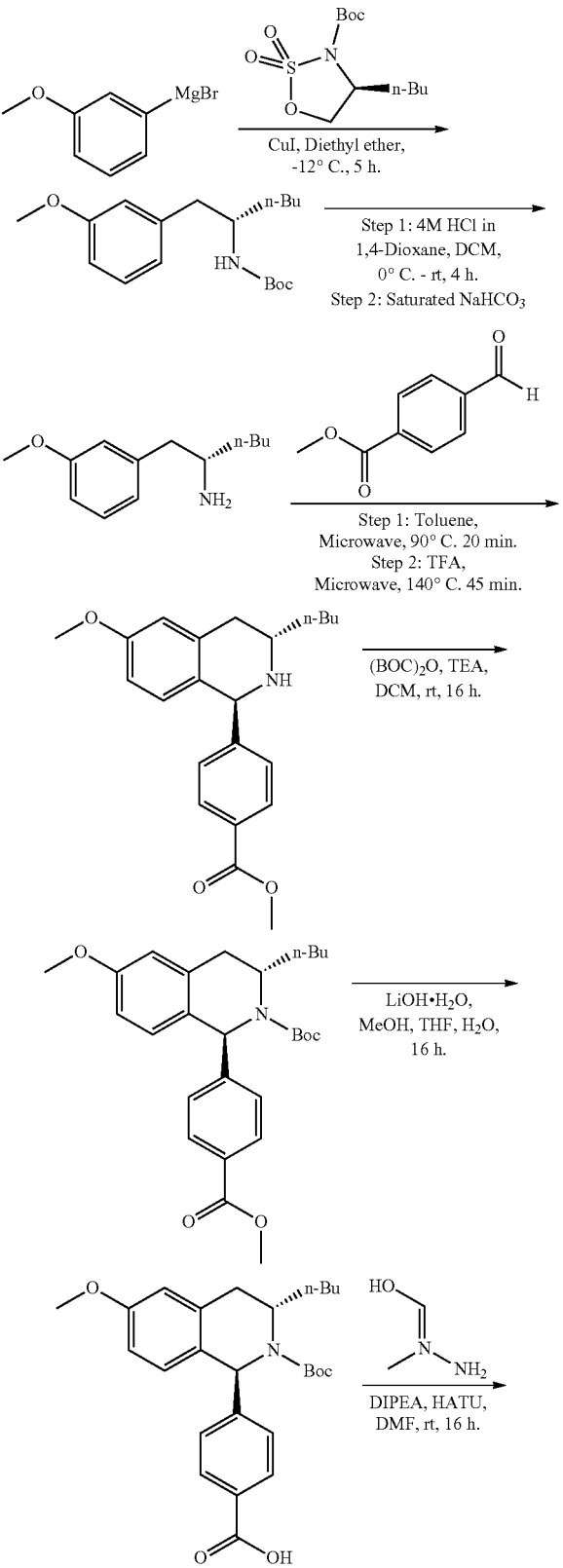

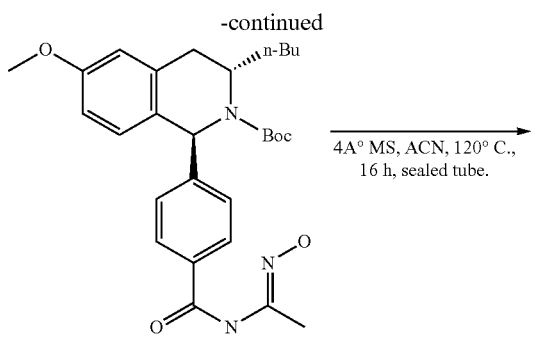

4Å MS, ACN, 120° C., 16 h, sealed tube.

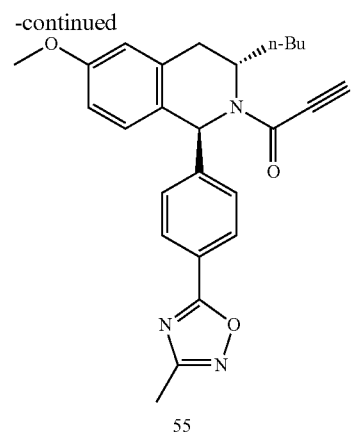

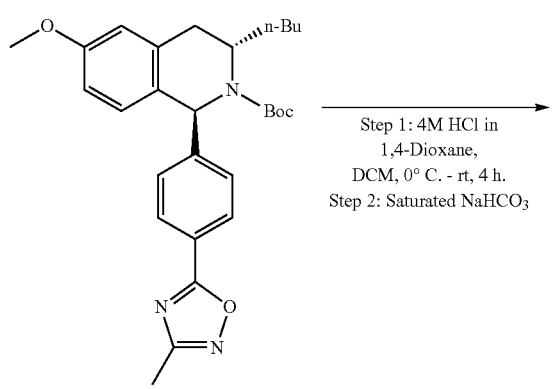

Step 1: 4M HCl in 1,4-Dioxane, DCM, 0° C. - rt, 4 h.
Step 2: Saturated NaHCO₃

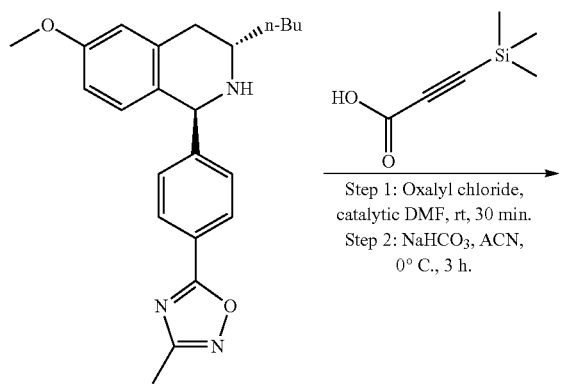

Step 1: Oxalyl chloride, catalytic DMF, rt, 30 min.
Step 2: NaHCO₃, ACN, 0° C., 3 h.

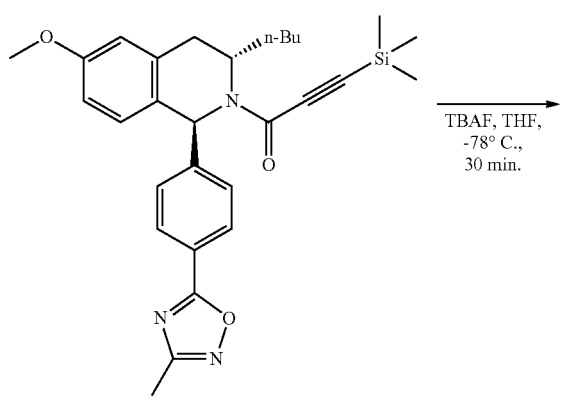

TBAF, THF, −78° C., 30 min.

tert-butyl (S)-(1-(3-methoxyphenyl)hexan-2-yl)carbamate: To a solution of copper iodide (0.510 g, 2.68 mmol, 0.1 eq) in diethyl ether (50 mL) was added (3-methoxyphenyl)magnesium bromide (1M in THF) (53 mL, 53.76 mmol, 2 eq) drop wise over a period of 10 min at −12° C. The reaction mixture was stirred for 30 min at −12° C. After this time, a solution of tert-butyl (S)-4-butyl-1,2,3-oxathiazolidine-3-carboxylate 2,2-dioxide (7.5 g, 26.88 mmol, 1 eq) in diethyl ether (15 mL) was added at −12° C. drop wise to the reaction mass. The resulting mixture was stirred for 4 h at −12° C. Finally, the reaction was quenched with 10% aqueous citric acid solution (15 mL) at −12° C. and diluted with ethyl acetate (100 mL). The organic layer was separated and washed with brine (50 mL), dried over anhydrous sodium sulfate, filtered and concentrated to give the crude product, which was purified by flash column chromatography using 15% ethyl acetate in n-hexane as an eluent to obtain tert-butyl (S)-(1-(3-methoxyphenyl)hexan-2-yl)carbamate. LC-MS (m/z): 252.0 [M+H]⁺

¹H NMR (400 MHz, CDCl₃): δ ppm 0.86-0.87 (m, 3H), 1.23-1.35 (m, 6H), 1.40 (s, 9H), 2.73 (bs, 2H), 3.78 (s, 3H), 4.29 (bs, 1H), 6.71-6.76 (m, 3H), 7.19 (t, J=7.8 Hz, 1H) Amide NH was not observed.

(S)-1-(3-methoxyphenyl)hexan-2-amine: To a solution of tert-butyl (S)-(1-(3-methoxyphenyl)hexan-2-yl)carbamate (10 g, 32.57 mmol, 1 eq) in dichloromethane (50 mL) was added 4M HCl in 1,4-Dioxane (20 mL, 64.10 mmol, 2 eq) at 0° C. The mixture was allowed to stir at room temperature for 16 h. The progress of the reaction was monitored by TLC, after completion of reaction; the reaction mixture was concentrated under reduced pressure. The obtained crude was dissolved with ice cold water (10 mL) and was basified by saturated aqueous solution of NaHCO₃. The compound was extracted with EtOAc (100 mL). Organic layer was washed with brine (10 mL), dried over anhydrous sodium sulfate, filtered and concentrated to obtain (S)-1-(3-methoxyphenyl)hexan-2-amine. LC-MS (m/z): 208.1 [M+H]⁺.

¹H NMR (400 MHz, CDCl₃): δ ppm 0.82-0.90 (m, 3H), 1.23-1.42 (m, 4H), 1.57-1.62 (m, 2H), 2.69-2.91 (m, 2H), 3.25-3.58 (m, 1H), 3.80 (s, 3H), 6.69-6.78 (m, 3H), 7.21 (t, J=8.0 Hz, 1H) NH₂ protons was not observed.

methyl 4-((1S,3S)-3-butyl-6-methoxy-1,2,3,4-tetrahydroisoquinolin-1-yl)benzoate: To a solution of (S)-1-(3-methoxyphenyl)hexan-2-amine (0.7 g, 3.37 mmol, 1 eq) and methyl 4-formylbenzoate (0.664 g, 4.05 mmol, 1 eq) in toluene (4 mL) was irradiated in microwave at 90° C. for 20 min. After this time, volatile portion was concentrated under reduced pressure and taken forward for cyclization step as such in TFA (4 mL) and irradiated in microwave at 140° C. for 45 min. After this time, volatile portion was concentrated under reduced pressure and obtained crude was diluted with saturated aqueous solution of NaHCO$_3$ (10 mL) and EtOAc (40 mL). The organic layer was separated, washed with brine (10 mL), dried over anhydrous MgSO4, filtered and concentrated under reduced pressure to obtain the crude product. The obtained crude product was purified by silica gel flash column chromatography (n-hexane/EtOAc) to give methyl 4-((1S,3S)-3-butyl-6-methoxy-1,2,3,4-tetrahydroisoquinolin-1-yl)benzoate. LC-MS (m/z): 208.1 [M+H]$^+$.

$^1$H NMR (400 MHz, CDCl$_3$): δ ppm 0.84-0.86 (m, 3H), 1.23-1.24 (m, 6H), 2.55-2.59 (m, 1H), 2.85-2.88 (m, 2H), 3.75 (s, 3H), 3.80 (s, 3H), 5.29 (s, 3H), 6.67-6.69 (m, 2H), 6.70-6.80 (m, 1H), 7.21-7.26 (s, 2H), 7.94-8.0 (m, 2H).

tert-butyl-(1S,3S)-6-methoxy-1-(4-(methoxycarbonyl) phenyl)-3-methyl-3,4-dihydroisoquinoline-2(1H)-carboxylate: To a solution of compound methyl 4-((1S,3S)-6-methoxy-3-methyl-1,2,3,4-tetrahydroisoquinolin-1-yl) benzoate (0.35 g, 1.12 mmol, 1 eq) in DCM (10 mL) was added triethylamine (0.45 g, 4.49 mmol, 4 eq) and di-tert-butyl dicarbonate (0.715 g, 2.24 mmol, 2 eq) at room temperature and the mixture was stirred for 16 h. TLC (50% EtOAc in hexane) showed the reaction was completed.

The reaction mixture was concentrated under reduced pressure, and the crude was diluted with EtOAc (50 mL), washed with water (2×50 mL). The organic layer was dried over anhydrous Na$_2$SO$_4$, concentrated under reduced pressure to crude product tert-butyl (1S,3S)-6-methoxy-1-(4-(methoxycarbonyl)phenyl)-3-methyl-3,4-dihydroisoquinoline-2(1H)-carboxylate. LC-MS (m/z): 356.0 [M-$^t$Bu+H]$^+$.

4-((1S,3S)-2-(tert-butoxycarbonyl)-6-methoxy-3-methyl-1,2,3,4-tetrahydroisoquinolin-1-yl)benzoic acid: To a solution of compound tert-butyl (1S,3S)-6-methoxy-1-(4-(methoxycarbonyl)phenyl)-3-methyl-3,4-dihydroisoquinoline-2(1H)-carboxylate (0.650 g, 1.57 mmol, 1 eq) in a mixture of THF:MeOH:H$_2$O (9 mL: 1 mL) were added lithium hydroxide (0.331 g, 7.89 mmol, 5 eq) and allowed to stirrer at room temperature for 16 h. TLC (50% EtOAc in hexane) showed the reaction was completed. The reaction mixture was concentrated under reduced pressure, and the crude was acidified with 5% citric acid solution (pH=9). Reaction mixture was diluted with EtOAc (50 mL) and the organic layer was separated and dried over anhydrous Na$_2$SO$_4$, concentrated under reduced pressure to give crude product 4-((1S,3S)-2-(tert-butoxycarbonyl)-6-methoxy-3-methyl-1,2,3,4-tetrahydroisoquinolin-1-yl)benzoic acid. LC-MS (m/z): 396.0 [M+H].

tert-butyl (1S,3S)-3-butyl-1-(4-(((E)-1-(hydroxyimino) ethyl)carbamoyl)phenyl)-6-methoxy-3,4-dihydroisoquinoline-2(1H)-carboxylate: To a solution of 4-((1S,3S)-2-(tert-butoxycarbonyl)-3-butyl-6-methoxy-1,2,3,4-tetrahydroisoquinolin-1-yl)benzoic acid (0.2 g, 0.45 mmol, 1 eq) in DMF (10 mL) was added DIPEA (0.15 mL, 0.91 mmol, 2 eq) and HATU (0.207 g, 5.46 mmol, 1.2 eq) at room temperature, stirred for 15 mins and then (E)—N'-hydroxyacetimidamide (0.043 g, 0.591 mmol, 1.3 eq) was added and the reaction mixture was stirred at room temperature for 3 h. The progress of the reaction was monitored by TLC (30% EtOAc in hexane). After the completion of the reaction, the reaction mixture was poured to crushed ice and then extracted with EtOAc (2×50 mL). Combined organic layer was dried over anhydrous sodium sulfate, filtered and concentrated under reduced pressure to obtain tert-butyl (1S, 3S)-3-butyl-1-(4-(((E)-1-(hydroxyimino)ethyl)carbamoyl) phenyl)-6-methoxy-3,4-dihydroisoquinoline-2(1H)-carboxylate. LC-MS (m/z)=496.0 [M+H]$^+$.

tert-butyl(1S,3S)-3-butyl-6-methoxy-1-(4-(3-methyl-1,2,4-oxadiazol-5-yl)phenyl)-3,4-dihydroisoquinoline-2(1H)-carboxylate: To a solution of tert-butyl (1S,3S)-3-butyl-1-(4-(((E)-1-(hydroxyimino)ethyl)carbamoyl)phenyl)-6-methoxy-3,4-dihydroisoquinoline-2(1H)-carboxylate (0.3 g, 0.606 mmol, 1 eq) in ACN (10 mL) was added 4 Å MS (0.1 g) and the reaction mixture was stirred at 120° C. for 3 h in a sealed tube. The progress of the reaction was monitored by TLC (50% EtOAc in hexane). After the completion of the reaction, the reaction mixture was filtered through sintered funnel and the filtrate obtained was concentrated under reduced pressure to obtain the crude. It was purified by silica gel column chromatography using 25-30% EtOAc in hexane as an eluent to afford tert-butyl (1S,3S)-3-butyl-6-methoxy-1-(4-(3-methyl-1,2,4-oxadiazol-5-yl)phenyl)-3,4-dihydroisoquinoline-2(1H)-carboxylate. LC-MS (m/z)=478.0 [M+H]$^+$.

5-(4-((1S,3S)-3-butyl-6-methoxy-1,2,3,4-tetrahydroisoquinolin-1-yl)phenyl)-3-methyl-1,2,4-oxadiazole: To a solution of tert-butyl (1S,3S)-3-butyl-6-methoxy-1-(4-(3-methyl-1,2,4-oxadiazol-5-yl)phenyl)-3,4-dihydroisoquinoline-2(1H)-carboxylate (0.185 g, 0.387 mmol, 1 eq) in dichloromethane (20 mL) was added 4 M HCl in 1,4-Dioxane (10 mL, 1.52 mmol, 2 eq) at 0° C. The mixture was allowed to stir at room temperature for 16 h. The progress of the reaction was monitored by TLC, after completion of reaction; the reaction mixture was concentrated under reduced pressure. The obtained crude was dissolved with ice cold water (20 mL) and was basified by saturated aqueous solution of NaHCO$_3$. The compound was extracted with EtOAc (100 mL). Organic layer was washed with brine (10 mL), dried over anhydrous sodium sulfate, filtered and concentrated to obtain 5-(4-((1S,3S)-3-butyl-6-methoxy-1,2,3,4-tetrahydroisoquinolin-1-yl)phenyl)-3-methyl-1,2,4-oxadiazole. LC-MS (m/z): 378.0 [M+H]$^+$.

1-((1S,3S)-3-butyl-6-methoxy-1-(4-(3-methyl-1,2,4-oxadiazol-5-yl)phenyl)-3,4-dihydroisoquinolin-2(1H)-yl)-3-(trimethylsilyl)prop-2-yn-1-one: To 3-(trimethylsilyl)propiolic acid (0.090 g, 0.260 mmol, 1 eq), DMF (0.0008 g, 0.010 mmol, 0.04 eq) and oxalyl chloride (0.05 mL, 0.969 mmol, 1.1 eq) was added and stirred for 30 mins. After this time reaction mixture was concentrated under reduced pressure to obtain crude 3-(trimethylsilyl)propioloyl chloride and this crude was diluted with ACN (1 mL) and added to a reaction mixture containing a stirred solution of 5-(4-((1S, 3S)-3-butyl-6-methoxy-1,2,3,4-tetrahydroisoquinolin-1-yl) phenyl)-3-methyl-1,2,4-oxadiazole (0.160 g, 0.424 mmol, 1 eq) and NaHCO$_3$ (0.267 g, 3.181 mmol, 7.5 eq) in ACN (5 mL) at 0° C. and stirred for 15 mins. LCMS and TLC (30% EtOAc in hexane) showed the reaction was completed. The reaction was filtered and concentrated under reduced pressure to give the crude product 1-((1S,3S)-3-butyl-6-methoxy-1-(4-(3-methyl-1,2,4-oxadiazol-5-yl)phenyl)-3,4-dihydroisoquinolin-2(1H)-yl)-3-(trimethylsilyl)prop-2-yn-1-one which was taken to next step without further purification. LC-MS (m/z): 502.0 [M+H]$^+$.

1-((1S,3S)-3-butyl-6-methoxy-1-(4-(3-methyl-1,2,4-oxadiazol-5-yl)phenyl)-3,4-dihydroisoquinolin-2(1H)-yl)prop-2-yn-1-one: To 1-((1S,3S)-3-butyl-6-methoxy-1-(4-(3-methyl-1,2,4-oxadiazol-5-yl)phenyl)-3,4-dihydroisoquinolin-2(1H)-yl)-3-(trimethylsilyl)prop-2-yn-1-one (0.100 g, 0.199 mmol, 1 eq) in THF (10.0 mL) TBAF (1M solution in THF) (0.104 mL, 0.399 mmol, 2 eq) was added and stirred for 30 mins. After this time reaction mixture was concentrated under reduced pressure, diluted with Ethylacetate (100 mL) and was washed with water (2×10 mL). The organic layers were dried over Na$_2$SO$_4$ and concentrated to give to obtain the crude product, which was further purified by preparative TLC chromatography using 20% EtOAc in hexane as an eluent to 1-((1S,3S)-3-butyl-6-methoxy-1-(4-(3-methyl-1,2,4-oxadiazol-5-yl)phenyl)-3,4-dihydroisoquinolin-2(1H)-yl)prop-2-yn-1-one. LC-MS (m/z): 430.1 [M+H]⁺.

¹H NMR (400 MHz, DMSO-d₆): δ 0.80-0.81 (m, 3H), 0.83-1.49 (m, 6H), 2.31 (s, 3H), 2.81-2.92 (m, 1H), 2.93-3.13 (m, 1H), 3.71 (s, 3H), 4.35 (s, 0.5H), 4.59 (s, 0.5H), 4.65-4.77 (bs, 1H), 6.13 (s, 0.7H), 6.41 (s, 0.5H), 6.78-6.86 (m, 2H), 7.49-7.53 (m, 2H), 7.68-7.70 (m, 1H), 7.92-8.00 (m, 2H).

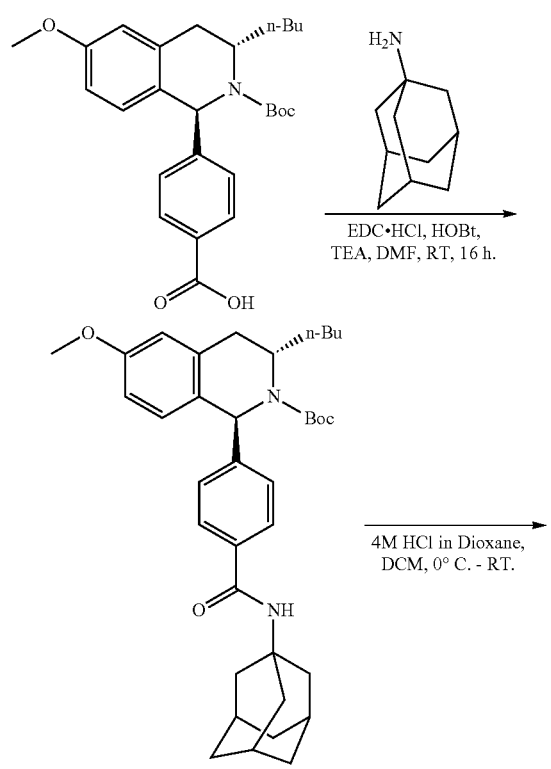

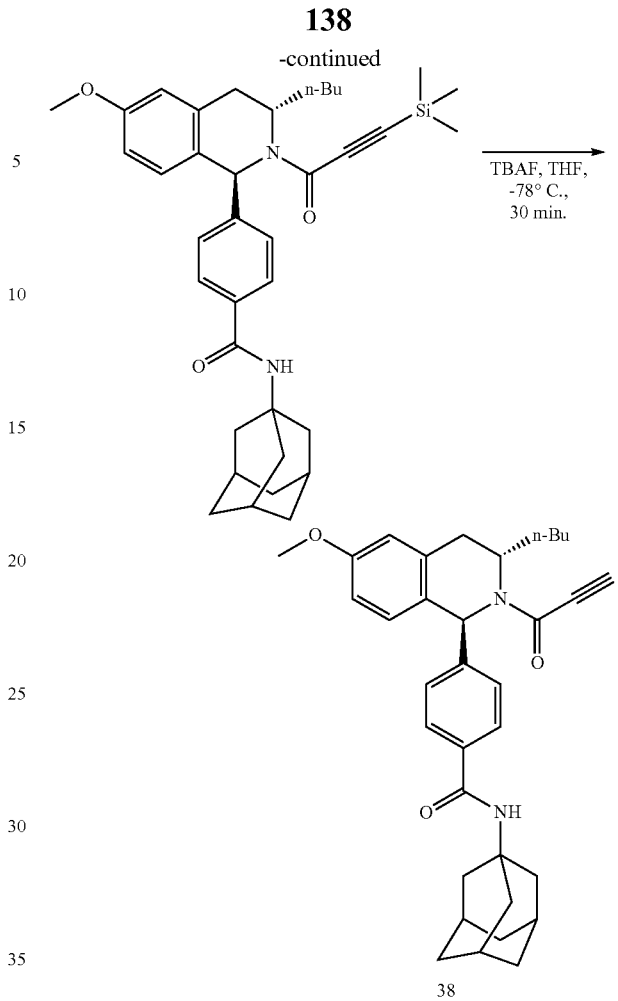

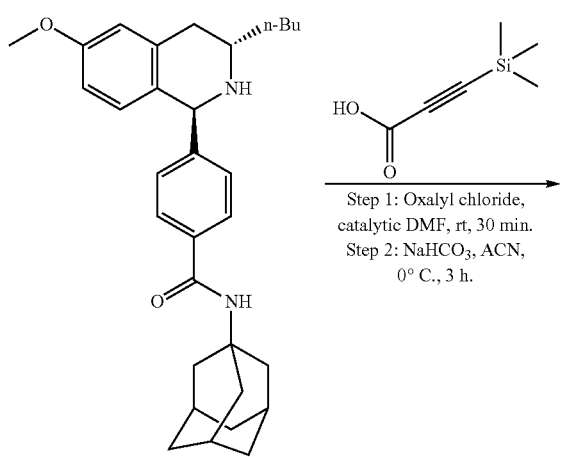

Procedure 19: Synthesis of Compound 38 tert-butyl(1S,3S)-1-(4-(((3R,5R,7R)-adamantan-1-yl)carbamoyl)phenyl)-3-butyl-6-methoxy-3,4-dihydroisoquinoline-2(1H)-carboxylate: To a solution of 4-((1S,3S)-2-(tert-butoxycarbonyl)-3-butyl-6-methoxy-1,2,3,4-tetrahydroisoquinolin-1-yl)benzoic acid (0.2 g, 0.45 mmol, 1 eq) in DCM (10 mL) was added TEA (0.2 mL, 1.36 mmol, 3 eq), (3s,5s,7s)-adamantan-1-amine (0.068 g, 0.45 mmol, 1 eq) and HOBt (0.092 g, 0.682 mmol, 1.5 eq) at room temperature, stirred for 15 mins and then EDC.HCl (0.13 g, 0.682 mmol, 1.5 eq) was added and the reaction mixture was stirred at room temperature for 16 h. The progress of the reaction was monitored by TLC (30% EtOAc in hexane). After the completion of the reaction, the reaction mixture was diluted with water and then extracted with DCM (2×50 mL). Combined organic layer was dried over anhydrous sodium sulfate, filtered and concentrated under reduced pressure to obtain tert-butyl(1S,3S)-1-(4-(((3R,5R,7R)-adamantan-1-yl)carbamoyl)phenyl)-3-butyl-6-methoxy-3,4-dihydroisoquinoline-2(1H)-carboxylate. LC-MS (m/z): 517.3 [M+H]⁺.

¹H NMR (400 MHz, DMSO-d₆): δ ppm 0.81 (s, 3H), 0.98-1.40 (m, 15H), 1.62 (s, 6H), 2.00 (s, 9H), 2.75 (s, 1H), 3.03 (s, 1H), 3.68 (s, 3H), 4.30-4.44 (m, 1H), 5.87 (s, 1H) 6.73 (s, 2H), 7.28 (s, 2H), 7.41 (s, 2H), 7.59 (s, 2H).

N—((3R,5R,7R)-adamantan-1-yl)-4-((1S,3S)-3-butyl-6-methoxy-1,2,3,4-tetrahydroisoquinolin-1-yl)benzamide: To a solution of tert-butyl(1S,3S)-1-(4-(((3R,5R,7R)-adamantan-1-yl)carbamoyl)phenyl)-3-butyl-6-methoxy-3,4-dihydroisoquinoline-2(1H)-carboxylate (0.23 g, 0.401 mmol, 1 eq) in dichloromethane (10 mL) was added 4M HCl in 1,4-dioxane (7 mL) at 0° C. The mixture was allowed to stir at room temperature for 3 h. The progress of the reaction was monitored by TLC, after completion of reaction; the reaction mixture was concentrated under reduced pressure. The obtained crude was dissolved with ice cold water (10 mL) and was basified by saturated aqueous solution of NaHCO$_3$. The compound was extracted with EtOAc (30 mL). Organic layer was washed with brine (10 mL), dried over anhydrous sodium sulfate, filtered and concentrated to obtain N—((3R,5R,7R)-adamantan-1-yl)-4-((1S,3S)-3-butyl-6-methoxy-1,2,3,4-tetrahydroisoquinolin-1-yl)benzamide. LC-MS (m/z): 473.7 [M+H]$^+$.

N—((3R,5R,7R)-adamantan-1-yl)-4-((1S,3S)-3-butyl-6-methoxy-2-(3-(trimethylsilyl)propioloyl)-1,2,3,4-tetrahydroisoquinolin-1-yl)benzamide: To 3-(trimethylsilyl)propiolic acid (0.085 g, 0.59 mmol, 1 eq), DMF (0.001 mL, 0.023 mmol, 0.04 eq) and oxalyl chloride (0.061 mL, 0.717 mmol, 1.2 eq) was added and stirred for 30 mins. After this time reaction mixture was concentrated under reduced pressure to obtain crude 3-(trimethylsilyl)propioloyl chloride, which was diluted with ACN (1 mL) and added to a reaction mixture containing a stirred solution of N—((3R,5R,7R)-adamantan-1-yl)-4-((1S,3S)-3-butyl-6-methoxy-1,2,3,4-tetrahydroisoquinolin-1-yl)benzamide (0.19 g, 0.401 mmol, 1 eq) and NaHCO$_3$ (0.253 g, 3.01 mmol, 7.5 eq) in ACN (5 mL) at 0° C. and stirred for 15 mins. LCMS and TLC (40% EtOAc in hexane) showed the reaction was completed. The reaction was filtered and concentrated under reduced pressure to give the crude product N—((3R,5R,7R)-adamantan-1-yl)-4-((1S,3S)-3-butyl-6-methoxy-2-(3-(trimethylsilyl)propioloyl)-1,2,3,4-tetrahydroisoquinolin-1-yl)benzamide which was taken to next step without further purification. LC-MS (m/z): 597.3 [M+H]$^+$.

N—((3R,5R,7R)-adamantan-1-yl)-4-((1S,3S)-3-butyl-6-methoxy-2-propioloyl-1,2,3,4-tetrahydroisoquinolin-1-yl)benzamide: To N—((3R,5R,7R)-adamantan-1-yl)-4-((1S,3S)-3-butyl-6-methoxy-2-(3-(trimethylsilyl)propioloyl)-1,2,3,4-tetrahydroisoquinolin-1-yl)benzamide (0.17 g, 0.284 mmol, 1 eq) in THF (10.0 mL) TBAF (1M solution in THF) (0.081 mL, 0.313 mmol, 1.1 eq) was added and stirred for 15 mins. After this time reaction mixture was concentrated under reduced pressure, diluted with Ethylacetate (30 mL) and was washed with water (2×10 mL). The organic layers were dried over Na$_2$SO$_4$ and concentrated to give to obtain the crude product, which was further purified by flash column chromatography using 20% EtOAc in hexane as an eluent to get N—((3R,5R,7R)-adamantan-1-yl)-4-((1S,3S)-3-butyl-6-methoxy-2-propioloyl-1,2,3,4-tetrahydroisoquinolin-1-yl)benzamide. LC-MS (m/z): 525.8 [M+H]$^+$.

$^1$H NMR (400 MHz, DMSO-d$_6$): δ 0.81 (t, J=6.0 Hz, 3H), 1.22 (s, 6H), 1.48-1.61 (m, 7H), 2.00 (s, 8H), 2.85-2.89 (m, 1H), 3.10-3.13 (m, 1H), 3.69 (d, J=6.0 Hz, 3H), 4.29 (s, 1H), 4.59 (bs, 1H), 6.06 (s, 1H), 6.76-6.84 (m, 2H), 7.25-7.29 (m, 2H), 7.41-7.47 (m, 2H), 7.55 (d, J=8.0 Hz, 1H), 7.62 (d, J=8.0 Hz, 1H).

Procedure 20: Synthesis of Compound 48

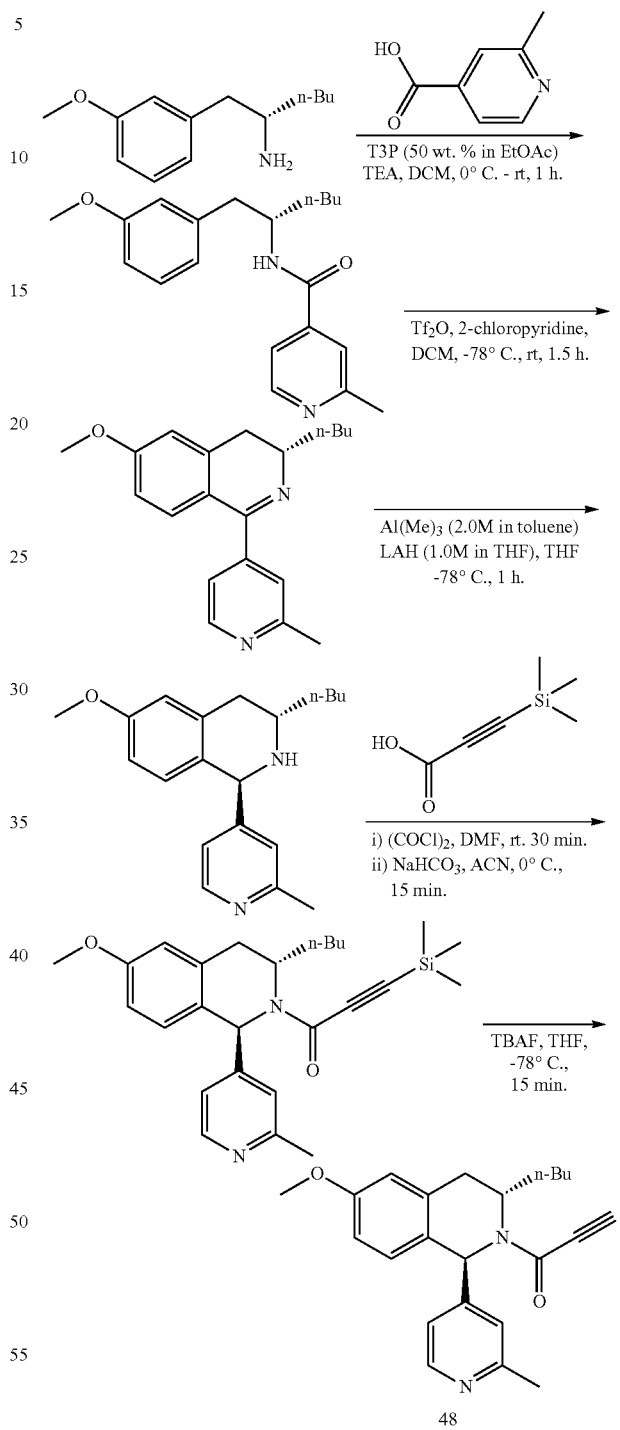

48

(S)—N—(1-(3-methoxyphenyl)hexan-2-yl)-2-methylisonicotinamide: To a solution of 2-methylisonicotinic acid (0.654 g, 4.77 mmol, 1.1 eq) in DCM (15 mL) was added TEA (2.5 mL, 17.36 mmol, 4 eq), stirred for 15 min and then T3P (50 wt. % in EtOAc) (4.2 mL, 6.51 mmol, 1.5 eq) was added at 0° C. and stirred for another 5 mins. Then (S)-1-(3-methoxyphenyl)hexan-2-amine (0.900 g, 4.34 mmol, 1 eq) was added to the reaction mixture and then reaction mixture was stirred at room temperature for 16 h. The progress of the reaction was monitored by TLC (40% ethyl acetate in hexane). The reaction mixture was diluted with DCM (30 mL) and saturated sodium bicarbonate solution (15 mL) Organic layer was separated, washed with brine solution (12 mL), dried over anhydrous sodium sulfate, filtered and concentrated under reduced pressure to obtain (S)—N—(1-(3-methoxyphenyl)hexan-2-yl)-2-methylisonicotinamide. LCMS (ES) (m/z)=327.3 [M+H]+

$^1$H NMR (400 MHz, CDCl$_3$) δ ppm 0.87-0.89 (m, 3H), 1.36-1.46 (m, 4H), 1.60-1.69 (m, 2H), 2.59 (s, 3H), 2.81-2.93 (m, 2H), 3.76 (s, 3H), 4.36-4.37 (m, 1H), 5.83 (d, J=7.2 Hz, 1H), 6.74-6.78 (m, 3H), 7.21 (t, J=7.6 Hz, 2H), 7.37 (s, 1H), 8.57 (d, J=4.8 Hz, 1H).

(S)-3-butyl-6-methoxy-1-(2-methylpyridin-4-yl)-3,4-dihydroisoquinoline: Trifluoromethanesulfonic anhydride (1.28 mL, 7.65 mmol, 2 eq) was added via syringe over a period of 1 min to a stirred mixture of (S)—N—(1-(3-methoxyphenyl)hexan-2-yl)-2-methylisonicotinamide (1.25 g, 3.82 mmol, 1 eq) and 2-chloropyridine (0.72 mL, 7.65 mmol, 2 eq) in dichloromethane (10 mL) at −78° C. After 5 min, the reaction mixture was placed in an ice-water bath and warmed to 0° C. After 5 min, the resulting solution was allowed to warm to 23° C. TLC (5% MeOH in DCM) showed the reaction was completed. After 1 h, aqueous sodium hydroxide solution (12 mL, 1N) was introduced to neutralize the trifluoromethanesulfonate salts. Dichloromethane (70 mL) was added to dilute the mixture and the layers were separated. The organic layer was washed with brine (10 mL), was dried over anhydrous sodium sulfate, and was filtered. The volatiles were removed under reduced pressure to give the crude product. The obtained crude product was purified by flash chromatography using ethyl acetate in hexane as an eluent to get the desired product (S)-3-butyl-6-methoxy-1-(2-methylpyridin-4-yl)-3,4-dihydroisoquinoline. LCMS (ES) m/z=309.4 [M+H]+

(1S,3S)-3-butyl-6-methoxy-1-(2-methylpyridin-4-yl)-1,2,3,4-tetrahydroisoquinoline: A solution of the (S)-3-butyl-6-methoxy-1-(2-methylpyridin-4-yl)-3,4-dihydroisoquinoline (0.54 g, 1.78 mmol, 1 eq) in anhydrous THF (4 mL) was added drop wise to a mixture of lithium aluminum hydride 1M in THF (17.8 mL, 17.8 mmol, 10 eq) and trimethylaluminum (2M in THF) (4.46 mL, 12.85 mmol, 5 eq) at −78° C. under nitrogen. The suspension was stirred at −78° C. for 1 h, and warmed to 0° C. over 1 h. TLC (5% MeOH in DCM) showed the reaction was completed. The reaction mixture was quenched with saturated aqueous sodium chloride (8 mL) followed by diluted with EtOAc (30 mL) and the precipitate was filtered off. Finally, filtrate was dried over anhydrous sodium sulfate, filtered and evaporated under reduced pressure. The residue was purified by silica gel flash chromatography using ethyl acetate in hexane as an eluent to give the (1S,3S)-3-butyl-6-methoxy-1-(2-methylpyridin-4-yl)-1,2,3,4-tetrahydroisoquinoline. LCMS (ES) m/z=311.3 [M+H]+

1-((1S,3S)-3-butyl-6-methoxy-1-(2-methylpyridin-4-yl)-3,4-dihydroisoquinolin-2(1H)-yl)-3-(trimethylsilyl)prop-2-yn-1-one: First step:— To a solution of 3-(trimethylsilyl)propiolic acid (206 mg, 1.44 mmol, 3 eq) in DMF (0.014 mL, 0.05 mmol, 0.04 eq) was added oxalyl chloride (0.13 mL, 1.59 mmol, 1.1 eq) at room temperature and stirred for 30 minutes. After this time, reaction mixture was concentrated under reduced pressure to get 3-(trimethylsilyl)propioloyl chloride. This acid chloride was carried to next step without any further purification.

Second step:— To a solution of (1S,3S)-3-butyl-6-methoxy-1-(2-methylpyridin-4-yl)-1,2,3,4-tetrahydroisoquinoline (0.15 g, 0.48 mmol, 1.0 eq) in acetonitrile (5.0 mL) was added sodium bicarbonate (0.30 g, 3.62 mmol, 7.5 eq) at 0° C. After stirring for 5 minutes, a solution of 3-(trimethylsilyl)propioloyl chloride in acetonitrile (3.0 mL) was added to the above reaction mass. The resulting mixture stirred at 0° C. for 15 min, progress of the reaction was monitored by TLC (55% ethyl acetate in n-hexane). After this time, reaction mass was diluted with EtOAc (15 mL) and water (5 mL). Organic layer was separated, washed with brine solution (5 mL), dried over anhydrous sodium sulfate, filtered and concentrated under reduced pressure to obtain the crude product. This crude product was carried to next step without any further purification. LCMS (ES) m/z=435.3 [M+H]+

1-((1S,3S)-3-butyl-6-methoxy-1-(2-methylpyridin-4-yl)-3,4-dihydroisoquinolin-2(1H)-yl)prop-2-yn-1-one: To a solution of 1-((1S,3S)-3-butyl-6-methoxy-1-(2-methylpyridin-4-yl)-3,4-dihydroisoquinolin-2(1H)-yl)-3-(trimethylsilyl)prop-2-yn-1-one (0.25 g, 0.576 mmol, 1 eq) in THF (5.0 mL) was added TBAF (1M solution in THF) (0.63 mL, 0.63 mmol, 1.1 eq) at −78° C. This reaction mixture was stirred at −78° C. for 15 minutes. Progress of the reaction was monitored by TLC (60% ethyl acetate in n-hexane). After this time, the reaction mixture was quenched with saturated aqueous NaHCO$_3$ solution (8 mL) and product was extracted with ethyl acetate (25 mL). Organic layers were dried over anhydrous sodium sulfate, filtered and concentrated under reduced pressure. The obtained crude product was purified by preparative TLC using 55% ethyl acetate in n-hexane as an eluent to obtain 1-((1S,3S)-3-butyl-6-methoxy-1-(2-methylpyridin-4-yl)-3,4-dihydroisoquinolin-2(1H)-yl)prop-2-yn-1-one. LCMS (ES) m/z=363.4 [M+H]+.

$^1$H NMR (400 MHz, DMSO-d$_6$) ppm δ 0.80 (d, 3H), 1.24 (s, 4H), 1.50 (s, 2H), 2.38 (s, 3H), 2.80-2.88 (m, 1H), 3.12-3.15 (m, 1H), 3.72 (s, 3H), 4.38 (s, 1H), 4.57-4.74 (m, 1H), 5.97 (s, 1H), 6.78 (s, 2H), 6.99-7.07 (m, 2H), 7.40-7.55 (m, 1H), 8.23-8.29 (m, 1H).

Procedure 21: Synthesis of Compound 49

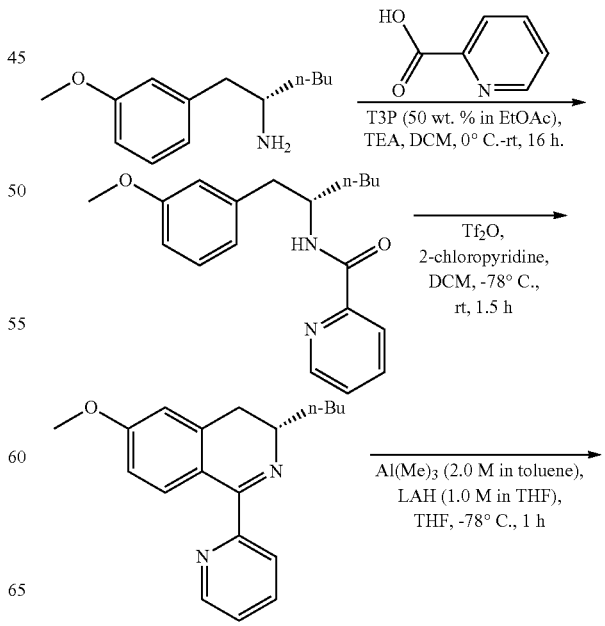

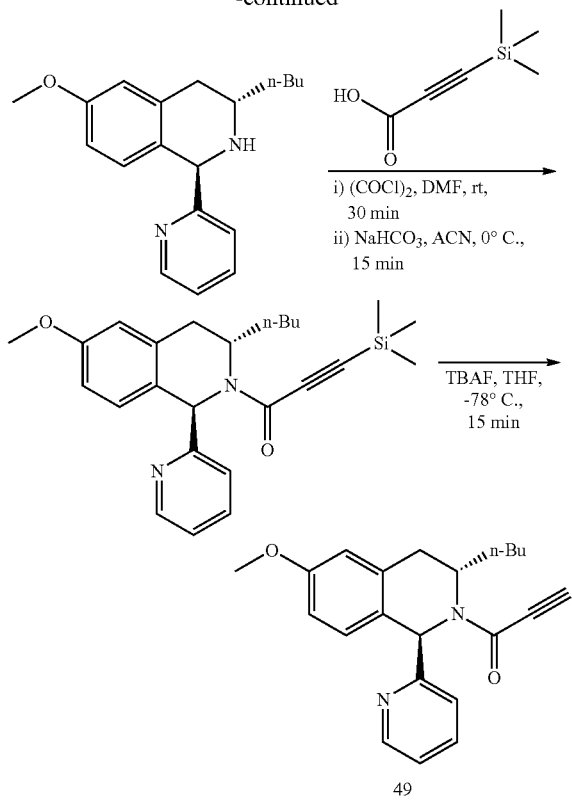

49

(S)—N—(1-(3-methoxyphenyl)hexan-2-yl)picolinamide: To a solution of picolinic acid (0.68 g, 5.54 mmol, 1.15 eq) in DCM (15 mL) was added TEA (2.7 mL, 19.29 mmol, 4 eq), stirred for 15 min and then T3P (50 wt. % in EtOAc) (4.6 mL, 7.23 mmol, 1.5 eq) was added at 0° C. and stirred for another 5 mins. Then (S)-1-(3-methoxyphenyl)hexan-2-amine (1.0 g, 4.82 mmol, 1 eq) was added to the reaction mixture and then reaction mixture was stirred at room temperature for 16 h. The progress of the reaction was monitored by TLC (40% ethyl acetate in hexane). The reaction mixture was diluted with DCM (30 mL) and saturated sodium bicarbonate solution (15 mL) Organic layer was separated, washed with brine solution (12 mL), dried over anhydrous sodium sulfate, filtered and concentrated under reduced pressure to obtain (S)—N—(1-(3-methoxyphenyl)hexan-2-yl)picolinamide. LC-MS (m/z)=313.4 [M+H]$^+$ $^1$H NMR (400 MHz, CDCl$_3$) δ ppm 0.84 (t, J=6.8 Hz, 3H), 1.23-1.60 (m, 6H), 2.81-2.94 (m, 2H), 3.74 (s, 3H), 4.35-4.36 (m, 1H), 6.73-6.82 (m, 3H), 7.17 (t, J=8.0 Hz, 1H), 7.39 (t, J=6.0 Hz, 1H), 7.82 (t, J=8.0 Hz, 1H), 7.91 (d, J=8.0 Hz, 1H), 8.17 (d, J=7.6 Hz, 1H), 8.52 (d, J=4.0 Hz, 1H).

(S)-3-butyl-6-methoxy-1-(pyridin-2-yl)-3,4-dihydroisoquinoline: Trifluoromethanesulfonic anhydride (1.55 mL, 9.28 mmol, 2.0 eq) was added via syringe over a period of 1 min to a stirred mixture of (S)—N—(1-(3-methoxyphenyl) hexan-2-yl)picolinamide (1.4 g, 4.64 mmol, 1 eq) and 2-chloropyridine (0.87 mL, 9.28 mmol, 2.0 eq) in dichloromethane (15 mL) at −78° C. After 5 min, the reaction mixture was placed in an ice-water bath and warmed to 0° C. After 5 min, the resulting solution was allowed to warm to 23° C. TLC (40% ethyl acetate in n-hexane) showed the reaction was completed. After 1 h, aqueous sodium hydroxide solution (12 mL, 1N) was introduced to neutralize the trifluoromethanesulfonate salts. Dichloromethane (50 mL) was added to dilute the mixture and the layers were separated. The organic layer was washed with brine (10 mL), was dried over anhydrous sodium sulfate, and was filtered. The volatiles were removed under reduced pressure to give the crude product. The obtained crude product was purified by flash chromatography using ethyl acetate in hexane as an eluent to get the desired product (S)-3-butyl-6-methoxy-1-(pyridin-2-yl)-3,4-dihydroisoquinoline. LC-MS (m/z)=295.1 [M+H]$^+$ $^1$H NMR (400 MHz, CDCl$_3$) δ ppm 0.93 (t, J=7.2 Hz, 3H), 1.26-1.43 (m, 4H), 1.65-1.88 (m, 2H), 2.58-2.65 (m, 1H), 2.79-2.87 (m, 1H), 3.58 (bs, 1H), 3.83 (s, 3H), 6.73-6.75 (m, 2H), 7.32-7.37 (m, 2H), 7.77-7.83 (m, 2H), 8.64-8.70 (m, 1H).

(1R,3S)-3-butyl-6-methoxy-1-(pyridin-2-yl)-1,2,3,4-tetrahydroisoquinoline: A solution of the (S)-3-butyl-6-methoxy-1-(pyridin-2-yl)-3,4-dihydroisoquinoline (0.1 g, 0.34 mmol, 1 eq) in anhydrous THF (4 mL) was added drop wise to a mixture of lithium aluminum hydride 1M in THF (3.4 mL, 3.40 mmol, 10 eq) and trimethylaluminum (2M in toluene) (0.85 mL, 1.70 mmol, 5 eq) at −78° C. under nitrogen. The suspension was stirred at −78° C. for 1 h, and warmed to 0° C. over 1 h. TLC (5% MeOH in DCM) showed the reaction was completed. The reaction mixture was quenched with saturated aqueous sodium chloride (4 mL) followed by diluted with EtOAc (15 mL) and the precipitate was filtered off. Finally, filtrate was dried over anhydrous sodium sulfate, filtered and evaporated under reduced pressure. The residue was purified by silica gel flash chromatography using ethyl acetate in hexane as an eluent to give the (1R,3S)-3-butyl-6-methoxy-1-(pyridin-2-yl)-1,2,3,4-tetrahydroisoquinoline. LC-MS (m/z)=311.3 [M+H]$^+$ 1-((1R,3S)-3-butyl-6-methoxy-1-(pyridin-2-yl)-3,4-dihydroisoquinolin-2(1H)-yl)-3-(trimethylsilyl)prop-2-yn-1-one: First step:— To a solution of 3-(trimethylsilyl)propiolic acid (0.10 g, 0.709 mmol, 3.0 eq.) in DMF (0.0007 mL 0.009 mmol, 0.04 equiv.), oxalyl chloride (0.02 mL, 0.26 mmol, 1.1 eq.) was added at room temperature and reaction was stirred for 30 minutes. After this time, the reaction mixture was concentrated under reduced pressure to yield 3-trimethylsilyl)propioloyl chloride. This acid chloride was carried to next step without further purification.

Second step:— To a solution of (1S,3S)-3-butyl-6-methoxy-1-(2-methylpyridin-4-yl)-1,2,3,4-tetrahydroisoquinoline (0.07 g, 0.236 mmol, 1.0 eq.) in acetonitrile (3.0 mL) was added sodium bicarbonate (0.149 g, 1.77 mmol, 7.5 eq.) at 0° C. After stirring for 5 minutes, a solution of 3-(trimethylsilyl)propioloyl chloride in acetonitrile (2.0 mL) was added to the above reaction mass. The resulting mixture stirred at 0° C. for 15 min, progress of the reaction was monitored by TLC (60% ethyl acetate in n-hexane). After this time, reaction mass was diluted with EtOAc (15 mL) and water (5 mL). Organic layer was separated, washed with brine solution (5 mL), dried over anhydrous sodium sulfate, filtered and concentrated under reduced pressure to obtain the crude product. This crude product was carried to next step without any further purification. LC-MS (m/z)=421.3 [M+H]$^+$ 1-((1R,3S)-3-butyl-6-methoxy-1-(pyridin-2-yl)-3,4-dihydroisoquinolin-2(1H)-yl)prop-2-yn-1-one: To a solution of 1-((1R,3S)-3-butyl-6-methoxy-1-(pyridin-2-yl)-3,4-dihydroisoquinolin-2(1H)-yl)-3-(trimethylsilyl)prop-2-yn-1-one (0.07 g, 0.166 mmol, 1.0 equiv.) in THF (4.0 mL) was added TBAF (1M solution in THF) (0.183 mL, 0.183 mmol, 1.1 equiv.) at −78° C. This reaction mixture was stirred at −78°

C. for 15 minutes. Progress of the reaction was monitored by TLC (50% ethyl acetate in n-hexane). After this time, the reaction mixture was quenched with saturated aqueous NaHCO₃ solution (2 mL) and product was extracted with ethyl acetate (25 mL). Organic layers were dried over anhydrous sodium sulfate, filtered and concentrated under reduced pressure. The obtained crude product was purified by preparative TLC using 50% ethyl acetate in n-hexane as an eluent to get 1-((1R,3S)-3-butyl-6-methoxy-1-(pyridin-2-yl)-3,4-dihydroisoquinolin-2(1H)-yl)prop-2-yn-1-one. LC-MS (m/z)=349.4 [M+H]⁺

¹H NMR (400 MHz, DMSO-d₆): δ 0.80 (t, J=6.8 Hz, 3H), 1.20-1.44 (m, 6H), 2.71-2.83 (m, 1H), 3.03 (s, 1H), 3.43-3.47 (m, 1H), 3.67-3.69 (m, 3H), 4.56-4.70 (m, 2H), 6.01-6.28 (m, 2H), 6.72-6.79 (m, 1H), 7.09-7.18 (m, 1H), 7.35-7.44 (m, 1H), 7.56-7.69 (m, 1H), 8.32-8.42 (m, 1H).

Procedure 22: Synthesis of Compound 50

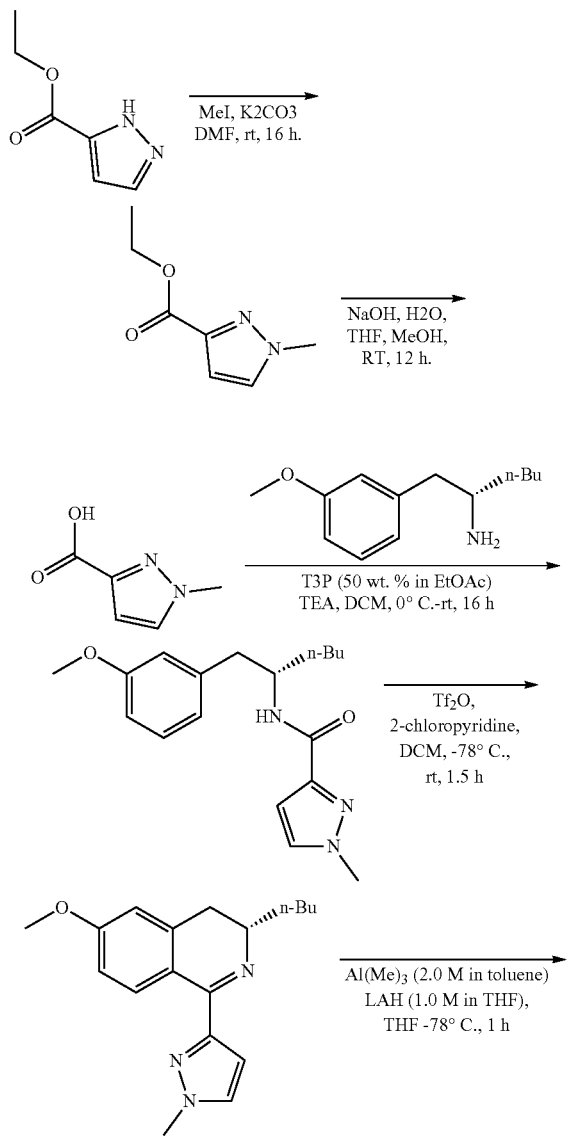

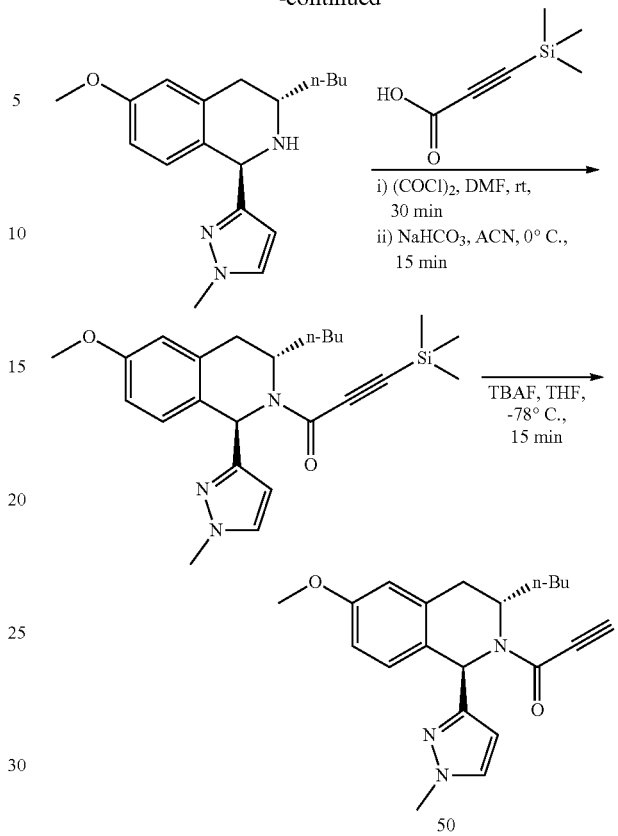

ethyl 1-methyl-1H-pyrazole-3-carboxylate: To a solution of ethyl 1H-pyrazole-5-carboxylate (4.0 g, 28.5 mmol, 1.0 eq) in DMF (40 mL), potassium carbonate (7.89 g, 57.1 mmol, 2 eq) and methyl iodide (3.55 mL, 57.1 mmol, 2 eq) were added at room temperature. The reaction mixture was stirred for 16 h at room temperature. The progress of the reaction was monitored by TLC (30% ethyl acetate in n-hexane). After this time, the reaction mixture was diluted with ice cold water (30 mL) and extracted with ethyl acetate (100 mL). The organic layer was separated, dried over anhydrous sodium sulphate, filtered and concentrated under reduced pressure to get crude product of ethyl 1-methyl-1H-pyrazole-3-carboxylate. LCMS (ES) m/z=155.1 [M+H]⁺

¹H NMR (400 MHz, CDCl₃) δ ppm 1.38 (t, J=7.2 Hz, 3H), 3.97 (s, 3H), 4.38 (q, J=6.8 Hz, 2H), 6.79 (d, J=1.6 Hz, 1H), 7.37 (d, J=1.2 Hz, 1H).

1-methyl-1H-pyrazole-3-carboxylic acid: To a solution of ethyl 1-methyl-1H-pyrazole-3-carboxylate (2.0 g, 13.0 mmol, 1 eq) in THF (10 mL) and methanol (10 mL), 2 M sodium hydroxide solution (15 mL) was added. The reaction mixture was stirred at room temperature for 16 h. The progress of the reaction was monitored by TLC (70% ethyl acetate in n-hexane). After reaction completion, the reaction mixture was concentrated to remove solvents. The reaction mixture was acidified using 1N HCl solution (pH 3) and extracted with ethyl acetate (120 mL). The organic layer was dried over anhydrous sodium sulphate, filtered and concentrated under reduced to yield crude 1-methyl-1H-pyrazole-5-carboxylic acid. LCMS (m/z)=127.1 [M+H]⁺

¹H NMR (400 MHz, DMSO-d₆) δ ppm 3.87 (s, 3H), 6.63-6.64 (m, 1H), 7.75 (s, 1H), 12.54 (s, 1H).

(S)—N—(1-(3-methoxyphenyl)hexan-2-yl)-1-methyl-1H-pyrazole-3-carboxamide: To a solution of (2S)-1-(3- methoxyphenyl)hexan-2-amine (1.6 g, 7.72 mmol, 1.0 eq) in DCM (10 mL) was added 1-methyl-1H-pyrazole-3-carboxylic acid (1.17 g, 9.26 mmol, 1.2 eq) and triethylamine (4.3 mL, 30.9 mmol, 4.0 eq). To this propanephosphonic acid anhydride (7.37 mL, 11.6 mmol, 1.5 eq) was added at 0° C. After the addition, the reaction mixture was stirred at room temperature for 16 h. The progress of the reaction was monitored by TLC (70% ethyl acetate in n-hexane). After reaction completion, the reaction mixture was quenched with aqueous NaHCO$_3$ solution (15 mL) and extracted with DCM (70 mL). Organic layer was dried over anhydrous Na$_2$SO$_4$, filtered and concentrated under reduced pressure to get crude N-[(2S)-1-(3-methoxyphenyl)hexan-2-yl]-1-methyl-1H-pyrazole-5-carboxamide. LCMS (m/z)=316.2 [M+H]$^+$ (3S)-3-butyl-6-methoxy-1-(1-methyl-1H-pyrazol-3-yl)-3,4-dihydroisoquinoline: Trifluoromethanesulfonic anhydride (3.19 mL, 19.0 mmol, 2.0 eq) was added via syringe over a period of 10 minutes to a stirred mixture of N-[(2S)-1-(3-methoxyphenyl)hexan-2-yl]-1-methyl-1H-pyrazole-3-carboxamide (3.0 g, 9.51 mmol, 1.0 eq) and 2-chloropyridine (1.8 mL, 19.0 mmol, 2.0 eq) in dichloromethane (20 mL) at −78° C. After 5 min, the reaction mixture was placed in an ice-water bath and warmed to 0° C. After 5 min, the resulting solution was allowed to warm to 23° C. The progress of the reaction was monitored by TLC (70% ethyl acetate in n-hexane). After 15 minutes aqueous sodium hydroxide solution (12 mL, 1N) was added to reaction mixture at 0° C. to neutralize the trifluoromethanesulfonate salts. Dichloromethane (50 mL) was added to dilute the mixture and the layers were separated. The organic layer was washed with brine (10 mL), was dried over anhydrous sodium sulfate, and was filtered. The volatiles were removed under reduced pressure to give the crude product. The obtained crude product was purified by flash chromatography using ethyl acetate in hexane as an eluent to get the desired product (3S)-3-butyl-6-methoxy-1-(1-methyl-1H-pyrazol-3-yl)-3,4-dihydroisoquinoline. LCMS (m/z)=298.1 [M+H]$^+$ $^1$H NMR (400 MHz, CDCl$_3$) δ ppm: 0.88 (t, J=6.4 Hz, 3H), 1.24-1.44 (m, 4H), 1.54-2.03 (m, 2H), 2.76-2.88 (m, 1H), 3.01-3.20 (m, 1H), 3.92 (s, 3H), 4.04 (s, 4H), 6.85 (d, J=1.2 Hz, 1H), 6.91 (d, J=8.8 Hz, 1H), 7.10 (s, 1H), 7.56 (s, 1H), 8.13 (d, J=8.8 Hz, 1H).

(1R,3S)-3-butyl-6-methoxy-1-(1-methyl-1H-pyrazol-3-yl)-1,2,3,4-tetrahydroisoquinoline: To a solution of trimethylaluminium (7.82 mL, 15.6 mmol, 5 eq) in tetrahydrofuran (8 mL) at −78° C. was added lithium aluminium hydride (31.3 mL, 31.3 mmol, 10 eq) at −78° C. followed by the addition of (3S)-3-butyl-6-methoxy-1-(1-methyl-1H-pyrazol-3-yl)-3,4-dihydroisoquinoline (0.93 g, 3.13 mmol, 1 eq) in THF (3 mL). The reaction was stirred at −78° C. for 1 h. The progress of the reaction was monitored by TLC (70% ethyl acetate in n-hexane). After 1 h, the reaction was completed. The reaction mixture was quenched with brine solution (10 mL) at 0° C., diluted with ethyl acetate (15 mL). It was then filtered through celite bed and washed with ethyl acetate (20 mL). Organic layer was separated from aqueous layer and concentrated under reduced pressure to get crude. The crude was purified by flash column chromatography on silica gel with an increasing polarity of 2-3% MeOH in DCM as solvent to get (1R,3S)-3-butyl-6-methoxy-1-(1-methyl-1H-pyrazol-3-yl)-1,2,3,4-tetrahydroisoquinoline (mixture of cis and trans). LCMS (m/z)=300.2 [M+H]$^+$ 1-[(3S)-3-butyl-6-methoxy-1-(1-methyl-1H-pyrazol-3-yl)-1,2,3,4-tetrahydroisoquinolin-2-yl]-3-(trimethylsilyl)prop-2-yn-1-one: First step: To a solution of 3-(trimethylsilyl)propiolic acid (0.2 g, 1.41 mmol, 1 eq) in DMF (0.004 mL, 0.056 mmol, 0.04 eq), oxalyl chloride (0.13 mL, 1.55 mmol, 1.1 eq) was added at room temperature and reaction was stirred for 30 minutes. After this time, the reaction mixture was concentrated under reduced pressure to yield 3-trimethylsilyl)propioloyl chloride. This acid chloride was carried to next step without further purification.

Second step: To a solution of (1S,3S)-3-butyl-6-methoxy-1-(2-methylpyridin-4-yl)-1,2,3,4-tetrahydroisoquinoline (0.42 g, 1.40 mmol, 1 eq) in acetonitrile (3.0 mL) was added sodium bicarbonate (0.88 g, 10.5 mmol, 7.5 eq) at 0° C. After stirring for 5 minutes, a solution of 3-(trimethylsilyl)propioloyl chloride in acetonitrile (2 mL) was added to the above reaction mass. The resulting mixture stirred at 0° C. for 15 min, progress of the reaction was monitored by TLC (60% ethyl acetate in n-hexane). After this time, reaction mass was diluted with EtOAc (20 mL) and water (5 mL). Organic layer was separated, washed with brine solution (5 mL), dried over anhydrous sodium sulfate, filtered and concentrated under reduced pressure to obtain the crude product. This crude product was carried to next step without any further purification. LCMS (m/z)=424.3 [M+H]$^+$.

1-[(1R,3S)-3-butyl-6-methoxy-1-(1-methyl-1H-pyrazol-3-yl)-1,2,3,4-tetrahydroisoquinolin-2-yl]prop-2-yn-1-one: To a solution of —[(3S)-3-butyl-6-methoxy-1-(1-methyl-1H-pyrazol-3-yl)-1,2,3,4-tetrahydroisoquinolin-2-yl]-3-(trimethylsilyl)prop-2-yn-1-one (0.5 g, 1.18 mmol, 1 eq) in THF (8.0 mL) was added TBAF (1M solution in THF (1.30 mL, 1.30 mmol, 1.1 eq) at −78° C. This reaction mixture was stirred at −78° C. for 15 minutes. Progress of the reaction was monitored by TLC (50% ethyl acetate in n-hexane). After this time, the reaction mixture was quenched with saturated aqueous NaHCO$_3$ solution (2 mL) and product was extracted with ethyl acetate (25 mL). Organic layers were dried over anhydrous sodium sulfate, filtered and concentrated under reduced pressure. The obtained crude product was purified by preparative TLC using 50% ethyl acetate in n-hexane as an eluent to get 1-[(1R,3S)-3-butyl-6-methoxy-1-(1-methyl-1H-pyrazol-3-yl)-1,2,3,4-tetrahydroisoquinolin-2-yl]prop-2-yn-1-one. LCMS (m/z)=352.4 [M+H]$^+$.

$^1$H NMR (400 MHz, DMSO-d$_6$): δ 0.79 (t, J=6.0 Hz, 3H), 0.94-1.43 (m, 6H), 2.71-2.83 (m, 1H), 2.93-2.98 (m, 0.5H), 3.25-3.26 (m, 0.5H), 3.64-3.70 (m, 6H), 4.30-4.56 (m, 2H), 5.91-6.20 (m, 2H), 6.73-6.79 (m, 2H), 7.26-7.47 (m, 2H).

Procedure 23: Synthesis of Compound 76

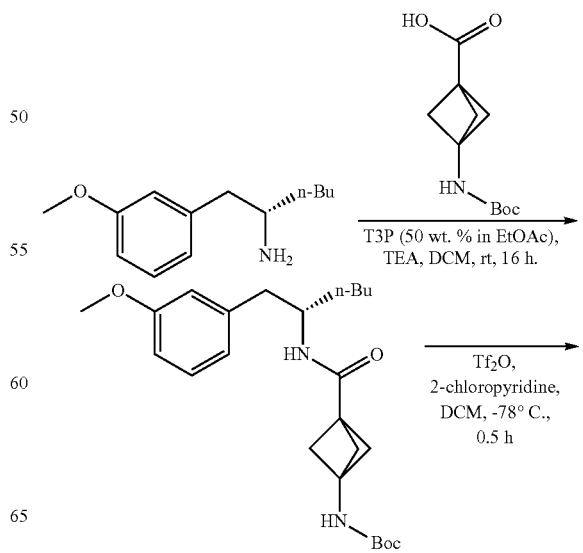

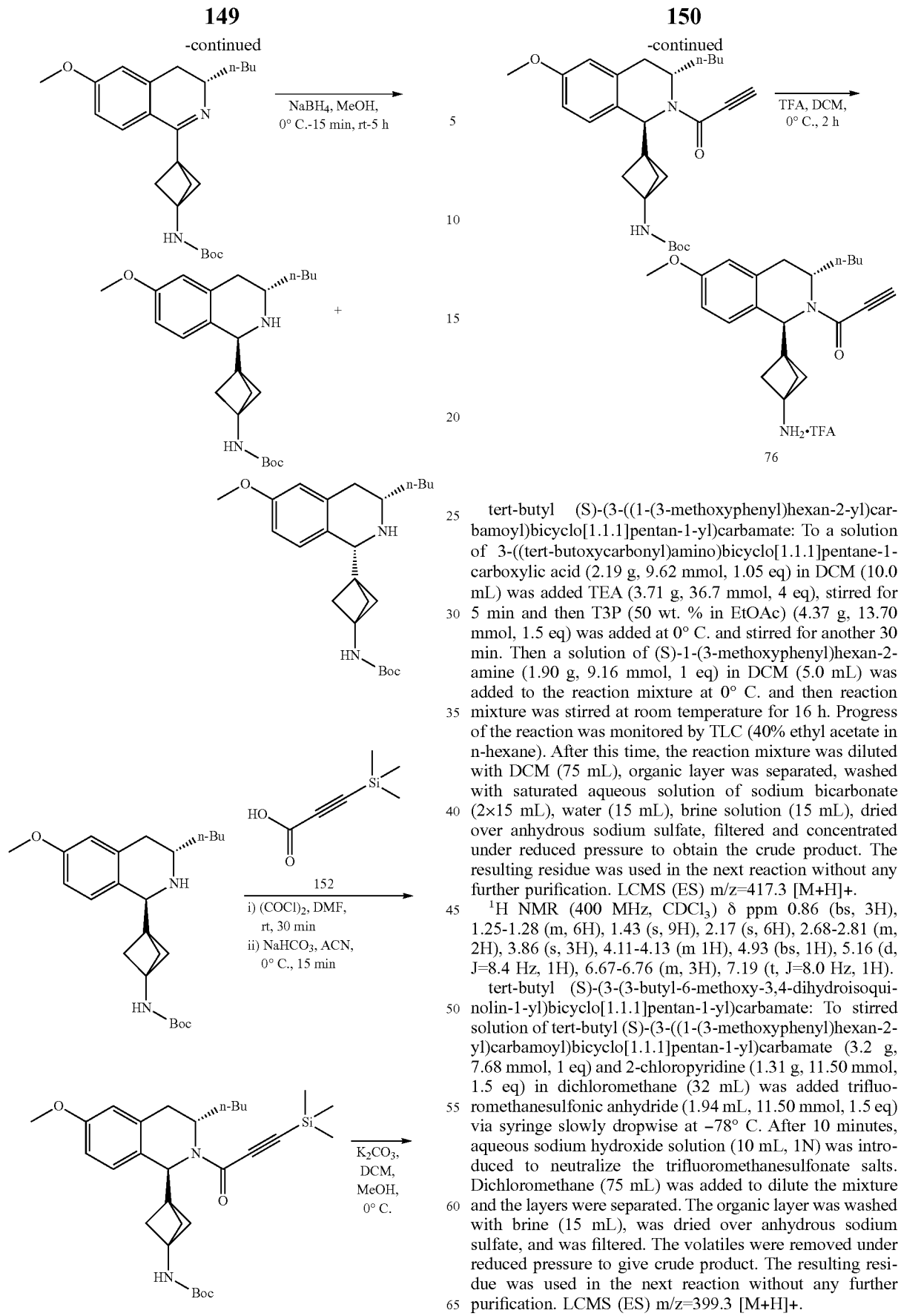

tert-butyl (S)-(3-((1-(3-methoxyphenyl)hexan-2-yl)carbamoyl)bicyclo[1.1.1]pentan-1-yl)carbamate: To a solution of 3-((tert-butoxycarbonyl)amino)bicyclo[1.1.1]pentane-1-carboxylic acid (2.19 g, 9.62 mmol, 1.05 eq) in DCM (10.0 mL) was added TEA (3.71 g, 36.7 mmol, 4 eq), stirred for 5 min and then T3P (50 wt. % in EtOAc) (4.37 g, 13.70 mmol, 1.5 eq) was added at 0° C. and stirred for another 30 min. Then a solution of (S)-1-(3-methoxyphenyl)hexan-2-amine (1.90 g, 9.16 mmol, 1 eq) in DCM (5.0 mL) was added to the reaction mixture at 0° C. and then reaction mixture was stirred at room temperature for 16 h. Progress of the reaction was monitored by TLC (40% ethyl acetate in n-hexane). After this time, the reaction mixture was diluted with DCM (75 mL), organic layer was separated, washed with saturated aqueous solution of sodium bicarbonate (2×15 mL), water (15 mL), brine solution (15 mL), dried over anhydrous sodium sulfate, filtered and concentrated under reduced pressure to obtain the crude product. The resulting residue was used in the next reaction without any further purification. LCMS (ES) m/z=417.3 [M+H]+.

$^1$H NMR (400 MHz, CDCl$_3$) δ ppm 0.86 (bs, 3H), 1.25-1.28 (m, 6H), 1.43 (s, 9H), 2.17 (s, 6H), 2.68-2.81 (m, 2H), 3.86 (s, 3H), 4.11-4.13 (m 1H), 4.93 (bs, 1H), 5.16 (d, J=8.4 Hz, 1H), 6.67-6.76 (m, 3H), 7.19 (t, J=8.0 Hz, 1H).

tert-butyl (S)-(3-(3-butyl-6-methoxy-3,4-dihydroisoquinolin-1-yl)bicyclo[1.1.1]pentan-1-yl)carbamate: To stirred solution of tert-butyl (S)-(3-((1-(3-methoxyphenyl)hexan-2-yl)carbamoyl)bicyclo[1.1.1]pentan-1-yl)carbamate (3.2 g, 7.68 mmol, 1 eq) and 2-chloropyridine (1.31 g, 11.50 mmol, 1.5 eq) in dichloromethane (32 mL) was added trifluoromethanesulfonic anhydride (1.94 mL, 11.50 mmol, 1.5 eq) via syringe slowly dropwise at −78° C. After 10 minutes, aqueous sodium hydroxide solution (10 mL, 1N) was introduced to neutralize the trifluoromethanesulfonate salts. Dichloromethane (75 mL) was added to dilute the mixture and the layers were separated. The organic layer was washed with brine (15 mL), was dried over anhydrous sodium sulfate, and was filtered. The volatiles were removed under reduced pressure to give crude product. The resulting residue was used in the next reaction without any further purification. LCMS (ES) m/z=399.3 [M+H]+.

tert-butyl (3-((1S,3S)-3-butyl-6-methoxy-1,2,3,4-tetrahydroisoquinolin-1-yl)bicyclo[1.1.1]pentan-1-yl)carbamate & tert-butyl (3-((1R,3S)-3-butyl-6-methoxy-1,2,3,4-tetrahydroisoquinolin-1-yl)bicyclo[1.1.1]pentan-1-yl)carbamate:
To a solution of tert-butyl (S)-(3-(3-butyl-6-methoxy-3,4-dihydroisoquinolin-1-yl)bicyclo[1.1.1]pentan-1-yl)carbamate (3.0 g, 7.53 mmol, 1 eq) in methanol (30 mL) was added sodium borohydride (0.854 mg, 22.60 mmol, 3 eq) portion wise at 0° C. The suspension was stirred at room temperature for 1 h. Progress of the reaction was monitored by TLC (50% EtOAc in n-hexane). After this time, the reaction mixture was concentrated under reduced pressure and obtained crude was diluted with EtOAc (100 mL) and water (20 mL). Organic layer was separated, washed with brine solution (20 mL), dried over anhydrous sodium sulfate, filtered and concentrated under reduced pressure to obtain the crude product. The obtained crude product was purified by flash column chromatography on silica gel using ethyl acetate in n-hexane as an eluent. Desired products were eluted with 30-70% ethyl acetate in n-hexane. Fractions containing products were combined and concentrated under reduced pressure to get tert-butyl (3-((1S,3S)-3-butyl-6-methoxy-1,2,3,4-tetrahydroisoquinolin-1-yl)bicyclo[1.1.1]pentan-1-yl)carbamate (1,3-trans isomer) and tert-butyl (3-((1R,3S)-3-butyl-6-methoxy-1,2,3,4-tetrahydroisoquinolin-1-yl)bicyclo[1.1.1]pentan-1-yl)carbamate (1,3-cis isomer).

Cis-isomer: LCMS (ES) m/z=401.3 [M+H]+.
$^1$H NMR (400 MHz, CDCl$_3$) δ ppm 0.92 (t, J=6.8 Hz, 3H), 1.23-1.29 (m, 3H), 1.36-1.37 (m, 3H), 1.43 (s, 9H), 1.93-2.04 (m, 6H), 2.37-2.44 (m, 1H), 2.64-2.68 (m, 1H), 2.76 (bs, 1H), 3.77 (s, 3H), 4.20 (s, 1H), 4.91 (bs, 1H), 6.59 (s, 1H), 6.68 (d, J=8.4 Hz, 1H), 7.05 (d, J=8.8 Hz, 1H).

Trans-isomer: LCMS (ES) m/z=401.3 [M+H]+.
$^1$H NMR (400 MHz, CDCl$_3$) δ ppm 0.93-0.94 (m, 3H), 1.25-1.28 (m, 5H), 1.36-1.47 (m, 10H), 1.93-1.98 (m, 6H), 2.43-2.50 (m, 1H), 2.69-2.72 (m, 1H), 3.13 (bs, 1H), 3.77 (s, 3H), 4.13 (s, 1H), 4.90 (bs, 1H), 6.60 (s, 1H), 6.65 (d, J=8.4 Hz, 1H), 6.89 (d, J=8.8 Hz, 1H).

To a solution of tert-butyl (3-((1S,3S)-3-butyl-6-methoxy-1,2,3,4-tetrahydroisoquinolin-1-yl)bicyclo[1.1.1]pentan-1-yl)carbamate (0.3 g, 0.749 mmol, 1 eq) in THF (4 mL) was added QuadraSil® AP extent of labeling: 1.5-2.0 mmol/g loading (480 mg) (calculated by amount of QuadraSil® required (for 1.0 eq)=mmol of copper catalyst used in the previous steps/mmol of scavenger loading) at room temperature and stirred for 1 h. After this time, solid portion was removed by passing through filter paper and filtrate was concentrated under reduced pressure to get tert-butyl (3-((1S,3S)-3-butyl-6-methoxy-1,2,3,4-tetrahydroisoquinolin-1-yl)bicyclo[1.1.1]pentan-1-yl)carbamate. LCMS (ES) m/z=401.3 [M+H]+.
$^1$H NMR (400 MHz, CDCl$_3$) δ ppm 0.93-0.94 (m, 3H), 1.25-1.28 (m, 5H), 1.36-1.47 (m, 10H), 1.93-1.98 (m, 6H), 2.43-2.50 (m, 1H), 2.69-2.72 (m, 1H), 3.13 (bs, 1H), 3.77 (s, 3H), 4.13 (s, 1H), 4.90 (bs, 1H), 6.60 (s, 1H), 6.65 (d, J=8.4 Hz, 1H), 6.89 (d, J=8.8 Hz, 1H).

tert-butyl (3-((1S,3S)-3-butyl-6-methoxy-2-(3-(trimethylsilyl)propioloyl)-1,2,3,4-tetrahydroisoquinolin-1-yl)bicyclo[1.1.1]pentan-1-yl)carbamate: First step: To a solution of 3-(trimethylsilyl)propiolic acid (155 mg, 1.09 mmol, 1.0 eq) in DMF (3.2 mg, 0.04 mmol, 0.04 eq) was added oxalyl chloride (152 mg, 1.2 mmol, 1.1 eq) at room temperature and stirred for 30 minutes. After this time, reaction mixture was concentrated under reduced pressure to get 3-(trimethylsilyl)propioloyl chloride. This acid chloride was carried to next step without any further purification.

Second step: To a solution of tert-butyl (3-((1S,3S)-3-butyl-6-methoxy-1,2,3,4-tetrahydroisoquinolin-1-yl)bicyclo[1.1.1]pentan-1-yl)carbamate (285 mg, 0.711 mmol, 1.0 eq) in acetonitrile (3.0 mL) was added sodium bicarbonate (448 mg, 5.34 mmol, 7.5 eq.) at 0° C. After stirring for 5 minutes, a solution of 3-(trimethylsilyl)propioloyl chloride (171 mg, 1.07 mmol, 1.5 eq) in acetonitrile (1 mL) was added to the above reaction mass at 0° C. The resulting mixture stirred at 0° C. for 15 min, progress of the reaction was monitored by TLC (50% ethyl acetate in n-hexane). After this time, reaction mass was diluted with EtOAc (40 mL) and water (10 mL). Organic layer was separated, washed with brine solution (7 mL), dried over anhydrous sodium sulfate, filtered and concentrated under reduced pressure to obtain the crude product. The obtained crude product was purified by preparative TLC by using 25% EtOAc in n-hexane as mobile phase to get tert-butyl (3-((1S,3S)-3-butyl-6-methoxy-2-(3-(trimethylsilyl)propioloyl)-1,2,3,4-tetrahydroisoquinolin-1-yl)bicyclo[1.1.1]pentan-1-yl)carbamate. LCMS (ES) m/z=525.3 [M+H]+.

$^1$H NMR (400 MHz, CDCl$_3$) δ ppm 0.25-0.28 (m, 9H), 0.80-0.84 (m, 3H), 1.16-1.26 (m, 6H), 1.39 (s, 9H), 1.73-1.82 (m, 6H), 2.67-2.71 (m, 1H), 2.92-2.96 (m, 1H), 3.02-3.11 (m, 1H), 3.80-3.81 (m, 3H), 4.44 (bs, 1H), 5.28 (s, 1H), 6.67-6.74 (m, 2H), 6.92 (d, J=8.4 Hz, 1H).

tert-butyl (3-((1S,3S)-3-butyl-6-methoxy-2-propioloyl-1,2,3,4-tetrahydroisoquinolin-1-yl)bicyclo[1.1.1]pentan-1-yl)carbamate: To a solution of tert-butyl (3-((1S,3S)-3-butyl-6-methoxy-2-(3-(trimethylsilyl)propioloyl)-1,2,3,4-tetrahydroisoquinolin-1-yl)bicyclo[1.1.1]pentan-1-yl)carbamate (145 mg, 0.276 mmol, 1 eq) in DCM (16 mL)/MeOH (3.3 mL) were added K$_2$CO$_3$ (232 mg, 1.66 mmol, 6.0 eq) at 0° C. The reaction mixture was stirred at 0° C. for 3 hr to give a white solution. Progress of the reaction was monitored by TLC (30% ethyl acetate in n-hexane). After this time, the reaction mixture was diluted with DCM (50 mL) and water (10 mL). Organic layer was separated, dried over Na$_2$SO$_4$ and concentrated under reduced pressure to give tert-butyl 3-((1S,3S)-3-butyl-6-methoxy-2-propioloyl-1,2,3,4-tetrahydroisoquinolin-1-yl)bicyclo[1.1.1]pentan-1-yl)carbamate. The resulting residue was used in the next reaction without any further purification. LCMS (ES) m/z=397.3 [M+H]+−56.

$^1$H NMR (400 MHz, CDCl$_3$) δ ppm 0.80-0.82 (m, 3H), 1.18-1.25 (m, 6H), 1.38-1.39 (m, 9H), 1.75-1.84 (m, 6H), 2.68-2.72 (m, 1H), 2.92-3.11 (m, 2H), 3.80-3.81 (m, 3H), 4.45 (bs, 1H), 4.84 (s, 1H), 5.27 (s, 1H), 6.67-6.73 (m, 2H), 6.92 (d, J=8.4 Hz, 1H).

1-((1S,3S)-1-(3-aminobicyclo[1.1.1]pentan-1-yl)-3-butyl-6-methoxy-3,4-dihydroisoquinolin-2(1H)-yl)prop-2-yn-1-one: To a solution of tert-butyl (3-((1S,3S)-3-butyl-6-methoxy-2-propioloyl-1,2,3,4-tetrahydroisoquinolin-1-yl)bicyclo[1.1.1]pentan-1-yl)carbamate (120 mg, 0.265 mmol, 1.0 eq) in DCM (10 mL) was added TFA (2.42 g, 21.2 mmol, 80 eq) at 0° C. The mixture was stirred at 0° C. for 1.5 hr. LCMS showed the reaction was completed. Then, the reaction mixture was concentrate under reduced pressure. Obtained residue was dissolved in water (5 mL) followed by lyophilize to give 1-((1S,3S)-1-(3-aminobicyclo[1.1.1]pentan-1-yl)-3-butyl-6-methoxy-3,4-dihydroisoquinolin-2(1H)-yl)prop-2-yn-1-one. LCMS (ES) m/z=353.3 [M+H]+.

$^1$H NMR (400 MHz, DMSO-d$_6$) δ ppm 0.77 (bs, 3H), 0.88-0.95 (m, 1H), 1.16-1.17 (m, 4H), 1.34 (bs, 1H), 1.58-1.77 (m, 6H), 2.78-2.89 (m, 2H), 3.73 (s, 3H), 4.32-4.43 (m, 1H), 4.57-4.62 (m, 1H), 5.19-5.29 (m, 1H), 6.79 (d, J=8.0 Hz, 1H), 6.87 (s, 1H), 6.05-7.14 (m, 1H), 8.37-8.44 (m, 3H).

Procedure 24: Synthesis of Compound 94

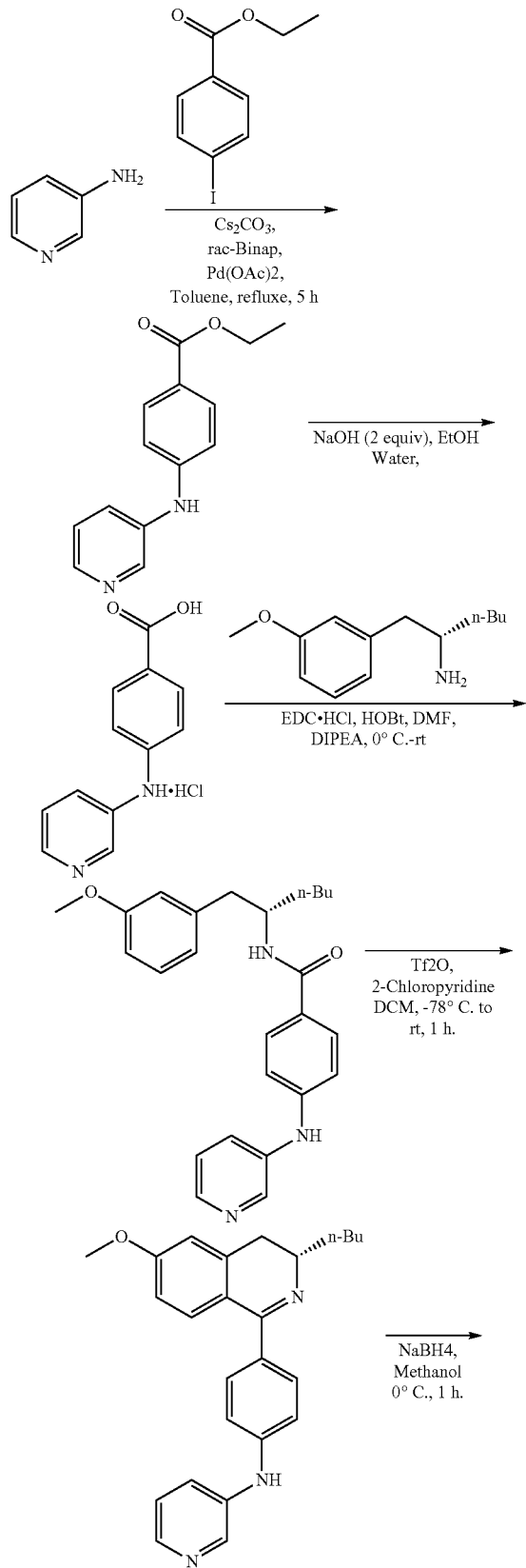

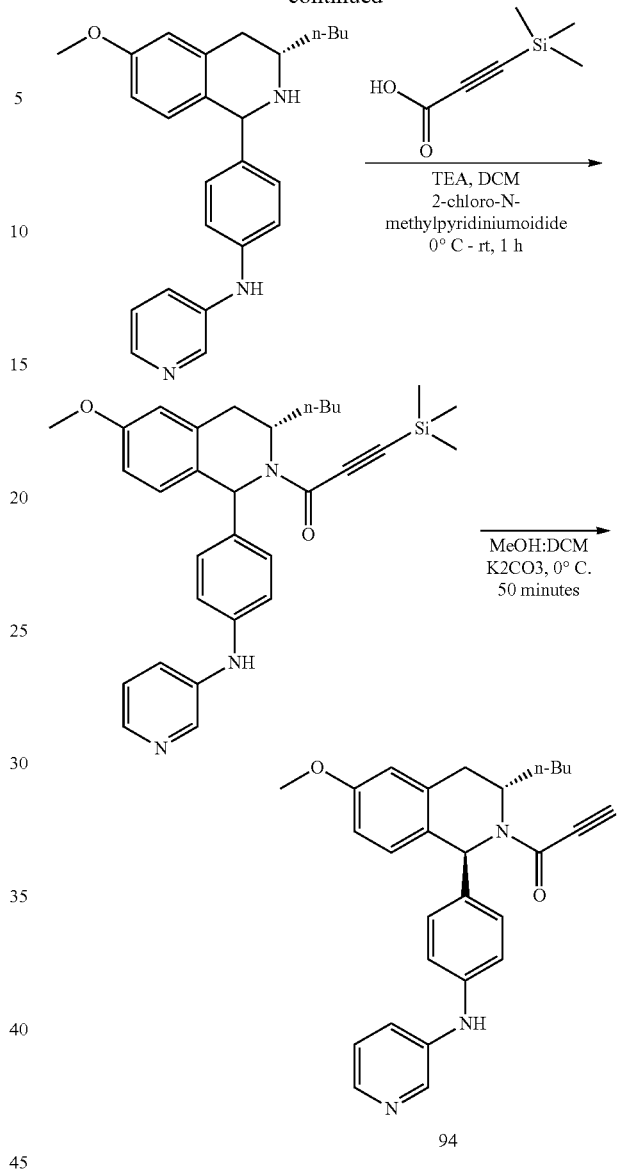

ethyl 4-[(pyridin-3-yl)amino]benzoate: To a solution of ethyl 4-iodobenzoate (5.0 g, 18.1 mmol, 1.0 eq) and pyridine-3-amine (2.05 g, 21.7 mmol, 1.2 eq) in Toluene (100 mL) was added cesium carbonate (11.8 g, 36.2 mmol, 2 eq) and binap (0.226 g, 0.362 mmol, 0.02 eq) at room temperature, purged the reaction mixture with nitrogen for 20 mins and then $Pd(OAc)_2$ (0.081 g, 0.362 mmol, 0.02 eq) added. Then reaction mixture was stirred under reflux condition for 30 h. The reaction mixture was cooled to room temperature, filtered through celite bed, washed the bed with EtOAc (200 mL) and the filtrate was concentrated under reduced pressure to get crude product. The obtained crude product was purified by flash column chromatography on silica gel using EtOAc in n-hexane. Product was isolated at 40-45% ethyl acetate in hexane as an eluent to afford ethyl 4-(pyridin-3-ylamino)benzoate. LCMS (ES) m/z=243.1 [M+H]+.

$^1$H NMR (400 MHz, DMSO-$d_6$): δ ppm 1.27 (t, J=6.8 Hz, 3H), 4.23 (q, J=7.2 Hz, 2H), 7.07 (d, J=8.8 Hz, 2H), 7.29-7.32 (m, 1H), 7.59 (d, J=6.8 Hz, 1H), 7.81 (d, J=8.4 Hz, 2H), 8.15-8.16 (m, 1H), 8.41-8.42 (m, 1H), 8.91 (s, 1H).

4-[(pyridin-3-yl)amino]benzoic acid hydrochloride: To a stirred solution of ethyl 4-[(pyridin-3-yl)amino]benzoate (2.5 g, 10.3 mmol, 1.0 eq) in ethanol (30 mL) was added sodium hydroxide (0.84 g, 20.6 mmol, 2.0 eq) in water (10 mL). The reaction mixture was stirred at 75° C. for 16 h. The progress of the reaction was monitored by TLC (70% ethyl acetate in n-hexane). After reaction completion, the reaction mixture was concentrated. Obtained crude was acidified with 1N HCl (pH~2) and evaporated under reduced pressure to get hydrochloride salt of crude product. Product was dried and taken for next step as hydrochloride salt. LCMS (ES) m/z=215.1 [M+H]+ free amine mass.

N-[(2S)-1-(3-methoxyphenyl)hexan-2-yl]-4-[(pyridin-3-yl)amino]benzamide: To a stirred solution of 4-(pyridin-3-ylamino)benzoic acid hydrochloride (3.10 g, 12.3 mmol, 1.6 eq) in DMF (30 mL) was added DIPEA (8.1 mL, 46.3 mmol, 6 eq) and stirred for 5 minutes, then EDC.HCl (2.2 g, 11.6 mmol, 1.5 eq) followed by (S)-1-(3-methoxyphenyl)hexan-2-amine (1.6 g, 7.72 mmol, 1 eq) was added at 0° C. After stirring for 5 minutes HOBt (1.56 g, 11.6 mmol, 1.5 eq) was added to the reaction mixture at 0° C. and then reaction mixture was stirred at room temperature for 16 h. After this time, the reaction mixture was diluted with EtOAc (60 mL), organic layer was washed with saturated sodium bicarbonate solution (20 mL), water (10 mL), brine solution (10 mL), dried over anhydrous sodium sulfate, filtered and concentrated under reduced pressure. The crude product was purified by flash column chromatography using 5% MeOH in DCM as an eluent to obtain N-[(2S)-1-(3-methoxyphenyl)hexan-2-yl]-4-[(pyridin-3-yl)amino]benzamide. LCMS(ES) m/z=404.4 [M+H]+.

$^1$H NMR (400 MHz, DMSO-$d_6$) δ ppm: 0.91 (bs, 3H), 1.23 (s, 4H), 1.49 (s, 2H), 2.71-2.81 (m, 2H), 3.66 (s, 3H), 4.11-4.12 (m, 1H), 6.69 (d, J=8.0 Hz, 1H), 6.76 (s, 2H), 7.04 (d, J=8.0 Hz, 2H), 7.11-7.13 (m, 1H), 7.26-7.28 (m, 1H), 7.52-7.53 (m, 1H), 7.71 (d, J=8.0 Hz, 2H), 7.92 (d, J=8.4 Hz, 1H), 8.07 (d, J=8.0 Hz, 1H), 8.37 (s, 1H), 8.66 (s, 1H).

N-{4-[(3S)-3-butyl-6-methoxy-3,4-dihydroisoquinolin-1-yl]phenyl}pyridin-3-amine: To stirred solution of N-[(2S)-1-(3-methoxyphenyl)hexan-2-yl]-4-[(pyridin-3-yl)amino] benzamide (2.4 g, 5.95 mmol, 1 eq) and 2-chloropyridine (1.69 mL, 17.8 mmol, 3.0 eq) in dichloromethane (30 mL) was added trifluoromethanesulfonic anhydride (3.0 mL, 17.8 mmol, 3.0 eq) via syringe slowly dropwise at −78° C. After 5 min, the reaction mixture was placed in an ice-water bath and warmed to 0° C. After 5 min, the resulting solution was allowed to warm to 23° C. Progress of the reaction was monitored by TLC (5% MeOH in DCM). After 1 h, reaction was quenched with aqueous sodium hydroxide solution (25 mL, 1N) to neutralize the trifluoromethanesulfonate salts. Dichloromethane (150 mL) was added to dilute the mixture and the layers were separated. The aqueous layer was extracted with DCM (100 mL). The combined organic layer was washed with brine (25 mL), was dried over anhydrous sodium sulfate, and was filtered. The volatiles were removed under reduced pressure to give the crude product. The obtained crude product was purified by flash chromatography using 5% MeOH in DCM as an eluent to get the desired product N-{4-[(3S)-3-butyl-6-methoxy-3,4-dihydroisoquinolin-1-yl]phenyl}pyridin-3-amine. LCMS (ES) m/z=386.2 [M+H]+.

N-{4-[(3S)-3-butyl-6-methoxy-1,2,3,4-tetrahydroisoquinolin-1-yl]phenyl}pyridin-3-amine: To a stirred solution of N-{4-[(3S)-3-butyl-6-methoxy-3,4-dihydroisoquinolin-1-yl]phenyl}pyridin-3-amine (1.9 g, 4.93 mmol, 1 eq) in methanol (45 mL) was added sodium borohydride (0.559 g, 14.8 mmol, 3 eq) portion wise at 0° C. The suspension was stirred at room temperature for 1 h. The reaction mixture was concentrated and obtained crude was diluted with EtOAc (300 mL) and water (100 mL). Organic layer was separated, washed with brine solution (100 mL), dried over anhydrous sodium sulfate, filtered and concentrated under reduced pressure to obtain the crude product. The obtained crude product was purified by flash chromatography using 5% methanol in DCM as an eluent to get N-{4-[(3S)-3-butyl-6-methoxy-1,2,3,4-tetrahydroisoquinolin-1-yl] phenyl}pyridin-3-amine. LCMS (ES) m/z=388.4 [M+H]+.

1-[(3S)-3-butyl-6-methoxy-1-{4-[(pyridin-3-yl)amino] phenyl}-1,2,3,4-tetrahydroisoquinolin-2-yl]-3-(trimethylsilyl)prop-2-yn-1-one: To a stirred solution of N-{4-[(3S)-3-butyl-6-methoxy-1,2,3,4-tetrahydroisoquinolin-1-yl] phenyl}pyridin-3-amine (0.400 g, 1.03 mmol, 1.0 eq) in DCM (12.0 mL) was added triethylamine (0.363 mL, 2.58 mmol, 2.5 eq), 3-(trimethylsilyl)propiolic acid (0.176 g, 1.24 mmol, 1.2 eq) and 2-Chloro-1-methylpyridinium iodide (0.316 g, 1.24 mmol, 1.2 eq) at room temperature and the reaction was stirred at room temperature for 1 h. The reaction mixture was diluted with DCM (25 mL), washed with water (10 mL) and brine (10 mL), dried over anhydrous sodium sulfate. Organic layer was filtered and concentrated under reduced pressure to get 1-[(3S)-3-butyl-6-methoxy-1-{4-[(pyridin-3-yl)amino]phenyl}-1,2,3,4-tetrahydroisoquinolin-2-yl]-3-(trimethylsilyl)prop-2-yn-1-one. LCMS (ES) m/z=512.3 [M+H]+.

1-[(1S,3S)-3-butyl-6-methoxy-1-{4-[(pyridin-3-yl) amino]phenyl}-1,2,3,4-tetrahydroisoquinolin-2-yl]prop-2-yn-1-one: To a stirred solution of 1-[(3S)-3-butyl-6-methoxy-1-{4-[(pyridin-3-yl)amino]phenyl}-1,2,3,4-tetrahydroisoquinolin-2-yl]-3-(trimethylsilyl)prop-2-yn-1-one (0.640 g, 1.25 mmol, 1.0 eq) in MeOH:DCM (1:5) (12 mL) mixture at 0° C., potassium carbonate (1.04 g, 7.50 mmol, 6.0 eq) was added. Then reaction mixture was stirred at 0° C. for 50 minutes. Then reaction mixture was diluted with DCM (25.0 mL), washed with water (10.0 mL). Organic layer was separated and dried over anhydrous sodium sulphate. Organic layer was filtered and concentrated under reduced pressure to get crude product, which was purified by flash column chromatography using ethyl acetate in hexane as eluent. Isolated mixture was further purified by preparative TLC using 60% ethyl acetate in hexane as eluent by running two times. Product fraction collected and concentrated under reduced pressure to get pure product. Obtained pure product kept under lyophilization by dissolving acetonitrile (1.0 mL) and water (2.0 mL) mixture for 16 h to get 1-[(1S,3S)-3-butyl-6-methoxy-1-{4-[(pyridin-3-yl)amino]phenyl}-1,2,3,4-tetrahydroisoquinolin-2-yl]prop-2-yn-1-one. LCMS m/z=440.5 [M+H]+.

$^1$H NMR (400 MHz, DMSO-$d_6$) δ ppm 0.79-0.80 (m, 3H), 1.21 (bs, 4H), 1.49 (s, 2H), 2.77-2.87 (m, 1.5H), 3.06-3.10 (m, 0.5H), 3.70-3.72 (m, 3H), 4.31 (s, 0.5H), 4.48 (s, 0.5H), 4.58 (s, 0.5H), 4.66 (s, 0.5H), 6.00 (s, 0.5H), 6.24 (s, 0.5H), 6.77-6.83 (m, 2H), 6.92-6.99 (m, 2H), 7.05-7.13 (m, 2H), 7.15-7.17 (m, 1H), 7.35-7.39 (m, 1.5H), 7.52-7.54 (m, 0.5H), 7.94-7.98 (m, 1H), 8.24-8.29 (m, 2H).

Procedure 25: Synthesis of Compound 100

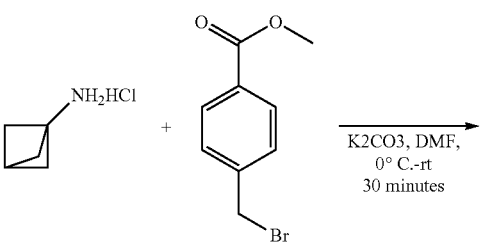

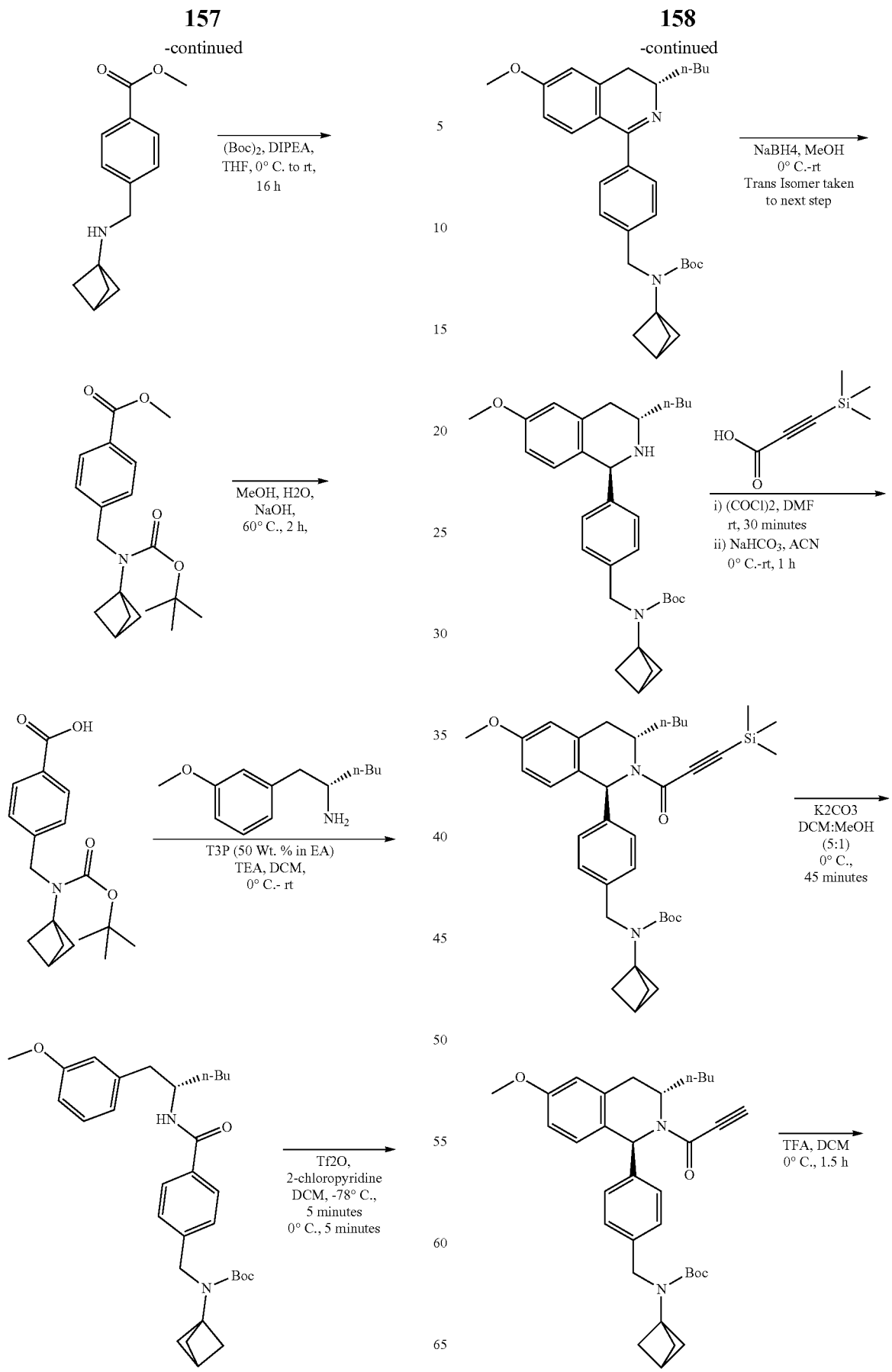

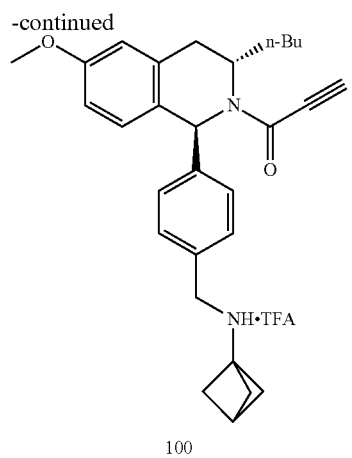

100 methyl 4-[({bicyclo[1.1.1]pentan-1-yl}amino)methyl] benzoate: To a stirred solution of bicyclo[1.1.1]pentan-1-amine hydrochloride (2.1 g, 17.6 mmol, 1.0 eq) in DMF (30.0 mL) at 0° C., potassium carbonate (7.3 g, 52.7 mmol, 3.0 eq) added. After stirring for 5 minutes methyl 4-(bromomethyl)benzoate (3.22 g, 14.0 mmol, 0.8 eq) added. Then reaction mixture was allowed to stir at room temperature for 30 minutes. Reaction mixture was diluted with water (30 mL), extracted in to ethyl acetate (2×30 mL). Combined organic layer was washed with cool water (40 mL), brine (20 mL), dried over anhydrous sodium sulphate. Organic layer was filtered and concentrated under reduced pressure to get crude product, which was purified by flash column chromatography on silica gel using ethyl acetate in hexane as eluent. Product was isolated at 15-18% ethyl acetate in hexane. Product fractions collected and concentrated under reduced pressure to get methyl 4-((bicyclo[1.1.1]pentan-1-ylamino)methyl)benzoate. LCMS (ES) m/z=232.2 [M+H]+.

$^1$H NMR (400 MHz, DMSO-d$_6$): δ ppm 1.64 (s, 6H), 2.28 (s, 1H), 3.69 (s, 2H), 3.74 (s, 3H), 7.45-7.48 (m, 2H), 7.86-7.88 (m, 2H).

methyl 4-[({bicyclo[1.1.1]pentan-1-yl}[(tert-butoxy)carbonyl]amino)methyl]benzoate: To a stirred solution of methyl 4-((bicyclo[1.1.1]pentan-1-ylamino)methyl)benzoate (2.2 g, 9.51 mmol, 1 eq) in THF (30 mL) at 0° C. added DIPEA (5 mL, 28.5 mmol, 3 eq) followed by boc anhydride (6.6 mL, 28.5 mmol, 3 eq). Then reaction mixture was allowed to stir at room temperature for 16 h. Reaction mixture was diluted with water (25 mL), extracted with ethyl acetate (2×30 mL). Combined organic layer was washed with water (20 mL), brine (20 mL), dried over anhydrous sodium sulphate. Organic layer was filtered and concentrated under reduced pressure to get crude product, which was purified by flash column chromatography on silica gel using ethyl acetate in hexane as eluent. Product was isolated at 12-16% ethyl acetate in hexane. Product fractions collected and concentrated under reduced pressure to get methyl 4-((bicyclo[1.1.1]pentan-1-yl(tert-butoxycarbonyl)amino)methyl)benzoate. LCMS (ES) m/z=332.2 [M+H]+ but observed 276.2 without tert butyl group.

4-[({bicyclo[1.1.1]pentan-1-yl}[(tert-butoxy)carbonyl]amino)methyl]benzoic acid: To a solution of methyl 4-((bicyclo[1.1.1]pentan-1-yl(tert-butoxycarbonyl)amino)methyl)benzoate (2.75 g, 8.30 mmol, 1 eq) in MeOH (20 mL) and water (10 mL) was added sodium hydroxide (0.680 g, 16.6 mmol, 2 eq) at room temperature and the reaction mixture was stirred at 60° C. for 2 h. Progress of the reaction was monitored by TLC (5% MeOH in DCM). After completion of the reaction, the reaction mixture was concentrated under reduced pressure to remove methanol from reaction mass and the remaining aqueous layer was acidified with 5% citric acid (pH~4) and then product was extracted with EtOAc (100 mL). Organic layer was dried over anhydrous sodium sulfate, filtered and concentrated under reduced pressure to get 4-((bicyclo[1.1.1]pentan-1-yl(tert-butoxycarbonyl)amino)methyl)benzoic acid. LCMS (ES) m/z=318.1 [M+H]+ but observed 262.1 without tert butyl group.

$^1$H NMR (400 MHz, DMSO-d$_6$): δ ppm 1.38 (s, 9H), 1.92 (s, 6H), 2.33 (s, 1H), 4.41 (s, 2H), 7.26 (d, J=8.4 Hz, 2H), 7.88 (d, J=8.4 Hz, 2H), 12.40 (bs, 1H).

tert-butyl N-{bicyclo[1.1.1]pentan-1-yl}—N-[(4-{[(2S)-1-(3-methoxyphenyl)hexan-2-yl]carbamoyl}phenyl)methyl]carbamate: To a solution of 4-((bicyclo[1.1.1]pentan-1-yl(tert-butoxycarbonyl)amino)methyl)benzoic acid (1.99 g, 6.27 mmol, 1 eq) in DCM (20 mL) was added TEA (2.64 mL, 18.8 mmol, 3 eq), stirred for 5 min and then T3P (50 wt. % in EtOAc) (6 mL, 9.41 mmol, 1.5 eq) was added at 0° C. and stirred for another 30 min. Then a solution of (S)-1-(3-methoxyphenyl)hexan-2-amine (1.3 g, 6.27 mmol, 1 eq) in DCM (10 mL) was added to the reaction mixture at 0° C. and then reaction mixture was stirred at room temperature for 2 h. Progress of the reaction was monitored by TLC (20% ethyl acetate in hexane). After this time, the reaction mixture was diluted with DCM (100 mL), washed with saturated sodium bicarbonate solution (40 mL), water (40 mL), brine solution (20 mL), dried over anhydrous sodium sulfate, filtered and concentrated under reduced pressure to obtain the crude product. The obtained crude product was purified by flash chromatography on silica gel. Desired product was eluted with 16-18% ethyl acetate in n-hexane. Fractions containing product were combined and concentrated under reduced pressure to get tert-butyl (S)-bicyclo[1.1.1]pentan-1-yl(4-((1-(3-methoxyphenyl)hexan-2-yl)carbamoyl)benzyl)carbamate. LCMS (ES) m/z=507.3 [M+H]+.

$^1$H NMR (400 MHz, DMSO-d$_6$): δ ppm 0.81 (s, 3H), 1.25-1.26 (m, 4H), 1.39 (s, 9H), 1.50 (s, 2H), 1.93 (s, 6H), 2.33 (s, 1H), 2.75 (bs, 2H), 3.65 (s, 3H), 4.12 (bs, 1H), 4.39 (s, 2H), 6.69 (d, J=8.0 Hz, 1H), 6.77 (s, 2H), 7.11-7.15 (m, 1H), 7.20-7.21 (m, 2H), 7.71 (d, J=7.2 Hz, 2H), 8.04 (bs, 1H).

tert-butyl N-{bicyclo[1.1.1]pentan-1-yl}—N—({4-[(3S)-3-butyl-6-methoxy-3,4-dihydroisoquinolin-1-yl] phenyl}methyl)carbamate: To stirred solution of tert-butyl (S)-bicyclo[1.1.1]pentan-1-yl(4-((1-(3-methoxyphenyl)hexan-2-yl)carbamoyl)benzyl)carbamate (2.3 g, 4.54 mmol, 1 eq) and 2-chloropyridine (1.30 mL, 13.6 mmol, 3.0 eq) in dichloromethane (25 mL) was added trifluoromethanesulfonic anhydride (2.3 mL, 13.6 mmol, 3 eq) via syringe slowly drop wise at −78° C. After 5 min, the reaction mixture was placed in an ice-water bath and warmed to 0° C. After 5 minutes reaction mixture was quenched with aqueous sodium hydroxide solution (1N, 20 mL) to neutralize the trifluoromethanesulfonate salts. Dichloromethane (150 mL) was added to dilute the mixture and the layers were separated. The aqueous layer was extracted with DCM (100 mL). The combined organic layer was washed with brine (25 mL), was dried over anhydrous sodium sulfate, filtered and concentrated under pressure to obtain the crude product, which was purified by flash column chromatography on silica gel using ethyl acetate in hexane as eluent. Product was isolated at 12-15% ethyl acetate in hexane. Product fractions collected and concentrated under reduced pressure to get tert-butyl N-{bicyclo[1.1.1]pentan-1-yl}—N—({4-[(3S)-3- butyl-6-methoxy-3,4-dihydroisoquinolin-1-yl]phenyl}methyl)carbamate. In Column purification N—({4-[(3S)-3-butyl-6-methoxy-3,4-dihydroisoquinolin-1-yl]phenyl}methyl)bicyclo[1.1.1]pentan-1-amine also isolated. LCMS (ES) m/z=489.3 [M+H]+.

$^1$H NMR (400 MHz, DMSO-$d_6$) δ ppm 0.87-0.91 (m, 3H), 1.32-1.40 (m, 12H), 1.56-1.67 (m, 3H), 1.95 (s, 6H), 2.30-2.34 (m, 1H), 2.41-2.48 (m, 2H), 2.74-2.78 (m, 1H), 3.78 (s, 3H), 4.42 (s, 2H), 6.80 (d, J=8.4 Hz, 1H), 6.90 (s, 1H), 7.07 (d, J=8.4 Hz, 1H), 7.23 (d, J=7.6 Hz, 2H), 7.45-7.46 (m, 2H).

tert-butyl N-{bicyclo[1.1.1]pentan-1-yl}—N—({4-[(1S,3S)-3-butyl-6-methoxy-1,2,3,4-tetrahydroisoquinolin-1-yl]phenyl}methyl)carbamate: To a solution of tert-butyl (S)-bicyclo[1.1.1]pentan-1-yl(4-(3-butyl-6-methoxy-3,4-dihydroisoquinolin-1-yl)benzyl)carbamate (0.850 g, 1.74 mmol, 1 eq) in methanol (10 mL) was added sodium borohydride (0.197 g, 5.22 mmol, 3 eq) portion wise at 0° C. The suspension was stirred at room temperature for 1 h. Progress of the reaction was monitored by TLC (20% EA in hexane). After this time, the reaction mixture was concentrated and obtained crude was diluted with EtOAc (20 mL) and water (10 mL). Organic layer was separated, washed with brine solution (10 mL), dried over anhydrous sodium sulfate, filtered and concentrated under reduced pressure to obtain the crude product. The obtained crude product was purified by Preparative TLC using 20% ethyl acetate in n-hexane. Product fraction collected and concentrated under reduced pressure to get tert-butyl N-{bicyclo[1.1.1]pentan-1-yl}—N—({4-[(1S,3S)-3-butyl-6-methoxy-1,2,3,4-tetrahydroisoquinolin-1-yl]phenyl}methyl)carbamate. LCMS (ES) m/z=491.3 [M+H]+.

$^1$H NMR (400 MHz, DMSO-$d_6$) δ ppm 0.75-0.78 (m, 3H), 1.08-1.17 (m, 6H), 1.36 (bs, 9H), 1.90 (s, 6H), 2.30 (s, 1H), 2.37 (s, 1H), 2.73-2.75 (m, 2H), 3.70 (s, 3H), 4.30 (s, 2H), 5.04 (bs, 1H), 6.64-6.69 (m, 2H), 6.75-6.77 (m, 1H), 7.04 (s, 4H).

tert-butyl N-{biicyclo[1.1.1]pentan-1-yl}—N—({4-[(1S,3S)-3-butyl-6-methoxy-2-[3-(trimethylsilyl)prop-2-ynoyl]-1,2,3,4-tetrahydroisoquinolin-1-yl]phenyl}methyl)carbamate: First step: To a solution of 3-(trimethylsilyl)propiolic acid (35 mg, 0.246 mmol, 1.0 eq) in DMF (0.001 mL, 0.009 mmol, 0.04 eq) was added oxalyl chloride (0.023 mL, 0.271 mmol, 1.1 eq) at room temperature and stirred for 30 minutes. Then reaction mixture was concentrated under reduced pressure to get 3-(trimethylsilyl)propioloyl chloride. This acid chloride was carried to next step without any further purification.

Second step: To a solution of tert-butyl N-{bicyclo[1.1.1]pentan-1-yl}—N—({4-[(1S,3S)-3-butyl-6-methoxy-1,2,3,4-tetrahydroisoquinolin-1-yl]phenyl}methyl)carbamate (0.085 g, 0.173 mmol, 1 eq) in acetonitrile (3 mL) was added sodium bicarbonate (0.118 g, 1.39 mmol, 8.0 eq) at 0° C. After stirring for 5 minutes, a solution of 3-(trimethylsilyl)propioloyl chloride (0.031 g, 0.191 mmol, 1.1 eq) in acetonitrile (2.0 mL) was added to the above reaction mass. The resulting mixture stirred at 0° C. for 1 h. Then reaction mixture was diluted with EtOAc (10 mL) and water (5 mL). Organic layer was separated, washed with brine solution (5 mL), dried over anhydrous sodium sulfate, filtered and concentrated under reduced pressure to obtain the crude product. This crude product was carried to next step without any further purification. LCMS (ES) m/z=615.3 [M+H]+ but observed 559.3 without tert butyl group tert-butyl N-{bicyclo[1.1.1]pentan-1-yl}—N—({4-[(1S,3S)-3-butyl-6-methoxy-2-(prop-2-ynoyl)-1,2,3,4-tetrahydroisoquinolin-1-yl]phenyl}methyl)carbamate: To a solution of tert-butyl bicyclo[1.1.1]pentan-1-yl(4-((1S,3S)-3-butyl-6-methoxy-2-(3-(trimethylsilyl)propioloyl)-1,2,3,4-tetrahydroisoquinolin-1-yl)benzyl)carbamate (85 mg, 0.138 mmol, 1 eq) in DCM (5 mL)/MeOH (1 mL) was added K2CO3 (115 mg, 0.829 mmol, 6 eq) at 0° C. The mixture was stirred at 0° C. for 45 minutes. Then reaction mixture was diluted with DCM (10 mL) and added water (2 mL). The organic layer was extracted with DCM (2×5 mL) and dried over anhydrous Na2SO4. Organic layer was filtered and concentrated to obtain the crude product, which product was purified by preparative TLC using 20% ethyl acetate in hexane as mobile phase. Product fraction collected and concentrated under reduced pressure to get tert-butyl bicyclo[1.1.1]pentan-1-yl(4-((1S,3S)-3-butyl-6-methoxy-2-propioloyl-1,2,3,4-tetrahydroisoquinolin-1-yl)benzyl)carbamate. LCMS (ES) m/z=543.3 [M+H]+ but observed without boc group.

N-{biicyclo[1.1.1]pentan-1-yl}—N—({4-[(1S,3S)-3-butyl-6-methoxy-2-(prop-2-ynoyl)-1,2,3,4-tetrahydroisoquinolin-1-yl]phenyl}methyl)-2,2,2-trifluoroacetamide: To a stirred solution of tert-butyl N-{bicyclo[1.1.1]pentan-1-yl}—N—({4-[(1S,3S)-3-butyl-6-methoxy-2-(prop-2-ynoyl)-1,2,3,4-tetrahydroisoquinolin-1-yl]phenyl}methyl)carbamate (0.040 g, 0.073 mmol, 1.0 eq) in DCM (1.0 mL) at 0° C. TFA (0.150 mL) was added. Then reaction mixture was stirred at 0° C. for 1.5 h. Reaction mixture was evaporated under reduced pressure keeping water bath temperature at 30° C. The obtained crude product kept under lyophilization by adding water (1.5 mL) and acetonitrile (0.5 mL) mixture for 16 h. Obtained product taken for analysis. LCMS (ES) m/z=443.3 [M+H]+ (observed free amine mass).

$^1$H NMR (400 MHz, DMSO-$d_6$) δ ppm 0.79-0.82 (m, 3H), 1.13-1.21 (m, 4H), 1.47 (bs, 2H), 1.97-1.98 (m, 6H), 2.65 (s, 1H), 2.77 (bs, 1H), 2.85-2.89 (m, 0.5H), 3.14-3.15 (m, 0.5H), 3.69-3.70 (m, 3H), 3.98 (s, 2H), 4.29 (s, 0.5H), 4.60 (s, 1H), 4.74 (s, 0.5H), 6.04 (s, 0.5H), 6.33 (s, 0.5H), 6.75-6.83 (m, 2H), 7.28-7.32 (m, 3H), 7.37-7.42 (m, 1.5H), 7.60-7.62 (m, 0.5H), 9.42 (bs, 2H).

Procedure 26: Synthesis of Compound 98

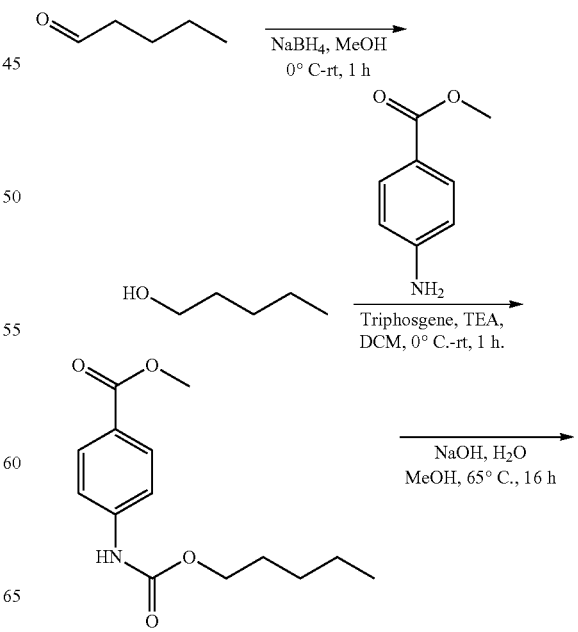

-continued

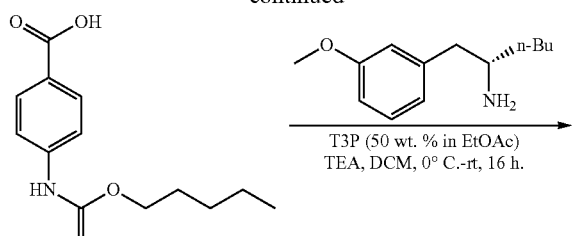

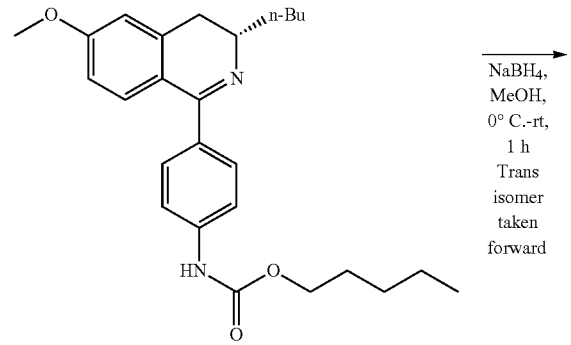

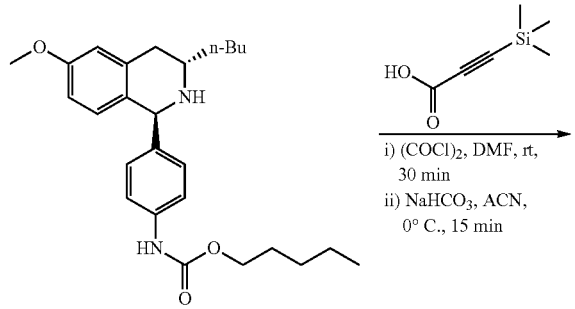

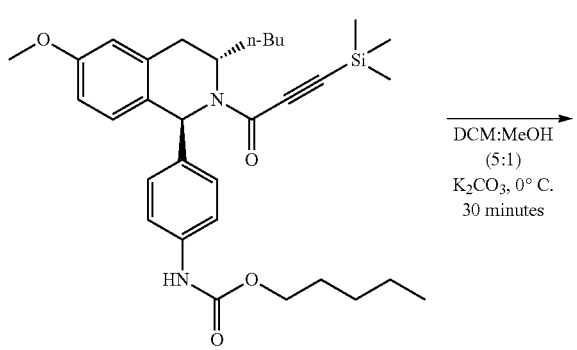

-continued

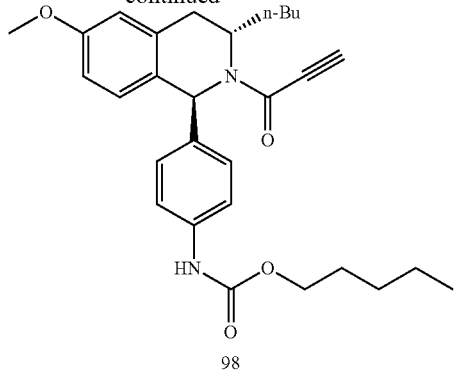

98 pentan-1-ol: To a solution of pentanal (8.0 g, 92.9 mmol, 1.0 eq) in methanol (50 mL) was added sodium borohydride (10.5 g, 279 mmol, 3.0 eq) at 0° C. portion wise. The reaction mixture was stirred at room temperature for 1 h. The progress of the reaction was monitored by TLC (20% ethyl acetate in n-hexane). After reaction completion, the reaction mixture was quenched with few drops of acetone, concentrated, diluted with water (35 mL) and extracted with ethyl acetate (2×50 mL). The organic layer was dried over anhydrous sodium sulphate, filtered and concentrated under reduced pressure to get crude pentan-1-ol.

$^1$H NMR (400 MHz, DMSO-$d_6$) δ ppm 0.84 (t, J=6.0 Hz, 3H), 1.13-1.24 (m, 4H), 1.37-1.42 (m, 2H), 3.31-3.37 (m, 2H), 4.30 (t, J=4.8 Hz, 1H).

methyl 4-{[(pentyloxy)carbonyl]amino}benzoate: To a solution of pentan-1-ol (5.0 g, 56.7 mmol, 1.0 eq) in DCM (75 mL) was added methyl-4-aminobenzoate (10.3 g, 68.1 mmol, 1.2 eq) and triethylamine (39.5 mL, 284 mmol, 5.0 eq). To this triphosgene (11.8 g, 23.8 mmol, 0.7 eq) was added at 0° C. portion wise. The reaction mixture was stirred at rt for 1 h. The progress of the reaction was monitored by TLC (15% ethyl acetate in n-hexane). After reaction completion, the reaction mixture was quenched with aqueous sodium bicarbonate solution (80 mL) and extracted with ethyl acetate (140 mL). The organic layer was dried over anhydrous sodium sulphate, filtered and concentrated under reduced pressure to get crude. The crude was purified by flash column chromatography on silica gel with an increasing polarity of 5-10% ethyl acetate in n-hexane to get methyl 4-(((pentyloxy)carbonyl)amino)benzoate.

$^1$H NMR (400 MHz, DMSO-$d_6$) δ ppm 0.86 (s, 3H), 1.31 (s, 4H), 1.60 (s, 2H), 3.78 (s, 3H), 4.07 (t, J=6.0 Hz, 2H), 7.57 (d, J=8.0 Hz, 2H), 7.85 (d, J=8.0 Hz, 2H), 10.0 (s, 1H).

4-{[(pentyloxy)carbonyl]amino}benzoic acid: To a solution of methyl 4-(((pentyloxy)carbonyl)amino)benzoate (6.6 g, 24.9 mmol, 1 eq) in methanol (70 mL) was added sodium hydroxide (1.53 g, 37.3 mmol, 1.5 eq.) and water (35 mL). The reaction mixture was stirred at 65° C. for 16 h. The progress of the reaction was monitored by TLC (40% ethyl acetate in n-hexane). After reaction completion, the reaction mixture was acidified with 10% citric acid solution up to pH=4 and extracted with ethyl acetate (160 mL). The organic layer was dried over anhydrous sodium sulphate, filtered and concentrated under reduced pressure to get crude 4-(((pentyloxy)carbonyl)amino)benzoic acid.

$^1$H NMR (400 MHz, DMSO-$d_6$) δ ppm 0.86 (t, J=7.2 Hz, 3H), 1.30-1.38 (m, 4H), 1.59-1.62 (m, 2H), 4.07 (t, J=6.4 Hz, 2H), 7.54 (d, J=8.8 Hz, 2H), 7.83 (d, J=8.4 Hz, 2H), 9.97 (s, 1H), 12.54 (s, 1H).

pentyl (S)-(4-((1-(3-methoxyphenyl)hexan-2-yl)carbamoyl)phenyl)carbamate: To a solution of 4-(((pentyloxy)carbonyl)amino)benzoic acid (2.06 g, 8.20 mmol, 1.0 eq) in DCM (35 mL) was added (4.61 mL, 32.8 mmol, 4 eq), stirred for 15 min and then T3P (50 wt. % in EtOAc) (7.8 mL, 12.3 mmol, 1.5 eq) was added at 0° C. and stirred for another 5 mins. Then (S)-1-(3-methoxyphenyl)hexan-2-amine (1.70 g, 8.20 mmol, 1.0 eq) was added to the reaction mixture and then reaction mixture was stirred at room temperature for 16 h. The progress of the reaction was monitored by TLC (40% ethyl acetate in hexane). The reaction mixture was diluted with DCM (70 mL) and saturated sodium bicarbonate solution (30 mL) Organic layer was separated, washed with brine solution (12 mL), dried over anhydrous sodium sulfate, filtered and concentrated under reduced pressure to obtain pentyl (S)-(4-((1-(3-methoxyphenyl)hexan-2-yl)carbamoyl)phenyl)carbamate. LCMS (ES) m/z=441.2 [M+H]+

$^1$H NMR (400 MHz, DMSO-$d_6$) δ ppm 0.80-0.86 (m, 6H), 1.21-1.31 (m, 8H), 1.47-1.72 (m, 4H), 2.65-2.79 (m, 2H), 3.65 (s, 3H), 4.06-4.13 (m, 3H), 6.67-6.77 (m, 3H), 7.12 (t, J=7.6 Hz, 1H), 7.47 (d, J=8.4 Hz, 2H), 7.70 (d, J=8.4 Hz, 2H), 7.98 (d, J=8.0 Hz, 1H), 9.81 (s, 1H).

pentyl (S)-(4-(3-butyl-6-methoxy-3,4-dihydroisoquinolin-1-yl)phenyl)carbamate: Trifluoromethanesulfonic anhydride (1.91 mL, 11.3 mmol, 2 eq) was added via syringe over a period of 1 min to a stirred mixture of pentyl (S)-(4-((1-(3-methoxyphenyl)hexan-2-yl)carbamoyl)phenyl)carbamate (2.50 g, 5.67 mmol, 1 eq) and 2-chloropyridine (1.07 mL, 11.3 mmol, 2 eq) in dichloromethane (20 mL) at −78° C. After 5 min, the reaction mixture was placed in an ice-water bath and warmed to 0° C. After 5 min, the resulting solution was allowed to warm to 23° C. TLC (20% ethyl acetate in n-hexane) showed the reaction was completed. After 1 h, aqueous sodium hydroxide solution (30 mL, 1N) was introduced to neutralize the trifluoromethanesulfonate salts. Dichloromethane (120 mL) was added to dilute the mixture and the layers were separated. The organic layer was washed with brine (20 mL), was dried over anhydrous sodium sulfate, and was filtered. The volatiles were removed under reduced pressure to give the crude product. The obtained crude product was purified by flash chromatography using ethyl acetate in hexane as an eluent to get the desired product pentyl (S)-(4-(3-butyl-6-methoxy-3,4-dihydroisoquinolin-1-yl)phenyl)carbamate. LCMS (ES) m/z=423.3 [M+H]+.

$^1$H NMR (400 MHz, DMSO-$d_6$) δ ppm 0.79-0.89 (m, 6H), 1.32-1.60 (m, 8H), 1.61-1.96 (m, 4H), 2.30-2.48 (m, 2H), 2.65-2.76 (m, 1H), 3.78 (s, 3H), 4.07 (t, J=6.4 Hz, 2H), 6.80 (d, J=8.4 Hz, 1H), 6.89 (s, 1H), 7.11 (d, J=8.4 Hz, 1H), 7.42 (d, J=8.8 Hz, 2H), 7.51 (d, J=8.8 Hz, 2H), 9.74 (s, 1H).

pentyl N-{4-[(1S,3S)-3-butyl-6-methoxy-1,2,3,4-tetrahydroisoquinolin-1-yl]phenyl}carbamate: To a solution of pentyl (S)-(4-(3-butyl-6-methoxy-3,4-dihydroisoquinolin-1-yl)phenyl)carbamate (0.300 g, 0.710 mmol, 1 eq) in methanol (6 mL) was added sodium borohydride (0.081 g, 2.13 mmol, 3 eq) portion wise at 0° C. The suspension was stirred at room temperature for 1 h. After this time, the reaction mixture was concentrated and obtained crude was diluted with EtOAc (30 mL) and water (10 mL). Organic layer was separated, washed with brine solution (10 mL), dried over anhydrous sodium sulfate, filtered and concentrated under reduced pressure to obtain the crude product. The obtained crude product was purified by preparative TLC using 30% ethyl acetate in n-hexane as eluent. Product fraction collected and concentrated under reduced pressure to get pentyl (4-((1S,3S)-3-butyl-6-methoxy-1,2,3,4-tetrahydroisoquinolin-1-yl)phenyl)carbamate. LCMS (ES) m/z=425.3 [M+H]+

$^1$H NMR (400 MHz, DMSO-$d_6$) δ ppm 0.79-0.85 (m, 6H), 1.17-1.35 (m, 10H), 1.58 (s, 2H), 2.77 (bs, 2H), 3.14-3.15 (m, 1H), 3.70 (s, 3H), 4.00-4.02 (m, 2H), 5.04 (s, 1H), 6.64-6.74 (m, 3H), 6.99 (d, J=8.0 Hz, 2H), 7.31 (d, J=7.6 Hz, 2H), 9.50 (s, 1H).

pentyl N-{4-[(1S,3S)-3-butyl-6-methoxy-2-[3-(trimethylsilyl)prop-2-ynoyl]-1,2,3,4-tetrahydroisoquinolin-1-yl]phenyl}carbamate: First step: To a solution of 3-(trimethylsilyl)propiolic acid (15 mg, 0.105 mmol, 1.0 eq) in DMF (0.0003 mL, 0.004 mmol, 0.04 eq) was added oxalyl chloride (0.010 mL, 0.116 mmol, 1.1 eq) at room temperature and stirred for 30 minutes. Then reaction mixture was concentrated under reduced pressure to get 3-(trimethylsilyl) propioloyl chloride. This acid chloride was carried to next step without any further purification.

Second step: To a solution of pentyl N-{4-[(1S,3S)-3-butyl-6-methoxy-1,2,3,4-tetrahydroisoquinolin-1-yl]phenyl}carbamate (0.035 g, 0.082 mmol, 1.0 eq) in acetonitrile (3 mL) was added sodium bicarbonate (0.057 g, 0.659 mmol, 8.0 eq) at 0° C. After stirring for 5 minutes, a solution of 3-(trimethylsilyl)propioloyl chloride (0.015 g, 0.090 mmol, 1.1 eq) in acetonitrile (2.0 mL) was added to the above reaction mass. The resulting mixture was stirred at 0° C. for 30 minutes, progress of the reaction was monitored by TLC (20% ethyl acetate in n-hexane). After this time, reaction mass was diluted with EtOAc (15 mL) and water (5 mL). Organic layer was separated, washed with brine solution (5 mL), dried over anhydrous sodium sulfate, filtered and concentrated under reduced pressure to obtain the crude product. This crude product was carried to next step without any further purification. LC-MS (ES) m/z=549.4 [M+H]+.

pentyl N-{4-[(1S,3S)-3-butyl-6-methoxy-2-(prop-2-ynoyl)-1,2,3,4-tetrahydroisoquinolin-1-yl]phenyl}carbamate: To a stirred solution of pentyl N-{4-[(1S,3S)-3-butyl-6-methoxy-2-[3-(trimethylsilyl)prop-2-ynoyl]-1,2,3,4-tetrahydroisoquinolin-1-yl]phenyl}carbamate (0.045 g, 0.082 mmol, 1 eq) in MeOH:DCM (1:5) (6 mL) mixture at 0° C., potassium carbonate (0.068 g, 0.492 mmol, 6 eq) was added. Then reaction mixture was stirred at 0° C. for 30 minutes. Then reaction mixture was diluted with DCM (15.0 mL), washed with water (3.0 mL). Organic layer was separated and dried over anhydrous sodium sulphate. Organic layer was filtered and concentrated under reduced pressure to get crude product, which was purified by preparative TLC using 20% ethyl acetate in hexane as eluent. Product fraction collected and concentrated under reduced pressure to get pure product. Obtained pure product kept under lyophilization by dissolving acetonitrile (1.0 mL) and water (2.0 mL) mixture for 16 h to get pentyl N-{4-[(1S,3S)-3-butyl-6-methoxy-2-(prop-2-ynoyl)-1,2,3,4-tetrahydroisoquinolin-1-yl]phenyl}carbamate. LCMS (ES) m/z: 477.3 [M+H]+.

$^1$H NMR (400 MHz, DMSO-$d_6$) δ ppm: 0.78-0.85 (m, 6H), 1.21-1.29 (m, 9H), 1.46-1.56 (m, 3H), 2.65 (s, 1H), 2.82-2.86 (m, 0.5H), 3.06-3.09 (m, 0.5H), 3.69-3.70 (m, 3H), 3.98-4.01 (m, 2H), 4.30 (s, 0.5H), 4.49 (s, 0.5H), 4.60 (s, 0.5H), 4.68 (s, 0.5H), 5.97 (s, 0.5H), 6.22 (s, 0.5H), 6.75-6.81 (m, 2H), 7.07-7.12 (m, 2H), 7.25-7.27 (m, 1H), 7.31-7.36 (m, 1.5H), 7.53-7.55 (m, 0.5H), 9.46 (s, 0.5H), 9.53 (s, 0.5H).

Procedure 27: Synthesis of Compound 101

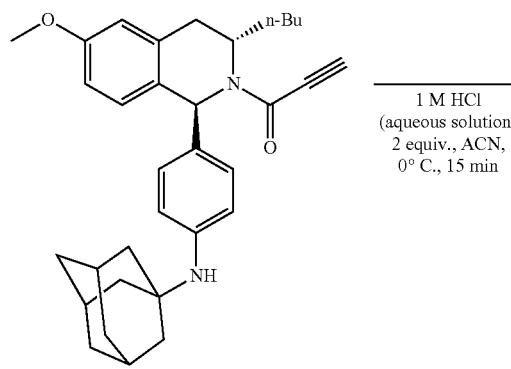

101

1-((1S,3S)-1-(4-(((3R,5R,7R)-adamantan-1-yl)amino) phenyl)-3-butyl-6-methoxy-3,4-dihydroisoquinolin-2(1H)-yl)prop-2-yn-1-one hydrochloride: To a solution of 1-((1S,3S)-1-(4-(((3R,5R,7R)-adamantan-1-yl)amino)phenyl)-3-butyl-6-methoxy-3,4-dihydroisoquinolin-2(1H)-yl)prop-2-yn-1-one (10 mg, 0.02 mmol, 1 eq) in ACN (1.0 mL) was added 1M HCl (aqueous solution) (0.04 mL, 0.04 mmol, 2 eq) at 0° C. and the mixture was stirred at 0° C. for 15 min. After this time, reaction mixture was diluted with water (2 mL), followed by cooled to −78° C. and lyophilize to get 1-((1S,3S)-1-(4-(((3R,5R,7R)-adamantan-1-yl)amino)phenyl)-3-butyl-6-methoxy-3,4-dihydroisoquinolin-2(1H)-yl) prop-2-yn-1-one hydrochloride. LCMS (ES) m/z=497.3 [M+H]+ excluding HCl salt mass.

$^{1}$H NMR (400 MHz, DMSO-d$_{6}$) δ ppm 0.80 (t, J=6.4 Hz, 3H), 1.19-1.21 (m, 6H), 1.47-1.60 (m, 7H), 1.75 (s, 5H), 2.07 (s, 3H), 2.64 (bs, 1H), 2.86-2.90 (m, 1H), 3.06-3.09 (m, 1H), 3.69-3.71 (m, 3H), 4.35 (s, 0.5H), 4.55 (bs, 0.5H), 4.65 (s, 0.5H), 4.72 (bs, 0.5H), 6.09 (s, 1H), 6.35 (bs, 0.5H), 6.78-6.84 (m, 2H), 7.15-7.30 (m, 2H), 7.41-7.47 (m, 2H), 7.60 (bs, 0.5H), 10.50-10.60 (m, 1H).

Procedure 28: Synthesis of Compound 97

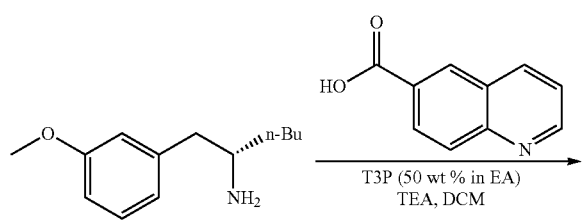

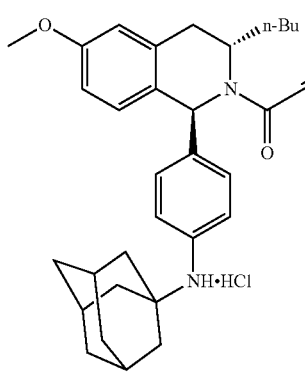

97

(S)—N—(1-(3-methoxyphenyl)hexan-2-yl)quinoline-6-carboxamide: To a solution of isoquinoline-6-carboxylic acid (0.735 g, 4.24 mmol, 1 eq) in DCM (10 mL) under nitrogen atmosphere was added 1-(3-methoxyphenyl)hexan-2-amine (0.968 g, 4.67 mmol, 1.1 eq) at 0° C., stirred for 10 mins and then Propanephosphonic acid anhydride (4.18 mL, 6.37 mmol, 1.5 eq) was added at 0° C. to the reaction mixture, stirred at 0° C. for 15 mins and then triethylamine (2.20 mL, 17 mmol, 4 eq) dissolved in DCM (10 mL) was added to the reaction mixture at 0° C. and then the reaction mixture was stirred at room temperature for 2 h. TLC (40% EtOAc in hexane) showed the reaction was completed after 2 h. The reaction mixture was diluted with ethyl acetate (100 mL), washed with saturated sodium bicarbonate solution (20 mL) and water (30 mL). Organic layer was dried over anhydrous Na2SO4, filtered and concentrated under reduced pressure to get (S)—N—(1-(3-methoxyphenyl)hexan-2-yl)quinoline-6-carboxamide crude. LCMS (ES) m/z=363 [M+H]+.

(S)-6-(3-butyl-6-methoxy-3,4-dihydroisoquinolin-1-yl)quinolone: To a solution of N-[(2S)-1-(3-methoxyphenyl)hexan-2-yl]quinoline-6-carboxamide (1 g, 2.76 mmol, 1 eq) in DCM (10 mL) under nitrogen atmosphere was added 2-Chloropyridine (0.783 mL, 8.28 mmol, 3 eq) at room temperature. Then trifluoromethanesulfonic anhydride (1.39 mL, 8.28 mmol, 3 eq) was added at −78° C., stirred for 5 mins, then warmed to 0° C., stirred for 30 mins at 0° C. and then the reaction mixture was stirred at room temperature for 1 h. TLC (5% MeOH in DCM) showed starting material along with new spots. Reaction was monitored by LCMS. The reaction mass was concentrated under reduced pressure to obtain the crude residue, obtained residue was quenched with 10% sodium hydroxide solution (15 mL), extracted with (2×150 mL) DCM, combined organic layers were dried with anhydrous Na2SO4, filtered and concentrated under reduced pressure to get crude product, which was purified by flash column chromatography using 5% MeOH in DCM as an eluent to obtain 6-[(3S)-3-butyl-6-methoxy-3,4-dihydroisoquinolin-1-yl]quinoline. LCMS (ES) m/z=345 [M+H]+.

$^1$H NMR (400 MHz, DMSO-$d_6$) δ ppm 0.90 (t, J=7.2 Hz, 3H), 1.46 (s, 1H), 1.61 (t, J=6.4 Hz, 3H), 1.73 (s, 2H), 2.65 (s, 1H), 2.80-2.83 (m, 1H), 3.42 (d, J=11.2 Hz, 1H), 3.80 (s, 3H), 6.83 (d, J=8.8 Hz, 1H), 6.95 (s, 1H), 7.17 (d, J=8.8 Hz, 1H), 7.54-7.57 (m, 1H), 7.91-8.10 (m, 3H), 8.45 (d, J=7.6 Hz, 1H), 8.93 (d, J=2.8 Hz, 1H).

6-((3S)-3-butyl-6-methoxy-1,2,3,4-tetrahydroisoquinolin-1-yl)quinolone: To a stirred solution of (S)-6-(3-butyl-6-methoxy-3,4-dihydroisoquinolin-1-yl)quinoline (0.5 g, 1.45 mmol, 1 eq) in MeOH (10 mL) was added sodium borohydride (0.165 g, 4.35 mmol, 3 eq) at 0° C. and the reaction was stirred at room temperature for 1 h. Reaction was monitored by TLC (70% EtOAc in hexane). Reaction was completed after this time. The reaction was concentrated under reduced pressure to remove methanol and the crude obtained was dissolved in EtOAc (100 mL) and was washed with water (10 mL). Organic layer was dried over anhydrous sodium sulfate, filtered and concentrated under reduced pressure to afford 6-((3S)-3-butyl-6-methoxy-1,2,3,4-tetrahydroisoquinolin-1-yl)quinoline. LCMS (ES) m/z=347.2 [M+H]+.

1-((3S)-3-butyl-6-methoxy-1-(quinolin-6-yl)-3,4-dihydroisoquinolin-2(1H)-yl)-3-(trimethylsilyl)prop-2-yn-1-one: Step 1: To 3-(trimethylsilyl)propiolic acid (0.195 g, 1.37 mmol, 1 eq) in DMF (0.004 mL, 0.054 mmol, 0.04 eq) was added oxalyl chloride (0.13 mL, 1.51 mmol, 1.1 eq) at room temperature and the reaction was stirred at room temperature for 30 mins. After this time the reaction mixture was concentrated under reduced pressure to afford 3-(trimethylsilyl)propioloyl chloride and the same was taken for the next step.

Step 2: To a stirred solution of 6-((3S)-3-butyl-6-methoxy-1,2,3,4-tetrahydroisoquinolin-1-yl)quinoline (0.35 g, 1.01 mmol, 1 eq) in ACN (8.0 mL) was added sodium bicarbonate (0.64 g, 7.58 mmol, 7.5 eq) at 0° C., stirred at 0° C. for 15 mins and then 3-(trimethylsilyl)propioloyl chloride (0.19 g, 1.21 mmol, 1.2 eq) in ACN (2.0 mL) was added at 0° C. and the reaction was stirred at room temperature for 30 mins. Reaction was monitored by TLC (70% EtOAc in hexane). After this time the reaction mixture was diluted with EtOAc (100 mL) and was washed with water (10 mL). Organic layer was dried over anhydrous sodium sulfate, filtered and concentrated under reduced pressure to afford 1-((3S)-3-butyl-6-methoxy-1-(quinolin-6-yl)-3,4-dihydroisoquinolin-2(1H)-yl)-3-(trimethylsilyl)prop-2-yn-1-one. LCMS (ES) m/z=471.3 [M+H]+.

1-((1S,3S)-3-butyl-6-methoxy-1-(quinolin-6-yl)-3,4-dihydroisoquinolin-2(1H)-yl)prop-2-yn-1-one: To a stirred solution of 1-((3S)-3-butyl-6-methoxy-1-(quinolin-6-yl)-3,4-dihydroisoquinolin-2(1H)-yl)-3-(trimethylsilyl)prop-2-yn-1-one (0.53 g, 1.13 mmol, 1 eq) in methanol (4 mL) and DCM (30 mL) was added potassium carbonate (0.93 g, 6.76 mmol, 6 eq) at 0° C. and the reaction was stirred at 0° C. for 1 h. Reaction was monitored by TLC (50% EtOAc in hexane). After this time, the reaction mixture was diluted with water (10 mL) and extracted with DCM (150 mL). Organic layer was dried over anhydrous sodium sulfate, filtered and concentrated under reduced pressure to get crude. The crude was purified twice by preparative TLC using 50% EtOAc in hexane as an eluent (eluted twice) to afford 1-((1S,3S)-3-butyl-6-methoxy-1-(quinolin-6-yl)-3,4-dihydroisoquinolin-2(1H)-yl)prop-2-yn-1-one. LCMS (ES) m/z=399.2 [M+H]+.

$^1$H NMR (400 MHz, DMSO-$d_6$) δ ppm 0.82 (t, J=7.0 Hz, 3H), 1.20-1.21 (m, 4H), 1.53 (bs, 2H), 2.80-2.84 (m, 1H), 2.90-2.94 (m, 1H), 3.68-3.70 (m, 3H), 4.25 (s, 0.38H), 4.62 (s, 0.73H), 4.68 (bs, 0.6H), 4.82 (bs, 0.8H), 6.21 (s, 0.6H), 6.49 (s, 0.4H), 6.77-6.86 (m, 2H), 7.44-7.52 (m, 2H), 7.71 (t, J=7.2 Hz, 1.5H), 7.79-7.91 (m, 2.5H), 8.28-8.36 (m, 1H), 8.78-8.82 (m, 1H).

Procedure 29: Synthesis of Compound 27

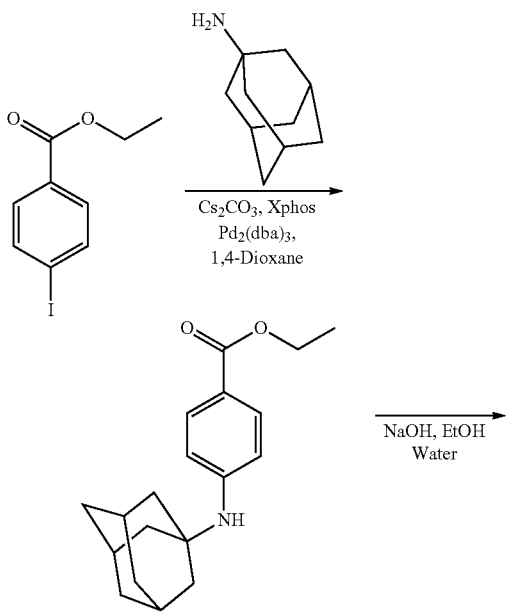

-continued

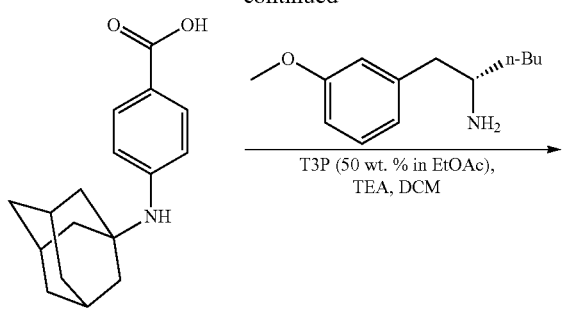

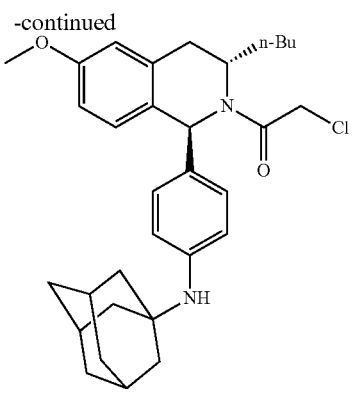

27

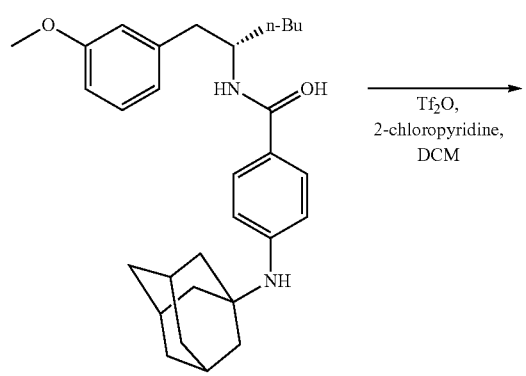

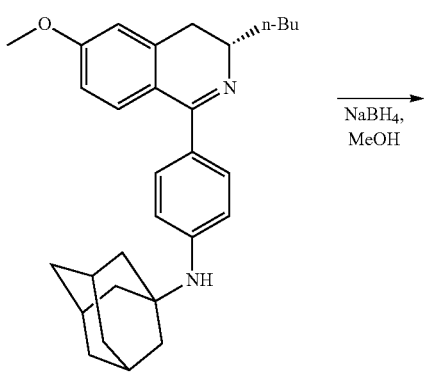

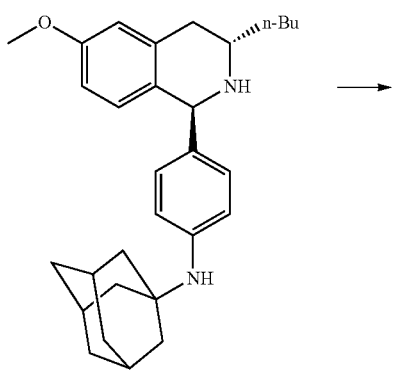

ethyl 4-(((3s,5s,7s)-adamantan-1-yl)amino)benzoate: To a solution of ethyl 4-iodobenzoate (30 g, 109 mmol, 1 eq) in 1,4-Dioxane (500 mL) was added adamantan-1-amine (19.7 g, 130 mmol, 1.2 eq), cesium carbonate (70.8 g, 217 mmol, 2 eq), dicyclohexyl[2',4',6'-tris(propan-2-yl)-[1,1'-biphenyl]-2-yl]phosphane (2.59 g, 5.43 mmol, 0.05 eq) at room temperature and the reaction mixture was purged under nitrogen atmosphere for 30 min. Then tris(dibenzylideneacetone)dipalladium (2.99 g, 3.26 mmol, 0.03 eq) was added to the mixture at room temperature. Then reaction mixture was allowed to warm to 110° C. for 16 h in a sealed tube. Progress of the reaction was monitored by TLC (10% EtOAc in n-hexane). After completion of the reaction, reaction mixture was cooled to room temperature and passed through celite bed and the filtrate was concentrated under reduced pressure to get crude. Obtained crude was extracted with EtOAc (500 mL) and washed with water (100 mL) and brine solution (100 mL). Organic layer was dried over anhydrous sodium sulfate, filtered and concentrated under reduced pressure to get crude product. The obtained crude product was purified by flash column chromatography on silica gel using 6-7% ethyl acetate in hexane. Fractions containing product was combined and concentrated under reduced pressure to get ethyl 4-[(adamantan-1-yl)amino]benzoate. LCMS (ES) m/z=300.2 [M+H]+.

$^1$H NMR (400 MHz, DMSO-$d_6$) δ ppm 1.25 (t, J=8 Hz, 3H), 1.48 (s, 6H), 1.90 (s, 6H), 2.04 (s, 3H), 4.15-4.22 (m, 2H), 5.95 (s, 1H), 6.73 (d, J=8 Hz, 2H), 7.59 (d, J=8 Hz, 2H).

4-(((3s,5s,7s)-adamantan-1-yl)amino)benzoic acid: To a solution of ethyl 4-[(adamantan-1-yl)amino]benzoate (8.20 g, 27.4 mmol, 1 eq) in ethanol (140 mL) was added sodium hydroxide (2.25 g, 54.8 mmol, 2 eq) in water (52 mL) at 0° C. Then reaction mixture was allowed to warm to 80° C. and stirred for 6 h. Progress of the reaction was monitored by TLC (5% Methanol in DCM). After completion of the reaction, reaction mixture was cooled to room temperature and organic solvent was removed under reduced pressure. Then, the resulting residue was acidified with 1 N HCl (pH=2) and extracted with DCM (200 mL). Organic layer was dried over anhydrous sodium sulfate, filtered and concentrated under reduced pressure to get 4-[(adamantan-1-yl)amino]benzoic acid. LCMS (ES) m/z=272.2 [M+H]+.

$^1$H NMR (400 MHz, DMSO-$d_6$) δ ppm 1.60-1.67 (m, 6H), 1.89 (d, J=9.2 Hz, 6H), 2.04 (s, 3H), 5.91 (s, 1H), 6.71 (d, J=8 Hz 2H), 7.57 (d, J=8.8 Hz, 2H), 12.21 (s, 1H).

4-(((3R,5R,7R)-adamantan-1-yl)amino)—N—((S)-1-(3-methoxyphenyl)hexan-2-yl)benzamide: To a solution of 4-[(adamantan-1-yl)amino]benzoic acid (3.6 g, 13.5 mmol, 1 eq) in DCM (25 mL) was added triethylamine (7.5 mL, 54.0 mmol, 4 eq) and the reaction mixture was cooled to 0° C. Tripropyl-1,3,5,2,4,6-trioxatriphosphinane-2,4,6-trione (12.0 mL, 20.3 mmol, 1.5 eq) was added to the reaction mixture at 0° C. and stirred for 30 min. Then a solution of (2S)-1-(3-methoxyphenyl)hexan-2-amine (2.8 g, 13.5 mmol, 1 eq) in DCM (5 mL) was added to the reaction mixture. Followed by the addition, reaction mixture was warmed to room temperature then stirred for 16 h. Progress of the reaction was monitored by TLC (5% MeOH in DCM). After completion of the reaction, reaction mixture was diluted with DCM (400 mL) and saturated sodium bicarbonate (50 mL). Organic layer was separated, washed with brine solution (25 mL), dried over anhydrous sodium sulfate, filtered and concentrated under reduced pressure. The obtained crude product was purified by flash column chromatography on silica gel using 20-27% ethyl acetate in hexane. Fractions containing product was combined and concentrated under reduced pressure to get 4-[(adamantan-1-yl)amino]—N-[(2S)-1-(3-methoxyphenyl)hexan-2-yl] benzamide. LCMS (ES) m/z=461.3 [M+H]+.

$^1$H NMR (400 MHz, DMSO-d$_6$) δ ppm 0.80 (s, 3H), 1.13-1.22 (m, 4H), 1.46 (s, 2H), 1.64 (s, 5H), 1.89 (s, 5H), 2.05 (s, 4H), 2.65-2.78 (m, 2H), 3.57 (s, 3H), 4.00-4.09 (m, 2H), 5.53 (s, 1H), 5.74 (s, 1H), 6.71 (t, J=4 Hz, 4H), 7.13 (d, J=8 Hz, 1H), 7.57 (d, J=4 Hz, 2H), 7.65 (d, J=8 Hz, 1H).

(3R,5R,7R)—N—(4-((S)-3-butyl-6-methoxy-3,4-dihydroisoquinolin-1-yl)phenyl)adamantan-1-amine: To a solution of 4-[(adamantan-1-yl)amino]—N-[(2S)-1-(3-methoxyphenyl)hexan-2-yl]benzamide (1.92 g, 4.17 mmol, 1 eq) in DCM (25 mL) was added 2-chloropyridine (1.18 mL, 12.5 mmol, 3 eq) at room temperature and the reaction mixture was cooled to −78° C. and trifluoromethanesulfonyl trifluoromethanesulfonate (2.97 mL, 12.5 mmol, 3 eq) was added to the mixture at −78° C. and stirred. After 10 min, reaction mixture was placed in an ice-water bath and warmed to 0° C. for 10 min. Then resulting solution was allowed to warm to room temperature and stirred for 1 hr. Progress of the reaction was monitored by TLC (70% EtOAc in n-hexane). After completion of the reaction, reaction mixture was quenched with 1M NaOH (10 mL) at 0° C. and then diluted with DCM (50 mL) and extracted with DCM (100 mL) and washed with water (5 mL). Organic layer was dried over anhydrous sodium sulfate, filtered and concentrated under reduced pressure to get crude product. The obtained crude product was purified by flash column chromatography on silica gel using 56-65% ethyl acetate in hexane. Fractions containing product was combined and concentrated under reduced pressure to afford N-{4-[(3S)-3-butyl-6-methoxy-3,4-dihydroisoquinolin-1-yl]phenyl}adamantan-1-amine. LCMS (ES) m/z=443.3 [M+H]+.

(3R,5R,7R)—N—(4-((1S,3S)-3-butyl-6-methoxy-1,2,3,4-tetrahydroisoquinolin-1-yl)phenyl)adamantan-1-amine: To a solution of N-{4-[(3S)-3-butyl-6-methoxy-3,4-dihydroisoquinolin-1-yl]phenyl}adamantan-1-amine (0.4 g, 0.904 mmol, 1 eq) in methanol (10 mL) was added sodium borohydride (0.103 g, 2.71 mmol, 3 eq) portion wise at 0° C. The suspension was stirred at room temperature for 30 min. Progress of the reaction was monitored by TLC (5% MeOH in DCM). Then the reaction mixture was concentrated and obtained crude was diluted with EtOAc (50 mL) and water (10 mL). Organic layer was separated, washed with brine solution (10 mL), and dried over anhydrous sodium sulfate, filtered and concentrated under reduced pressure to obtain the crude product. The obtained crude product was purified by preparative TLC using 60% ethyl acetate in n-hexane as eluent to get N-{4-[(1S,3S)-3-butyl-6-methoxy-1,2,3,4-tetrahydroisoquinolin-1-yl]cyclohexyl}adamantan-1-amine. LCMS (ES) m/z=445.3 [M+H]+.

$^1$H NMR (400 MHz, DMSO-d$_6$) δ ppm 1.12-1.31 (m, 9H), 1.59 (s, 6H), 1.80 (s, 6H), 2.03 (d, J=3H), 3.27 (s, 1H), 3.69 (s, 3H), 6.62 (t, J=8 Hz 4H), 6.74 (t, J=8.8 Hz, 3H).

1-((1S,3S)-1-(4-(((3R,5R,7R)-adamantan-1-yl)amino)phenyl)-3-butyl-6-methoxy-3,4-dihydroisoquinolin-2(1H)-yl)-2-chloroethan-1-one: To a solution of N-{4-[(1S,3S)-3-butyl-6-methoxy-1,2,3,4-tetrahydroisoquinolin-1-yl]phenyl}adamantan-1-amine (0.030 g, 0.067 mmol, 1 eq) in DCM (5 mL) was added sodium bicarbonate (8.5 mg, 0.101 mmol, 1.5 eq) and cooled to 0° C. and stirred for 10 minutes. After that 2-Chloro acetyl chloride (0.003 mL, 0.067 mmol, 1 eq) was added at 0° C. and warmed to room temperature stirred for 30 minutes. Progress of the reaction was monitored by TLC (70% EtOAc in n-hexane). After completion of the reaction, reaction mixture was quenched with 1M NaOH (5 mL) at 0° C. and then diluted with DCM (5 mL) and extracted with DCM (100 mL) and washed with water (5 mL). Organic layer was dried over anhydrous sodium sulfate, filtered and concentrated under reduced pressure to get crude product. The obtained crude product was purified by preparative TLC using 70% ethyl acetate in n-hexane as an eluent. Product fraction was collected and concentrated under reduced pressure to get 1-[(1S,3S)-1-{4-[(adamantan-1-yl)amino]phenyl}-3-butyl-6-methoxy-1,2,3,4-tetrahydroisoquinolin-2-yl]-2-chloroethan-1-one. LCMS (ES) m/z=521.5 [M+H]+.

$^1$H NMR (400 MHz, DMSO-d$_6$) δ ppm 0.78 (s, 3H), 1.29 (d, J=6.8 Hz, 6H), 1.40 (bs, 2H), 1.58 (s, 3H), 1.78 (s, 3H), 1.99 (s, 2H), 2.15 (bs, 1H), 2.65-2.83 (m, 3H), 3.69 (s, 3H), 3.79-3.82 (m, 1H), 4.47-4.93 (m, 5H), 5.89-5.93 (m, 1H), 6.56-6.65 (m, 2H), 6.76 (d, J=8 Hz, 2H), 6.87 (s, 2H), 7.36 (d, J=8 Hz, 1H).

Procedure 30: Synthesis of Compound 102

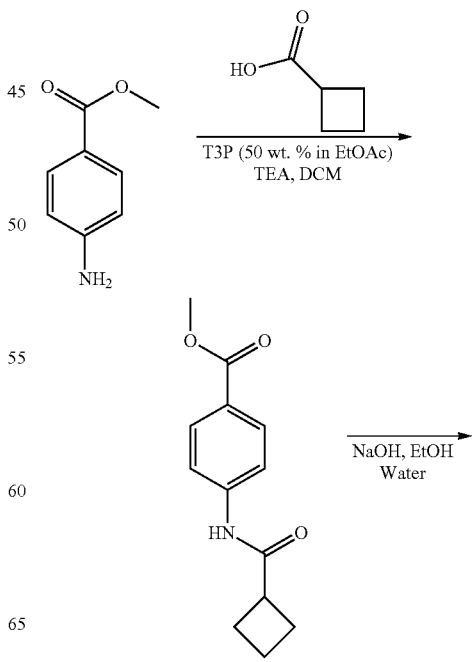

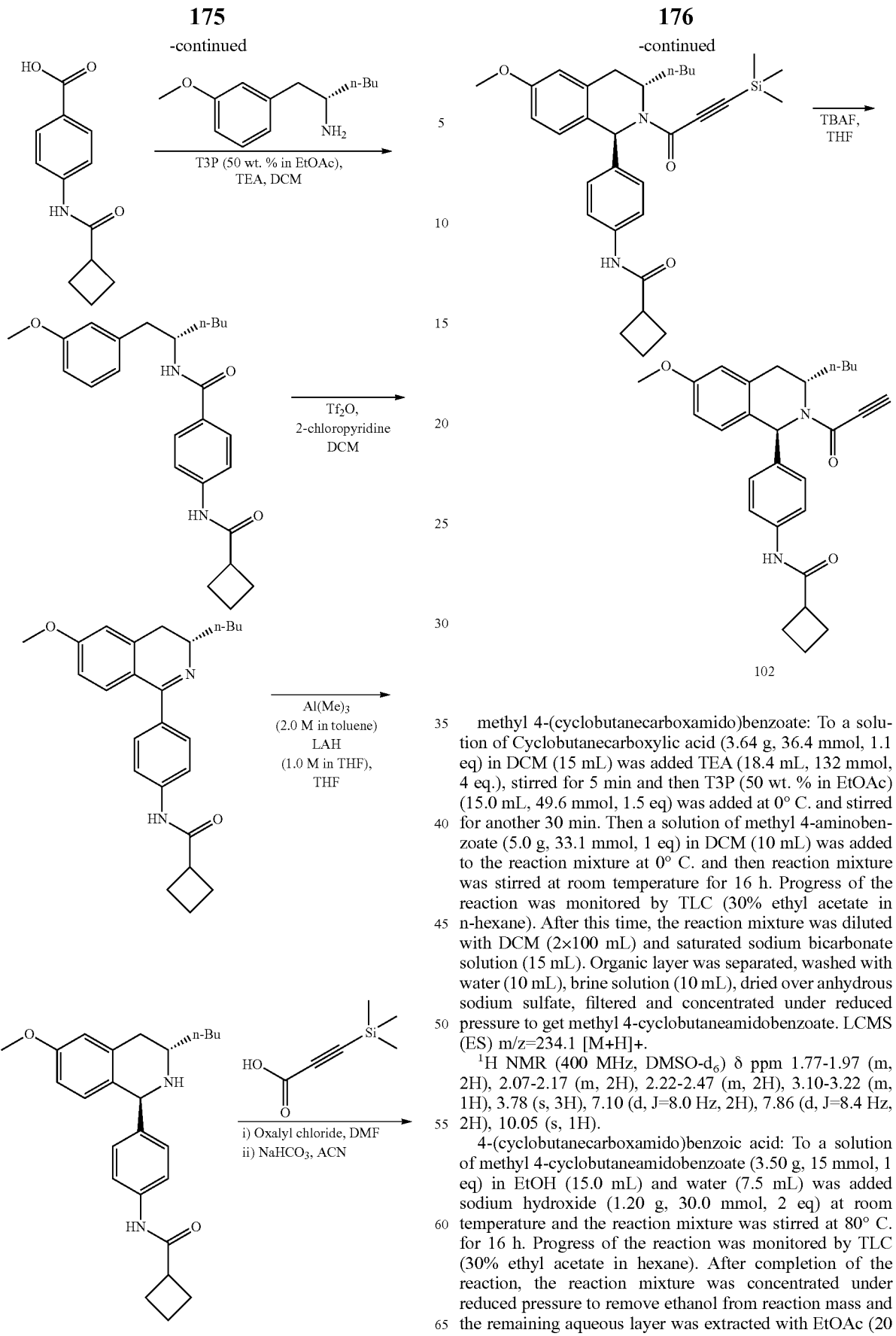

methyl 4-(cyclobutanecarboxamido)benzoate: To a solution of Cyclobutanecarboxylic acid (3.64 g, 36.4 mmol, 1.1 eq) in DCM (15 mL) was added TEA (18.4 mL, 132 mmol, 4 eq.), stirred for 5 min and then T3P (50 wt. % in EtOAc) (15.0 mL, 49.6 mmol, 1.5 eq) was added at 0° C. and stirred for another 30 min. Then a solution of methyl 4-aminobenzoate (5.0 g, 33.1 mmol, 1 eq) in DCM (10 mL) was added to the reaction mixture at 0° C. and then reaction mixture was stirred at room temperature for 16 h. Progress of the reaction was monitored by TLC (30% ethyl acetate in n-hexane). After this time, the reaction mixture was diluted with DCM (2×100 mL) and saturated sodium bicarbonate solution (15 mL). Organic layer was separated, washed with water (10 mL), brine solution (10 mL), dried over anhydrous sodium sulfate, filtered and concentrated under reduced pressure to get methyl 4-cyclobutaneamidobenzoate. LCMS (ES) m/z=234.1 [M+H]+.

$^1$H NMR (400 MHz, DMSO-d$_6$) δ ppm 1.77-1.97 (m, 2H), 2.07-2.17 (m, 2H), 2.22-2.47 (m, 2H), 3.10-3.22 (m, 1H), 3.78 (s, 3H), 7.10 (d, J=8.0 Hz, 2H), 7.86 (d, J=8.4 Hz, 2H), 10.05 (s, 1H).

4-(cyclobutanecarboxamido)benzoic acid: To a solution of methyl 4-cyclobutaneamidobenzoate (3.50 g, 15 mmol, 1 eq) in EtOH (15.0 mL) and water (7.5 mL) was added sodium hydroxide (1.20 g, 30.0 mmol, 2 eq) at room temperature and the reaction mixture was stirred at 80° C. for 16 h. Progress of the reaction was monitored by TLC (30% ethyl acetate in hexane). After completion of the reaction, the reaction mixture was concentrated under reduced pressure to remove ethanol from reaction mass and the remaining aqueous layer was extracted with EtOAc (20 mL). Finally, the aqueous layer was acidified with 5% citric acid (pH~4) and then product was extracted with EtOAc (2×80 mL). Organic layer was dried over anhydrous sodium sulfate, filtered and concentrated under reduced pressure to get the product which was triturated with n-pentane (10 mL) for 5 minutes, decanted the pentane layer and dried under high vacuum to afford 4-cyclobutaneamidobenzoic acid. LCMS (ES) m/z=220.3 [M+H]+.

(S)-4-(cyclobutanecarboxamido)—N—(1-(3-methoxyphenyl)hexan-2-yl)benzamide: To a solution of 4-cyclobutaneamidobenzoic acid (2.12 g, 9.65 mmol, 1 eq) in DCM (15 mL) under nitrogen atmosphere was added triethylamine (5.42 mL, 38.6 mmol, 4 eq) at 0° C., stirred for 10 mins and then propanephosphonic acid anhydride (50 wt. % in ethyl acetate) (4.6 g, 14.5 mmol, 1.5 eq) was added at 0° C. to the reaction mixture, stirred at 0° C. for 15 mins and then (2S)-1-(3-methoxyphenyl)hexan-2-amine (2 g, 9.65 mmol, 1 eq) dissolved in DCM (5 mL) was added to the reaction mixture at 0° C. and then the reaction mixture was stirred at room temperature for 16 h. TLC (50% EtOAc in hexane) showed the reaction was completed after 16 h. The reaction mixture was diluted with DCM (80 mL), washed with saturated sodium bicarbonate solution (20 mL) and water (10 mL). Organic layer was dried over anhydrous Na2SO4, filtered and concentrated under reduced pressure to get 4-cyclobutaneamido—N-[(2S)-1-(3-methoxyphenyl)hexan-2-yl]benzamide. LCMS (ES) m/z=409.3 [M+H]+.

(S)—N—(4-(3-butyl-6-methoxy-3,4-dihydroisoquinolin-1-yl)phenyl)cyclobutanecarboxamide: To a solution of 4-cyclobutaneamido—N-[(2S)-1-(3-methoxyphenyl)hexan-2-yl]benzamide (0.1 g, 0.245 mmol, 1 eq) in DCM (5 mL) was added 2-chloropyridine (0.046 mL, 0.490 mmol, 2 eq) at room temperature and the reaction mixture was cooled to −78° C. and trifluoromethanesulfonyl trifluoromethanesulfonate (0.082 mL, 0.49 mmol, 2 eq) was added to the mixture at −78° C. and stirred. After 10 min, reaction mixture was placed in an ice-water bath and warmed to 0° C. for 10 min. Then resulting solution was allowed to warm to room temperature and stirred for 1 h. Progress of the reaction was monitored by TLC (70% EtOAc in n-hexane). After completion of the reaction, reaction mixture was quenched with 1M NaOH (5 mL) at 0° C. and then diluted with DCM (5 mL) and extracted with DCM (25 mL) and washed with water (5 mL). Organic layer was dried over anhydrous sodium sulfate, filtered and concentrated under reduced pressure to afford (S)—N—(4-(3-butyl-6-methoxy-3,4-dihydroisoquinolin-1-yl)phenyl)cyclobutanecarboxamide. LCMS (ES) m/z=391.3 [M+H]+.

N—(4-((1S,3S)-3-butyl-6-methoxy-1,2,3,4-tetrahydroisoquinolin-1-yl)phenyl)cyclobutanecarboxamide: To a solution of N-{4-[(3S)-3-butyl-6-methoxy-3,4-dihydroisoquinolin-1-yl]phenyl}cyclobutanecarboxamide (1.40 g, 3.58 mmol, 1 eq) in MeOH (20 mL) under nitrogen atmosphere was added sodium borohydride (0.396 g, 10.8 mmol, 3 eq) at 0° C. and then the reaction mixture was stirred at room temperature for 1 h. Reaction was monitored by TLC (70% EtOAc in hexane) and LC-MS. After completion of the reaction, reaction mixture was quenched with acetone and concentrated under reduced pressure then extracted with EtOAc (50 mL) and washed with water (10 mL). Organic layer was dried over anhydrous sodium sulfate, filtered and concentrated under reduced pressure to get crude product. The obtained crude product was purified by flash column chromatography with 45-55% ethyl acetate in hexane as an eluent. Fractions containing product was combined and concentrated under reduced pressure to get a crude of cis and trans mixture. Again the crude was purified by preparative TLC using 60% ethyl acetate in n-hexane as eluent to get N-{4-[(1S,3S)-3-butyl-6-methoxy-1,2,3,4-tetrahydroisoquinolin-1-yl]phenyl}cyclobutanecarboxamide. LCMS (ES) m/z=393.3 [M+H]+.

N—(4-((1S,3S)-3-butyl-6-methoxy-2-(3-(trimethylsilyl)propioloyl)-1,2,3,4-tetrahydroisoquinolin-1-yl)phenyl)cyclobutanecarboxamide: Step 1: To a solution of 3-(trimethylsilyl)propiolic acid (0.1 g, 0.703 mmol, 1 eq) in DMF (0.002 mL, 0.028 mmol, 0.04 eq) was added oxalyl chloride (0.072 mL, 0.844 mmol, eq) at room temperature and stirred for 30 minutes. Then reaction mixture was concentrated under reduced pressure to get 3 (trimethylsilyl)propioloyl chloride.

Step 2: To a solution of N-{4-[(1S,3S)-3-butyl-6-methoxy-1,2,3,4-tetrahydroisoquinolin-1-yl]phenyl}cyclobutanecarboxamide (0.2 g, 0.509 mmol, 1 eq) in acetonitrile (7.0 mL) was added sodium bicarbonate (0.325 g, 3.82 mmol, 7.5 eq) at 0° C. After stirring for 5 minutes, a solution of 3-(trimethylsilyl)propioloyl chloride (0.123 g, 0.764 mmol, 1.5 equiv.) in acetonitrile (3 mL) was added to the above reaction mass at 0° C. The resulting mixture was stirred at 0° C. for 45 min, progress of the reaction was monitored by TLC (25% ethyl acetate in n-hexane). After this time, reaction mass was diluted with EtOAc (20 mL) and water (5 mL). Organic layer was separated, washed with brine solution (7.0 mL), dried over anhydrous sodium sulfate, filtered and concentrated under reduced pressure to obtain the crude product. LCMS (ES) m/z=517.3 [M+H]+.

N—(4-((1S,3S)-3-butyl-6-methoxy-2-propioloyl-1,2,3,4-tetrahydroisoquinolin-1-yl)phenyl)cyclobutanecarboxamide: To a solution of N-{4-[(1S,3S)-3-butyl-6-methoxy-2-[3-(trimethylsilyl)prop-2-ynoyl]-1,2,3,4-tetrahydroisoquinolin-1-yl]phenyl}cyclobutanecarboxamide (0.2 g, 0.387 mmol, 1 eq) in THF (5 mL) was added TBAF (1M solution in THF) (0.968 mL, 0.968 mmol, 2.5 eq) at −78° C. This reaction mixture was stirred at −78° C. for 15 minutes. Progress of the reaction was monitored by TLC (25% ethyl acetate in n-hexane). After this time, the reaction mixture was quenched with saturated aqueous NaHCO3 solution (10 mL) at −78° C. and product was extracted with ethyl acetate (2×50 mL). Combined organic layers was dried over anhydrous sodium sulfate, filtered and concentrated under reduced pressure. The obtained crude product was purified by preparative TLC using 30% ethyl acetate in n-hexane as an eluent. Product fraction was collected and concentrated under reduced pressure to get N-{4-[(1S,3S)-3-butyl-6-methoxy-2-(prop-2-ynoyl)-1,2,3,4-tetrahydroisoquinolin-1-yl]phenyl}cyclobutanecarboxamide. LCMS (ES) m/z=445.2 [M+H]+.

$^1$H NMR (400 MHZ, DMSO-$d_6$) δ ppm: rotamer pattern observed along with additional peaks (minor impurity). $^1$H NMR (400 MHz, DMSO-$d_6$) δ ppm 0.65-0.68 (m, 3H), 0.75 (bs, 1H), 1.09-1.11 (m, 4H), 1.25 (s, 1H), 1.54 (s, 1H), 1.78-1.86 (m, 1H), 1.89-1.93 (m, 1H), 2.05-2.07 (m, 2H), 2.20-2.25 (m, 2H), 2.63-2.66 (m, 0.5H), 2.99-3.01 (m, 0.5H), 3.13-3.18 (m, 1H), 3.74-3.76 (m, 3H), 4.04 (s, 0.5H), 4.53-4.59 (m, 1.5H), 6.50-6.55 (m, 1H), 6.77-6.79 (m, 0.5H), 6.84 (s, 1H), 6.90-6.94 (m, 2H), 7.03 (d, J=8.0 Hz, 1H), 7.26 (d, J=8.4 Hz, 0.5H), 7.47-7.54 (m, 2H), 9.67-9.72 (m, 1H).

Procedure 31: Synthesis of Compound 96
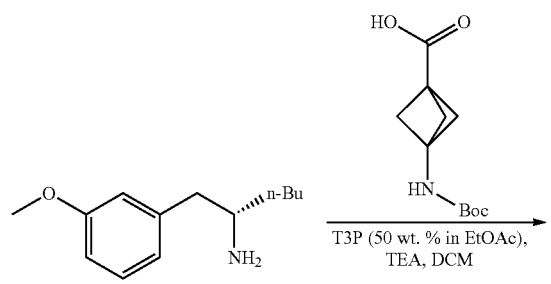
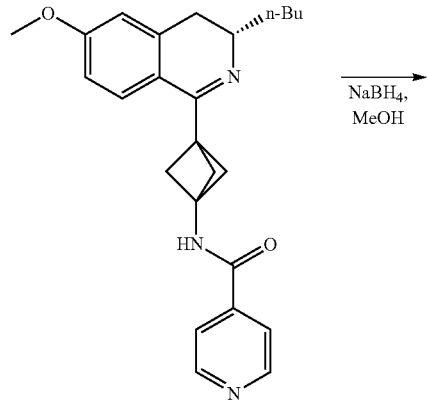
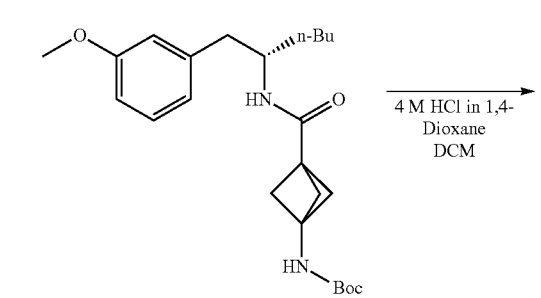
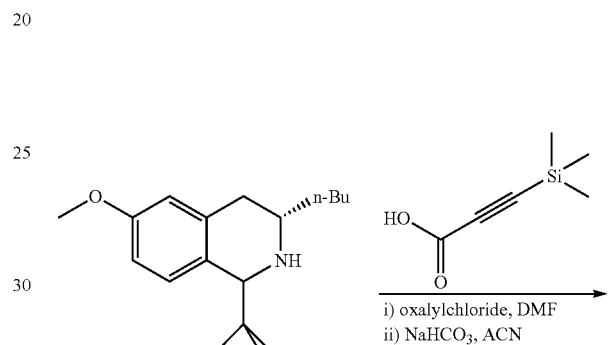
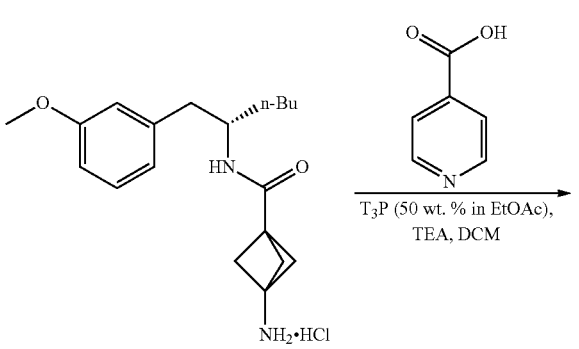
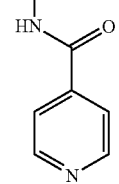
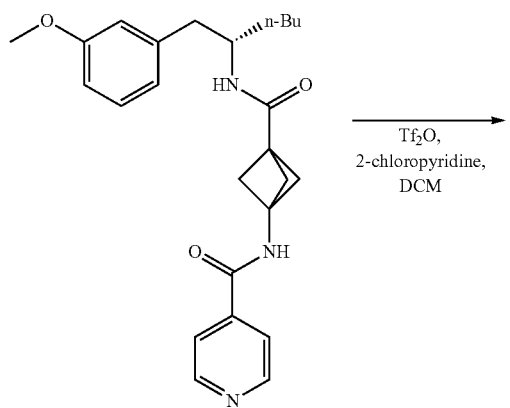
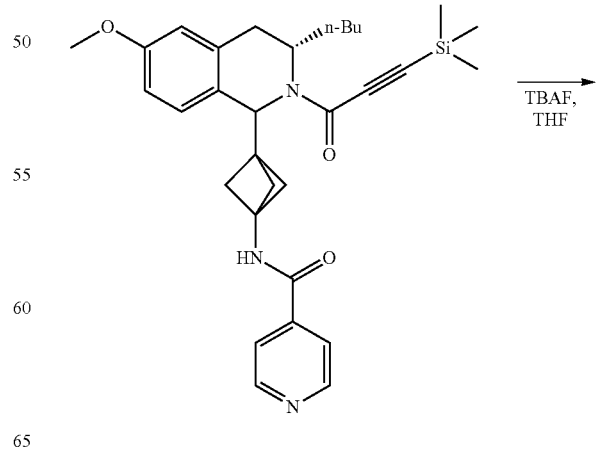

-continued

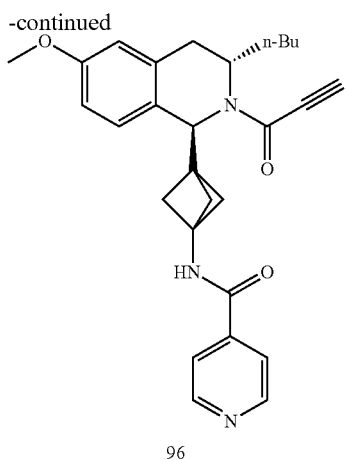

96 tert-butyl (S)-(3-((1-(3-methoxyphenyl)hexan-2-yl)carbamoyl)bicyclo[1.1.1]pentan-1-yl)carbamate: To a solution of 3-((tert-butoxycarbonyl)amino)bicyclo[1.1.1]pentane-1-carboxylic acid (2.3 g, 10.1 mmol, 1.05 eq) in DCM (30 mL) was added TEA (4.04 mL, 28.9 mmol, 3 eq), stirred for 5 min and then T3P (50 wt. % in EtOAc) (4.85 mL, 14.5 mmol, 1.5 eq) was added at 0° C. and stirred for another 30 min. Then a solution of (S)-1-(3-methoxyphenyl)hexan-2-amine (2 g, 9.65 mmol, 1 eq) in DCM (10 mL) was added to the reaction mixture at 0° C. and then reaction mixture was stirred at room temperature for 16 h. Progress of the reaction was monitored by TLC (40% ethyl acetate in n-hexane). After this time, the reaction mixture was diluted with DCM (50 mL), organic layer was washed with saturated aqueous solution of sodium bicarbonate (2×10 mL), water (10 mL), brine solution (10 mL), dried over anhydrous sodium sulfate, filtered and concentrated under reduced pressure to obtain the crude product. Obtained crude was purified by flash chromatography using 0-30% EtOAc in n-hexane as an eluent to give tert-butyl (S)-(3-((1-(3-methoxyphenyl)hexan-2-yl)carbamoyl)bicyclo[1.1.1]pentan-1-yl)carbamate. LCMS (ES) m/z=417.5 [M+H]+.

$^1$H NMR (400 MHz, CDCl$_3$) δ ppm 0.84 (bs, 3H), 1.27 (bs, 6H), 1.42 (s, 9H), 2.16 (s, 6H), 2.67-2.79 (m, 2H), 3.77 (s, 3H), 4.11 (bs, 1H), 4.92 (bs, 1H), 5.15 (d, J=8.4 Hz, 1H), 6.66-6.57 (m, 3H), 7.18 (t, J=8.0 Hz, 1H).

(S)-3-amino—N—(1-(3-methoxyphenyl)hexan-2-yl)bicyclo[1.1.1]pentane-1-carboxamide hydrochloride: To a solution of tert-butyl (S)-(3-((1-(3-methoxyphenyl)hexan-2-yl)carbamoyl)bicyclo[1.1.1]pentan-1-yl)carbamate (3 g, 7.20 mmol, 1 eq) in dichloromethane (50 mL) was added 4 M HCl in 1,4-dioxane (5 mL) at 0° C. The mixture was allowed to warm at room temperature and stirred for 12 h. The progress of the reaction was monitored by TLC (60% EtOAc in hexane), after completion of the reaction, the reaction mixture was concentrated under reduced pressure to obtain the crude, which was triturated with mixture of diethyl ether (10 mL) and n-pentane (10 mL) and decanted the solvent, dried under reduced pressure to obtain (S)-3-amino—N—(1-(3-methoxyphenyl)hexan-2-yl)bicyclo[1.1.1]pentane-1-carboxamide hydrochloride. LCMS (ES) m/z=317 [M+H]+.

$^1$H NMR (400 MHz, DMSO-d$_6$) δ ppm 0.81 (s, 3H), 1.09-1.21 (m, 4H), 1.37-1.40 (m, 2H), 2.05 (s, 6H), 2.56-2.64 (m, 2H), 3.7 (s, 3H), 3.84 (bs, 1H), 6.70-6.72 (m, 3H), 7.13 (t, J=7.6 Hz, 1H), 7.56 (d, J=8.8 Hz, 1H), 8.73 (bs, 3H).

(S)—N—(3-((1-(3-methoxyphenyl)hexan-2-yl)carbamoyl)bicyclo[1.1.1]pentan-1-yl)isonicotinamide: To a solution of 3-amino—N-[(2S)-1-(3-methoxyphenyl)hexan-2-yl] bicyclo[1.1.1]pentane-1-carboxamide hydrochloride (0.6 g, 1.70 mmol, 1 eq) & pyridine-4-carboxylic acid (0.251 g, 2.04 mmol, 1.2 eq) in DCM (10 mL) was added triethylamine (1.32 mL, 10.2 mmol, 6 eq), stirred for 5 min and then T3P (50 wt. % in EtOAc) (2.03 mL, 3.40 mmol, 2 eq) was added at 0° C. and stirred for another 30 min and then reaction mixture was stirred at room temperature for 3 h. Progress of the reaction was monitored by TLC (60% ethyl acetate in n-hexane). After this time, the reaction mixture was diluted with DCM (20 mL), organic layer was washed with saturated aqueous solution of sodium bicarbonate (2×10 mL), water (10 mL), brine solution (10 mL), dried over anhydrous sodium sulfate, filtered and concentrated under reduced pressure to obtain the crude product. The crude was purified by silica gel column chromatography using 35-40% EtOAc in hexane as an eluent to afford N—(3-{[(2S)-1-(3-methoxyphenyl)hexan-2-yl] carbamoyl}bicyclo[1.1.1]pentan-1-yl)pyridine-4-carboxamide. LCMS (ES) m/z=422.3 [M+H]+

(S)—N—(3-(3-butyl-6-methoxy-3,4-dihydroisoquinolin-1-yl)bicyclo[1.1.1]pentan-1-yl)isonicotinamide: To a stirred solution of N—(3-{[(2S)-1-(3-methoxyphenyl)hexan-2-yl] carbamoyl}bicyclo[1.1.1]pentan-1-yl)pyridine-4-carboxamide (0.4 g, 0.949 mmol, 1 eq) in DCM (10 mL) under nitrogen atmosphere was added 2-chloropyridine (0.18 mL, 1.90 mmol, 2 eq) at room temperature and the resulting reaction mixture was cooled to −78° C. and then trifluoromethane sulfonic anhydride (0.32 mL, 1.90 mmol, 2 eq) was added dropwise. The reaction mixture was then stirred at −78° C. for 5 mins, then warmed to 0° C. and stirred for 10 mins, then warmed to room temperature and stirred for 1.5 h. Reaction was monitored by TLC (5% MeOH/DCM). After this time the reaction was neutralized with 1N NaOH solution and was extracted with DCM (2×50 mL). Combined organic layer was washed with water (10 mL), separated the layers. Organic layer was dried over anhydrous sodium sulfate, filtered and concentrated under reduced pressure to obtain the crude. Obtained crude was purified by flash chromatography using 15-20% EtOAc in n-hexane as an eluent to give to afford N-{3-[(3S)-3-butyl-6-methoxy-3,4-dihydroisoquinolin-1-yl]bicyclo[1.1.1]pentan-1-yl}pyridine-4-carboxamide. LCMS (ES) m/z=404.3 [M+H]+.

N—(3-((3S)-3-butyl-6-methoxy-1,2,3,4-tetrahydroisoquinolin-1-yl)bicyclo[1.1.1]pentan-1-yl)isonicotinamide: To a solution of N-{3-[(3S)-3-butyl-6-methoxy-3,4-dihydroisoquinolin-1-yl]bicyclo[1.1.1]pentan-1-yl}pyridine-4-carboxamide (0.27 g, 0.669 mmol, 1 eq) in methanol (10 mL) was added sodium borohydride (0.076 g, 2.01 mmol, 3 eq) at 0° C. portion wise. The suspension was stirred at 0° C. for 3 h. After this time, the reaction mixture was concentrated and obtained crude was diluted with EtOAc (50 mL) and water (10 mL). Organic layer was separated, washed with brine solution (5 mL), dried over anhydrous sodium sulfate, filtered and concentrated under reduced pressure to afford N—(3-((3S)-3-butyl-6-methoxy-1,2,3,4-tetrahydroisoquinolin-1-yl)bicyclo[1.1.1]pentan-1-yl)isonicotinamide. LCMS (ES) m/z=406.2 [M+H]+.

N—(3-((3S)-3-butyl-6-methoxy-2-(3-(trimethylsilyl)propioloyl)-1,2,3,4-tetrahydroisoquinolin-1-yl)bicyclo[1.1.1] pentan-1-yl)isonicotinamide: Step 1: To a solution of 3-(trimethylsilyl)propiolic acid (0.05 g, 0.352 mmol, 1 eq) in DMF (0.001 mL, 0.014 mmol, 0.04 eq) was added oxalyl chloride (0.033 mL, 0.387 mmol, 1.1 eq) at room temperature and stirred for 30 minutes. After this time, reaction mixture was concentrated under reduced pressure to get 3-(trimethylsilyl)propioloyl chloride.

Step 2: To a solution of N-{3-[(1S,3S)-3-butyl-6-methoxy-1,2,3,4-tetrahydroisoquinolin-1-yl]bicyclo[1.1.1]pentan-1-yl}pyridine-4-carboxamide (0.220 g, 0.542 mmol, 1 eq) in acetonitrile (3.0 mL) was added sodium bicarbonate (0.346 g, 4.07 mmol, 7.5 eq) at 0° C. After stirring for 5 minutes, a solution of 3-(trimethylsilyl)propioloyl chloride (0.131 g, 0.814 mmol, 1.5 eq) in acetonitrile (1.0 mL) was added to the above reaction mass at 0° C. The resulting mixture stirred at 0° C. for 15 min, progress of the reaction was monitored by TLC (5% MeOH/DCM). Desired product mass was observed in LCMS. After this time, the reaction was quenched with saturated sodium bicarbonate solution (10 ml), diluted with EtOAc (20 mL), stirred at room temperature for 5 mins. Then the layers were separated. Aqueous layer was extracted with EtOAc (2×50 mL). Combined organic layer was washed with water (15 mL), separated the layers. Then the organic layer was dried over anhydrous sodium sulfate, filtered and concentrated under reduced pressure to obtain product N-{3-[(1S,3S)-3-butyl-6-methoxy-2-[3-(trimethylsilyl)prop-2-ynoyl]-1,2,3,4-tetrahydroisoquinolin-1-yl]bicyclo[1.1.1]pentan-1-yl}pyridine-4-carboxamide. LCMS (ES) m/z=530.2 [M+H]+.

N—(3-((1S,3S)-3-butyl-6-methoxy-2-propioloyl-1,2,3,4-tetrahydroisoquinolin-1-yl)bicyclo[1.1.1]pentan-1-yl)isonicotinamide: To a stirred solution of N—(3-((1S,3S)-3-butyl-6-methoxy-2-(3-(trimethylsilyl)propioloyl)-1,2,3,4-tetrahydroisoquinolin-1-yl)bicyclo[1.1.1]pentan-1-yl) isonicotinamide (0.25 g, 0.47 mmol, 1 eq) in Methanol (3 mL) and DCM (20 mL) was added potassium carbonate (0.39 g, 2.83 mmol, 6 eq) at 0° C. and the reaction was stirred at 0° C. for 1 h. Reaction was monitored by TLC (5% MeOH-DCM) After this time, the reaction mixture was diluted with water (10.0 mL) and extracted with DCM (150 mL). Organic layer was dried over anhydrous sodium sulfate, filtered and concentrated under reduced pressure to get crude. The crude was purified twice by preparative TLC using 4% MeOH-DCM as an eluent (eluted thrice) to isolate the desired product. It was re-purified by preparative HPLC using the following condition. (Analytical Conditions: Column: X-BridgeC-18 (250 mm×4.6 mm×5 μm); mobile phase (A): 0.1% ammonia in water; mobile phase (B): acetonitrile; flow rate: 1.0 mL/min; gradient B: 0/10, 12/60, 22/95, 25/95, 27/10, 30/10). Fractions obtained from preparative HPLC was concentrated under reduced pressure and lyophilized to afford N—(3-((1S,3S)-3-butyl-6-methoxy-2-propioloyl-1,2,3,4-tetrahydroisoquinolin-1-yl)bicyclo[1.1.1]pentan-1-yl) isonicotinamide. LCMS (ES) m/z=458.3 [M+H]+.

Procedure 32: Synthesis of Compound 54

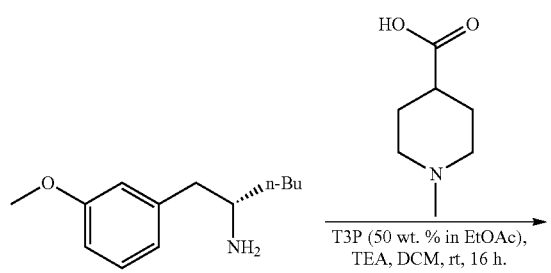

(S)—N—(1-(3-methoxyphenyl)hexan-2-yl)-1-methylpiperidine-4-carboxamide: To a solution of 1-methylpiperidine-4-carboxylic acid (0.64 g, 3.76 mmol, 1.2 eq) in DCM (20 mL) was added TEA (1.75 mL, 12.56 mmol, 4 eq), stirred for 15 min and then T3P (50 wt. % in EtOAc) (9.9 mL, 4.71 mmol, 1.5 eq) was added at 0° C. and stirred for another 5 mins. Then (S)-1-(3-methoxyphenyl)hexan-2-amine (0.65 g, 3.14 mmol, 1 eq) was added to the reaction mixture and then reaction mixture was stirred at room temperature for 16 h. The progress of the reaction was monitored by TLC (70% ethyl acetate in hexane). The reaction mixture was diluted with DCM (50 mL) and saturated sodium bicarbonate solution (20 mL) Organic layer was separated, washed with brine solution (20 mL), dried over anhydrous sodium sulfate, filtered and concentrated under reduced pressure to obtain the crude product, which was purified by silica gel flash chromatography using 70% EtOAc/n-hexane as an eluent to give the (S)—N—(1-(3-methoxyphenyl)hexan-2-yl)-1-methylpiperidine-4-carboxamide. LCMS (ES) m/z=333 [M+H]$^+$ $^1$H NMR (400 MHz, DMSO-d$_6$) δ ppm 0.80-0.90 (m, 3H), 1.18-1.30 (m, 6H), 1.39-1.52 (m, 4H), 1.73-1.82 (m, 2H), 1.92-1.96 (m, 1H), 2.12 (s, 3H), 2.58-2.65 (m, 2H), 2.70-2.75 (m, 2H), 3.69 (s, 3H), 3.86 (bs, 1H), 6.70-6.71 (m, 3H), 7.11-7.15 (m, 1H), 7.48 (d, J=7.6 Hz, 1H).

(S)-3-butyl-6-methoxy-1-(1-methylpiperidin-4-yl)-3,4-dihydroisoquinoline: To a stirred solution of (S)—N—(1-(3-methoxyphenyl)hexan-2-yl)-1-methylpiperidine-4-carboxamide (0.3 g, 0.90 mmol, 1 eq) in POCl3 (0.1 mL, 1.08 mmol, 1.2 eq) was stirred at 80° C. for 1 hour, reaction progress was checked by TLC monitoring, after completion of the reaction, reaction was cooled to room temperature, reaction mass was concentrated under reduced pressure to obtain the crude residue obtained residue was basified with 10% aq NaOH solution (pH=8), aqueous layer was extracted with (2×20) mL of Ethylacetate, combined organic layers were dried with anhydrous Na2SO4, filtered and concentrated under reduced pressure to get the (S)-3-butyl-6-methoxy-1-(1-methylpiperidin-4-yl)-3,4-dihydroisoquinoline. LC-MS (m/z)=315 [M+H]$^+$ (3S)-3-butyl-6-methoxy-1-(1-methylpiperidin-4-yl)-1,2,3,4-tetrahydroisoquinoline: To a solution of tert-butyl (S)-3-butyl-6-methoxy-1-(1-methylpiperidin-4-yl)-3,4-dihydroisoquinoline (0.2 g, 0.63 mmol, 1.0 eq) in methanol (10 mL) was added sodium borohydride (0.07 g, 1.91 mmol, 3 eq) portion wise at 0° C. The suspension was stirred at room temperature for 15 mins. Progress of the reaction was monitored by TLC (10% MeOH in DCM). After this time, the reaction mixture was concentrated and obtained crude was diluted with EtOAc (15 mL) and water (8 mL). Organic layer was separated, washed with brine solution (7 mL), dried over anhydrous sodium sulfate, filtered and concentrated under reduced pressure to obtain the crude product, which was purified by flash column chromatography using 8% MeOH in DCM as mobile phase to get (3S)-3-butyl-6-methoxy-1-(1-methylpiperidin-4-yl)-1,2,3,4-tetrahydroisoquinoline. LCMS (ES) m/z=317 [M+H]+.

$^1$H NMR (400 MHz, DMSO-d$_6$) δ ppm 0.87 (bs, 3H), 1.21-1.45 (m, 10H), 2.11-2.14 (m, 3H), 1.76 (bs, 2H), 2.60-2.80 (m, 4H), 3.48 (bs, 1H), 3.67 (s, 3H), 3.91 (s, 1H), 6.30 (bs, 1H), 6.59-6.69 (m, 2H), 7.02-7.04 (m, 2H).

1-((3S)-3-butyl-6-methoxy-1-(1-methylpiperidin-4-yl)-3,4-dihydroisoquinolin-2(1H)-yl)-3-(trimethylsilyl)prop-2-yn-1-one: First step: To a solution of 3-(trimethylsilyl)propiolic acid (0.1 g, 0.70 mmol, 1.0 eq) in DMF (0.002 mL, 0.028 mmol, 0.04 eq) was added oxalyl chloride (0.065 mL, 0.77 mmol, 1.1 eq) at room temperature and stirred for 30 minutes. After this time, reaction mixture was concentrated under reduced pressure to get 3-(trimethylsilyl)propioloyl chloride. Obtained acid chloride was carried to next step without any further purification.

Second step: To a solution of (3S)-3-butyl-6-methoxy-1-(1-methylpiperidin-4-yl)-1,2,3,4-tetrahydroisoquinoline (0.18 g, 0.5696 mmol, 1.0 eq) in acetonitrile (10 mL) was added sodium bicarbonate (0.35 g, 4.27 mmol, 7.5 eq) at 0° C. After stirring for 5 minutes, a solution of 3-(trimethylsilyl)propioloyl chloride (0.109 g, 0.62 mmol, 1.2 eq) in acetonitrile (5 mL) was added to the above reaction mass at 0° C. The resulting mixture stirred at 0° C. for 15 min, progress of the reaction was monitored by TLC (5% MeOH in DCM). After this time, reaction mass was diluted with EtOAc (40 mL) and water (8 mL). Organic layer was separated, washed with brine solution (7 mL), dried over anhydrous sodium sulfate, filtered and concentrated under reduced pressure to obtain the crude product, it was carried to next step without any further purification. LCMS (ES) m/z=441 [M+H]+.

1-((3S)-3-butyl-6-methoxy-1-(1-methylpiperidin-4-yl)-3,4-dihydroisoquinolin-2(1H)-yl)prop-2-yn-1-one: To a solution of 1-((3S)-3-butyl-6-methoxy-1-(1-methylpiperidin-4-yl)-3,4-dihydroisoquinolin-2(1H)-yl)-3-(trimethylsilyl)prop-2-yn-1-one (0.2 g, 0.45 mmol, 1.0 eq) in MeOH (15 mL) was added K$_2$CO$_3$ (0.187 g, 1.36 mmol, 3 eq) at 0° C. The reaction mixture was stirred at 0° C. for 15 mins to give a white solution. Progress of the reaction was monitored by TLC (10% MeOH in DCM). After this time, the reaction mixture was diluted with DCM (5 mL) and water (5 mL). Organic layer was separated, dried over Na2SO4 and concentrated under reduced pressure to obtain the crude product, which was purified by following preparative HPLC conditions. Analytical Conditions: column: X-BridgeC-18 (250 mm×4.6 mm×5 μm); mobile phase (A): 0.1% ammonia in water; mobile phase (B): CAN; flow rate: 1.0 mL/min.

Product fractions collected and concentrated under reduced pressure to get 1-((3S)-3-butyl-6-methoxy-1-(1-methylpiperidin-4-yl)-3,4-dihydroisoquinolin-2(1H)-yl)prop-2-yn-1-one. LCMS (ES) m/z=369 [M+H]+.

$^1$H NMR (400 MHz, CDCl$_3$) δ ppm 0.80-0.87 (m, 3H), 1.15-1.20 (m, 2H), 1.22-1.32 (m, 4H), 1.60-1.66 (m, 3H), 1.72-1.77 (m, 2H), 1.95-2.04 (m, 1H), 2.07-2.08 (m, 3H), 2.73-2.80 (m, 2H), 3.06-3.17 (m, 2H), 3.71 (s, 3H), 3.90 (bs, 1H), 4.08 (bs, 1H), 4.53-4.55 (m, 1H), 4.91-4.93 (m, 1H), 6.67-6.72 (m, 1H), 6.81 (s, 1H), 7.00-7.05 (m, 1H).

Procedure 33: Synthesis of Compound 99

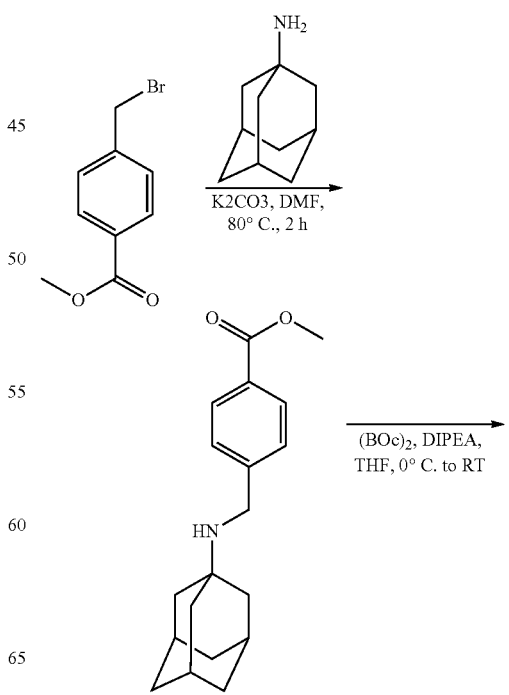

187
-continued
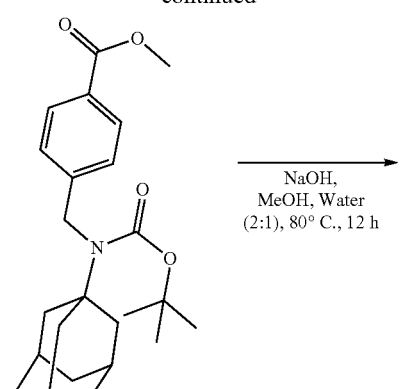
→ NaOH, MeOH, Water (2:1), 80° C., 12 h
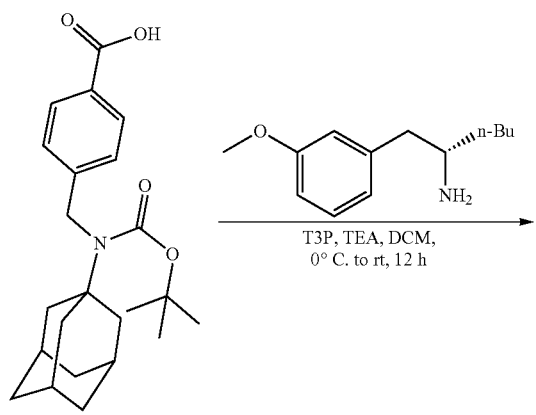
+ 
→ T3P, TEA, DCM, 0° C. to rt, 12 h
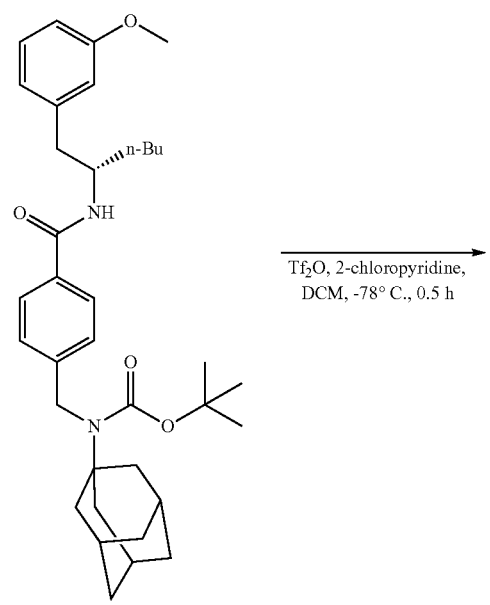
→ Tf₂O, 2-chloropyridine, DCM, -78° C., 0.5 h
188
-continued
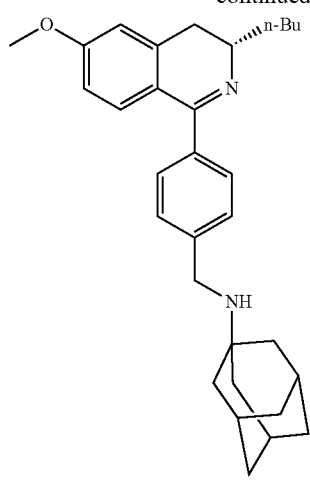
→ (Boc)2O, DIPEA, THF, 0° C., 16 h
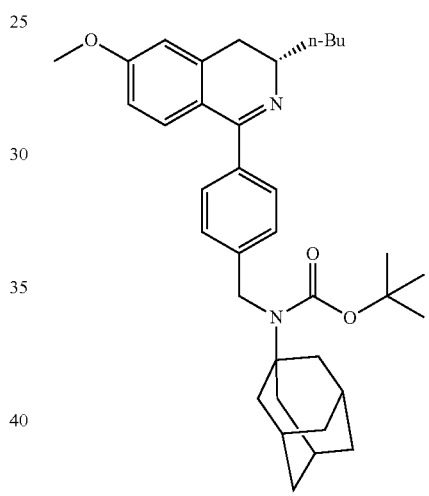
→ NaBH4, MeOH, 0° C. to rt, 1 h
Trans isomer was taken to the next step
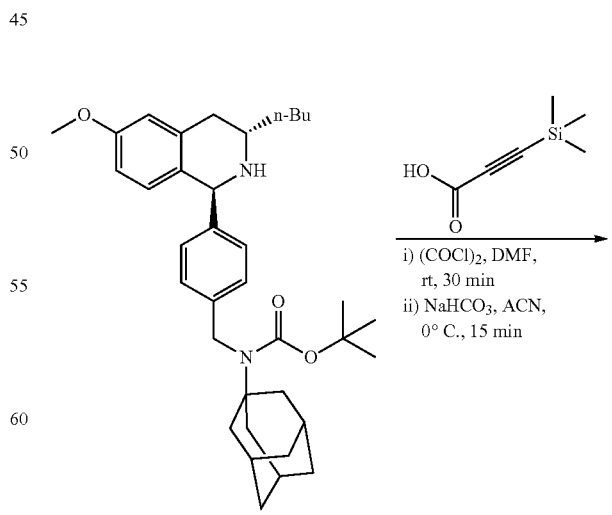
→ 
i) (COCl)₂, DMF, rt, 30 min
ii) NaHCO₃, ACN, 0° C., 15 min

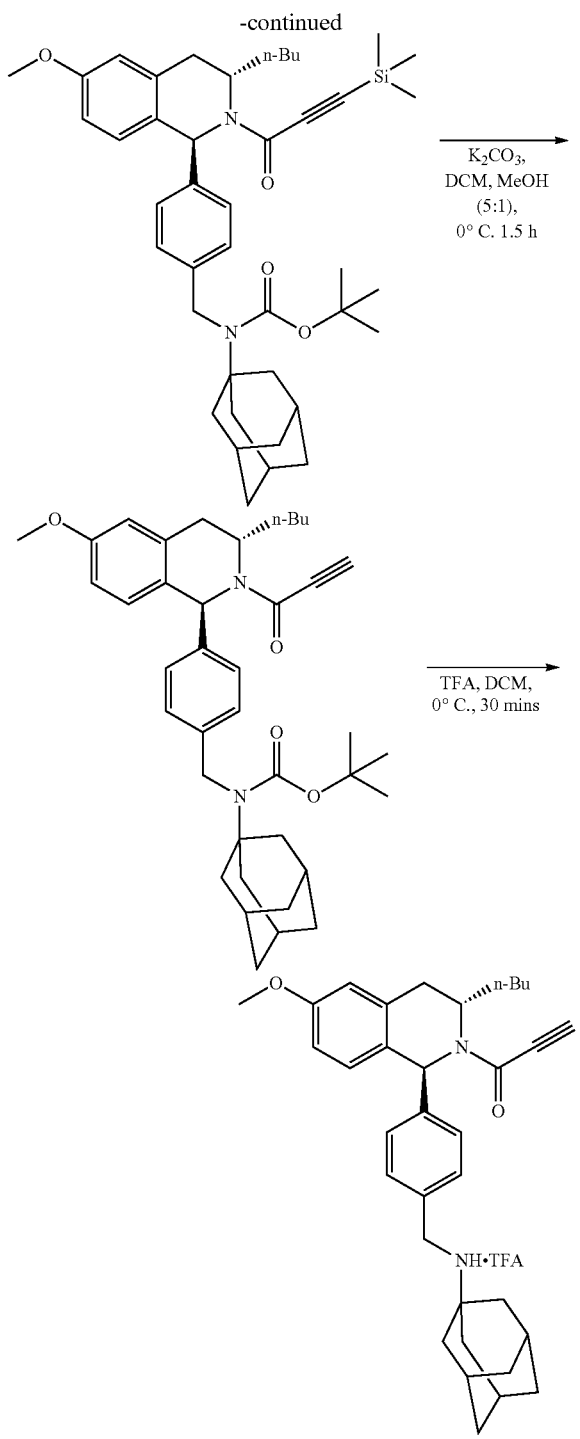

99 methyl 4-((((3s,5s,7s)-adamantan-1-yl)amino)methyl) benzoate: To a stirred solution of (3s,5s,7s)-adamantan-1-amine (1.98 g, 13.1 mmol, 1.0 eq) in DMF (30.0 mL) at 0° C., potassium carbonate (2.71 g, 19.6 mmol, 1.5 eq) added. After stirring for 5 minutes methyl 4-(bromomethyl)benzoate (2.7 g, 11.8 mmol, 0.9 eq) added. Then reaction mixture was allowed to stirred at 80° C. for 2 h. After completion of the reaction, reaction mixture was cool to room temperature, Reaction mixture was diluted with water (30 mL), extracted in to ethyl acetate (2×30 mL). Combined organic layer was washed with cool water (40 mL), brine (20 mL), dried over anhydrous sodium sulphate. Organic layer was filtered and concentrated under reduced pressure to get crude product, which was purified by flash column chromatography on silica gel using ethyl acetate in hexane as eluent. Product was isolated at 15-20% ethyl acetate in hexane.

Product fractions collected and concentrated under reduced pressure to get methyl 4-((((3s,5s,7s)-adamantan-1-yl)amino)methyl)benzoate. LCMS (ES) m/z=300 [M+H]+.

methyl 4-{[(adamantan-1-yl)[(tert-butoxy)carbonyl] amino]methyl}benzoate: To a solution of methyl 4-{[(adamantan-1-yl)amino]methyl}benzoate (3 g, 10.0 mmol, 1 eq) in THF (30 mL) was added N,N-diisopropylethylamine (5.25 mL, 30.1 mmol, 3 eq) and di-tert-butyl dicarbonate (6.91 mL, 30.1 mmol, 3 eq) at 0° C. The reaction was stirred at room temperature for 16 h. TLC (30% EtOAc in hexane) showed the reaction was completed. After this time, reaction mixture was concentrated under reduced pressure and obtained crude was diluted with saturated aqueous NaHCO$_3$ solution (15 mL) and ethyl acetate (30 mL). Organic layer was separated, washed with water (20 mL), brine solution (10 mL), dried over anhydrous sodium sulfate, filtered and concentrated under reduced pressure to get crude (9 g), which was purified by flash chromatography using 0-25% EtOAc in hexane as an eluent to give methyl 4-{[(adamantan-1-yl)[(tert-butoxy)carbonyl]amino]methyl}benzoate. LCMS (ES) m/z=300 [M+H]+, Boc group cleaved mass was observed.

$^1$H NMR (400 MHz, CDCl$_3$) δ ppm 1.42 (s, 9H), 1.52-1.72 (m, 6H), 1.98-2.03 (m, 3H), 1.52-1.72 (m, 6H), 2.16-2.19 (m, 3H), 4.62-4.67 (m, 2H), 7.27 (d, J=8.8 Hz, 2H), 7.97 (d, J=6.8 Hz, 2H).

4-((((3s,5s,7s)-adamantan-1-yl)(tert-butoxycarbonyl) amino)methyl)benzoic acid: To a solution of methyl 4-((((3s,5s,7s)-adamantan-1-yl)(tert-butoxycarbonyl)amino)methyl) benzoate (3 g, 7.51 mmol, 1 eq) in MeOH (30 mL) and water (15 mL) was added sodium hydroxide (0.616 g, 15 mmol, 2.0 eq) at room temperature and the reaction mixture was stirred at 80° C. for 12 h. Progress of the reaction was monitored by TLC (60% E. A in hexane). After completion of the reaction, the reaction mixture was concentrated under reduced pressure to remove Methanol from reaction mass and the remaining aqueous layer was extracted with EtOAc (50 mL). Finally the aqueous layer was acidified with 5% citric acid (pH=4) and then product was extracted with EtOAc (250 mL). Organic layer was dried over anhydrous sodium sulfate, filtered and concentrated under reduced pressure to get the product which was triturated with n-pentane (20 mL), decanted the pentane layer and dried under high vacuum to afford 4-((((3s,5s,7s)-adamantan-1-yl)(tert-butoxycarbonyl)amino)methyl)benzoic acid. LCMS (ES) m/z=286 [M+H]+(without boc mass was observed).

$^1$H NMR (400 MHz, DMSO-d$_6$): δ ppm 1.33 (s, 9H), 1.88-2.20 (m, 9H), 4.58 (s, 2H), 7.28 (d, J=8 Hz, 2H), 7.87 (d, J=8 Hz, 2H), 12.79 (bs, 1H).

4-((((1R,3R)-adamantan-1-yl)amino)methyl)—N—((S)-1-(3-methoxyphenyl)hexan-2-yl)benzamide: To a solution of 4-((((3s,5s,7s)-adamantan-1-yl)(tert-butoxycarbonyl) amino)methyl)benzoic acid (2.66 g, 6.27 mmol, 1.1 eq) in DCM (20 mL) was added TEA (2.63 mL, 18.8 mmol, 3 eq), stirred for 5 min and then T3P (50 wt. % in EtOAc) (3.15 mL, 9.41 mmol, 1.5 eq) was added at 0° C. and stirred for another 30 min. Then a solution of (S)-1-(3-methoxyphenyl) hexan-2-amine (1.3 g, 6.27 mmol, 1 eq) in DCM (10 mL) was added to the reaction mixture at 0° C. and then reaction mixture was stirred at room temperature for 12 h. Progress of the reaction was monitored by TLC (60% ethyl acetate in n-hexane). After this time, the reaction mixture was diluted with DCM (50 mL), organic layer was washed with saturated aqueous solution of sodium bicarbonate (2×10 mL), water (10 mL), brine solution (10 mL), dried over anhydrous sodium sulfate, filtered and concentrated under reduced pressure to obtain the crude product, which was purified by flash chromatography using 25-30% EtOAc in n-hexane as an eluent to give 4-((((1R,3R)-adamantan-1-yl)amino) methyl)—N—((S)-1-(3-methoxyphenyl)hexan-2-yl)benzamide. LCMS (ES) m/z=576 [M+H]+.

$^1$H NMR (400 MHz, DMSO-$d_6$) δ ppm 0.80-0.87 (m, 3H), 1.12-1.35 (m, 9H), 1.52 (bs, 5H), 1.97-2.03 (m, 6H), 2.74 (bs, 1H), 3.64 (s, 3H), 4.11 (bs, 1H), 3.8 (bs, 1H), 4.11 (bs, 1H), 4.55 (bs, 2H), 6.70-6.76 (m, 2H), 7.13-7.22 (m, 3H), 7.71 (m, 1H), 8.09 (bs, 1H).

N—({4-[(3S)-3-butyl-6-methoxy-3,4-dihydroisoquinolin-1-yl]phenyl}methyl)adamantan-1-amine: To stirred solution of 4-((((1R,3R)-adamantan-1-yl)amino)methyl)—N—((S)-1-(3-methoxyphenyl)hexan-2-yl)benzamide (2.2 g, 3.83 mmol, 1 eq) and 2-chloropyridine (3.6 mL, 38.32 mmol, 10.0 eq) in dichloromethane (5 mL) was added trifluoromethanesulfonic anhydride (1.9 mL, 11.49 mmol, 3.0 eq) via syringe slowly dropwise at −78° C. After 5 min, the reaction mixture was placed in an ice-water bath and warmed to 0° C. After 5 min, the resulting solution was allowed to warm to 23° C. for 1 h. Progress of the reaction was monitored by TLC (30% EA in hexane). After 30 minutes, reaction was quenched with aqueous sodium hydroxide solution (3 mL, 1N) to neutralize the trifluoromethanesulfonate salts. Dichloromethane (15 mL) was added to dilute the mixture and the layers were separated. The aqueous layer was extracted with DCM (2×50 mL). The combined organic layer was washed with brine (5 mL), was dried over anhydrous sodium sulfate, filtered and concentrated under reduced pressure to give the crude product. LCMS (ES) m/z=457 [M+H]+.

tert-butyl N—(adamantan-1-yl)—N—({4-[(3S)-3-butyl-6-methoxy-3,4-dihydroisoquinolin-1-yl]phenyl}methyl)carbamate: To a stirred solution of (1R,3R)—N—(4-((S)-3-butyl-6-methoxy-3,4-dihydroisoquinolin-1-yl)benzyl) adamantan-1-amine (2.1 g, 4.60 mmol, 1.0 eq) in THF (20.0 mL) at 0° C. was added DIPEA (2.46 mL, 13.8 mmol, 3.0 eq) followed by boc anhydride (3.17 mL, 13.8 mmol, 3.0 eq). Then reaction mixture was allowed to stir at room temperature for 16 h. Reaction mixture was diluted with water (25 mL), extracted with ethyl acetate (2×30 mL). Combined organic layer was washed with water (20 mL), brine (20 mL), dried over anhydrous sodium sulphate. Organic layer was filtered and concentrated under reduced pressure to get crude product, which was purified by silica gel column chromatography 30% ethylacetate in hexane as an eluent to give the tert-butyl ((1R,3R)-adamantantan-1-yl)(4-((S)-3-butyl-6-methoxy-3,4-dihydroisoquinolin-1-yl) benzyl)carbamate. LCMS (ES) m/z=557 [M+H]+

$^1$H NMR (400 MHz, DMSO-$d_6$) δ ppm 0.89 (t, J=7.2 Hz, 3H), 1.3 (s, 9H), 1.54-1.65 (m, 9H), 1.99-2.10 (m, 9H), 2.4-2.6 (m, 2H), 2.74-2.77 (m, 1H), 3.78 (s, 3H), 4.58 (s, 2H), 6.79-6.81 (m, 1H), 6.90 (s, 1H), 7.07-7.09 (m, 1H), 7.23-7.25 (m, 2H), 7.44-7.46 (m, 1H).

tert-butyl N—(adamantan-1-yl)—N—({4-[(1S,3S)-3-butyl-6-methoxy-1,2,3,4-tetrahydroisoquinolin-1-yl] phenyl}methyl)carbamate: To a solution of tert-butyl ((1R, 3R)-adamantan-1-yl)(4-((S)-3-butyl-6-methoxy-3,4-dihydroisoquinolin-1-yl)benzyl)carbamate (0.8 g, 1.44 mmol, 1 eq) in methanol (15 mL) was added sodium borohydride (0.159 g, 4.31 mmol, 3 eq) portion wise at 0° C. The suspension was stirred at room temperature for 30 mins. Progress of the reaction was monitored by TLC (20% EA in hexane). After this time, the reaction mixture was quenched with acetone (10 mL), concentrated and obtained crude was diluted with EtOAc (20 mL) and water (5 mL). Organic layer was separated, washed with brine solution (10 mL), dried over anhydrous sodium sulfate, filtered and concentrated under reduced pressure to obtain the crude product. The obtained crude product was purified by prep TLC using 20% ethyl acetate in n-hexane as an eluent to get tert-butyl ((1R,3R)-adamantan-1-yl)(4-((1S,3S)-3-butyl-6-methoxy-1,2,3,4-tetrahydroisoquinolin-1-yl)benzyl)carbamate (1,3 trans isomer). LCMS (ES) m/z=559 [M+H]+.

$^1$H NMR (400 MHz, CDCl$_3$) δ ppm 0.8-0.9 (m, 3H), 1.1-1.3 (m, 5H), 1.39 (s, 9H), 1.59-1.70 (m, 9H), 2.02 (bs, 3H), 2.10 (s, 5H), 2.73 (bs, 2H), 2.88-2.99 (m, 2H), 3.79 (s, 3H), 4.55 (s, 2H), 5.29 (s, 2H), 6.68 (s, 2H), 6.84 (bs, 1H), 7.11 (bs, 3H).

tert-butyl N—(adamantan-1-yl)—N—({4-[(1S,3S)-3-butyl-6-methoxy-2-[3-(trimethylsilyl)prop-2-ynoyl]-1,2,3, 4-tetrahydroisoquinolin-1-yl]phenyl}methyl)carbamate:

First step: To a solution of 3-(trimethylsilyl)propiolic acid (0.043 g, 0.302 mmol, 1.0 eq) in DMF (0.00094 mL, 0.012 mmol, 0.04 eq) was added oxalyl chloride (0.028 mL, 0.33 mmol, 1.1 eq) at room temperature and stirred for 30 minutes. Then the reaction mixture was concentrated under reduced pressure to get 3-(trimethylsilyl)propioloyl chloride. This acid chloride crude was carried to next step without any further purification.

Second step: To a solution of tert-butyl ((1R,3R)-adamantan-1-yl)(4-((1S,3S)-3-butyl-6-methoxy-1,2,3,4-tetrahydroisoquinolin-1-yl)benzyl)carbamate (0.080 g, 0.143 mmol, 1.0 eq) in acetonitrile (10 mL) was added sodium bicarbonate (0.091 g, 1.07 mmol, 7.5 eq) at 0° C. After stirring for 5 minutes, a solution of 3-(trimethylsilyl)propioloyl chloride (0.025 g, 0.157 mmol, 1.1 eq) in acetonitrile (5.0 mL) was added to the above reaction mass. The resulting mixture stirred at 0° C. for 1 h, progress of the reaction was monitored by TLC (20% ethyl acetate in n-hexane). After this time, reaction mass was diluted with EtOAc (100 mL) and water (50 mL). Organic layer was separated, washed with brine solution (10 mL), dried over anhydrous sodium sulfate, filtered and concentrated under reduced pressure. This crude product was carried to next step without any further purification. LCMS (ES) m/z=583 [M+H]+ (without Boc group mass was observed).

tert-butyl N—(adamantan-1-yl)—N—({4-[(1S,3S)-3-butyl-6-methoxy-2-(prop-2-ynoyl)-1,2,3,4-tetrahydroisoquinolin-1-yl]phenyl}methyl)carbamate: To a solution of tert-butyl ((1R,3R)-adamantan-1-yl)(4-((1S,3S)-3-butyl-6-methoxy-2-(3-(trimethylsilyl)propioloyl)-1,2,3,4-tetrahydroisoquinolin-1-yl)benzyl)carbamate (171 mg, 0.25 mmol, 1 eq) in DCM (10 mL)/MeOH (2 mL) were added K$_2$CO$_3$ (207 mg, 1.50 mmol, 6 eq) at 0° C. The mixture was stirred at 0° C. for 2 h, after completion of the reaction, the reaction mixture was diluted with DCM (5 mL) and added H2O (3 mL). The organic layer was extracted with DCM (3×10 mL) and dried over Na$_2$SO$_4$ and concentrated. The residue was purified by prep-TLC, using 20% E. A in hexane to give tert-butyl ((1R,3R)-adamantan-1-yl)(4-((1S,3S)-3-butyl-6-methoxy-2-propioloyl-1,2,3,4-tetrahydroisoquinolin-1-yl) benzyl)carbamate. LCMS (ES) m/z=511.2 [M+H]+. (without group mass was showing).

$^1$H NMR (400 MHz, CDCl$_3$) δ ppm 0.81-0.85 (m, 3H), 0.93-0.95 (m, 1H), 1.2-1.2 (m, 6H), 1.38-1.56 (m, 9H), 1.68-1.71 (m, 2H), 1.91-2.0 (m, 3H), 2.01 (bs, 5H), 2.17 (s, 1H), 2.67-2.82 (m, 2H), 2.88 (s, 1H), 3.80-3.81 (m, 3H), 4.48-4.61 (m, 4H), 6.29 (d, J=14 Hz, 1H), 6.69 (s, 1H), 6.78-6.84 (m, 1H), 6.93-7.08 (m, 4H), 7.33 (d, J=8.4 Hz, 1H).

N—(adamantan-1-yl)—N—({4-[(1S,3S)-3-butyl-6-methoxy-2-(prop-2-ynoyl)-1,2,3,4-tetrahydroisoquinolin-1-yl]phenyl}methyl)-2,2,2-trifluoroacetamide: To a stirred solution of tert-butyl ((1R,3R)-adamantan-1-yl)(4-((1S,3S)-3-butyl-6-methoxy-2-propioloyl-1,2,3,4-tetrahydroisoquinolin-1-yl)benzyl)carbamate (0.06 g, 0.098 mmol, 1 eq) in DCM (15 mL) was added TFA (0.2 mL) drop wise under cooling (0° C.) conditions, reaction mixture was stirred at 0° C. for 2 h, reaction progress was checked by TLC (70% EA in hexane), after completion of the reaction, reaction mixture was concentrated under reduced pressure to obtain the crude product, which was further purified by prep HPLC purification by using following analytical condition to get the 1-((1S,3S)-1-(4-((((1R,3R)-adamantan-1-yl)(2,2,2-trifluoroacetyl)-14-azaneyl)methyl)phenyl)-3-butyl-6-methoxy-3,4-dihydroisoquinolin-2(1H)-yl)prop-2-yn-1-one. Analytical Conditions: column: X-BridgeC-18 (250 mm×4.6 mm×5 µm); mobile phase(A): 0.1% TFA in water; mobile phase (B): acetonitrile; flow rate: 1.0 mL/min; gradient B: 0/20, 12/60, 22/95, 25/95, 27/20, 30/20. LCMS (ES) m/z=511.1 [M+H]+.

$^1$H NMR (400 MHz, CDCl$_3$) δ ppm 0.80-0.84 (m, 3H), 0.90-1.2 (m, 7H), 1.5-1.67 (m, 6H), 1.86 (s, 4H), 1.90-2.1 (m, 2H), 2.76-2.90 (m, 2H), 3.0-3.16 (m, 1H), 3.70-3.80 (m, 4H), 4.01 (bs, 2H), 4.59-4.75 (m, 2H), 6.75-6.81 (m, 2H), 7.07-7.12 (m, 1H), 7.27-7.44 (m, 4H), 8.46 (bs, 2H).

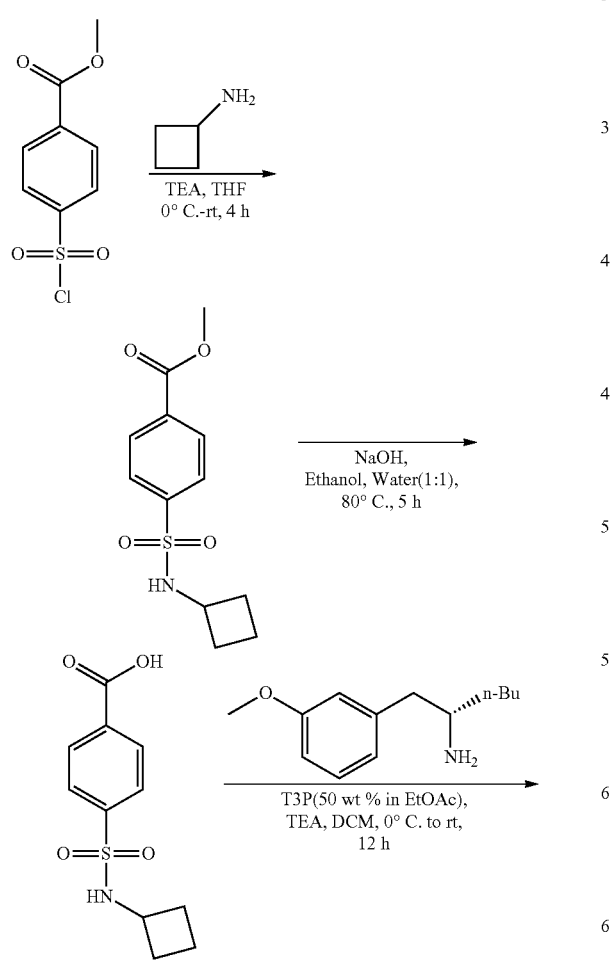

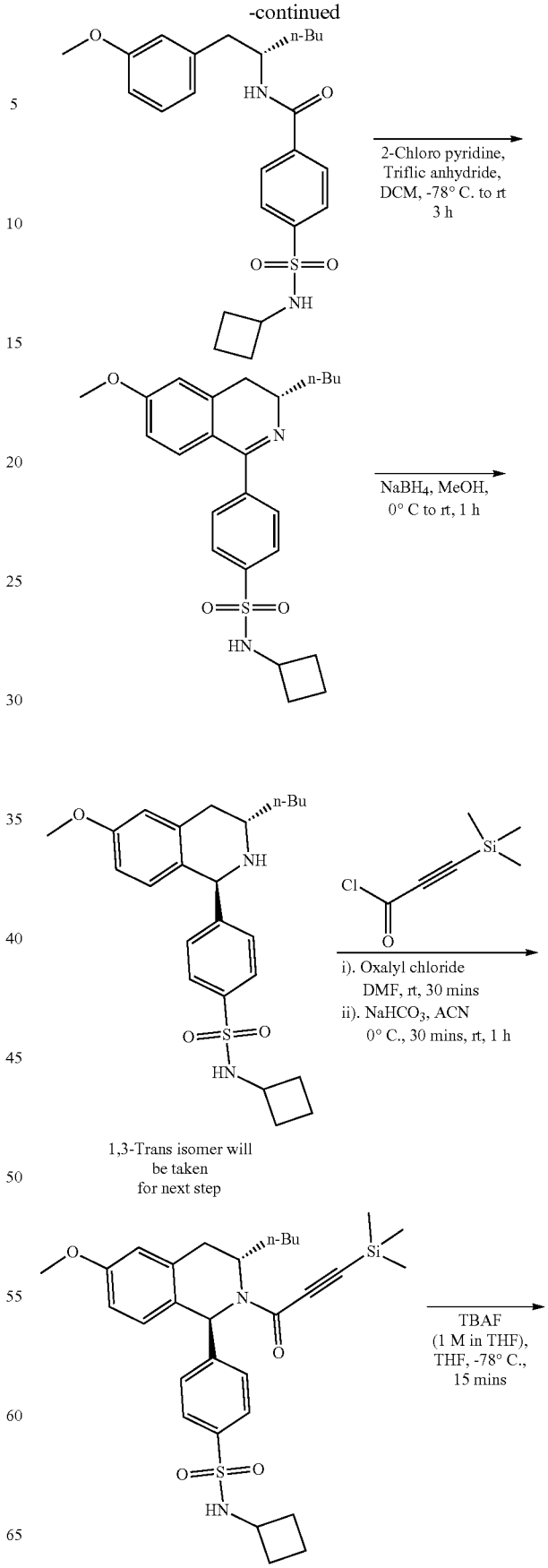

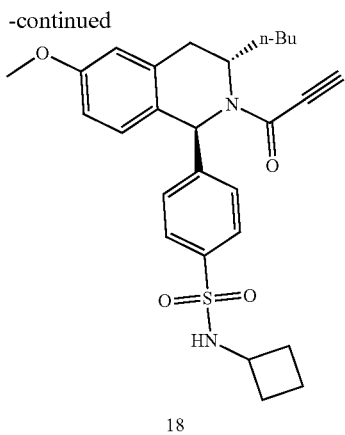

18 methyl 4-(cyclobutylsulfamoyl)benzoate: To a solution of methyl 4-(chlorosulfonyl)benzoate (5.0 g, 21.3 mmol, 1.0 eq) in THF (50 mL) was added triethylamine (8.92 mL, 63.9 mmol, 3.0 eq) and cyclobutanamine (1.83 mL, 21.3 mmol, 1.0 eq) at room temperature and the mixture was stirred at room temperature for 3 h, TLC (30% EtOAc in hexane) showed the reaction was completed. The reaction mixture was concentrated under reduced pressure and the obtained crude was diluted with EtOAc (250 mL), washed with water (2×50 mL). The organic layer was dried over anhydrous Na2SO4, concentrated under reduced pressure to get crude product. The crude was purified by flash chromatography using 15-20% EtOAc in hexane as an eluent to give methyl 4-(N-cyclobutylsulfamoyl)benzoate. LCMS (ES) m/z: 270.1 [M+H]+.

$^1$H NMR (400 MHz, DMSO-$d_6$) δ 1.56-1.67 (m, 2H), 1.71-1.76 (m, 2H), 2.10-2.14 (m, 2H), 3.78-3.86 (m, 1H), 3.95 (s, 3H), 4.67-4.69 (m, 1H), 7.92 (d, J=8.4 Hz, 2H), 8.15 (d, J=8.4 Hz, 2H).

4-(cyclobutylsulfamoyl)benzoic acid: To a stirred solution of methyl 4-(cyclobutylsulfamoyl)benzoate (5 g, 18.6 mmol, 1 eq) in EtOH (25 mL) and water (25 mL) was added sodium hydroxide (1.49 g, 37.1 mmol, 2 eq) at room temperature and the reaction was stirred at 80° C. for 6 h. TLC (70% in EtOAc in hexane) showed that the reaction was completed after 6 h. The reaction mixture was cooled to room temperature, concentrated the reaction mixture under reduced pressure. The obtained aqueous layer was extracted with EtOAc (2×20 mL) and then the aqueous layer was acidified with 2 N HCl (pH~5) and then extracted with EtOAc (50 mL). Organic layer was dried over anhydrous sodium sulfate, filtered and concentrated under reduced pressure to afford the title compound 4-(cyclobutylsulfamoyl)benzoic acid. LCMS (ES) m/z=254 [M−H]−.

$^1$H NMR (400 MHz, DMSO-$d_6$) δ ppm 1.20-1.45 (m, 2H), 1.68-1.72 (m, 2H), 1.60-1.88 (m, 2H), 1.74-1.78 (m, 4H), 3.60-3.66 (m, 1H), 7.86-7.88 (m, 2H), 8.09-8.13 (m, 3H), 4.37 (bs, 1H), 13.5 (bs, 1H).

4-(cyclobutylsulfamoyl)—N-[(2S)-1-(3-methoxyphenyl) hexan-2-yl]benzamide: To a solution of 4-(cyclobutylsulfamoyl)benzoic acid (3.69 g, 14.5 mmol, 1 eq) in DCM (30 mL) under nitrogen atmosphere was added triethylamine (6.06 mL, 43.4 mmol, 3.0 eq) at 0° C., stirred for 10 mins and then propanephosphonic acid anhydride (50 wt. % in ethyl acetate) (9.69 mL, 8.57 mmol, 2.0 eq) was added at 0° C. to the reaction mixture, stirred at 0° C. for 15 mins and then (2S)-1-(3-methoxyphenyl)hexan-2-amine (3.0 g, 14.5 mmol, 1 eq) dissolved in DCM (20.0 mL) was added to the reaction mixture at 0° C. and then the reaction mixture was stirred at room temperature for 16 h. TLC (40% EtOAc in hexane) showed the reaction was completed after 16 h. The reaction mixture was diluted with DCM (150 mL), washed with saturated sodium bicarbonate solution (20 mL) and water (30 mL). Organic layer was dried over anhydrous Na$_2$SO$_4$, filtered and concentrated under reduced pressure to get 4-(cyclobutylsulfamoyl)—N-[(2S)-1-(3-methoxyphenyl)hexan-2-yl]benzamide. LCMS (ES) m/z=445.2 [M+H]+.

$^1$H NMR (400 MHz, CDCl$_3$) δ ppm 0.87-0.89 (m, 3H), 1.32-1.36 (m, 4H), 1.49-1.54 (m, 1H), 1.74-1.78 (m, 4H), 2.1 (bs, 2H), 2.86-2.94 (m, 2H), 3.75-3.78 (m, 4H), 4.37 (bs, 1H), 4.76 (bs, 3H), 5.58-5.89 (m, 1H), 6.74-6.67 (m, 3H), 7.19-7.25 (m, 1H), 7.74-7.75 (m, 2H), 7.84-7.86 (m, 2H).

(S)-4-(3-butyl-6-methoxy-3,4-dihydroisoquinolin-1-yl)—N-cyclobutylbenzenesulfonamide: To a solution of (S)-4-(N-cyclobutylsulfamoyl)—N—(1-(3-methoxyphenyl) hexan-2-yl)benzamide (3 g, 6.75 mmol, 1 eq) in DCM (30 mL) under nitrogen atmosphere was added 2-chloropyridine (1.28 mL, 13.5 mmol, 2 eq) at room temperature. Then trifluoromethanesulfonic anhydride (2.27 mL, 13.5 mmol, 2 eq) was added at −78° C., stirred for 5 mins, then warmed to 0° C., stirred for 30 mins at 0° C. and then the reaction mixture was stirred at room temperature for 3 h. TLC (100% EtOAc) showed starting material along with new spots. Reaction was monitored by LC-MS. The reaction mass was concentrated under reduced pressure to obtain the crude residue, obtained residue was quenched with 10% sodium hydroxide solution (15 mL), extracted with (2×150 mL) of ethyl acetate, combined organic layers were dried with anhydrous Na$_2$SO$_4$, filtered and concentrated under reduced pressure to get crude product, which was purified by flash column chromatography using 100% ethyl acetate in hexane as an eluent to obtain (S)-4-(3-butyl-6-methoxy-3,4-dihydroisoquinolin-1-yl)—N-cyclobutylbenzenesulfonamide. LCMS (ES) m/z=427.1 [M+H]+.

$^1$H NMR (400 MHz, CDCl$_3$) δ ppm: 7.88 (d, J=7.6 Hz, 2H), 7.70 (d, J=8 Hz, 2H), 7.05 (d, J=8.8 Hz, 1H), 6.78 (s, 1H), 6.72 (d, J=8 Hz, 1H), 4.68-4.67 (m, 1H), 3.89 (s, 3H), 3.56-3.52 (m, 1H), 2.82-2.71 (m, 1H), 2.82-2.71 (m, 1H), 2.62-2.46 (m, 1H), 2.18-2.16 (m, 1H), 1.83-1.75 (m, 4H), 1.61-1.56 (m, 3H), 1.49-1.35 (m, 2H), 0.95-0.91 (m, 3H).

4-((1S,3S)-3-butyl-6-methoxy-1,2,3,4-tetrahydroisoquinolin-1-yl)—N-cyclobutylbenzenesulfonamide: To a solution of (S)-4-(3-butyl-6-methoxy-3,4-dihydroisoquinolin-1-yl)—N-cyclobutylbenzenesulfonamide (1.5 g, 3.52 mmol, 1 eq) in methanol (15 mL) was added sodium borohydride (0.388 g, 10.5 mmol, 3 eq) portion wise at 0° C. The suspension was stirred at room temperature for 1 h. Progress of the reaction was monitored by TLC (50% EA in hexane). After this time, the reaction mixture was quenched with acetone (10 mL), concentrated and the obtained crude product was diluted with EtOAc (30 mL) and water (20 mL). The organic layer was separated, washed with brine solution (10 mL), dried over anhydrous sodium sulfate, filtered and concentrated under reduced pressure to obtain the crude product. The obtained crude product was purified by prep TLC using 50% ethyl acetate in n-hexane as an eluent to get 4-((1S,3S)-3-butyl-6-methoxy-1,2,3,4-tetrahydroisoquinolin-1-yl)—N-cyclobutylbenzenesulfonamide (1,3 trans isomer). LCMS (ES) (m/z)=429 [M+H]+.

4-((1S,3S)-3-butyl-6-methoxy-2-(3-(trimethylsilyl)propioloyl)-1,2,3,4-tetrahydroisoquinolin-1-yl)—N-cyclobutylbenzenesulfonamide: First step: To a solution of 3-(trimethylsilyl)propiolic acid (0.2 g, 1.41 mmol, 1 eq) in DMF (0.04 mL, 0.56 mmol, 0.04 eq) was added oxalyl chloride (0.15 mL, 1.69 mmol, 1.2 eq) at room temperature and stirred for 30 minutes. Then the reaction mixture was concentrated under reduced pressure to get 3-(trimethylsilyl)propioloyl chloride. This acid chloride crude was carried to next step without any further purification.

Second step: To a solution of 4-((1S,3S)-3-butyl-6-methoxy-1,2,3,4-tetrahydroisoquinolin-1-yl)—N-cyclobutylbenzenesulfonamide (0.2 g, 0.467 mmol, 1 eq) in Acetonitrile (10 mL) was added sodium hydrogen carbonate (0.298 g, 3.5 mmol, 7.5 eq) at 0° C., followed by 3-(trimethylsilyl)propioloyl chloride (0.09 g, 0.56 mmol, 1.2 eq) in Acetonitrile (5 mL). The mixture was stirred at 0° C. for 5 minutes then allowed to stirred at room temperature for 1 h. Then the reaction mixture was diluted water (5 mL) and was extracted with ethyl acetate (2×15 mL). The organic layer was dried over anhydrous $Na_2SO_4$, filtered and concentrated under reduced pressure to obtain the crude of 4-((1S,3S)-3-butyl-6-methoxy-2-(3-(trimethylsilyl)propioloyl)-1,2,3,4-tetrahydroisoquinolin-1-yl)—N-cyclobutylbenzenesulfonamide. LCMS (ES) (m/z)=553 [M+H]+.

4-((1S,3S)-3-butyl-6-methoxy-2-propioloyl-1,2,3,4-tetrahydroisoquinolin-1-yl)—N-cyclobutylbenzenesulfonamide: Trans-isomer: To a stirred solution of 4-((1S,3S)-3-butyl-6-methoxy-2-(3-(trimethylsilyl)propioloyl)-1,2,3,4-tetrahydroisoquinolin-1-yl)—N-cyclobutylbenzenesulfonamide (0.200 g, 0.362 mmol, 1.0 eq) in THF (5.0 mL) was added tetra butyl ammonium fluoride (1M in THF) (0.43 mL, 0.43 mmol, 1.2 eq) at −78° C. The reaction mixture was stirred at same temperature for 30 minutes. The reaction mixture was quenched with saturated sodium bicarbonate solution (5 mL), extracted with ethyl acetate (2×20 mL). Combined organic layer was washed with water (10 mL), brine (10 mL) and dried over with anhydrous sodium sulfate, filtered and concentrated under reduced pressure to get crude. The obtained crude product was purified by flash chromatography using 60% ethyl acetate in n-hexane as an eluent to get the desired product 4-((1S,3S)-3-butyl-6-methoxy-2-propioloyl-1,2,3,4-tetrahydroisoquinolin-1-yl)—N-cyclobutylbenzenesulfonamide. LCMS (ES) m/z=481.3 [M+H]+.

$^1$H NMR (400 MHz, DMSO-$d_6$) δ ppm 0.80-0.81 (m, 3H), 0.90-0.95 (m, 1H), 1.20-1.39 (m, 4H), 1.40-1.49 (m, 3H), 1.71-1.76 (m, 2H), 1.88-1.90 (m, 2H), 2.81-2.94 (m, 1H), 3.06-3.17 (m, 1H), 3.55-3.57 (m, 1H), 3.77 (s, 3H), 4.44 (s, 1H), 4.75 (s, 1H), 6.06 (s, 1H), 6.77-6.83 (m, 2H), 7.37-7.43 (m, 2H), 7.60-7.69 (m, 3H).

Procedure 35: Synthesis of Compound 95

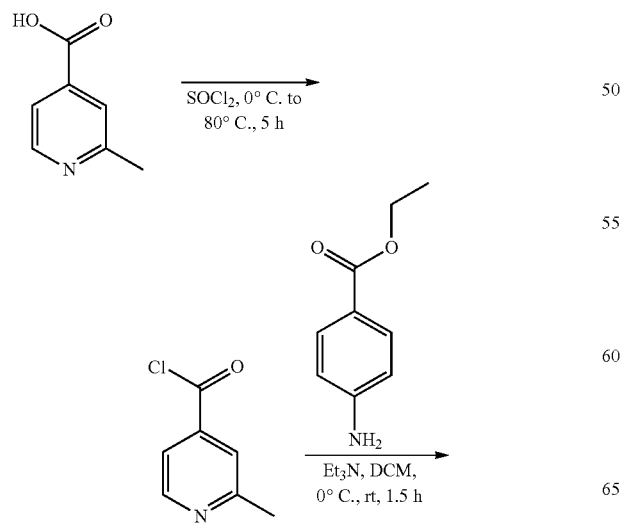

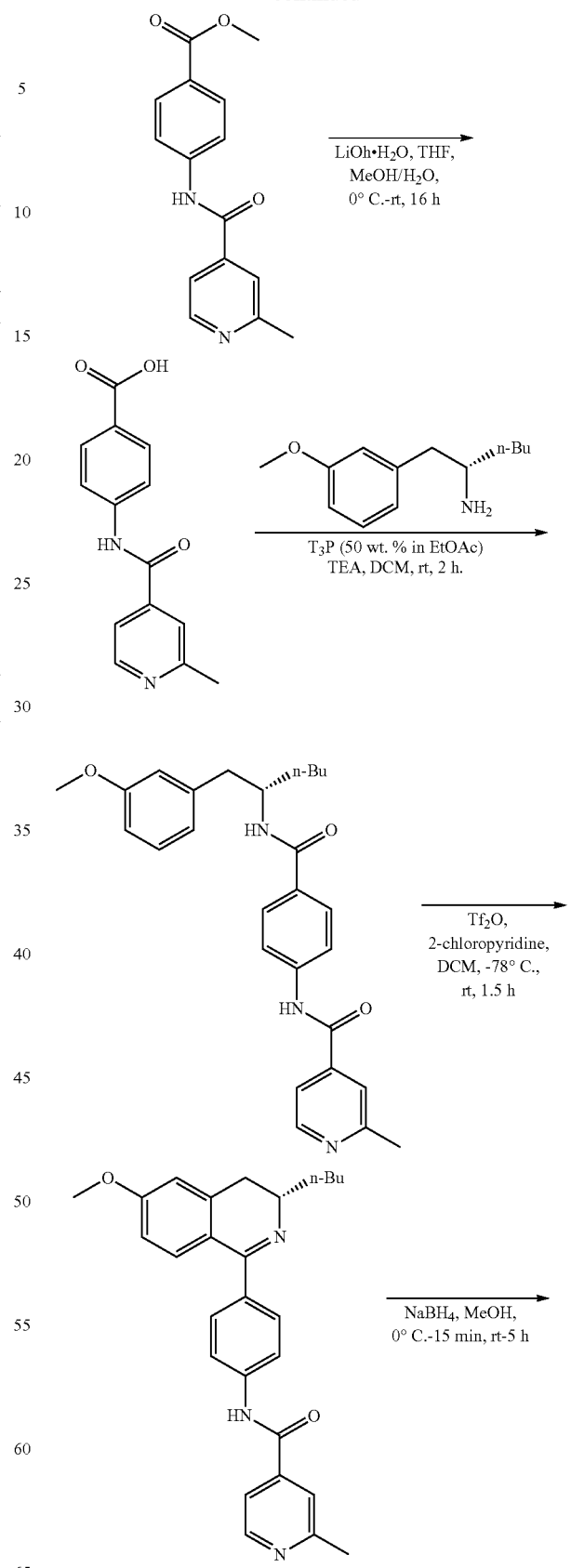

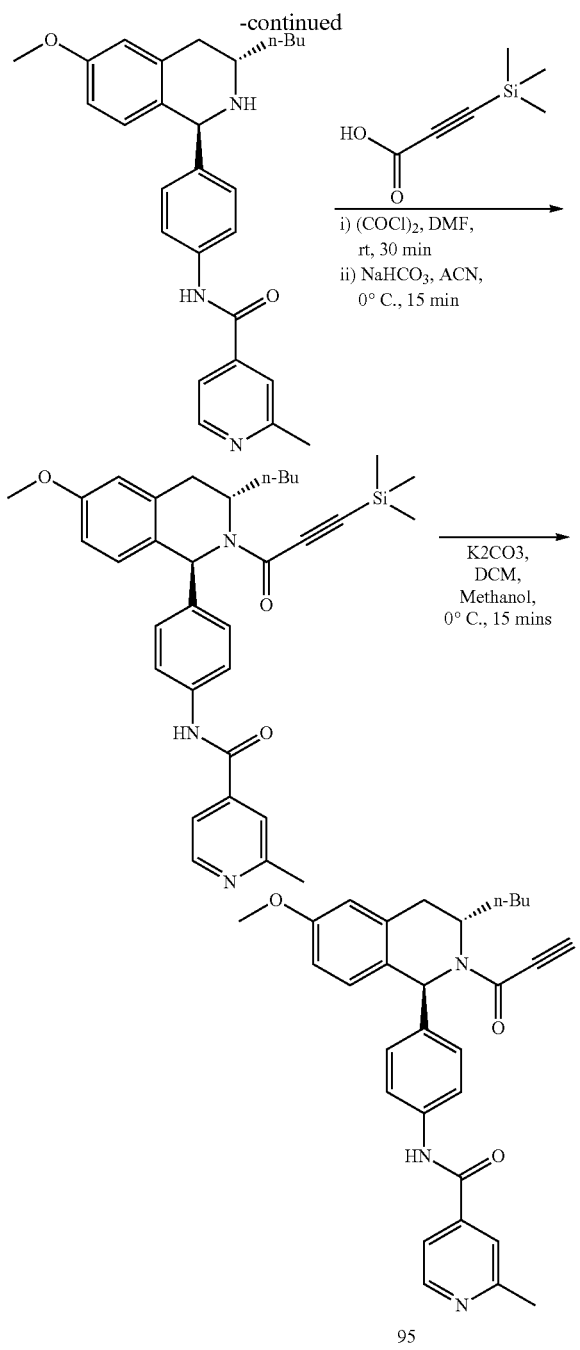

2-methylpyridine-4-carbonyl chloride: To a solution of 2-methylpyridine-4-carboxylic acid (3.00 g, 21.9 mmol, 1.0 eq) in N,N-dimethylformamide (0.067, 0.87 mmol, 0.04 eq) was added SOCl2 (40.0 mL) at 0° C., This mixture was refluxed for 3 h at 80° C., and the excess of thionyl chloride was concentrated under reduced pressure to get 2-methylpyridine-4-carbonyl chloride. This crude product carried to next step without any further purification.

ethyl 4-(2-methylpyridine-4-amido)benzoate: To a stirred solution of ethyl 4-aminobenzoate (3.19 g, 19.3 mmol, 1.0 eq) in DCM (40.0 mL) was added triethylamine (15.0 mL, 116 mmol, 6 eq) 0° C. and the reaction was stirred for 15 mins. Then 2-methylpyridine-4-carbonyl chloride (20 ml DCM) (3.00 g, 19.3 mmol, 1 eq) was added slowly. After this time, the reaction was stirred at room temperature for 12 h. After completion of the reaction, the reaction mixture was slowly quenched with water, diluted with DCM (100 mL), stirred at room temperature for 5 mins. Then the layers were separated. Aqueous layer was extracted with DCM (2×100.0 mL). Combined organic layer was washed with water (50.0 mL), separated the layers. Then the organic layer was dried over anhydrous sodium sulfate, filtered and concentrated under reduced pressure to obtain the crude. The crude was purified by column chromatography using 10% MeOH/DCM as an eluent to afford ethyl 4-(2-methylpyridine-4-amido)benzoate. LCMS (ES) m/z=285.2 [M+H]+.

$^1$H NMR (400 MHz, DMSO-$d_6$) δ ppm 1.28-1.31 (m, 3H), 2.48 (s, 3H), 4.25-4.30 (m, 2H), 7.62 (d, J=4.8 Hz, 1H), 7.76 (s, 1H), 7.89-7.97 (m, 4H), 8.61 (d, J=5.2 Hz, 1H), 10.72 (s, 1H), 4-(2-methylpyridine-4-amido)benzoic acid: To a stirred solution of ethyl 4-(2-methylpyridine-4-amido)benzoate (2.50 g, 8.79 mmol, 1.0 eq) in MeOH (20.0 mL), THF (20.0 mL) and Water (15.0 mL) was added LiOH.H2O (0.76 g, 17.6 mmol, 2.0 eq) and the reaction was stirred at rt for 16 h. Reaction was monitored by TLC (5% MeOH/DCM). After this time reaction mixture was concentrated under reduced pressure at rt and the aqueous layer was extracted with EtOAc (2×50 mL). The aqueous layer was then acidified with 5% citric acid (Ph=5), filtered and dried under reduced pressure to get the 4-(2-methylpyridine-4-amido)benzoic acid. LC-MS (ES) (m/z)=257.2 [M+H]+.

$^1$H NMR (400 MHz, DMSO-$d_6$) δ ppm 7.57-7.64 (m, 1H), 7.71 (s, 1H), 7.87-7.95 (m, 4H), 8.63 (d, J=4.8 Hz, 1H), 10.69 (s, 1H), 12.71 (s, 1H).

N—(4-{[(2S)-1-(3-methoxyphenyl)hexan-2-yl]carbamoyl}phenyl)-2-methylpyridine-4-carboxamide: To a solution of (2S)-1-(3-methoxyphenyl)hexan-2-amine (1.0 g, 4.82 mmol, 1.0 eq), 4-(2-methylpyridine-4-amido)benzoic acid (1.48 g, 5.79 mmol, 1.2 eq) in DCM (20.0 mL) was added Triethylamine (2.69 mL, 19.3 mmol, 4 eq), stirred for 5 min and then T3P (50 wt. % in EtOAc) (2.15 ml, 7.24 mmol, 1.5 eq) was added at 0° C. and stirred for another 30 min. Progress of the reaction was monitored by TLC (5% MeOH/DCM). After the completion of the reaction, the reaction mixture was quenched with water (20.0 mL) and extracted with DCM (2×25 mL). The combined organic extracts were washed with water (15 mL) and brine solution (15 mL) and dried over anhydrous Na$_2$SO$_4$, concentrated under reduced pressure to obtain the crude compound. The crude was purified by flash column chromatography using 3-5% methanol in DCM as an eluent to yield ethyl (S)—N—(4-((1-(3-methoxyphenyl)hexan-2-yl)carbamoyl)phenyl)-2-methylisonicotinamide. LC-MS (m/z)=446.3 [M+H]+.

$^1$H NMR (400 MHz, DMSO-$d_6$) δ ppm: 0.82 (d, J=6.8 Hz, 3H), 1.13-1.31 (m, 5H), 1.50 (d, J=6.0 Hz, 2H), 2.65 (s, 3H), 2.71-2.81 (m, 2H), 3.67 (s, 3H), 4.08-4.15 (m, 1H), 6.69 (d, J=8.8 Hz, 1H), 6.78 (d, J=6.4 Hz, 2H), 7.13 (t, J=8.0 Hz, 1H), 7.63 (d, J=4.8 Hz, 1H), 7.72 (s, 1H), 7.80 (s, 4H), 8.09 (d, J=8.8 Hz, 1H), 8.62 (d, J=5.2 Hz, 1H), 10.59 (s, 1H).

N-{4-[(3S)-3-butyl-6-methoxy-3,4-dihydroisoquinolin-1-yl]phenyl}-2-methylpyridine-4-carboxamide: To stirred solution of (S)—N—(4-((1-(3-methoxyphenyl)hexan-2-yl)carbamoyl)phenyl)-2-methylisonicotinamide (1.2 g, 2.69 mmol, 1 eq) and 2-chloropyridine (1.02 mL, 10.8 mmol, 4.0 eq) in dichloromethane (25.0 mL) was added trifluoromethanesulfonic anhydride (1.81 mL, 10.8 mmol, 4.0 eq) slowly dropwise at −78° C. After 5 min, the reaction mixture was placed in an ice-water bath and warmed to 0° C. and the resulting solution was allowed to stir at 0° C. After 1.5 h, reaction was quenched with aqueous 1.0 N sodium hydroxide solution (15 mL) to neutralize the trifluoromethanesulfonate salts. Dichloromethane (2×15 mL) was added to dilute the reaction mixture and the layers were separated. The combined organic layer was washed with brine (5 mL), dried over anhydrous sodium sulfate, and was filtered. The volatiles were removed under reduced pressure to give the crude product of (S)—N—(4-(3-butyl-6-methoxy-3,4-dihydroisoquinolin-1-yl)phenyl)-2-methylisonicotinamide. LCMS (ES) m/z=428.3 [M+H]+.

N-{4-[(1S,3S)-3-butyl-6-methoxy-1,2,3,4-tetrahydroisoquinolin-1-yl]phenyl}-2-methylpyridine-4-carboxamide: To a solution of N-{4-[(3S)-3-butyl-6-methoxy-3,4-dihydroisoquinolin-1-yl]phenyl}-2-methylpyridine-4-carboxamide (260 mg, 0.608 mmol, 1 eq) in methanol (10 mL) was added sodium borohydride (69.0 mg, 1.82 mmol, 3 eq) portion wise at 0° C. The suspension was stirred at room temperature for 1 h. Progress of the reaction was monitored by TLC (5% methanol in DCM). After this time, the reaction mixture was concentrated and obtained crude was diluted with EtOAc (20 mL) and water (10 mL). Organic layer was separated, washed with brine solution (10 mL), dried over anhydrous sodium sulfate, filtered and concentrated under reduced pressure to obtain the crude product. The obtained crude product was purified by preparative TLC using 5% methanol in DCM. Product fraction was collected and concentrated under reduced pressure to get tert-butyl N-{biicyclo[1.1.1]pentan-1-yl}—N—({4-[(1S,3S)-3-butyl-6-methoxy-1,2,3,4-tetrahydroisoquinolin-1-yl]phenyl}methyl)carbamate.

N-{4-[(1S,3S)-3-butyl-6-methoxy-2-[3-(trimethylsilyl)prop-2-ynoyl]-1,2,3,4-tetrahydroisoquinolin-1-yl]phenyl}-2-methylpyridine-4-carboxamide: First step: To a solution of 3-(trimethylsilyl)prop-2-ynoic acid (20 mg, 0.0141 mmol, 1.0 eq) in DMF (0.00043 mL, 0.00562 mmol, 0.04 eq) was added oxalyl chloride (0.013 mL, 0.155 mmol, 1.1 eq) at room temperature and stirred for 30 minutes. After this time, reaction mixture was concentrated under reduced pressure to get 3-(trimethylsilyl)prop-2-ynoyl chloride. This acid chloride was carried forward to the next step without any further purification.

Second step: To a solution of N—(4-((1S,3S)-3-butyl-6-methoxy-1,2,3,4-tetrahydroisoquinolin-1-yl)phenyl)-2-methylisonicotinamide (40 mg, 0.093 mmol, 1 eq) in acetonitrile (4.0 mL) was added sodium bicarbonate (59.4 mg, 0.698 mmol, 7.5 eq) at 0° C. After stirring for 5 minutes, a solution of 3-(trimethylsilyl)prop-2-ynoyl chloride (22.4 mg, 0.140 mmol, 1.5 eq) in acetonitrile (2.0 mL) was added to the above reaction mass at 0° C. The resulting mixture was stirred at 0° C. for 15 min. Progress of the reaction was monitored by TLC (50% ethyl acetate in n-hexane). After this time, reaction mass was diluted with EtOAc (20 mL) and water (10 mL). Organic layer was separated, washed with brine solution (7.0 mL), dried over anhydrous sodium sulfate, filtered and concentrated under reduced pressure to obtain the crude of N—(4-((1S,3S)-3-butyl-6-methoxy-2-(3-(trimethylsilyl)propioloyl)-1,2,3,4-tetrahydroisoquinolin-1-yl)phenyl)-2-methylisonicotinamide. LCMS (ES) m/z=554.4 [M+H]+.

N-{4-[(1S,3S)-3-butyl-6-methoxy-2-(prop-2-ynoyl)-1,2,3,4-tetrahydroisoquinolin-1-yl]phenyl}-2-methylpyridine-4-carboxamide: To a solution of N—(4-((1S,3S)-3-butyl-6-methoxy-2-(3-(trimethylsilyl)propioloyl)-1,2,3,4-tetrahydroisoquinolin-1-yl)phenyl)-2-methylisonicotinamide (0.14 g, 0.253 mmol, 1 eq) in dichloromethane (10 mL) and methanol (2 mL) was added potassium carbonate (0.213 g, 1.52 mmol, 6.0 eq) at 0° C. This reaction mixture was stirred at 0° C. for 30 minutes. Progress of the reaction was monitored by LC-MS. After completion of starting material, the reaction mixture was diluted with Dichloromethane (2×10.0 mL) and separated with water (10.0 mL) and the combined organic layer was dried over anhydrous sodium sulfate, filtered and concentrated under reduced pressure to obtain the crude compound. The obtained crude product was purified by prep HPLC purification method by using following analytical condition to afford N—(4-((1S,3S)-3-butyl-6-methoxy-2-propioloyl-1,2,3,4-tetrahydroisoquinolin-1-yl)phenyl)-2-methylisonicotinamide. Analytical Conditions: Column: X-BridgeC-18 (250 mm×4.6 mm×5 μm); mobile phase (A): 0.1% ammonia in water; mobile phase (B): acetonitrile; Flow rate: 1.0 mL/min; gradient B: 0/10, 12/60, 22/95, 25/95, 27/10, 30/10. LCMS (ES) m/z=482.5 [M+H]+.

$^1$H NMR (400 MHz, DMSO-$d_6$) δ ppm: 0.81 (t, J=6.8 Hz, 3H), 1.22 (bs, 5H), 1.50 (bs, 2H), 2.53 (s, 3H), 2.79 (s, 1H), 3.12 (s, 1H), 3.70 (d, J=5.6 Hz, 2H), 4.30 (s, 1H), 4.59 (s, 1H), 6.03 (s, 1H), 6.28 (s, 1H), 6.80 (t, J=8.0 Hz, 1H), 7.21 (t, J=8.4 Hz, 2H), 7.41 (d, J=7.6 Hz, 1H), 7.57 (d, J=8.4 Hz, 2H), 7.64 (d, J=8.8 Hz, 2H), 8.58 (d, J=4.8 Hz, 1H), 10.32 (s, 1H).

Compounds shown in Table 1, can be or were, synthesized according to the procedures described above using the appropriate reagents and starting materials. Select data are shown in Table 2.

TABLE 2

| No. | MS [M+ H]+ | No. | MS [M+ H]+ | No. | MS [M+ H]+ |
|---|---|---|---|---|---|
| 1 | 385.3 | 3 | 402 | 5 | 413.3 |
| 2 | 402 | 4 | 389 | 6 | 388.1 |
| 7 | 388.1 | 34 | 418.89 | 76 | 353.3 |
| 8 | 348.3 | 35 | 358.83 | 93 | 434.95 |
| 9 | 324 | 36 | 428.93 | 94 | 440 |
| 10 | 324.3 | 38 | 525.8 | 95 | 482 |
| 11 | 390 | 39 | 354.6 | 96 | 458 |
| 12 | 365 | 40 | 432.83 | 97 | 399 |
| 13 | 469 | 42 | 408.87 | 98 | 477 |
| 14 | 448 | 48 | 363.4 | 99 | 610 |
| 15 | 445 | 49 | 349.4 | 100 | 541 |
| 18 | 481.3 | 50 | 352.4 | 101 | 498 |
| 27 | 521.5 | 54 | 369 | 102 | 445 |
| 28 | 497 | 55 | 429.5 | | |
| 33 | 415.93 | 57 | 349 | | |

BIOLOGICAL EXAMPLES

Example 1: Cell Proliferation (Alamar Blue) Assay

A cell viability assay was performed to assess the potency of the compounds in human cancer cell lines 786-O (renal cell carcinoma), SJSA-1 (osteosarcoma), and/or A431 (epidermoid carcinoma). Additional cell lines, such as pancreatic cancer cell lines (e.g., Panc 02.13, BxPC-3, Panc 12, Panc 02.03, Panc 6.03, PSN-1, HPAC, and Capan-1), prostate cancer cell lines (e.g., PC-3, DU145, 22Rv1, NCI-H660, BPH1, LNCaP, BM-1604, and MDA PCa 2b), etc., can be tested in a similar method.

Cells (SJSA-1, 786-O and/or A431) were seeded (5000 cells/100 μL/well) in 96-well tissue culture plate and incubated at 37° C./5% $CO_2$ for 16-24 hours. The cells were then treated with compounds (25 μL of 5×). The compound concentrations were 10-0.0005 μM prepared in 3-fold serial dilutions with final DMSO concentration of 1%. The plates were then incubated for 24h at 37° C./5% $CO_2$ in a moist environment. Then Alamar Blue™ reagent (final concentration 1×—12.5 μL) was added to each well and incubated for 1.5 hours at 37° C./5% $CO_2$. The plates were read on fluorescence reader at 540 nm excitation and 590 nm emission wavelengths. The $IC_{50}$ values were subsequently determined using a sigmoidal dose-response curve (variable slope) in GraphPad Prism® 5 software. Table 3 shows cell proliferation data for exemplary compounds as described herein.

TABLE 3

| | $IC_{50}$ (μM) | | |
|---|---|---|---|
| No. | 786-O | SJSA-1 | A431 |
| 1 | 2 | 2.8 | — |
| 2 | 0.742 | 0.855 | 8.7 |
| 3 | 0.512 | 0.736 | >10 |
| 4 | 0.588 | 1 | — |
| 5 | 0.212 | 0.382 | — |
| 6 | 3 | 3.2 | >10 |
| 7 | 0.137 | 0.22 | 7.8 |
| 8 | 0.181 | 0.183 | 7.9 |
| 9 | 0.223 | 0.436 | 4.9 |
| 10 | 0.164 | 0.278 | 8.6 |
| 11 | 0.016 | 0.018 | >10 |
| 12 | 0.014 | 0.025 | 3.5 |
| 13 | 0.002 | 0.005 | 3.6 |
| 14 | 0.024 | 0.07 | 7.6 |
| 15 | 0.010 | 0.018 | 3.5 |
| 18 | 0.004 | 0.008 | 8.9 |
| 27 | 0.004 | 0.006 | 8.4 |
| 28 | 0.004 | 0.016 | 2.9 |
| 33 | 0.2591 | — | — |
| 34 | 0.5917 | — | — |
| 35 | — | 2.56 | — |
| 38 | 0.005 | 0.010 | 10 |
| 39 | 0.158 | 0.170 | >10 |
| 44 | 0.592 | 0.599 | — |
| 45 | 5.891 | >3 | — |
| 46 | — | 2.56 | — |
| 47 | 0.259 | 0.329 | — |
| 48 | 0.053 | 0.050 | 5 |
| 49 | 0.023 | 0.040 | 6.6 |
| 50 | 0.065 | 0.101 | >10 |
| 54 | 0.743 | 0.659 | 5.8 |
| 55 | 0.027 | 0.032 | 2.3 |
| 57 | 0.023 | 0.040 | 6.6 |
| 76 | 0.187 | 0.623 | >10 |
| 94 | 0.108 | 0.047 | >10 |
| 95 | 0.037 | 0.2 | >10 |
| 96 | 0.163 | 0.368 | >10 |
| 97 | 0.026 | 0.068 | >10 |
| 98 | 0.024 | 0.053 | 8.92 |
| 99 | 0.002 | 0.002 | 2.77 |
| 100 | 0.013 | 0.021 | 4.06 |
| 101 | 0.008 | 0.0115 | 6.87 |
| 102 | 0.021 | 0.021 | 6.13 |

Selected compounds were also assayed (counter-screened) in a human lung cancer cell line, A549, a less sensitive cell line to GPX4 inhibitors, as a control to assess differential activity. Cells at a density of 800-2,000 cells/well were seeded in 96-well plates and incubated at 37° C. overnight. A series of nine different concentrations of compound stocks (500×) were created by 3-fold serial dilution in DMSO. These compounds were further diluted in culture media and then added to cells so that the final DMSO concentration was equal to 0.25% or less. After 96 hours of incubation, 50 μL of CellTiter Glo reagent (Promega) was added to each well and luminescence was measured after 10 minutes using EnVision (PerkinElmer). RSL3 (a prototype GPX4 inhibitor, also known as RSL-3) was used as a reference compound titrated from top concentration of up to 30 μM. All compounds were tested initially from 3 μM as the top concentration in duplicates (range of 4.6 nM-30 μM). The top concentration was then adjusted to higher (from up to 1000 μM) or lower for compounds that showed potency out of the initial range. Luminescence from cells treated with DMSO alone was set as Max and % of inhibition was calculated as follows: Inhibition %=(Max−Sample value)/Max*100. Data was analyzed using XL-fit software (ID Business Solutions Ltd.). $IC_{50}$, relative $IC_{50}$, or % of top inhibition was calculated. Data shown in Table 4.

TABLE 4

| | $IC_{50}$ (μM) | |
|---|---|---|
| No | A549 | KP4 |
| 40 | 6.238 (RSL3 3.078) | 0.019 (RSL3 0.002) |
| 41 | 1.315 (RSL3 3.078) | 0.042 (RSL3 0.002) |
| 42 | 5.05 (RSL3 3.078) | 0.0618 (RSL3 0.002) |
| 43 | 10.3 (RSL3 3.078) | 0.525 (RSL3 0.003) |
| 44 | 6.575 (RSL3 2.735) | — |
| 45 | 4.742 (RSL3 2.735) | — |
| 46 | 3.825 (RSL3 3.667) | — |
| 47 | 6.575 (RSL3 2.735) | — |

Example 2: GPX4 Inhibition Assay

Table 5 shows that compounds provided herein are GPX4 inhibitors. Studies have shown that lipophilic antioxidants, such as Ferrostatin, can rescue cells from GPX4 inhibition-induced ferroptosis. For instance, mesenchymal state GPX4-knockout cells can survive in the presence of Ferrostatin, however, when the supply of Ferrostatin is terminated, these cells undergo ferroptosis (see, e.g., Viswanathan et al., Nature 547:453-7, 2017). It has also been experimentally determined that that GPX4i can be rescued by blocking other components of the ferroptosis pathways, such as lipid ROS scavengers (Ferrostatin, Liproxstatin), lipoxygenase inhibitors, iron chelators and caspase inhibitors, which an apoptotic inhibitor does not rescue. These findings are suggestive of non-apoptotic, iron-dependent, oxidative cell death (i.e., ferroptosis). Accordingly, the ability of a molecule to induce ferroptotic cancer cell death, and that such ability is admonished by the addition of Ferrostatin, is clear indication that the molecule is an GPX4 inhibitor. The data in Table 5 shows that compounds provided herein lost inhibitory activity in the presence of Ferrostatin and are thus effective GPX4 inhibitors.

TABLE 5

| | 786-O ($IC_{50}$, μM) | | SJSA-1 ($IC_{50}$, μM) | |
|---|---|---|---|---|
| Compound No. | Without Ferrostatin | 2 μM Ferrostatin | Without Ferrostatin | 2 μM Ferrostatin |
| 4 | 0.588 | 5.731 | 1 | 3.563 |
| 5 | 0.212 | >10.00 | 0.382 | >10.00 |
| 8 | 0.181 | >10.00 | 0.183 | >10.00 |
| 9 | 0.223 | >10.00 | 0.436 | 3.744 |

Example 3: Method and Results of Western Blot—Gel Mobility Shift of GPX4

A mobility shift of GPX4 Western blot assay was established to assess target engagement directly in cell-based assay after incubation with compounds and in tumors from mice treated with compounds. Mobility shift can be used as a pharmacodynamic marker for GPX4 irreversible inhibitors. For cell-based assay, cells that are sensitive to GPX4 inhibitors (e.g. MiaPaCa-2) were seeded in 10 cm (2-8×10⁶ cells) and grown overnight. Cell seeding number can be adjusted proportionally based on the surface area if smaller dishes are used. Next day, cells were treated with DMSO and various compounds at indicated concentrations for a period of time (e.g. 0.5, 1, 2, 4, 6, or up to 72 hours). Cells were then lysed in 0.3-0.5 mL of RIPA buffer (Sigma) supplemented with protease inhibitors (Roche) and phosphatase inhibitors (Sigma). Lysates were assayed for protein concentration using BCA kit (Pierce). Normalized amount of lysates (20-40 μg protein/lane) were run on 4-12% or 12% NuPage gel (Life Technologies) and the proteins were transferred to the polyvinylidene fluoride (PVDF) or nitrocellulose membrane using iBlot Transfer Stack (Life Technologies). The membranes were probed with primary antibodies shown in Table 6 at 4° C. overnight after blocking with 1×TBST containing 5% non-fat milk for one hour at room temperature. Similar antibodies from other vendors could also be used in Western blot analysis. After washing 5 times with 1×TBS containing 0.1% Tween20, the membranes were probed with a second application of antibody (e.g. Anti-mouse-HRP, Anti-rabbit-HRP, Anti-Goat-HRP, Anti-mouse IgG Dylight 800 conjugate or Anti-rabbit IgG DyLight 680 conjugate) (1:10000; Cell signaling or similar IR to the antibodies from different vendors) at room temperature for one hour. After washing 5 times, the membranes were scanned using ImageQuant-LAS-4010 (chemiluminiscence) (GE Healthcare) if HRP-conjugated secondary antibodies were used or Odyssey® Imaging System (Licor Biosciences) if infrared conjugated secondary antibodies were used.

TABLE 6

Primary antibodies used for Western blot analysis

| Antibody Name | Vendor | Cat No. | Species | MW | Dilution |
|---|---|---|---|---|---|
| β-Actin (loading control) | Sigma | A5441 | Mouse | 43 kd | 1:10000 |
| Vinculin (loading control) | Sigma | V9131 | Mouse | 116 KD | 1:2000 |
| GPX4 | Abcam | ab125066 | Rabbit | 22 kd | 1:1000 |
| GPX4 | Abcam | ab41787 | Rabbit | 22 kd | 1:1000 |

Compound 40 was evaluated in cell-based Western blot analysis of GPX4 and the result is shown in FIG. 1. In DMSO treated sample, GPX4 ran as doublet—the major lower free or unbound GPX4 band and the minor upper band (likely glutathione-bound GPX4 (Cozza et al., Free Radical Biology and Medicine, Vol 112, pages 1-11, 2017)). The amount of upper band can be reduced if samples were boiled in excess amount of reducing agent dithiothreitol (DTT). GPX4 in SDS-PAGE reducing gel moved slower (appear as a larger molecular weight protein) when treated with covalent, irreversible inhibitors of GPX4 (e.g. RSL-3 and ML162) but not reversible inhibitors (e.g. ML210), presumably due to addition of the covalently linked small molecule to GPX4. Unlike glutathione-bound GPX4, the irreversible inhibitor bound GPX4 upper band cannot be reduced by excess amount of DTT. Further, distance of the GPX4 mobility shift is correlated with the molecular weight of the irreversible GPX4 inhibitor-shifted distance is bigger with larger irreversible inhibitors. Thus, this simple mobility shift of GPX4 Western blot can be used to conveniently assess direct target engagement in vitro, in cells and in tumors by irreversible inhibitors. As shown in FIG. 1, treatment of MiaPaCa-2 cells with Compound 40 resulted in dose-dependent mobility shift of GPX4 from the lower unbound to upper bound bands. At concentrations greater than 50 nM, Compound 40 converted nearly all GPX4 to the upper bands.

Example 4: Kinact/Ki Determination for GPX4 Inhibitors

The following example shows that target engagement with GPX4 is very rapid.

Day 1— seed cells: Cells were seeded with $5 \times 10^5$ Calu6 cells/well into 5×6-well plates.

Day 2— treat cells with Cmpd, prepare samples for gels: Cells were treated with 1, 0.75, 0.5, 0.25 and 0.1 μM inhibitor+2 μM Ferrostatin-1 for 0, 10, 20, 30, 45, 60 minutes. 10 μL of 1000×DMSO stock solutions were prepared for each compound dilution (1, 0.75, 0.5, 0.25, 0.1 mM). Complete cell culture media (EMEM+10% FBS) was prepared with 2 μM Ferrostatin-1 final conc. Drug solutions were prepared by adding 1000× inhibitors to Ferrostatin-1-supplemented media at 1× final concentration (1, 0.75, 0.5, 0.25, 0.1 μM) plus DMSO for use as a negative control.

Cell lysis buffer was prepared by diluting 5× cell lysis buffer (Cell Signaling Technology #9803) and 100× protease/phosphatase inhibitor cocktail (Cell Signaling Technology #5872) to 1× with deionized water.

Cells were treated with drug solutions in 1-hour time course. One concentration of drug added to each 6-well plate at t=60, 45, 30, 20, 10, 0 minutes. Media was aspirated from cells in 1 well of each 6-well plate and add 1 mL of media w/drug+Ferrostatin (t=60 min). Cells were returned to incubator between time points. Media was aspirated and drug added to cells at each subsequent time point. At t=10 min DMSO was added negative control to additional well.

At t=0 media was aspirated from cells, cells were washed with ice cold PBS and aspirated, 75 μL of 1× cell lysis buffer was added per well, bottom of plates scraped with cell scraper, and lysates transferred to 1.5 mL Eppendorf tubes at store at −20° C.

SDS-PAGE running buffer was prepared (2 L of 1×MES Bolt running buffer (ThermoFisher Scientific #B0002), Store at 4° C. overnight for use the next day).

Day 3— perform BCA assay and run gels: Lysates were thawed on ice, centrifuged at 18,000×g at 4° C. for 10 minutes, and BCA assay was performed on supernatant following manufacturer protocol (ThermoFisher Scientific #23225). 3.6×LDS/BME sample buffer was prepared by mixing Bolt 4×LDS sample buffer (ThermoFisher Scientific #B0008) with 2-mercaptoethanol at a 10:1 ratio. In 96-well PCR plate 19 μL 3.6×LDS/BME sample buffer was added and 50 μL lysate samples. Lysates diluted to 1 mg/mL with 1×LDS/BME, plates heated at 95° C. for 10 min in PCR machine, loaded 15 μL/well (15 μg total lysate) into 12% Bis-Tris Bolt gels, and gels were run at 200V for ~35 minutes (until dye front reaches bottom of gel) with cold 1×MES running buffer. After which time, gels were washed 5 minutes in water, 10 minutes in 20% Ethanol/water, and transferred to membrane with iBlot2 (ThermoFisher Scientific). Membrane was blocked 1h at RT with Licor TBS blocking buffer (Licor #927-60001) and incubated with 1:1000 dilution of anti-GPX4 antibody (Abcam #ab125066) in Licor TBS blocking buffer at 4° C. overnight with gentle rocking.

Day 4— develop blots, quantify gel shift: Membrane was washed with 1×TBST for 30 minutes (change wash buffer 3-4 times), incubated with Licor secondary antibody (Licor #926-68021) 1:40,000 in Licor TBS blocking buffer for 1h at RT with gentle rocking, washed with 1×TBST for 30 minutes, scraped with Licor imager and bands were quantized with Image studio.

Figure 2:
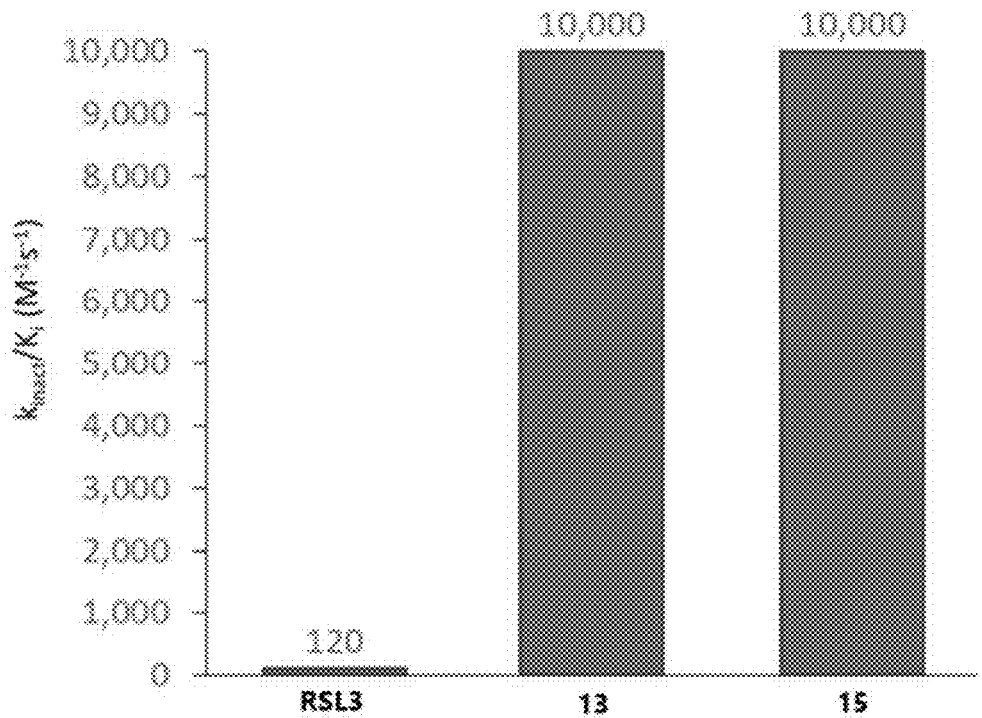
FIG. 2 shows Kinact/Ki data for compounds as described herein.

Kinact/Ki data for RSL3 and Compounds 13 and 15 shown in FIG. 2.

Example 5: Pharmacokinetics Studies

Institutional Animal Ethical Committee (IAEC) of Jubilant Biosys (IAEC/JDC/2019/188R (for Mice) and IAEC/JDC/2019/189R (for Rat) nominated by CPCSEA (Committee for the Purpose of Control and Supervision of Experiments on Animals) approved the mice and rat pharmacokinetic experiments. Male Balb/c mice (~6-8 weeks old with body weight range of 22-25 g) and male SD rats (6-8 weeks old with body weight range of 200-250 g) were procured from Vivo Biotech, Hyderabad, India. Animals were quarantined in Jubilant Biosys Animal House for a period of 7 days with a 12:12 h light: dark cycles, and prior to the study the animals were stratified as per body weight.

Housing: The animals were group housed in standard polycarbonate cages, with stainless steel top grill where pelleted food and drinking water bottle are placed; corn cob was used as bedding material and changed at least twice a week or as required.

Diet ad libitum: Rodent feed manufactured by Altromin Spezialfutter GmbH & Co. KG., ImSeelenkamp20. D-32791 Lage, was provided.

Water ad libitum: Purified water was provided ad libitum to animals in polycarbonate bottles with stainless steel sipper tubes.

A) Procedure for Mice: Intravenous, oral and intraperitoneal pharmacokinetics study was done at doses of 5, 20 and 10 mg/kg respectively at dose volume of 10 mL/Kg for PO and IP while 5 mL/kg for IV route. Sparse sampling was done and at each time point three mice were used for blood sampling (~100 μL) were collected from retro-orbital plexus at 0.083 (Only for IV), 0.25, 0.5, 1, 2, 4, 8, 10 (only for PO) and 24 h. Blood samples collected in tubes containing $K_2$.EDTA as anticoagulant and centrifuged for 5 min at 10,000 rpm in a refrigerated centrifuge (Biofuge, Heraeus, Germany) maintained at 4° C. for plasma separation.

Group I (IV) received test compound intravenously by tail vein at 5 mg/Kg in solution formulation prepared using 30% Kolliphore EL in WFI; dose volume: 5 mL/Kg; strength: 1 mg/mL.

Group II (PO) received test compound by per oral route using oral gavage needle at 20 mg/Kg in solution formulation prepared using 30% Kolliphore EL in WFI; dose volume: 10 mL/Kg; strength: 2 mg/mL.

Group III (IP) received test compound by intraperitoneal route at 10 mg/Kg in solution formulation prepared using 30% Kolliphore EL in WFI; dose volume: 10 mL/Kg; strength: 1 mg/mL.

B) Procedure for rat: Intravenous and oral pharmacokinetics study was done at a dose 2 and 10 mg/kg at dose volume of 2 and 10 mL/Kg. Serial blood sampling was done and at each time point (~200 μL) were collected from retro-orbital plexus at 0.083 (only for IV), 0.25, 0.5, 1, 2, 4, 8, 10 (only for PO) and 24 h. Blood samples collected in tubes containing $K_2$.EDTA as anticoagulant and centrifuged for 5 min at 10,000 rpm in a refrigerated centrifuge (Biofuge, Heraeus, Germany) maintained at 4° C. for plasma separation.

Group I (IV) received test compound intravenously by tail vein at 2 mg/Kg in solution formulation prepared using 30% Kolliphore EL in WFI; dose volume: 2 mL/Kg; strength: 1 mg/mL.

Group II (PO) received test compound using oral gavage needle at 10 mg/Kg (solution formulation prepared using 30% Kolliphore EL in WFI; dose volume: 10 mL/Kg: strength: 1 mg/mL.

Blood concentration-time data of test compound was analyzed by non-compartmental method using Phoenix WinNonlin Version 8.1. Data is shown below in Table 7.

TABLE 7

| Compound | 12 | 28 |
|---|---|---|
| Mouse IV-PK (5 mg/kg) | $T_{1/2}$: 0.5 h, $C_{max}$: 882 ng/mL, AUC: 181 ng * h/mL, CL: 454 mL/min/kg, Vd: 19.5 L/kg. | $T_{1/2}$: 3.5 h, $C_{max}$: 5446 ng/mL, AUC: 1635 ng * h/mL, CL: 49 mL/min/kg, Vd: 14.7 L/kg |
| Rat IV-PK (2 mg/kg): | | $T_{1/2}$: 3.15 h, $C_{max}$: 3529 ng/mL, AUC: 1082 ng * h/mL, CL: 30 mL/min/kg, Vd: 8.2 L/kg |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A compound of Formula I or a tautomer, stereoisomer, mixture of stereoisomers, isotopically enriched analog, or pharmaceutically acceptable salt thereof:

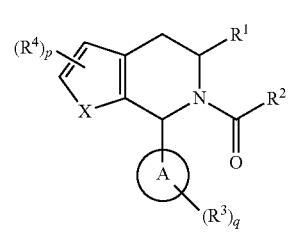

wherein:
ring A is $C_4$-$C_{10}$cycloalkyl, heterocyclyl, aryl, or heteroaryl;
X is—O—, —S—, —$NR^9$—, —$CR^5$=$CR^5$—, or—$CR^5$=N—;
p is 0, 1 or 2;
q is 0, 1, 2 or 3;
$R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —$OR^7$, —C(O)$OR^6$, —C(O)N($R^7$)$_2$, —OC(O)$R^6$, —S(O)$_2R^8$, —S(O)$_2$N($R^7$)$_2$, —S(O)N($R^7$)$_2$, —S(O)$R^8$, —N($R^7$)$_2$, —$NO_2$, —$C_1$-$C_6$alkyl—$OR^7$, or—Si($R^{15}$)$_3$;
$R^2$ is—$C_1$-$C_2$haloalkyl, —$C_2$-$C_3$alkenyl, —$C_2$-$C_3$haloalkenyl, $C_2$alkynyl, or—$CH_2$OS(O)$_2$-phenyl, wherein the $C_1$-$C_2$alkylhalo and—$C_2$-$C_3$alkenylhalo are optionally substituted with one or two —$CH_3$, and the $C_2$alkynyl and phenyl are optionally substituted with one —$CH_3$;

each $R^3$ is independently halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{12})_3$, —$SF_5$, —$C(O)OR^6$, —$C(O)N(R^7)_2$, —$NR^{12}C(O)R^8$, —$NR^{12}C(O)OR^8$, —$OC(O)N(R^7)_2$, —$OC(O)R^8$, —$C(O)R^6$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, -$C_1$-$C_6$alkylheteroaryl, or —$C_2$-$C_6$alkenylheteroaryl of $R^3$ is independently optionally substituted with one to three $R^{10}$;

each $R^4$ is independently halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{15})_3$, —$C(O)OR^6$, —$C(O)N(R^7)_2$, —$NR^{12}C(O)R^8$, —$OC(O)R^8$, —$C(O)R^6$, —$NR^{12}C(O)OR^8$, —$OC(O)N(R^7)_2$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^4$ is independently optionally substituted with one to three $R^{10}$;

each $R^5$ is independently hydrogen, halo, —CN, —OH, —$OR^8$, —$NH_2$, —$NHR^8$, —$N(R^8)_2$, —$S(O)_2R^8$, —$S(O)R^8$, —$S(O)_2N(R^7)_2$, —$S(O)N(R^7)_2$, —$NO_2$, —$Si(R^{15})_3$, —$C(O)OR^6$, —$C(O)N(R^7)_2$, —$NR^{12}C(O)R^8$, —$OC(O)R^8$, —$C(O)R^6$, —$NR^{12}C(O)OR^8$, —$OC(O)N(R^7)_2$, —$OC(O)CHR^8N(R^{12})_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^5$ is independently optionally substituted with one to three $R^{10}$;

each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $R^6$ is independently optionally further substituted with one to three $R^{11}$;

each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl, or two $R^7$, together with the nitrogen atom to which they are attached, form a 4 to 7 membered heterocyclyl; wherein each $R^7$ or ring formed thereby is independently optionally further substituted with one to three $R^{11}$;

each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl; wherein each $R^8$ is independently optionally further substituted with one to three $R^{11}$;

$R^9$ is hydrogen or $C_1$-$C_6$alkyl;

each $R^{10}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{11}$;

each $R^{11}$ is independently halo, —CN, —$OR^{12}$, —$NO_2$, —$N(R^{12})_2$, —$S(O)R^{13}$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl;

each $R^{12}$ is independently hydrogen, $C_1$-$C_6$alkyl or $C_3$-$C_{10}$cycloalkyl;

each $R^{13}$ is independently $C_1$-$C_6$alkyl or $C_3$-$C_{10}$cycloalkyl; and each $R^{15}$ is independently $C_1$-$C_6$alkyl, $C_2$-$C_6$alkenyl, aryl, heteroaryl, —$C_1$-$C_6$alkylaryl, —$C_2$-$C_6$alkenylaryl, —$C_1$-$C_6$alkylheteroaryl, or —$C_2$-$C_6$alkenylheteroaryl; provided that at least one of the following is true:

1) $R^1$ is other than —$C(O)OCH_3$;

2) $R^2$ is —$C_2$alkynyl optionally substituted with one —$CH_3$; or 3) when $R^1$ is —$C(O)OCH_3$ and $R^2$ is —$CH_2Cl$, then the moiety

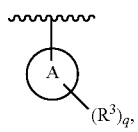

is other than 1,3-benzodioxol-5-yl, 4-nitrophenyl, 4-bromophenyl, cyclohexyl, furyl, or 4-methoxyphenyl.

2. The compound of claim 1, represented by a compound of Formula II, or a tautomer, stereoisomer, mixture of stereoisomers, isotopically enriched analog, or pharmaceutically acceptable salt thereof:

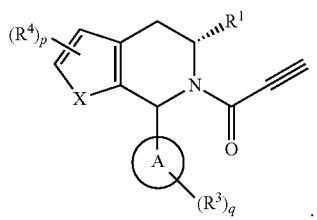

3. The compound of claim 1, represented by a compound of Formula III, or a tautomer, stereoisomer, mixture of stereoisomers, isotopically enriched analog, or pharmaceutically acceptable salt thereof:

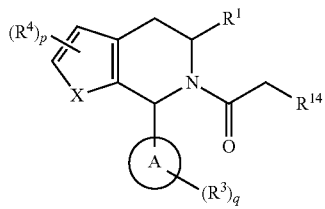

wherein $R^{14}$ is halo.

4. The compound of claim 1, or a tautomer, stereoisomer, mixture of stereoisomers, isotopically enriched analog, or pharmaceutically acceptable salt thereof, wherein ring A is $C_4$-$C_{10}$cycloalkyl.

5. The compound of claim 1, or a tautomer, stereoisomer, mixture of stereoisomers, isotopically enriched analog, or pharmaceutically acceptable salt thereof, wherein ring A is heterocyclyl.

6. The compound of claim 1, or a tautomer, stereoisomer, mixture of stereoisomers, isotopically enriched analog, or pharmaceutically acceptable salt thereof, wherein ring A is aryl.

7. The compound of claim 1, or a tautomer, stereoisomer, mixture of stereoisomers, isotopically enriched analog, or pharmaceutically acceptable salt thereof, wherein ring A is heteroaryl.

8. The compound of claim 1, represented by a compound of Formula VIII, or a tautomer, stereoisomer, mixture of stereoisomers, isotopically enriched analog, or pharmaceutically acceptable salt thereof:

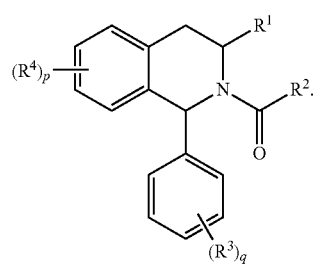

9. The compound of claim 1, wherein $R^1$ is $C_1$-$C_6$alkyl, $C_2$-$C_6$alkenyl, $C_2$-$C_6$alkynyl, $C_1$-$C_6$haloalkyl, $C_3$-$C_{10}$cycloalkyl, —CN, —C(O)OR$^6$, —C(O)N(R$^7$)$_2$, —N(R$^7$)$_2$, —OR$^7$, or —C$_1$-C$_6$alkyl-OR$^7$.

10. The compound of claim 1, or a tautomer, stereoisomer, mixture of stereoisomers, isotopically enriched analog, or pharmaceutically acceptable salt thereof, wherein $R^1$ is —C(O)OR$^6$ or —C(O)N(R$^7$)$_2$.

11. The compound of claim 1, or a tautomer, stereoisomer, mixture of stereoisomers, isotopically enriched analog, or pharmaceutically acceptable salt thereof, wherein $R^1$ is $C_1$-$C_6$alkyl.

12. The compound of claim 1, or a tautomer, stereoisomer, mixture of stereoisomers, isotopically enriched analog, or pharmaceutically acceptable salt thereof, wherein p is 0 or 1.

13. The compound of claim 1, represented by a compound of Formula IX, or a tautomer, stereoisomer, mixture of stereoisomers, isotopically enriched analog, or pharmaceutically acceptable salt thereof:

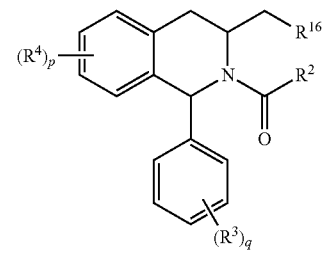

wherein $R^{16}$ is hydrogen or $C_2$-$C_5$alkyl.

14. The compound of claim 1, or a tautomer, stereoisomer, mixture of stereoisomers, isotopically enriched analog, or pharmaceutically acceptable salt thereof, wherein q is 2 or 3.

15. The compound of claim 1, or a tautomer, stereoisomer, mixture of stereoisomers, isotopically enriched analog, or pharmaceutically acceptable salt thereof, wherein each $R^4$ is independently halo, —CN, —OH, —OR$^8$, $C_1$-$C_6$alkyl, $C_2$-$C_6$alkynyl, or $C_3$-$C_{10}$cycloalkyl; wherein each $C_1$-$C_6$alkyl, $C_2$-$C_6$alkynyl, or $C_3$-$C_{10}$cycloalkyl of $R^4$ is independently optionally substituted with one to three $R^{10}$.

16. The compound of claim 1, or a tautomer, stereoisomer, mixture of stereoisomers, isotopically enriched analog, or pharmaceutically acceptable salt thereof, wherein q is 0.

17. A pharmaceutical composition comprising a compound, or a tautomer, stereoisomer, mixture of stereoisomers, isotopically enriched analog, or pharmaceutically acceptable salt thereof, of claim 1, and a pharmaceutically acceptable carrier.

18. The compound of claim 1, or a tautomer, stereoisomer, mixture of stereoisomers, isotopically enriched analog, or pharmaceutically acceptable salt thereof, wherein the compound is:

213
214
-continued
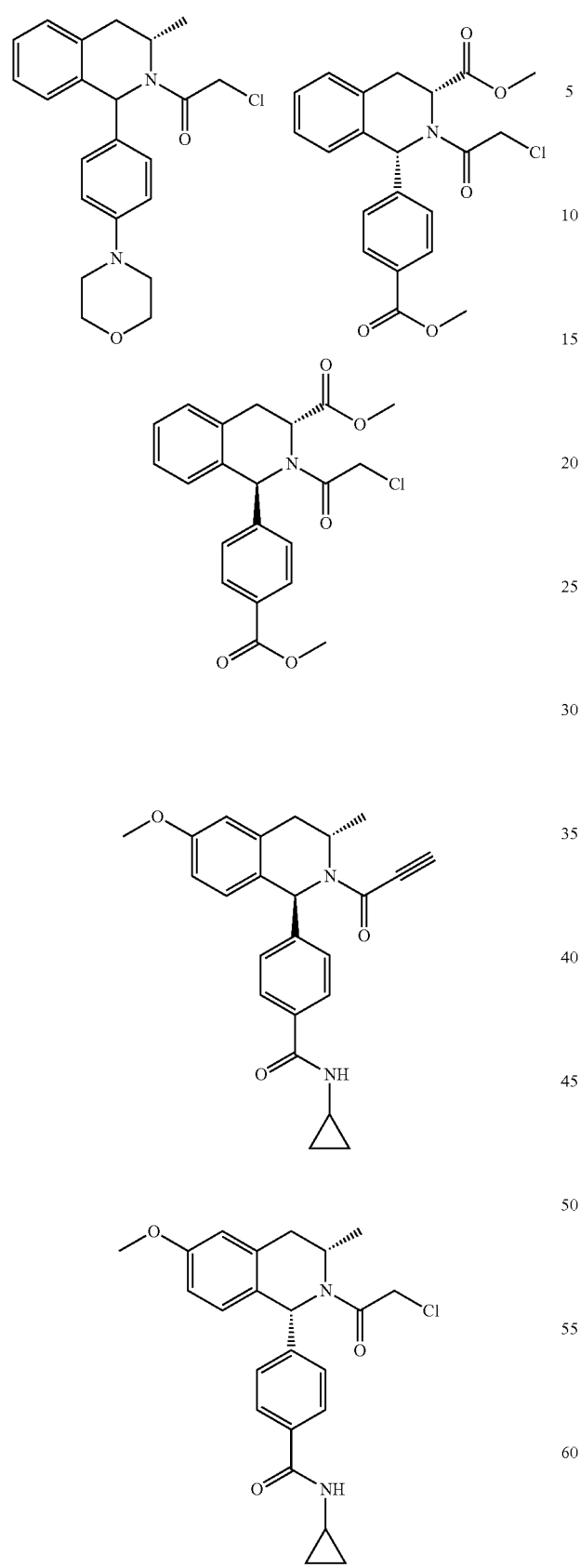
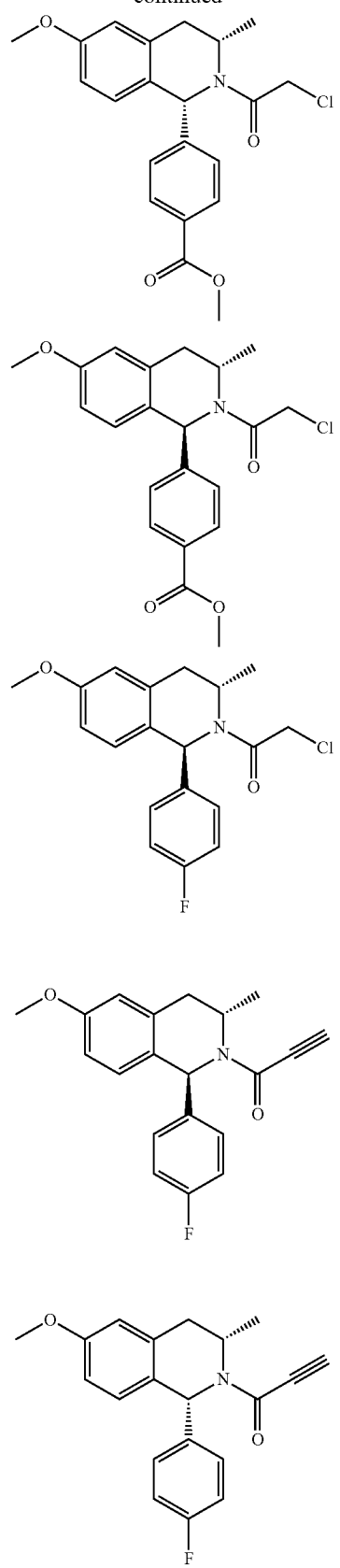

215
-continued
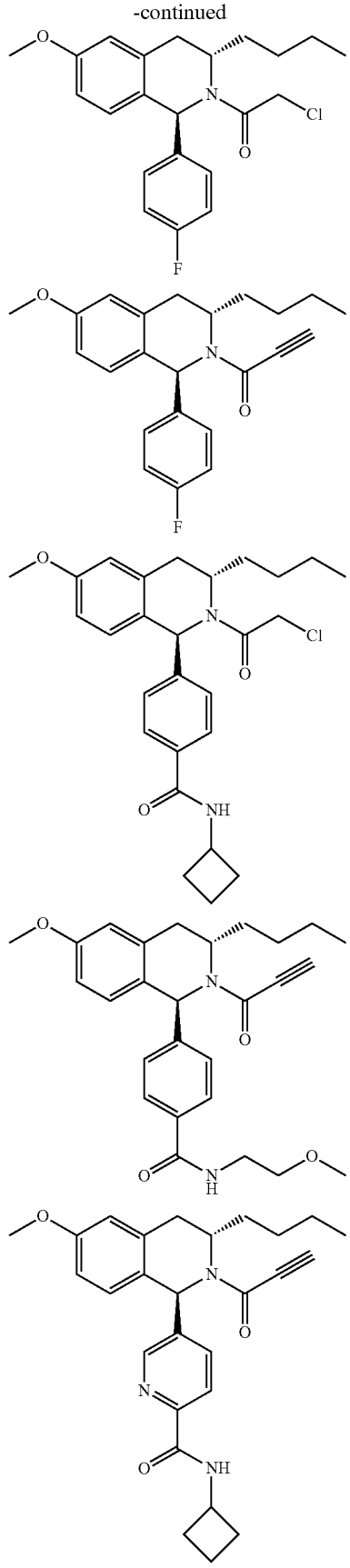
216
-continued
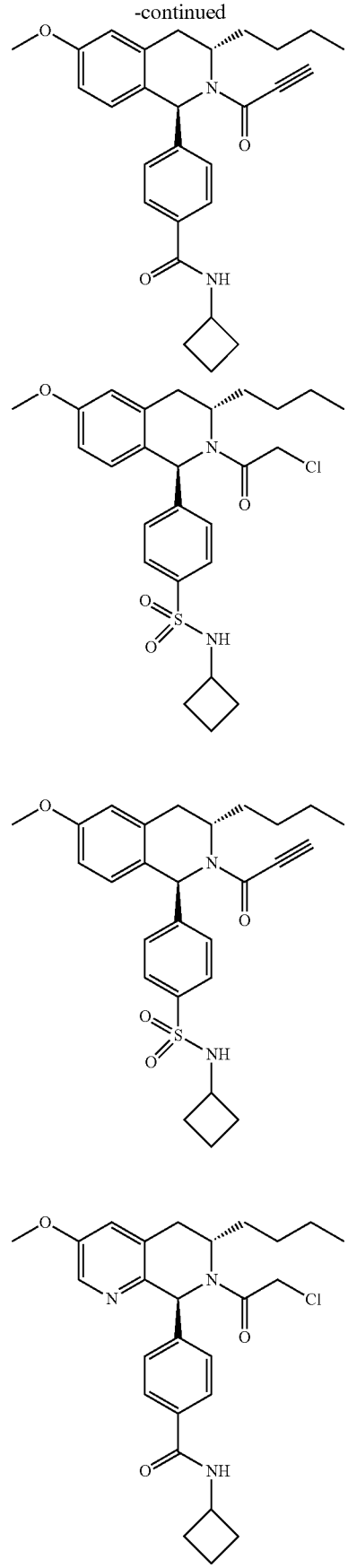

217
-continued
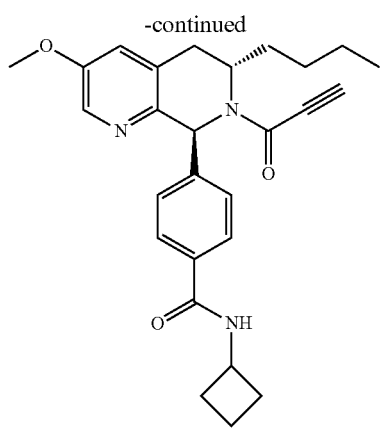
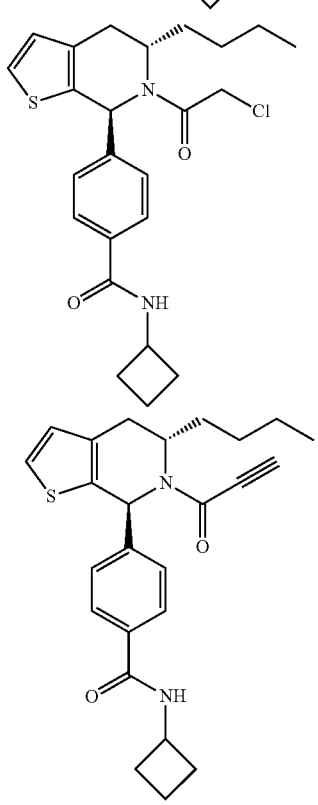
or
19. The compound of claim 1, or a tautomer, stereoisomer, mixture of stereoisomers, isotopically enriched analog, or pharmaceutically acceptable salt thereof, wherein the compound is:
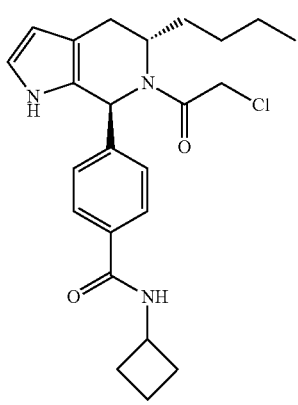
218
-continued
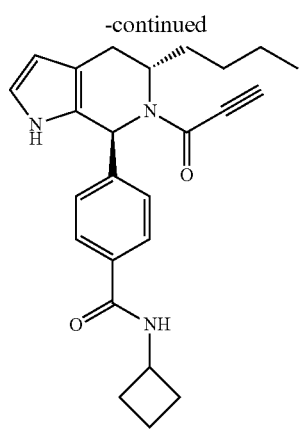
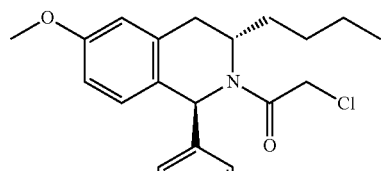
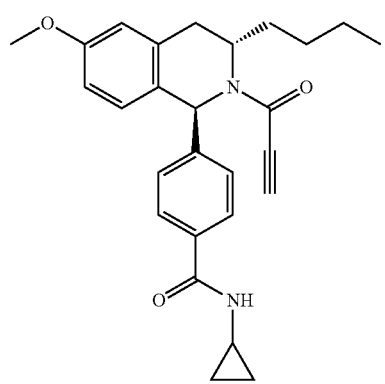
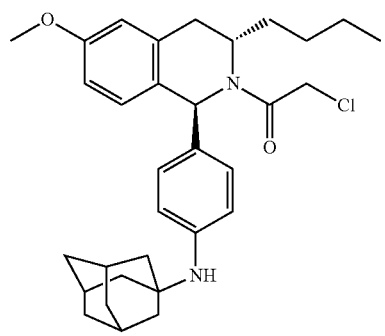

219
-continued
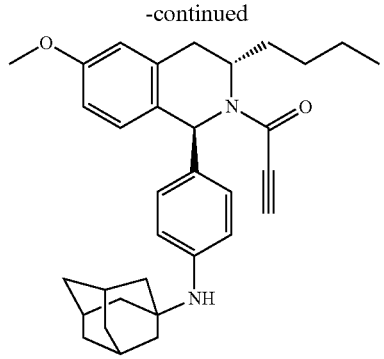
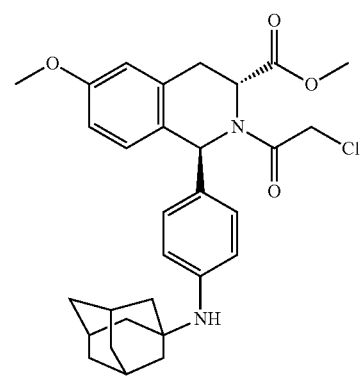
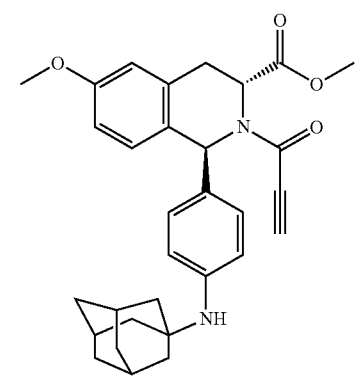
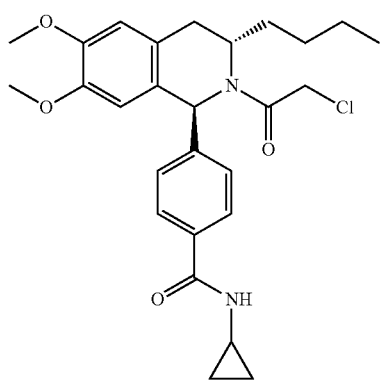
220
-continued
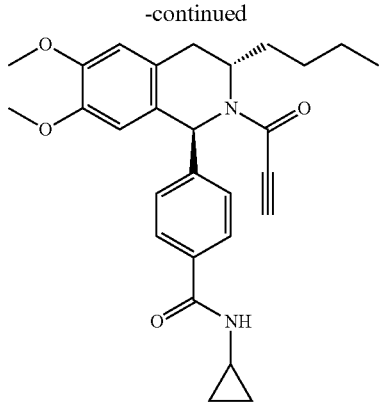
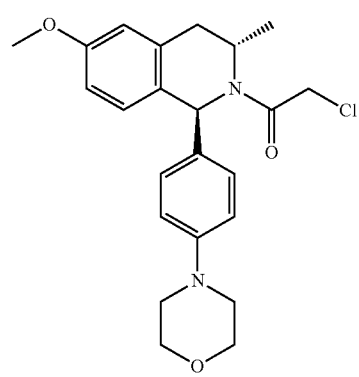
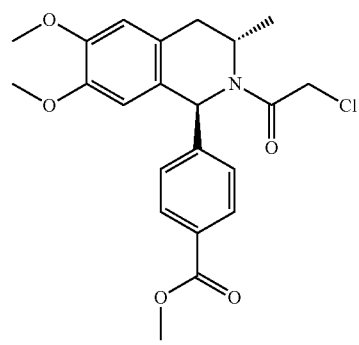
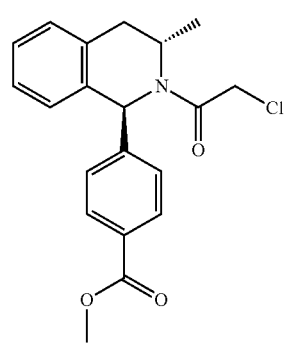
or 221
-continued
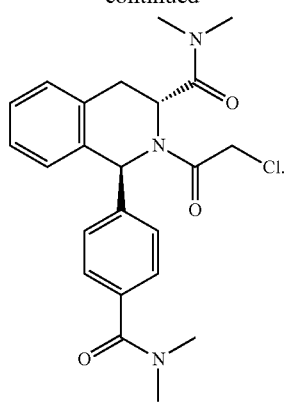
222
-continued
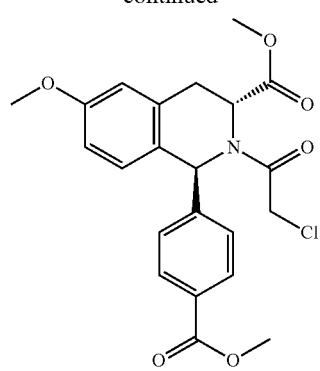
20. The compound of claim 1, or a tautomer, stereoisomer, mixture of stereoisomers, isotopically enriched analog, or pharmaceutically acceptable salt thereof, wherein the compound is:
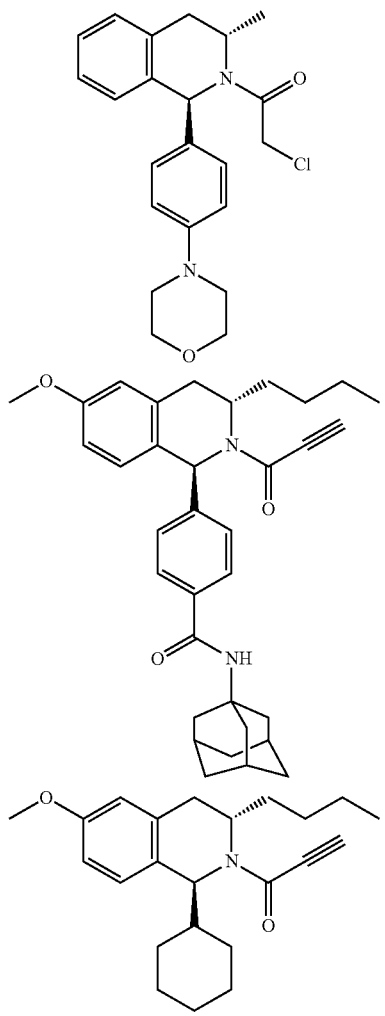
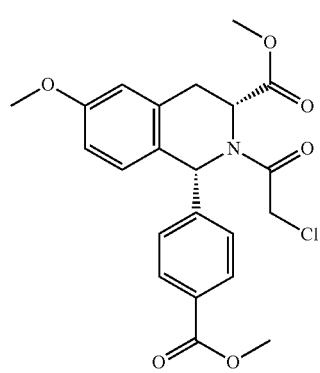
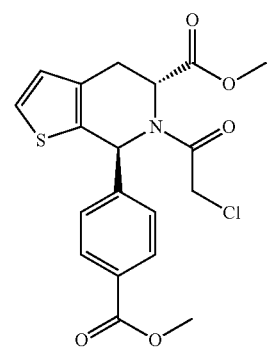
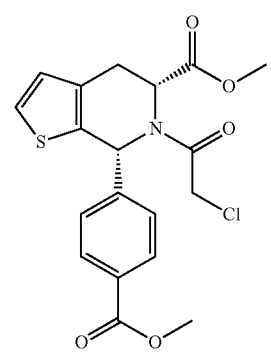

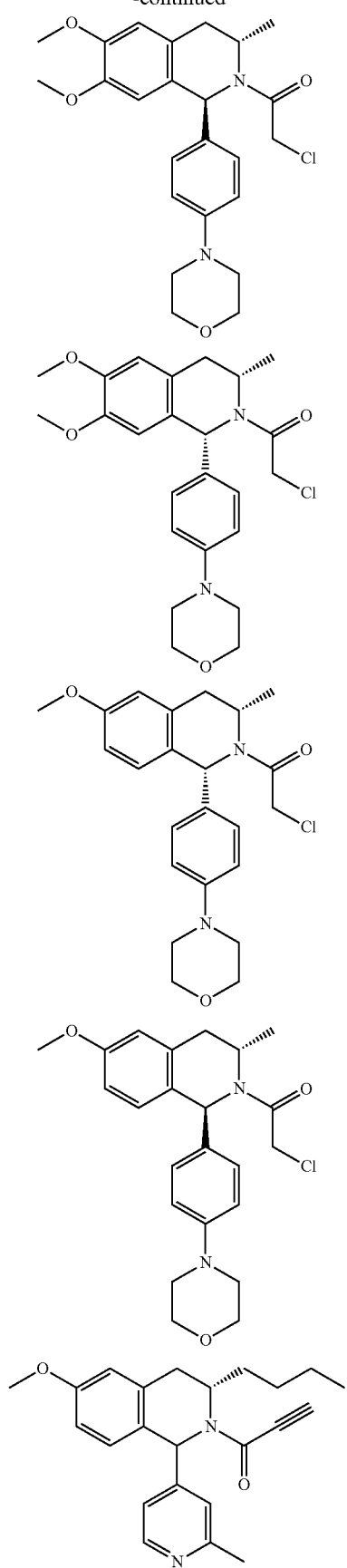
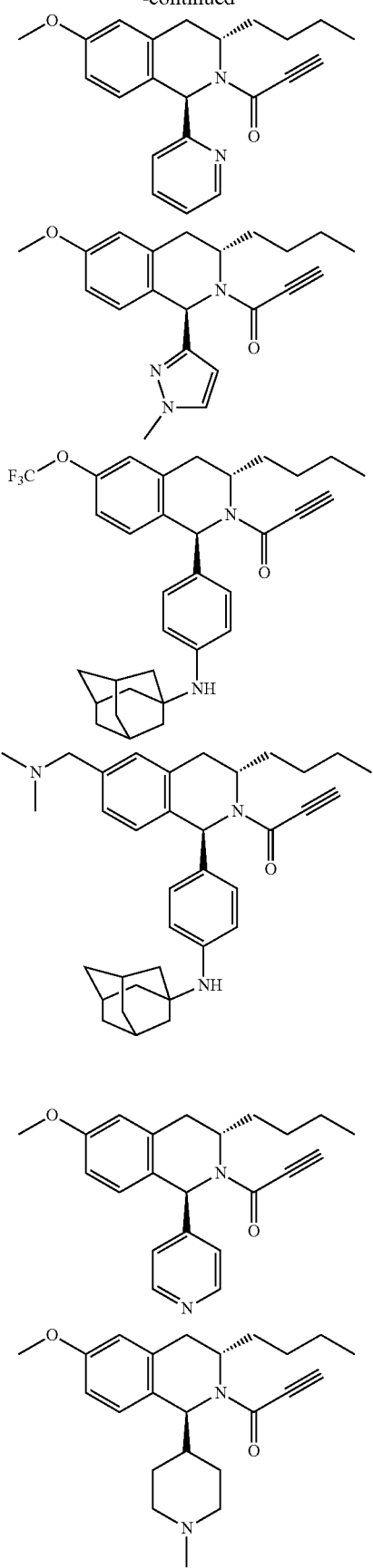

225
-continued
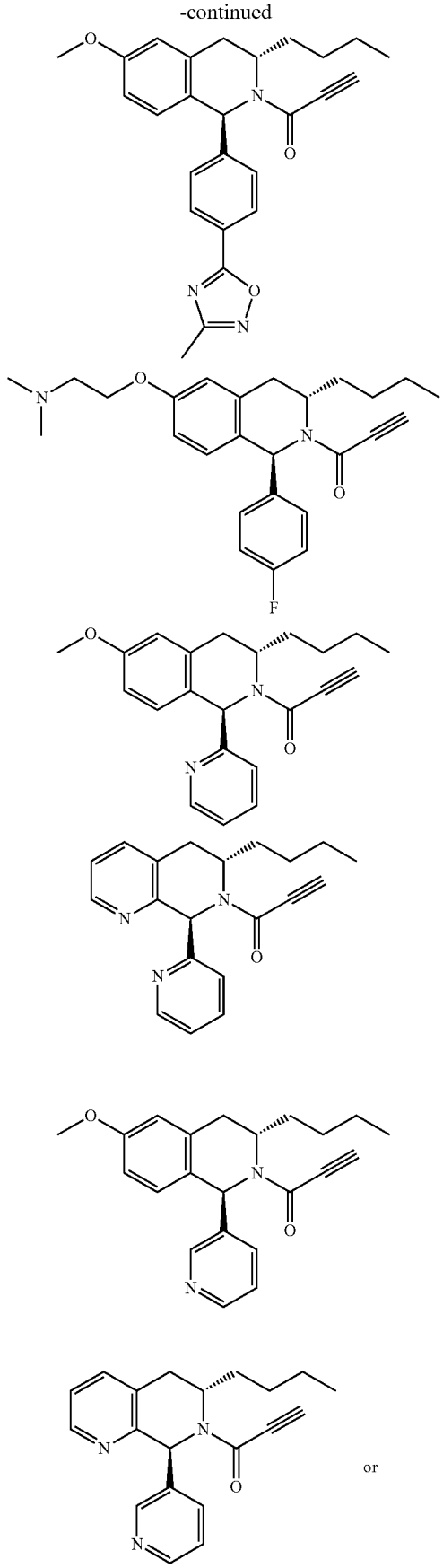
226
-continued
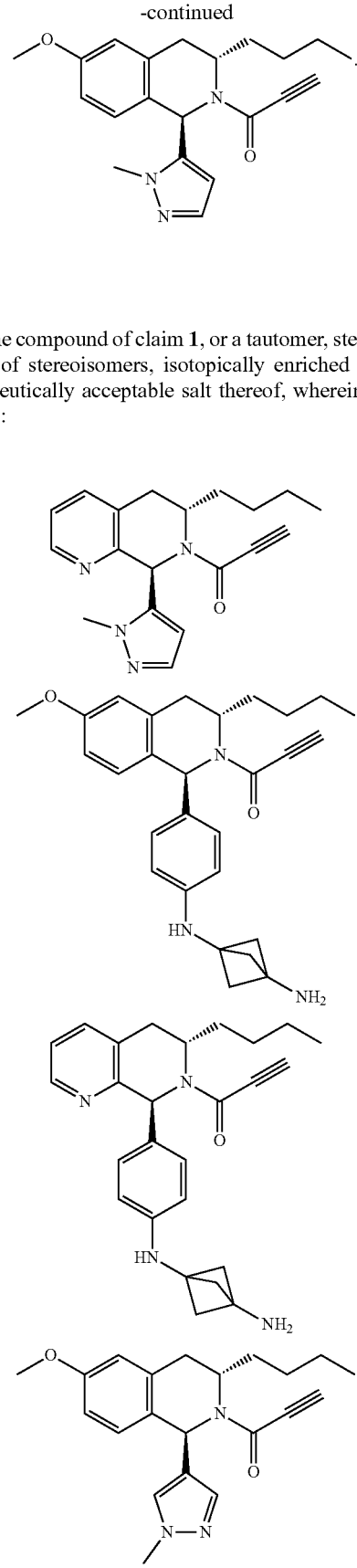
21. The compound of claim 1, or a tautomer, stereoisomer, mixture of stereoisomers, isotopically enriched analog, or pharmaceutically acceptable salt thereof, wherein the compound is:
or 227
-continued
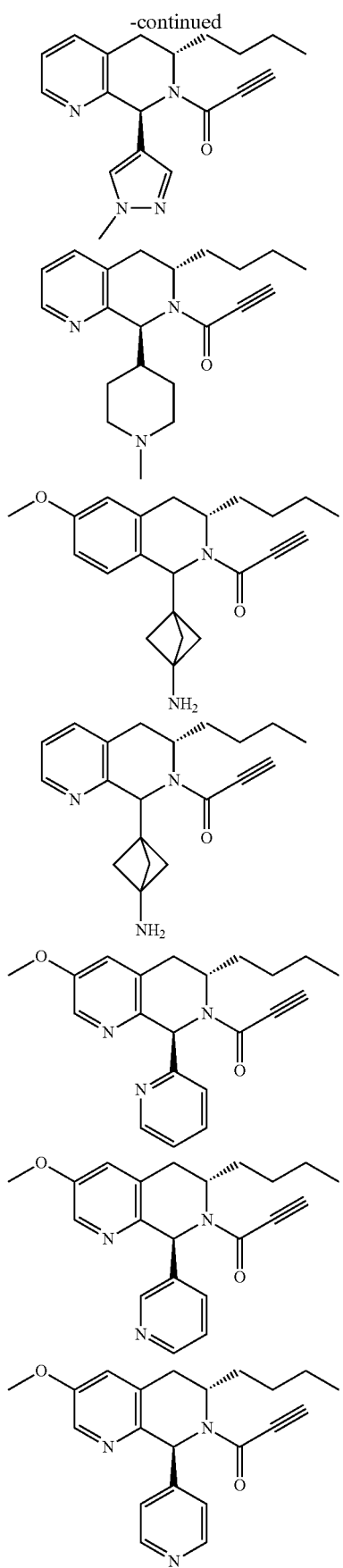
228
-continued
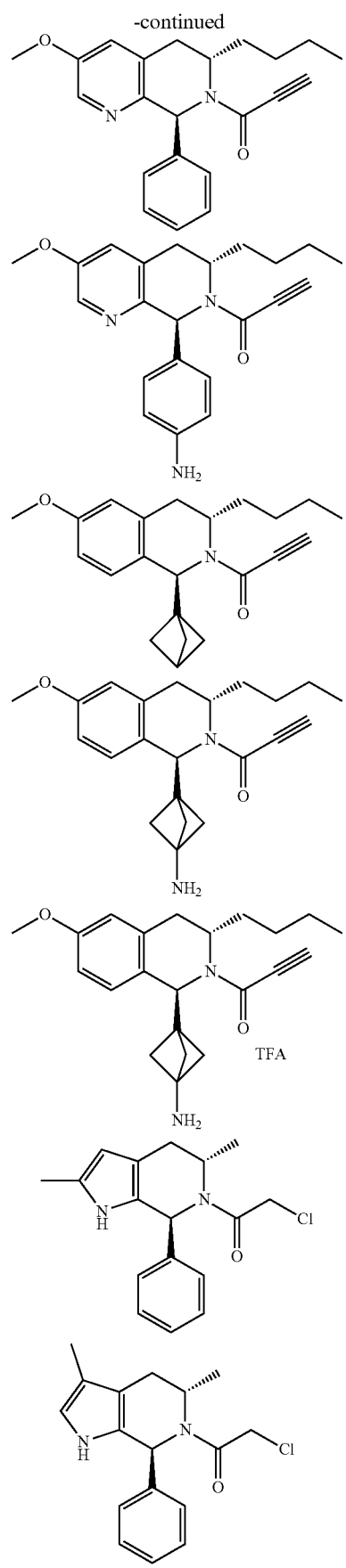

229
-continued
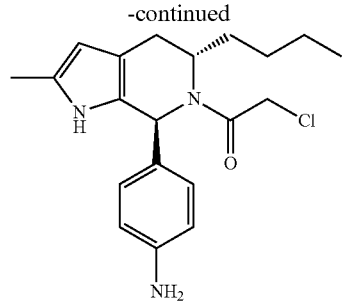
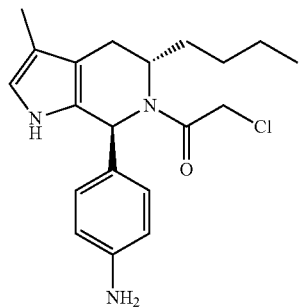
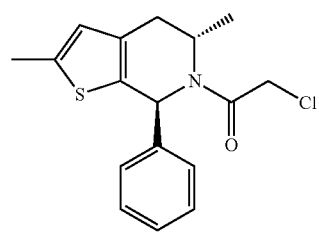
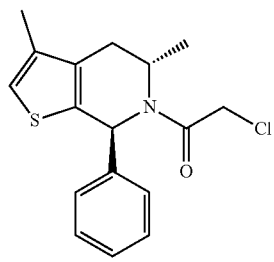
230
-continued
22. The compound of claim 1, or a tautomer, stereoisomer, mixture of stereoisomers, isotopically enriched analog, or pharmaceutically acceptable salt thereof, wherein the compound is:
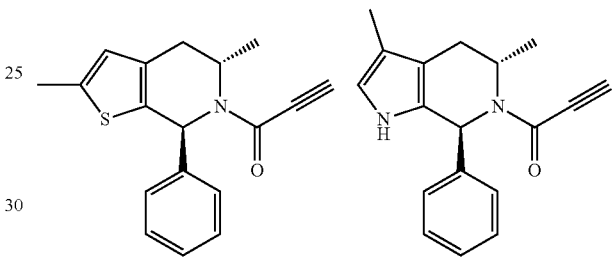
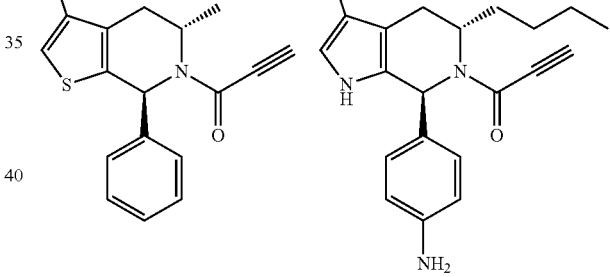
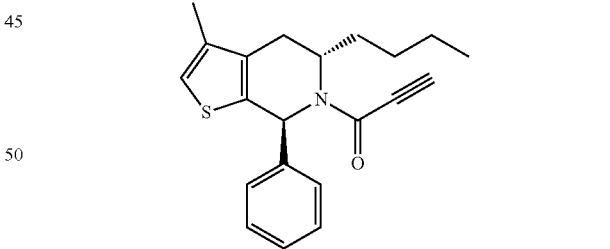
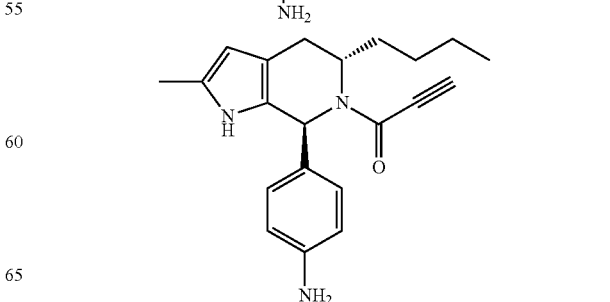

| 231 | 232 |
|---|---|
| 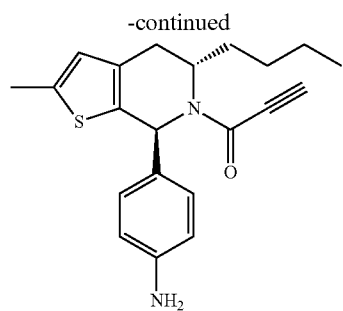 | 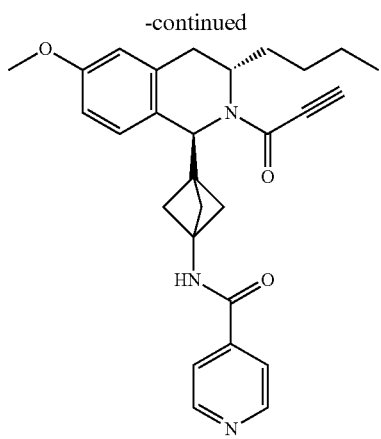 |
| 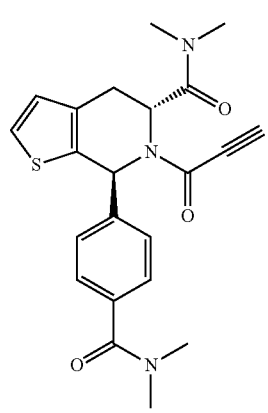 [SMILES: C#CC(=O)N1[C@@H](c2ccc(C(=O)N(C)C)cc2)c2sccc2C[C@@H]1C(=O)N(C)C] | 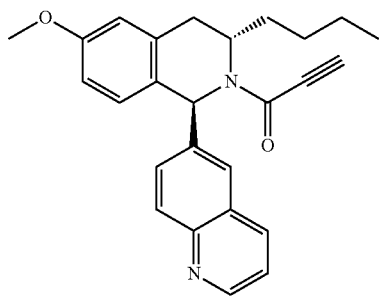 |
| 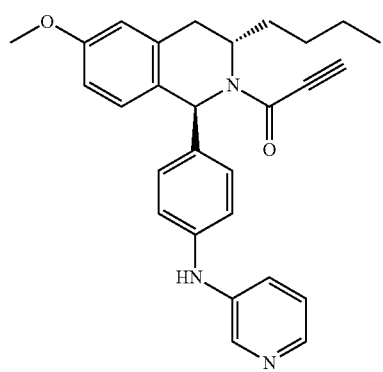 | 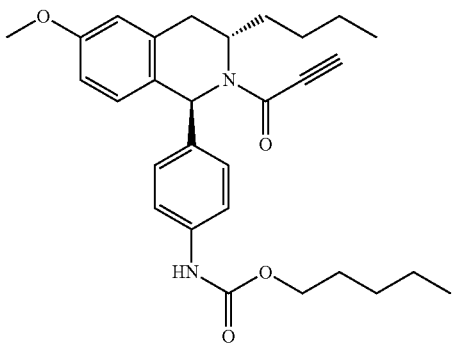 |
| 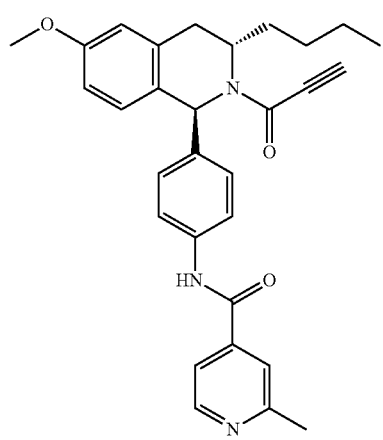 | 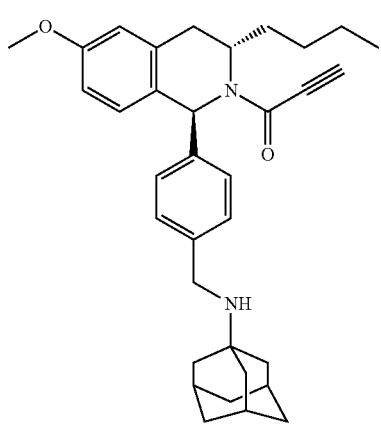 |

233
-continued
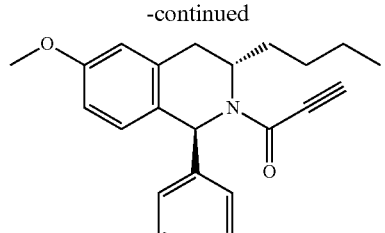
TFA
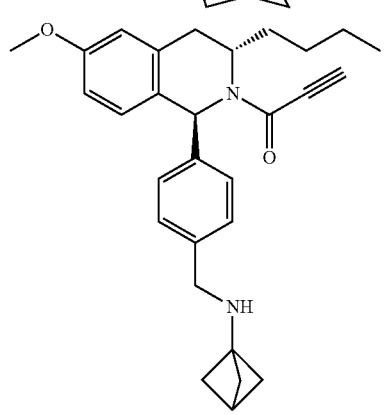
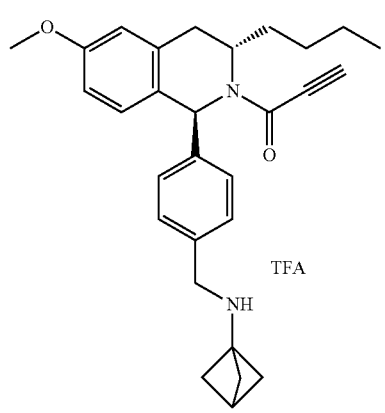
TFA
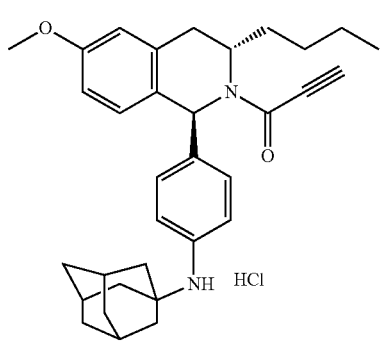
HCl
or
234
-continued
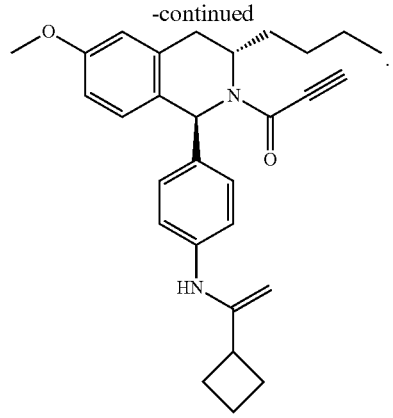
23. A compound which is:
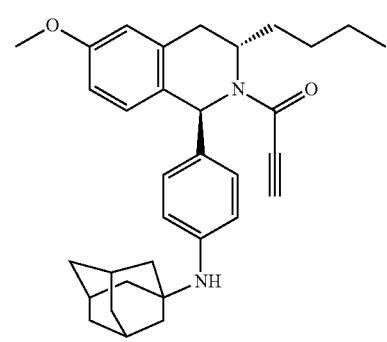 [SMILES: C#CC(=O)N1[C@@H](CCCC)Cc2cc(OC)ccc2[C@@H]1c1ccc(NC23CC4CC(CC(C4)C2)C3)cc1]
or pharmaceutically acceptable salt thereof.
24. A compound which is:
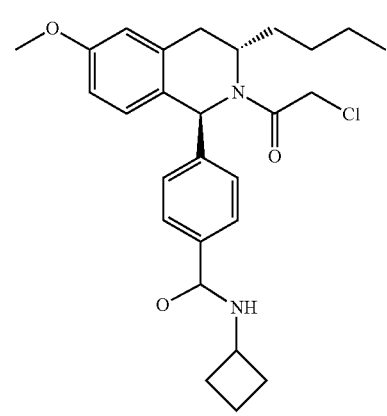 [SMILES: CCCC[C@H]1Cc2cc(OC)ccc2[C@H](c2ccc(C(O)NC3CCC3)cc2)N1C(=O)CCl]
or pharmaceutically acceptable salt thereof.

25. A compound which is:
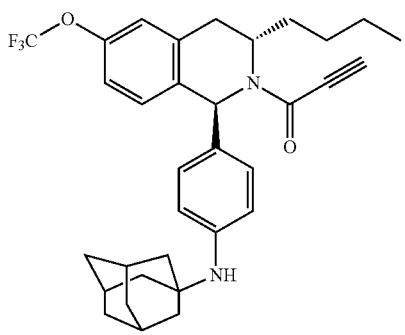 [SMILES: C#CC(=O)N1[C@@H](CCCC)Cc2cc(OC(F)(F)F)ccc2[C@@H]1c1ccc(NC23CC4CC(CC(C4)C2)C3)cc1]
or pharmaceutically acceptable salt thereof.
26. A compound which is:
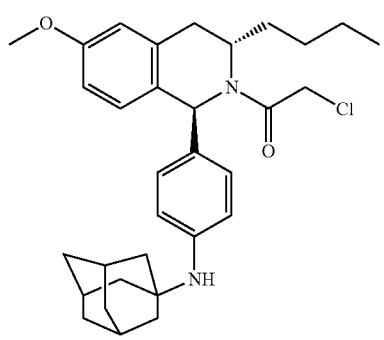 [SMILES: CCCC[C@H]1Cc2cc(OC)ccc2[C@H](c2ccc(NC34CC5CC(CC(C5)C3)C4)cc2)N1C(=O)CCl]
or pharmaceutically acceptable salt thereof.
27. A compound which is:
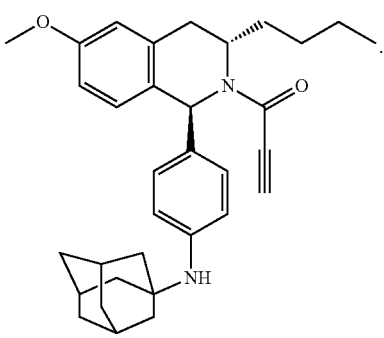 [SMILES: C#CC(=O)N1[C@@H](CCCC)Cc2cc(OC)ccc2[C@@H]1c1ccc(NC23CC4CC(CC(C4)C2)C3)cc1]
28. A compound which is:
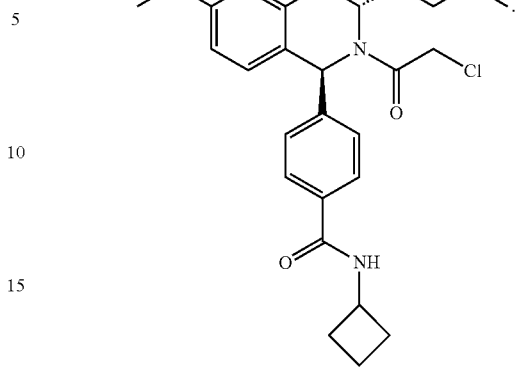
29. A compound which is:
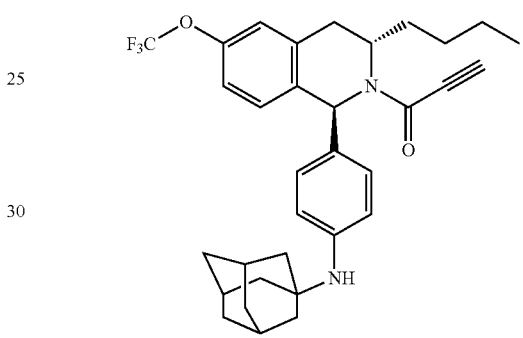
30. A compound which is:
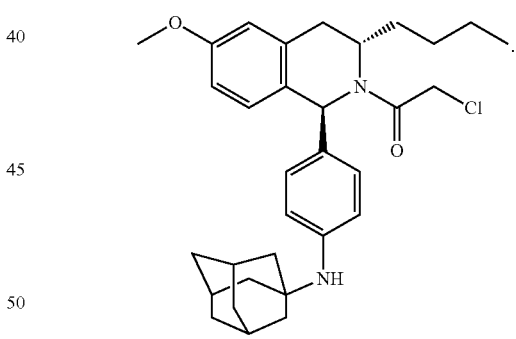
* * * * *